US006465634B1

(12) United States Patent
Dubensky, Jr. et al.

(10) Patent No.: US 6,465,634 B1
(45) Date of Patent: Oct. 15, 2002

(54) RECOMBINANT ALPHAVIRUS-BASED VECTORS WITH REDUCED INHIBITION OF CELLULAR MACROMOLECULAR SYNTHESIS

(75) Inventors: Thomas W. Dubensky, Jr., Del Mod, CA (US); John M. Polo, Encinitas, CA (US); Barbara A. Belli, San Diego, CA (US); Sondra Schlesinger, St. Louis, MO (US); Sergey A. Dryga, Fort Collins, CO (US); Ilya Frolov, St. Louis, MO (US)

(73) Assignees: Chiron Corporation, Emeryville, CA (US); Washington University, St. Louis, MO (US)

( * ) Notice: Subject to any disclaimer, the term of this patent is extended or adjusted under 35 U.S.C. 154(b) by 0 days.

(21) Appl. No.: 09/415,900

(22) Filed: Oct. 8, 1999

Related U.S. Application Data

(60) Division of application No. 08/944,645, filed on Oct. 6, 1997, which is a continuation-in-part of application No. 08/833,148, filed on Apr. 4, 1997, now abandoned, which is a continuation-in-part of application No. 08/679,640, filed on Jul. 12, 1996, now abandoned, which is a continuation-in-part of application No. 08/668,953, filed on Jun. 24, 1996, now abandoned, which is a continuation-in-part of application No. 08/628,594, filed on Apr. 5, 1996, now abandoned.

(51) Int. Cl.$^7$ .............................................. C07H 21/04
(52) U.S. Cl. .................................. 536/23.72; 435/320.1
(58) Field of Search ........................ 435/320.1; 514/44; 536/23.72

(56) References Cited

U.S. PATENT DOCUMENTS

| 5,026,686 A | 6/1991 | Schlesinger et al. | 514/17 |
|---|---|---|---|
| 5,091,309 A | 2/1992 | Schlesinger et al. | 435/69.1 |
| 5,185,440 A | 2/1993 | Davis et al. | 536/237.2 |
| 5,217,879 A | 6/1993 | Huang et al. | 435/69.1 |
| 5,505,947 A | 4/1996 | Johnston et al. | 424/218.1 |
| 5,532,154 A | 7/1996 | Brown | 435/235.1 |
| 5,591,579 A | 1/1997 | Olivo et al. | 435/6 |
| 5,614,404 A | 3/1997 | Mazzara et al. | 435/236 |
| 5,643,576 A | 7/1997 | Johnston et al. | 424/199.1 |
| 5,691,177 A | 11/1997 | Guber et al. | 435/172.3 |
| 5,739,026 A | 4/1998 | Garoff et al. | 435/240.2 |
| 5,766,602 A | 6/1998 | Xiong et al. | 424/218.1 |
| 5,789,245 A | 8/1998 | Dubensky, Jr. et al. | 435/320.1 |
| 5,792,462 A | 8/1998 | Johnston et al. | 424/199.1 |

FOREIGN PATENT DOCUMENTS

| WO | WO 88/00472 | 1/1988 |
|---|---|---|
| WO | WO 92/10578 | 6/1992 |
| WO | WO 94/17813 | 8/1994 |
| WO | WO 95/07994 | 3/1995 |
| WO | WO 95/17525 | 6/1995 |
| WO | WO 95/19990 | 7/1995 |
| WO | WO 95/25788 | 9/1995 |
| WO | WO 95/27044 | 10/1995 |
| WO | WO 95/27069 | 10/1995 |
| WO | WO 95/31565 | 11/1995 |
| WO | WO 95/32733 | 12/1995 |
| WO | WO 96/17072 | 6/1996 |
| WO | WO 96/37616 | 11/1996 |
| WO | WO 96/39830 | 12/1996 |
| WO | WO 97/38087 | 10/1997 |

OTHER PUBLICATIONS

Lastarza et al., Deletion and Duplication Mutations in the C–terminal Nonconserved Region of Sindbis Virus NsP3: Effects on Phosphorylation and on Virus Replication in Vertebrate and Invertebrate Cells. *Virology* 202:224–232, 1994.*

Dryga et al, "Identification of Mutations in a Sindbis Virus Variant able to Establish Persistent Infection in BHK Cells: the Importance of a Mutation in the nsP2 Gene" *Virology* 228:74–83, 1997.

Baumann and Schendel, "Interleukin–11 Regulates the Hepatic Expression of the Same Plasma Protien Genes as Interleukin–6" *J. Biological Chemistry* 266: 20424–20427, 1991.

Beier et al., "Association of Human, Class I MHC Alleles with the Adenovirus E3/19K Protein" *J. Immunology* 152:3862–3872, 1994.

Berglund et al., "Alphaviruses as Vectors for Gene Delivery" *Trends in Biotechnology* 14:130–134, 1996.

Berglund et al., "Semliki Forest Virus Expression System: Production of Conditionally Infectious Recombinant Particles" *Bio/Technology* 11:916–920, 1993.

Beauchemin et al., "Isolation and Characterization of Full–Length Functional cDNA Clones for Human Carcinoembryonic Antigen" *Molecular and Cellular Biology* 7(9):3221–3230, 1987.

Boyer and Haenni, "Infectious Transcripts and cDNA Clones of RNA Viruses" *Virology* 198:415–426, 1994.

Bredenbeek and Rice, "Animal RNA Virus Expression Systems" *Seminars in Virology* 3:297–310, 1992.

(List continued on next page.)

*Primary Examiner*—Donna C. Wortman
(74) *Attorney, Agent, or Firm*—Anne S. Dollard; Robert P. Blackburn; Dahna Pasternak

(57) ABSTRACT

Isolated nucleic acid molecules are disclosed, comprising an alphavirus nonstructural protein gene which, when operably incorporated into a recombinant alphavirus particle, eukaryotic layered vector initiation system, or RNA vector replicon, has a reduced level of vector-specific RNA synthesis, as compared to wild-type, and the same or greater level of proteins encoded by RNA transcribed from the viral junction region promoter, as compared to a wild-type recombinant alphavirus particle. Also disclosed are RNA vector replicons, alphavirus vector constructs, and eukaryotic layered vector initiation systems which contain the above-identified nucleic acid molecules.

25 Claims, 63 Drawing Sheets

OTHER PUBLICATIONS

Bredenbeek et al., "Sindbis Virus Expression Vectors: Packaging of RNA Replicons by Using Defective Helper RNAs" *J. Virology* 67(11):6439–6446, 1993.

Browne et al., "A Complex Between the MHC Class I Homologue Encoded by Human Cytomegalovirus and $\beta_2$ Microglobulin" *Nature* 347:770–772, 1990.

Culver and Blaese, "Gene Therapy for Cancer" *TIG* 10(5):174–178, 1994.

Davis et al., "In Vitro Synthesis of Infectious Venezuelan Equine Encephalitis Virus RNA from a cDNA Clone: Analysis of a Viable Deletion Mutant" *Virology* 171:189–204, 1989.

Davis et al., "Protection Against Influenza in Mice by Vaccination with a Venezuelan Equine Encephalitis Virus Vector Expressing the HA Protein" *J. Cell Biochem. Suppl.* 19A(10): Abstract No. J2–308, 1995.

Driver et al., "Layered Amplification of Gene Expression with a DNA Gene Delivery System" *Annals of New York Academy of Science* 772(1):261–264, 1995.

Dubensky et al., "Polynucleotide Based Gene Transfer Vector Derived from an Alphavirus" *J. Cellular Biochemistry Supplement* 0(21A):406, Abstract No. C6–413, 1995.

Dubensky, Jr. et al., "Sindbis Virus DNA–Based Expression Vectors: Utility for in vitro and in vivo Gene Transfer" *J. Virology* 70(1):508–519, 1996.

Dubuisson and Rice, "Sindbis Virus Attachment" Isolation and Characterization of Mutants with Impaired Binding to Vertebrate Cells *Journal Virology* 67(6):3363–3374, 1993.

Frolov and Schlesinger, "Comparison of the Effects of Sindbis and Sindbis Virus Replicons on Host Cell Protein Synthesis and Cytopathogenicity in BHK Cells" *J. Virology* 68(3):1721–1727, 1994.

Gassman et al., "Analysis of the *Borrelia Burgdorferi* GeHo fla Gene and Antigenic Characterization of its Gene Product" *J. Bacteriology* 173(4):1452–1459, 1991.

Geigenmüller–Gnirke et al., "Complementation between Sindbis Viral RNAs Produces Infectious Particles with a Bipartite Genome" *Proc. Natl. Acad. Sci. USA* 88:3253–3257, 1991.

Grakoui et al., "A cis–acting Mutation in the Sindbis Virus Junction Region which Affects Subgenomic RNA Synthesis" *J. Virology* 63(12):5216–5227, 1989.

Hahn et al., "Infectious Sindbis Virus Transient Expression Vectors for Studying Antigen Processing and Presentation" *Proc. Natl. Acad. Sci. USA* 89:2679–2683, 1992.

Hertz and Huang, "Utilization of Heterologous Alphavirus Junction Sequences as Promoters by Sindbis Virus" *J. Virology* 66(2):957–864, 1992.

Herweijer et al., "A Plasmid–Based Self–Amplifying Sindbis Virus Vector" *Human Gene Therapy* 6:1161–1167, 1995.

Hodgson, Advances in Vector Systems for Gene Therapy, *Exp. Opin. Ther. Patents* 5(5):459–468, 1995.

Huang et al., "RNA Viruses as Gene Expression Vectors" *Virus Genes* 3(1):85–91, 1989.

Huang and Li, "Liposomal Gene Delivery: A Complex Package" *Nature Biotechnology* 15:620–621, 1997.

Johanning et al., "A Sindbis Virus mRNA Polynucleotide Vector Achieves Prolonged and High Level Heterologous Gene Expression in vivo" *Nucleic Acids Research* 23(9):1495–1501, 1995.

Kuhn et al., Infectious RNA Transcripts from Ross River Virus cDNA Clones and the Construction and Characterization of Defined Chimers with Sindbis Virus: *Virology* 182:430–441, 1991.

Kuo et al., "An Assay for Circulating Antibodies to a Major Etiologic Virus of Human Non–A, Non–B Hepatits" *Science* 244:362–364, 1989.

Lemm et al., "Mutations which Alter the Level or Structure of nsP4 can Affect the Efficiency of Sindbis Virus Replication in a Host–Dependent Manner" *J. Virology* 64(6):3001–3011, 1990.

Lemm et al., "Polypepetide Requirements for Assembly of Functional Sindbis Virus Replication Complexes: a Model for the Temporal Regulation of Minus– and Plus–Strand RNA Synthesis" *The EMBO J.* 13(12):2925–2934, 1994.

Levis et al., "Deletion Mapping of Sindbis Virus DI RNAs Dervied from cDNAs Defines the Sequences Essential for Replication and Packaging" *Cell* 44:137–145, 1986.

Levis et al., "Engineered Defective Interfering RNAs of Sindbis Virus Express Bacterial Chloramphenicol Acetyltransferase in Avian Cells" *Proc. Natl. Acad. Sci. USA* 84:4811–4815, 1987.

Levis et al., "Promoter for Sindbis Virus RNA–Dependent Subgenomic RNA Transcription" *J. Virology* 64(4):1726–1733, 1990.

Liljeström and Garoff, "A New Generation of Animal Cell Expression Vectors Based on the Semliki Forest Virus Replicon" *Bio/Technology* 9:1356–1361, 1991.

Liljeström, "Alphavirus Expression Systems" *Current Opinion Biotechnology* 5: 495–500, 1994.

London et al., "Infectious Enveloped RNA Virus Antigenic Chimerase" *Proc. Natl. Acad. Sci USA* 89:207–211, 1992.

Marshall, "Gene Therapy's Growing Pains" *Science* 269:1050–1055, 1995.

Miller and Vile, "Targeted Vectors for Gene Therapy" *FASEB J.* 9:190–199, 1995.

Oker–Blom and Summers, "Expression of Sindbis Virus 26S cDNA in *Spodoptera frugiperda* (Sf9) Cells, Using a Baculovirus Expression Vector" *J. Virology* 63(3):1256–1264, 1989.

Olivo et al., "Cell Line that Expresses a Reporter Gene in Response to Infection by Sindbis Virus: a Prototype for Detection of Positive Strand RNA Viruses" *Virology* 198:381–384, 1994.

Orkin and Motulsky, Report and Recommendations of the Panel to Assess the NIH Investment in Research on Gene Therapy: www.nih.gov/news/panelrep.html (Accessed Sep. 11, 1998).

Owen and Kuhn, "Identification of a Region in the Sindbis Virus Nucleocapsid Protein that is Involved in Specificity of RNA Encapsidation" *J. Virology* 70(5):2757–2763, 1996.

Polo et al., "Alphavirus Mediated Delivery of Ribozyme Therapeutics" *J. Cell Biochem. Suppl.* 19A:228, Abstract No. A6–413, 1995.

Racaniello and Baltimore, "Cloned Poliovirus Complementary DNA is Infectious in Mammalian Cells" *Science* 214:916–919, 1981.

Raju and Huang, "Analysis of Sindbis Virus Promoter Recognition in vivo, Using Novel Vectors with Two Subgeonomic mRNA Promoters" *J. Virology* 65(5):2501–2510, 1991.

Rice et al., "Expression of Sindbis Virus Structural Proteins via Recombinant Vaccinia Virus: Synthesis, Processing, and Incorporation into Mature Sindbis Virions" *J. Virology* 56(1):227–239, 1985.

Rice et al., "Production of Infectious RNA Transcripts from Sindbis Virus cDNA Clones: Mapping of Lethal Mutatins, Rescue of a Temperature–Sensitive Marker, and in vitro Mutagenesis to Generate Defined Mutants" *J. Virology* 61(2):3809–3819, 1987.

Rolls et al., "Expression of Additional Genes in a Vector Derived from a Minimal RNA Virus" *Virology* 218:406–411, 1996.

Rolls et al., "Novel Infectious Particles Generated by Expression of the Vesicular Stomatitis Virus Glycoprotein from a Self–Replicating RNA" *Cell* 79:497–506, 1994.

Sarver and Stollar, "Sindbis Virus–Induced Cytopathic Effect in Clones of *Aedes albopictus* (Singh) Cells" *Virology* 80:390–400, 1977.

Schlesinger, "Alphaviruses–Vectors for the Expression of heterologous Genes" *Trends in Biotechnology* 11:18–22, 1993.

Schowalter et al., "Heterologous Expression of Adenovirus E3–gp19K in an E1a–deleted Adenovirus Vector Inhibits MHC I Expression in vitro, but does not Prolong Transgene Expression in vivo" *Gene Therapy* 4:351–360, 1997.

Semler et al., "Production of Infectious Poliovirus from Cloned cDNA is Dramatically Increased by SV40 Transcription and Replication Signals" *Nucleic Acids Research* 12(12): 5123–5141, 1984.

Shirako and Strauss, "Regulation of Sindbis Virus RNA Replication: Uncleaved P123 an nsP4 Function in Minus–Strand RNA Synthesis, Whereas Cleaved Products from P123 are Required for Efficient Plus–Strand RNA Synthesis" *J. Virology* 68(3):1874–1885, 1994.

Strauss and Strauss, "The Alphaviruses: Gene Expression, Replication, and Evolution" *Microbiological Reviews* 58(3):491–562, 1994.

Strauss et al., "Complete Nucleotide Sequence of the Genomic RNA of Sindbis Virus" *Virology* 133:92–110, 1984.

Strauss et al. "Identification of the Active Site Residues in the nsP2 Proteinase of Sindbis Virus" *Virology* 191:932–940, 1992.

Tysoe–Calnon et al., "Molecular Comparisons of the $\beta_2$–microglobulin–binding site in Class I major–histocompatibility–complex $\alpha$–chains and Proteins of Related Sequences" *Biochemistry* 277:359–369, 1991.

Watson et al., "A Mutant CHO–K1 Strain with Resistance to *Pseudomonas* Exotoxin A and Alphaviruses Fails to Cleave Sindbis Virus Glycoprotein PE2" *J. Virology* 65(5):2332–2339, 1991.

Weiss and Schlesinger, "Defective Interfering Particles of Sindbis Virus do not Interfere with a Homologous Virus Obtaining from Persistently Infected BHK Cells but do Interfere with Semliki Forest Virus" *J. Virology* 37(2):840–844, 1981.

Weiss and Schlesinger, "Recombination Between Sindbis Virus RNAs" *J. Virology* 65(8):4017–4025, 1991.

Weiss et al ., "Establishment and Maintenance of Persistent Infection by Sindbis Virus in BHK Cells" *J. Virology* 33(1):463–474, 1980.

Weiss et al., "Evidence for Specificity in the Encapsidation of Sindbis Virus RNAs" *J. Virology* 63:5310–5318, 1989.

Weiss et al., "Interactions Between Sindbis Virus RNAs and a 68 Amino Acid Derivative of the Viral Capsid Protein Further Defines the Capsid Binding Site" *Nucleic Acids Research* 22(5):780–786, 1994.

Wen and Schllesinger, "Regulated Expression of Sindbis and Vesicular Stomatitis Virus Glycoproteins in *Saccharomyces cerevisiae*" *Proc. Natl. Acad. Sci. USA* 83:3639–3643, 1986.

Xiong et al., "Sindbis Virus: and Efficient, Broad Host Range Vector for Gene Expression in Animal Cells" *Science* 243:1188–1191, 1989.

Zhou et al., "Generation of Cytotoxic and Humoral Immune Responses by Nonreplicative Recombinant Semliki Forest Virus" *Proc. Natl. Acad. Sci. USA* 92:3009–3013, 1995.

Zhou et al., "Self–Replicating Semliki Forest Virus RNA as Recombinant Vaccine" *Vaccine* 12(16):1510–1514, 1994.

International Search Report, PCT Patent Application No. PCT/US94/10469, May 4, 1995.

European Search Report, EP Patent Application No. 95115460.8, Nov. 15, 1996.

* cited by examiner

```
ATTGACGGCG TAGTACACAC TATTGAATCA AACAGCCGAC CAATCGCACT ACCATCACAA    60
TGGAGAAGCC AGTAGTAAAC GTAGACGTAG ACCCCCAGAG TCCGTTTGTC GTGCAACTGA   120
AAAAAAGCTT CCCGCAATTT GAGGTAGTAG CACAGCAGGT CACTCCAAAT GACCATGCTA   180
ATGCCAGAGC ATTTTCGCAT CTGGCCAGTA AACTAATCGA GCTGGAGGTT CCTACCACAG   240
CGACGATCTT GGACATAGGC AGCGCACCGG CTCGTAGAAT GTTTTCCGAG CACCAGTATC   300
ATTGTGTCTG CCCCATGCGT AGTCCAGAAG ACCGGACCG CATGATGAAA TACGCCAGTA   360
AACTGGCGGA AAAAGCGTGC AAGATTACAA ACAAGAACTT GCATGAGAAG ATTAAGGATC   420
TCCGGACCGT ACTTGATACG CCGGATGCTG AAACACCATC GCTCTGCTTT CACAACGATG   480
TTACCTGCAA CATGCGTGCC GAATATTCCG TCATGCAGGA CGTGTATATC AACGCTCCCG   540
GAACTATCTA TCATCAGGCT ATGAAAGCG TGCGGACCCT GTACTGGATT GGCTTCGACA   600
CCACCCAGTT CATGTTCTCG GCTATGGCAG GTTCGTACCC TGCGTACAAC ACCAACTGGG   660
CCGACGAGAA AGTCCTTGAA GCGCGTAACA TCGGACTTTG CAGCACAAAG CTGAGTGAAG   720
GTAGGACAGG AAAATTGTCG ATAATGAGGA AGAAGGAGTT GAAGCCCGGG TCGCGGGTTT   780
ATTTCTCCGT AGGATCGACA CTTTATCCAG AACACAGAGC CAGCTTGCAG AGCTGGCATC   840
TTCCATCGGT GTTCCACTTG AATGGAAAGC AGTCGTACAC TTGCCGCTGT GATACAGTGG   900
TGAGTTGCGA AGGCTACGTA GTGAAGAAAA TCACCATCAG TCCCGGGATC ACGGGAGAAA   960
CCGTGGGATA CGCGGTTACA CACAATAGCG AGGGCTTCTT GCTATGCAAA GTTACTGACA  1020
CAGTAAAAGG AGAACGGGTA TCGTTCCCTG TGTGCACGTA CATCCCGGCC ACCATATGCG  1080
ATCAGATGAC TGGTATAATG CCACGGATA TATCACCTGA CGATGCACAA AAACTTCTGG  1140
TTGGGCTCAA CCAGCGAATT GTCATTAACG GTAGGACTAA CAGGAACACC AACACCATGC  1200
AAAATTACCT TCTGCCGATC ATAGCACAAG GGTTCAGCAA ATGGGCTAAG GAGCGCAAGG  1260
ATGATCTTGA TAACGAGAAA ATGCTGGTA CTAGAGAACG CAAGCTTACG TATGGCTGCT  1320
TGTGGGCGTT TCGCACTAAG AAAGTACATT CGTTTTATCG CCCACCTGGA ACGCAGACCT  1380
GCGTAAAAGT CCCAGCCTCT TTTAGCGCTT TTCCCATGTC GTCCGTATGG ACGACCTCTT  1440
TGCCCATGTC GCTGAGGCAG AAATTGAAAC TGGCATTGCA ACCAAAGAAG GAGGAAAAAC  1500
TGCTGCAGGT CTCGGAGGAA TTAGTCATGG AGGCCAAGGC TGCTTTTGAG GATGCTCAGG  1560
AGGAAGCCAG AGCGGAGAAG CTCCGAGAAG CACTTCCACC ATTAGTGGCA GACAAAGGCA  1620
TCGAGGCAGC CGCAGAAGTT GTCTGCGAAG TGGAGGGCT CCAGGCGGAC ATCGGAGCAG  1680
CATTAGTTGA AACCCCGCGC GGTCACGTAA GGATAATACC TCAAGCAAAT GACCGTATGA  1740
TCGGACAGTA TATCGTTGTC TCGCCAAACT CTGTACTGAA GAATGCCAAA CTCGCACCAG  1800
CGCACCCGCT AGCAGATCAG GTTAAGATCA TAACACACTC CGGAAGATCA GGAAGGTACG  1860
CGGTCGAACC ATACGACGCT AAAGTACTGA TGCCAGCAGG AGGTGCCGTA CCATGGCAG  1920
AATTCCTAGC ACTGAGTGAG AGCGCCACGT TAGTGTACAA CGAAAGAGAG CTTGTGAACC  1980
GCAAACTATA CCACATTGCC ATGCATGGCC CGCCAAGAA TACAGAAGAG GAGCAGTACA  2040
AGGTTACAAA GGCAGAGCTT GCAGAAACAG AGTACGTGTT TGACGTGGAC AAGAAGCGTT  2100
GCGTTAAGAA GGAAGAAGCC TCAGGTCTGG TCCTCTCGGG AGAACTGACC AACCCTCCCT  2160
ATCATGAGCT AGCTCTGGAG GGACTGAAGA CCCGACCTGC GGTCCCGTAC AAGGTCGAAA  2220
CAATAGGAGT GATAGGCACA CCGGGGTCGG GCAAGTCAGC TATTATCAAG TCAACTGTCA  2280
CGGCACGAGA TCTTGTTACC AGCGGAAAGA AAGAAAATTG TCGCGAAATT GAGGCCGACG  2340
TGCTAAGACT GAGGGGTATG CAGATTACGT CGAAGACAGT AGATTCGGTT ATGCTCAACG  2400
GATGCCACAA AGCCGTAGAA GTGCTGTACG TTGACGAAGC GTTCGCGTGC CACGCAGGAG  2460
CACTACTTGC CTTGATTGCT ATCGTCAGGC CCCGCAAGAA GGTAGTACTA TGCGGAGACC  2520
```

FIG. 6A

```
CCATGCAATG CGGATTCTTC AACATGATGC AACTAAAGGT ACATTTCAAT CACCCTGAAA    2580
AAGACATATG CACCAAGACA TTCTACAAGT ATATCTCCCG GCGTTGCACA CAGCCAGTTA    2640
CAGCTATTGT ATCGACACTG CATTACGATG GAAAGATGAA AACCACGAAC CCGTGCAAGA    2700
AGAACATTGA AATCGATATT ACAGGGGCCA CAAAGCCGAA GCCAGGGGAT ATCATCCTGA    2760
CATGTTTCCG CGGGTGGGTT AAGCAATTGC AAATCGACTA TCCCGGACAT GAAGTAATGA    2820
CAGCCGCGGC CTCACAAGGG CTAACCAGAA AAGGAGTGTA TGCCGTCCGG CAAAAAGTCA    2880
ATGAAAACCC ACTGTACGCG ATCACATCAG AGCATGTGAA CGTGTTGCTC ACCCGCACTG    2940
AGGACAGGCT AGTGTGGAAA ACCTTGCAGG GCGACCCATG GATTAAGCAG CTCACTAACA    3000
TACCTAAAGG AAACTTTCAG GCTACTATAG AGGACTGGGA AGCTGAACAC AAGGGAATAA    3060
TTGCTGCAAT AAACAGCCCC ACTCCCCGTG CCAATCCGTT CAGCTGCAAG ACCAACGTTT    3120
GCTGGGCGAA AGCATTGGAA CCGATACTAG CCACGGCCGG TATCGTACTT ACCGGTTGCC    3180
AGTGGAGCGA ACTGTTCCCA CAGTTTGCGG ATGACAAACC ACATTCGCC ATTTACGCCT     3240
TAGACGTAAT TTGCATTAAG TTTTTCGGCA TGGACTTGAC AAGCGGACTG TTTTCTAAAC    3300
AGAGCATCCC ACTAACGTAC CATCCCGCCG ATTCAGCGAG GCCGGTAGCT CATTGGGACA    3360
ACAGCCCAGG AACCCGCAAG TATGGGTACG ATCACGCCAT TGCCGCCGAA CTCTCCCGTA    3420
GATTTCCGGT GTTCCAGCTA GCTGGGAAGG GCACACAACT TGATTTGCAG ACGGGGAGAA    3480
CCAGAGTTAT CTCTGCACAG CATAACCTGG TCCCGGTGAA CCGCAATCTT CCTCACGCCT    3540
TAGTCCCCGA GTACAAGGAG AAGCAACCCG GCCGGTCGA AAAATTCTTG AACCAGTTCA     3600
AACACCACTC AGTACTTGTG GTATCAGAGG AAAAAATTGA AGCTCCCCGT AAGAGAATCG    3660
AATGGATCGC CCCGATTGGC ATAGCCGGTG CAGATAAGAA CTACAACCTG GCTTTCGGGT    3720
TTCCGCCGCA GGCACGGTAC GACCTGGTGT TCATCAACAT TGGAACTAAA TACAGAAACC    3780
ACCACTTTCA GCAGTGCGAA GACCATGCGG CGACCTTAAA AACCCTTTCG CGTTCGGCCC    3840
TGAATTGCCT TAACTCAGGA GGCACTCTCG TGGTGAAGTC CTATGGCTAC GCCGACCGCA    3900
ACAGTGAGGA CGTAGTCACC GCTCTTGCCA GAAAGTTTGT CAGGGTGTCT GCAGCGAGAC    3960
CAGATTGTGT CTCAAGCAAT ACAGAAATGT ACCTGATTTT CCGACAACTA GACAACAGCC    4020
GTACACGGCA ATTCACCCCG CACCATCTGA ATTGCGTGAT TTCGTCCGTG TATGAGGGTA    4080
CAAGAGATGG AGTTGGAGCC GCGCCGTCAT ACCGCACCAA AAGGGAGAAT ATTGCTGACT    4140
GTCAAGAGGA AGCAGTTGTC AACGCAGCCA ATCCGCTGGG TAGACCAGGC AAGGAGTCT     4200
GCCGTGCCAT CTATAAACGT TGGCCGACCA GTTTTACCGA TTCAGCCACG GAGACAGGCA    4260
CCGCAAGAAT GACTGTGTGC CTAGGAAAGA AAGTGATCCA CGCGGTCGGC CCTGATTTCC    4320
GGAAGCACCC AGAAGCAGTA GCCTTGAAAT TGCTACAAAA CGCCTACCAT GCAGTGGCAG    4380
ACTTAGTAAA TGAACATAAC ATCAAGTCTG TCGCCATTCC ACTGCTATCT ACAGGCATTT    4440
ACGCAGCCGG AAAAGACCGC CTTGAAGTAT CACTTAACTG CTTGACAACC GCGCTAGACA    4500
GAACTGACGC GGACGTAACC ATCTATTGCC TGGATAAGAA GTGGAAGGAA AGAATCGACG    4560
CGGCACTCCA ACTTAAGGAG TCTGTAACAG AGCTGAAGGA TGAAGATATG GAGATCGACG    4620
ATGAGTTAGT ATGGATCCAT CCAGACAGTT GCTTGAAGGG AAGAAAGGGA TTCAGTACTA    4680
CAAAAGGAAA ATTGTATTCG TACTTCGAAG GCACCAAATT CCATCAAGCA GCAAAAGACA    4740
TGGCGGAGAT AAAGGTCCTG TTCCTAATG ACCAGGAAAG TAATGAACAA CTGTGTGCCT     4800
ACATATTGGG TGAGACCATG GAAGCAATCC GCGAAAAGTG CCCGGTCGAC CATAACCCGT    4860
CGTTTAGCCC GCCCAAAACG TTGCCGTGCC TTTGCATGTA TGCCATGACG CCAGAAAGGG    4920
TCCACAGACT TAGAAGCAAT AACGTCAAAG AAGTTACAGT ATGCTCCTCC ACCCCCCTTC    4980
CTAAGCACAA AATTAAGAAT GTTCAGAAGG TTCAGTGCAC GAAAGTAGTC CTGTTTAATC    5040
```

```
CGCACACTCC CGCATTCGTT CCCGCCCGTA AGTACATAGA AGTGCCAGAA CAGCCTACCG    5100
CTCCTCCTGC ACAGGCCGAG GAGGCCCCCG AAGTTGTAGC GACACCGTCA CCATCTACAG    5160
CTGATAACAC CTCGCTTGAT GTCACAGACA TCTCACTGGA TATGGATGAC AGTAGCGAAG    5220
GCTCACTTTT TTCGAGCTTT AGCGGATCGG ACAACTCTAT TACTAGTATG GACAGTTGGT    5280
CGTCAGGACC TAGTTCACTA GAGATAGTAG ACCGAAGGCA GGTGGTGGTG GCTGACGTTC    5340
ATGCCGTCCA AGAGCCTGCC CCTATTCCAC CGCCAAGGCT AAAGAAGATG GCCCGCCTGG    5400
CAGCGGCAAG AAAAGAGCCC ACTCCACCGG CAAGCAATAG CTCTGAGTCC CTCCACCTCT    5460
CTTTTGGTGG GGTATCCATG TCCCTCGGAT CAATTTTCGA CGGAGAGACG GCCCGCCAGG    5520
CAGCGGTACA ACCCCTGGCA ACAGGCCCCA CGGATGTGCC TATGTCTTTC GGATCGTTTT    5580
CCGACGGAGA GATTGATGAG CTGAGCCGCA GAGTAACTGA GTCCGAACCC GTCCTGTTTG    5640
GATCATTTGA ACCGGCGAA GTGAACTCAA TTATATCGTC CCGATCAGCC GTATCTTTTC    5700
CTCTACGCAA GCAGAGACGT AGACGCAGGA GCAGGAGGAC TGAATACTGA CTAACCGGGG    5760
TAGGTGGGTA CATATTTTCG ACGGACACAG GCCCTGGGCA CTTGCAAAAG AAGTCCGTTC    5820
TGCAGAACCA GCTTACAGAA CCGACCTTGG AGCACAATGT CCTGGAAAGA ATTCATGCCC    5880
CGGTGCTCGA CACGTCGAAA GAGGAACAAC TCAAACTCAG GTACCAGATG ATGCCCACCG    5940
AAGCCAACAA AAGTAGGTAC CAGTCTCGTA AAGTAGAAAA TCAGAAAGCC ATAACCACTG    6000
AGCGACTACT GTCAGGACTA CGACTGTATA ACTCTGCCAC AGATCAGCCA GAATGCTATA    6060
AGATCACCTA TCCGAAACCA TTGTACTCCA GTAGCGTACC GGCGAACTAC TCCGATCCAC    6120
AGTTCGCTGT AGCTGTCTGT AACAACTATC TGCATGAGAA CTATCCGACA GTAGCATCTT    6180
ATCAGATTAC TGACGAGTAC GATGCTTACT TGGATATGGT AGACGGGACA GTCGCCTGCC    6240
TGGATACTGC AACCTTCTGC CCCGCTAAGC TTAGAAGTTA CCCGAAAAAA CATGAGTATA    6300
GAGCCCCGAA TATCCGCAGT GCGGTTCCAT CAGCGATGCA GAACACGCTA CAAAATGTGC    6360
TCATTGCCGC AACTAAAAGA AATTGCAACG TCACGCAGAT GCGTGAACTG CCAACACTGG    6420
ACTCAGCGAC ATTCAATGTC GAATGCTTTC GAAAATATGC ATGTAATGAC GAGTATTGGG    6480
AGGAGTTCGC TCGGAAGCCA ATTAGGATTA CCACTGAGTT TGTCACCGCA TATGTAGCTA    6540
GACTGAAAGG CCCTAAGGCC GCCGCACTAT TTGCAAAGAC GTATAATTTG GTCCCATTGC    6600
AAGAAGTGCC TATGGATAGA TTCGTCATGG ACATGAAAAG AGACGTGAAA GTTACACCAG    6660
GCACGAAACA CACAGAAGAA AGACCGAAAG TACAAGTGAT ACAAGCCGCA GAACCCCTGG    6720
CGACTGCTTA CTTATGCGGG ATTCACCGGG AATTAGTGCG TAGGCTTACG GCCGTCTTGC    6780
TTCCAAACAT TCACACGCTT TTTGACATGT CGGCGGAGGA TTTTGATGCA ATCATAGCAG    6840
AACACTTCAA GCAAGGCGAC CCGGTACTGG AGACGGATAT CGCATCATTC GACAAAAGCC    6900
AAGACGACGC TATGGCGTTA ACCGGTCTGA TGATCTTGGA GGACCTGGGT GTGGATCAAC    6960
CACTACTCGA CTTGATCGAG TGCGCCTTTG GAGAAATATC ATCCACCCAT CTACCTACGG    7020
GTACTCGTTT TAAATTCGGG GCGATGATGA AATCCGGAAT GTTCCTCACA CTTTTTGTCA    7080
ACACAGTTTT GAATGTCGTT ATCGCCAGCA GAGTACTAGA AGAGCGGCTT AAAACGTCCA    7140
GATGTGCAGC GTTCATTGGC GACGACAACA TCATACATGG AGTAGTATCT GACAAAGAAA    7200
TGGCTGAGAG GTGCGCCACC TGGCTCAACA TGGAGGTTAA GATCATCGAC GCAGTCATCG    7260
GTGAGAGACC ACCTTACTTC TGCGGCGGAT TTATCTTGCA AGATTCGGTT ACTTCCACAG    7320
CGTGCCGCGT GGCGGATCCC CTGAAAAGGC TGTTTAAGTT GGGTAAACCG CTCCCAGCCG    7380
ACGACGAGCA AGACGAAGAC AGAAGACGCG CTCTGCTAGA TGAAACAAAG GCGTGGTTTA    7440
GAGTAGGTAT AACAGGCACT TTAGCAGTGG CCGTGACGAC CCGGTATGAG GTAGACAATA    7500
TTACACCTGT CCTACTGGCA TTGAGAACTT TTGCCCAGAG CAAAAGAGCA TTCCAAGCCA    7560
```

FIG. 6C

```
TCAGAGGGGA AATAAAGCAT CTCTACGGTG GTCCTAAATA GTCAGCATAG TTCATTTCAT    7620
CTGACTAATA CTACAACACC ACCACCATGA ATAGAGGATT CTTTAACATG CTCGGCCGCC    7680
GCCCCTTCCC GGCCCCCACT GCCATGTGGA GGCCGCGGAG AAGGAGGCAG GCGGCCCCGA    7740
TGCCTGCCCG CAACGGGCTG GCTTCTCAAA TCCAGCAACT GACCACAGCC GTCAGTGCCC    7800
TAGTCATTGG ACAGGCAACT AGACCTCAAC CCCCATGTCC ACGCCCGCCA CCGCGCCAGA    7860
AGAAGCAGGC GCCCAAGCAA CCACCGAAGC CGAAGAAACC AAAAACGCAG GAGAAGAAGA    7920
AGAAGCAACC TGCAAAACCC AAACCCGGAA AGAGACAGCG CATGGCACTT AAGTTGGAGG    7980
CCGACAGATT GTTCGACGTC                                                8000
```

FIG. 6D

| | | | | | | |
|---|---|---|---|---|---|---|
|ATTGACGGCG|TAGTACACAC|TATTGAATCA|AACAGCCGAC|CAATTGCACT|ACCATCACAA|60|
|TGGAGAAGCC|AGTAGTAAAC|GTAGACGTAG|ACCCCCAGAG|TCCGTTTGTC|GTGCAACTGC|120|
|AAAAAAGCTT|CCCGCAATTT|GAGGTAGTAG|CACAGCAGGT|CACTCCAAAT|GACCATGCTA|180|
|ATGCCAGAGC|ATTTTCGCAT|CTGGCCAGTA|AACTAATCGA|GCTGGAGGTT|CCTACCACAG|240|
|CGACGATCTT|GGACATAGGC|AGCGCACCGG|CTCGTAGAAT|GTTTTCCGAG|CACCAGTATC|300|
|ATTGTGTCTG|CCCCATGCGT|AGTCCAGAAG|ACCCGGACCG|CATGATGAAA|TACGCCAGTA|360|
|AACTGGCGGA|AAAAGCGTGC|AAGATTACAA|ACAAGAACTT|GCATGAGAAG|ATTAAGGATC|420|
|TCCGGACCGT|ACTTGATACG|CCGGATGCTG|AAACACCATC|GCTCTGCTTT|CACAACGATG|480|
|TTACCTGCAA|CATGCGTGCC|GAATATTCCG|TCATGCAGGA|CGTGTATATC|AACGCTCCCG|540|
|GAACTATCTA|TCATCAGGCT|ATGAAAGGCG|TGCGGACCCT|GTACTGGATT|GGCTTCGACA|600|
|CCACCCAGTT|CATGTTCTCG|GCTATGGCAG|GTTCGTACCC|TGCGTACAAC|ACCAACTGGG|660|
|CCGACGAGAA|AGTCCTTGAA|GCGCGTAACA|TCGGACTTTG|CAGCACAAAG|CTGAGTGAAG|720|
|GTAGGACAGG|AAAATTGTCG|ATAATGAGGA|AGAAGGAGTT|GAAGCCCGGG|TCGCGGGTTT|780|
|ATTTCTCCGT|AGGATCGACA|CTTTATCCAG|AACACAGAGC|CAGCTTGCAG|AGCTGGCATC|840|
|TTCCATCGGT|GTTCCACTTG|AATGGAAAGC|AGTCGTACAC|TTGCCGCTGT|GATACAGTGG|900|
|TGAGTTGCGA|AGGCTACGTA|GTGAAGAAAA|TCACCATCAG|TCCCGGGATC|ACGGAGAAA|960|
|CCGTGGGATA|CGCGGTTACA|CACAATAGCG|AGGGCTTCTT|GCTATGCAAA|GTTACTGACA|1020|
|CAGTAAAAGG|AGAACGGGTA|TCGTTCCCTG|TGTGCACGTA|CATCCCGGCC|ACCATATGCG|1080|
|ATCAGATGAC|TGGTATAATG|GCCACGGATA|TATCACCTGA|CGATGCACAA|AAACTTCTGG|1140|
|TTGGGCTCAA|CCAGCGAATT|GTCATTAACG|GTAGGACTAA|CAGGAACACC|AACACCATGC|1200|
|AAAATTACCT|TCTGCCGATC|ATAGCACAAG|GGTTCAGCAA|ATGGGCTAAG|GAGCGCAAGG|1260|
|ATGATCTTGA|TAACGAGAAA|ATGCTGGGTA|CTAGAGAACG|CAAGCTTACG|TATGGCTGCT|1320|
|TGTGGGCGTT|TCGCACTAAG|AAAGTACATT|CGTTTTATCG|CCCACCTGGA|ACGCAGACCT|1380|
|GCGTAAAAGT|CCCAGCCTCT|TTTAGCGCTT|TTCCCATGTC|GTCCGTATGG|ACGACCTCTT|1440|
|TGCCCATGTC|GCTGAGGCAG|AAATTGAAAC|TGGCATTGCA|ACCAAAGAAG|GAGGAAAAAC|1500|
|TGCTGCAGGT|CTCGGAGGAA|TTAGTCATGG|AGGCCAAGGC|TGCTTTTGAG|GATGCTCAGG|1560|
|AGGAAGCCAG|AGCGGAGAAG|CTCCGAGAAG|CACTTCCACC|ATTAGTGGCA|GACAAAGGCA|1620|
|TCGAGGCAGC|CGCAGAAGTT|GTCTGCGAAG|TGGAGGGGCT|CCAGGCGGAC|ATCGGAGCAG|1680|
|CATTAGTTGA|AACCCCGCGC|GGTCACGTAA|GGATAATACC|TCAAGCAAAT|GACCGTATGA|1740|
|TCGGACAGTA|TATCGTTGTC|TCGCCAAACT|CTGTGCTGAA|GAATGCCAAA|CTCGCACCAG|1800|
|CGCACCCGCT|AGCAGATCAG|GTTAAGATCA|TAACACACTC|CGGAAGATCA|GGAAGGTACG|1860|
|CGGTCGAACC|ATACGACGCT|AAAGTACTGA|TGCCAGCAGG|AGGTGCCGTA|CCATGGCCAG|1920|
|AATTCCTAGC|ACTGAGTGAG|AGCGCCACGT|TAGTGTACAA|CGAAAGAGAG|TTTGTGAACC|1980|
|GCAAACTATA|CCACATTGCC|ATGCATGGCC|CCGCCAAGAA|TACAGAAGAG|GAGCAGTACA|2040|
|AGGTTACAAA|GGCAGAGCTT|GCAGAAACAG|AGTACGTGTT|TGACGTGGAC|AAGAAGCGTT|2100|
|GCGTTAAGAA|GGAAGAAGCC|TCAGGTCTGG|TCCTCTCGGG|AGAACTGACC|AACCCTCCCT|2160|
|ATCATGAGCT|AGCTCTGGAG|GGACTGAAGA|CCCGACCTGC|GGTCCCGTAC|AAGGTCGAAA|2220|
|CAATAGGAGT|GATAGGCACA|CCGGGGTCGG|GCAAGTCAGC|TATTATCAAG|TCAACTGTCA|2280|
|CGGCACGAGA|TCTTGTTACC|AGCGGAAAGA|AAGAAAATTG|TCGCGAAATT|GAGGCCGACG|2340|
|TGCTAAGACT|GAGGGGTATG|CAGATTACGT|CGAAGACAGT|AGATTCGGTT|ATGCTCAACG|2400|
|GATGCCACAA|AGCCGTAGAA|GTGCTGTACG|TTGACGAAGC|GTTCGCGTGC|CACGCAGGAG|2460|
|CACTACTTGC|CTTGATTGCT|ATCGTCAGGC|CCCGCAAGAA|GGTAGTACTA|TGCGGAGACC|2520|

FIG. 7A

```
CCATGCAATG CGGATTCTTC AACATGATGC AACTAAAGGT ACATTTCAAT CACCCTGAAA    2580
AAGACATATG CACCAAGACA TTCTACAAGT ATATCTCCCG GCGTTGCACA CAGCCAGTTA    2640
CAGCTATTGT ATCGACACTG CATTACGATG GAAAGATGAA AACCACGAAC CCGTGCAAGA    2700
AGAACATTGA AATCGATATT ACAGGGGCCA CAAAGCCGAA GCCAGGGGAT ATCATCCTGA    2760
CATGTTTCCG CGGGTGGGTT AAGCAATTGC AAATCGACTA TCCCGGACAT GAAGTAATGA    2820
CAGCCGCGGC CTCACAAGGG CTAACCAGAA AAGGAGTGTA TGCCGTCCGG CAAAAAGTCA    2880
ATGAAAACCC ACTGTACGCG ATCACATCAG AGCATGTGAA CGTGTTGCTC ACCCGCACTG    2940
AGGACAGGCT AGTGTGGAAA ACCTTGCAGG GCGACCCATG GATTAAGCAG CCCACTAACA    3000
TACCTAAAGG AAACTTTCAG GCTACTATAG AGGACTGGGA AGCTGAACAC AAGGGAATAA    3060
TTGCTGCAAT AAACAGCCCC ACTCCCCGTG CCAATCCGTT CAGCTGCAAG ACCAACGTTT    3120
GCTGGGCGAA AGCATTGGAA CCGATACTAG CCACGGCCGG TATCGTACTT ACCGGTTGCC    3180
AGTGGAGCGA ACTGTTCCCA CAGTTTGCGG ATGACAAACC ACATTCGCC ATTTACGCCT     3240
TAGACGTAAT TTGCATTAAG TTTTTCGGCA TGGACTTGAC AAGCGGACTG TTTTCTAAAC    3300
AGAGCATCCC ACTAACGTAC CATCCCGCCG ATTCAGCGAG GCCGGTAGCT CATTGGGACA    3360
ACAGCCCAGG AACCCGCAAG TATGGGTACG ATCACGCCAT TGCCGCCGAA CTCTCCCGTA    3420
GATTTCCGGT GTTCCAGCTA GCTGGGAAGG GCACACAACT TGATTTGCAG ACGGGAGAA     3480
CCAGAGTTAT CTCTGCACAG CATAACCTGG TCCCGGTGAA CCGCAATCTT CCTCACGCCT    3540
TAGTCCCCGA GTACAAGGAG AAGCAACCCG GCCCGGTCAA AAAATTCTTG AACCAGTTCA    3600
AACACCACTC AGTACTTGTG GTATCAGAGG AAAAAATTGA AGCTCCCCGT AAGAGAATCG    3660
AATGGATCGC CCCGATTGGC ATAGCCGGTG CAGATAAGAA CTACAACCTG GCTTTCGGGT    3720
TTCCGCCGCA GGCACGGTAC GACCTGGTGT TCATCAACAT TGGAACTAAA TACAGAAACC    3780
ACCACTTTCA GCAGTGCGAA GACCATGCGG CGACCTTAAA AACCCTTTCG CGTTCGGCCC    3840
TGAATTGCCT TAACCCAGGA GGCACCCTCG TGGTGAAGTC CTATGGCTAC GCCGACCGCA    3900
ACAGTGAGGA CGTAGTCACC GCTCTTGCCA GAAAGTTTGT CAGGGTGTCT GCAGCGAGAC    3960
CAGATTGTGT CTCAAGCAAT ACAGAAATGT ACCTGATTTT CCGACAACTA GACAACAGCC    4020
GTACACGGCA ATTCACCCCG CACCATCTGA ATTGCGTGAT TTCGTCCGTG TATGAGGGTA    4080
CAAGAGATGG AGTTGGAGCC GCGCCGTCAT ACCGCACCAA AAGGGAGAAT ATTGCTGACT    4140
GTCAAGAGGA AGCAGTTGTC AACGCAGCCA ATCCGCTGGG TAGACCAGGC AAGGAGTCT     4200
GCCGTGCCAT CTATAAACGT TGGCCGACCA GTTTTACCGA TTCAGCCACG GAGACAGGCA    4260
CCGCAAGAAT GACTGTGTGC CTAGGAAAGA AAGTGATCCA CGCGGTCGGC CCTGATTTCC    4320
GGAAGCACCC AGAAGCAGAA GCCTTGAAAT TGCTACAAAA CGCCTACCAT GCAGTGGCAG    4380
ACTTAGTAAA TGAACATAAC ATCAAGTCTG TCGCCATTCC ACTGCTATCT ACAGGCATTT    4440
ACGCAGCCGG AAAAGACCGC CTTGAAGTAT CACTTAACTG CTTGACAACC GCGCTAGACA    4500
GAACTGACGC GGACGTAACC ATCTATTGCC TGGATAAGAA GTGGAAGGAA AGAATCGACG    4560
CGGCACTCCA ACTTAAGGAG TCTGTAACAG AGCTGAAGGA TGAAGATATG GAGATCGACG    4620
ATGAGTTAGT ATGGATCCAT CCAGACAGTT GCTTGAAGGG AAGAAAGGGA TTCAGTACTA    4680
CAAAAGGAAA ATTGTATTCG TACTTCGAAG GCACCAAATT CCATCAAGCA GCAAAAGACA    4740
TGGCGGAGAT AAAGGTCCTG TTCCCTAATG ACCAGGAAAG TAATGAACAA CTGTGTGCCT    4800
ACATATTGGG TGAGACCATG GAAGCAATCC GCGAAAAGTG CCCGGTCGAC CATAACCCGT    4860
CGTCTAGCCC GCCCAAAACG TTGCCGTGCC TTTGCATGTA TGCCATGACG CCAGAAAGGG    4920
TCCACAGACT TAGAAGCAAT AACGTCAAAG AAGTTACAGT ATGCTCCTCC ACCCCCCTTC    4980
CTAAGCACAA AATTAAGAAT GTTCAGAAGG TTCAGTGCAC GAAAGTAGTC CTGTTTAATC    5040
```

FIG. 7B

```
CGCACACTCC CGCATTCGTT CCCGCCCGTA AGTACATAGA AGTGCCAGAA CAGCCTACCG   5100
CTCCTCCTGC ACAGGCCGAG GAGGCCCCCG AAGTTGTAGC GACACCGTCA CCATCTACAG   5160
CTGATAACAC CTCGCTTGAT GTCACAGACA TCTCACTGGA TATGGATGAC AGTAGCGAAG   5220
GCTCACTTTT TTCGAGCTTT AGCGGATCGG ACAACTCTAT TACTAGTATG GACAGTTGGT   5280
CGTCAGGACC TAGTTCACTA GAGATAGTAG ACCGAAGGCA GGTGGTGGTG GCTGACGTTC   5340
ATGCCGTCCA AGAGCCTGCC CCTATTCCAC CGCCAAGGCT AAAGAAGATG GCCCGCCTGG   5400
CAGCGGCAAG AAAAGAGCCC ACTCCACCGG CAAGCAATAG CTCTGAGTCC CTCCACCTCT   5460
CTTTTGGTGG GGTATCCATG TCCCTCGGAT CAATTTTCGA CGGAGAGACG GCCCGCCAGG   5520
CAGCGGTACA ACCCCTGGCA ACAGGCCCCA CGGATGTGCC TATGTCTTTC GGATCGTTTT   5580
CCGACGGAGA GATTGATGAG CTGAGCCGCA GAGTAACTGA GTCCGAACCC GTCCTGTTTG   5640
GATCATTTGA ACCGGGCGAA GTGAACTCAA TTATATCGTC CCGATCAGCC GTATCTTTTC   5700
CACTACGCAA GCAGAGACGT AGACGCAGGA GCAGGAGGAC TGAATACTGA CTAACCGGGG   5760
TAGGTGGGTA CATATTTTCG ACGGACACAG GCCCTGGGCA CTTGCAAAAG AAGTCCGTTC   5820
TGCAGAACCA GCTTACAGAA CCGACCTTGG AGCGCAATGT CCTGGAAAGA ATTCATGCCC   5880
CGGTGCTCGA CACGTCGAAA GAGGAACAAC TCAAACTCAG GTACCAGATG ATGCCCACCG   5940
AAGCCAACAA AAGTAGGTAC CAGTCTCGTA AAGTAGAAAA TCAGAAAGCC ATAACCACTG   6000
AGCGACTACT GTCAGGACTA CGACTGTATA ACTCTGCCAC AGATCAGCCA GAATGCTATA   6060
AGATCACCTA TCCGAAACCA TTGTACTCCA GTAGCGTACC GGCGAACTAC TCCGATCCAC   6120
AGTTCGCTGT AGCTGTCTGT AACAACTATC TGCATGAGAA CTATCCGACA GTAGCATCTT   6180
ATCAGATTAC TGACGAGTAC GATGCTTACT GGATATATGT AGACGGGACA GTCGCCTGCC   6240
TGGATACTGC AACCTTCTGC CCCGCTAAGC TTAGAAGTTA CCCGAAAAAA CATGAGTATA   6300
GAGCCCCGAA TATCCGCAGT GCGGTTCCAT CAGCGATGCA GAACACGCTA CAAAATGTGC   6360
TCATTGCCGC AACTAAAAGA AATTGCAACG TCACGCAGAT GCGTGAACTG CCAACACTGG   6420
ACTCAGCGAC ATTCAATGTC GAATGCTTTC GAAAATATGC ATGTAATGAC GAGTATTGGG   6480
AGGAGTTCGC TCGGAAGCCA ATTAGGATTA CCACTGAGTT TGTCACCGCA TATGTAGCTA   6540
GACTGAAAGG CCCTAAGGCC GCCGCACTAT TTGCAAAGAC GTATAATTTG GTCCCATTGC   6600
AAGAAGTGCC TATGGATAGA TTCGTCATGG ACATGAAAAG AGACGTGAAA GTTACACCAG   6660
GCACGAAACA CACAGAAGAA AGACCGAAAG TACAAGTGAT ACAAGCCGCA GAACCCCTGG   6720
CGACTGCTTA CTTATGCGGG ATTCACCGGG AATTAGTGCG TAGGCTTACG GCCGTCTTGC   6780
TTCCAAACAT TCACACGCTT TTTGACATGT CGGCGGAGGA TTTTGATGCA ATCATAGCAG   6840
AACACTTCAA GCAAGGCGAC CCGGTACTGG AGACGGATAT CGCATCATTC GACAAAAGCC   6900
AAGACGACGC TATGGCGTTA ACCGGTCTGA TGATCTTGGA GGACCTGGGT GTGGATCAAC   6960
CACTACTCGA CTTGATCGAG TGCGCCTTTG GAGAAATATC ATCCACCCAT CTACCTACGG   7020
GTACTCGTTT TAAATTCGGG GCGATGATGA AATCCGGAAT GTTCCTCACA CTTTTTGTCA   7080
ACACAGTTTT GAATGTCGTT ATCGCCAGCA GAGTACTAGA AGAGCGGCTT AAAACGTCCA   7140
GATGTGCAGC GTTCATTGGC GACGACAACA TCATACATGG AGTAGTATCT GACAAAGAAA   7200
TGGCTGAGAG GTGCGCCACC TGGCTCAACA TGGAGGTTAA GATCATCGAC GCAGTCATCG   7260
GTGAGAGACC ACCTTACTTC TGCGGCGGAT TTATCTTGCA AGATTCGGTT ACTTCCACAG   7320
CGTGCCGCGT GGCGGATCCC CTGAAAGGC TGTTTAAGTT GGGTAAACCG CTCCCAGCCG   7380
ACGACGAGCA AGACGAAGAC AGAAGACGCG CTCTGCTAGA TGAAACAAAG GCGTGGTTTA   7440
GAGTAGGTAT AACAGGCACT TTAGCAGTGG CCGTGACGAC CCGGTATGAG GTAGACAATA   7500
TTACACCTGT CCTACTGGCA TTGAGAACTT TTGCCCAGAG CAAAAGAGCA TTCCAAGCCA   7560
```

FIG. 7C

```
TCAGAGGGGA AATAAAGCAT CTCTACGGTG GTCCTAAATA GTCAGCATAG TACATTTCAT    7620
CTGACTAATA CTACAACACC ACCACCATGA ATAGAGGATT CTTTAACATG CTCGGCCGCC    7680
GCCCCTTCCC GGCCCCCACT GCCATGTGGA GGCCGCGGAG AAGGAGGCAG GCGGCCCCGA    7740
TGCCTGCCCG CAACGGGCTG GCTTCTCAAA TCCAGCAACT GACCACAGCC GTCAGTGCCC    7800
TAGTCATTGG ACAGGCAACT AGACCTCAAC CCCCACGTCC ACGCCCGCCA CCGCGCCAGA    7860
AGAAGCAGGC GCCCAAGCAA CCACCGAAGC CGAAGAAACC AAAAACGCAG GAGAAGAAGA    7920
AGAAGCAACC TGCAAAACCC AAACCCGGAA AGAGACAGCG CATGGCACTT AAGTTGGAGG    7980
CCGACAGATT GTTCGACGTC                                                8000
```

FIG. 7D

| | | | | | | |
|---|---|---|---|---|---|---|
|ATTGACGGCG|TAGTACACAC|TATTGAATCA|AACAGCCGAC|CAATTGCACT|ACCATCACAA|60|
|TGGAGAAGCC|AGTAGTAAAC|GTAGACGTAG|ACCCCAGAG|TCCGTTTGTC|GTGCAACTGC|120|
|AAAAAAGCTT|CCCGCAATTT|GAGGTAGTAG|CACAGCAGGT|CACTCCAAAT|GACCATGCTA|180|
|ATGCCAGAGC|ATTTTCGCAT|CTGGCCAGTA|AACTAATCGA|GCTGGAGGTT|CCTACCACAG|240|
|CGACGATCTT|GGACATAGGC|AGCGCACCGG|CTCGTAGAAT|GTTTCCGAG|CACCAGTATC|300|
|ATTGTGTCTG|CCCCATGCGT|AGTCCAGAAG|ACCCGGACCG|CATGATGAAA|TACGCCAGTA|360|
|AACTGGCGGA|AAAAGCGTGC|AAGATTACAA|ACAAGAACTT|GCATGAGAAG|ATTAAGGATC|420|
|TCCGGACCGT|ACTTGATACG|CCCGATGCTG|AAACACCATC|GCTCTGCTTT|CACAACGATG|480|
|TTACCTGCAA|CATGCGTGCC|GAATATTCCG|TCATGCAGGA|CGTGTATATC|AACGCTCCCG|540|
|GAACTATCTA|TCATCAGGCT|ATGAAAGGCG|TGCGGACCCT|GTACTGGATT|GGCTTCGACA|600|
|CCACCCAGTT|CATGTTCTCG|GCTATGGCAG|GTTCGTACCC|TGCGTACAAC|ACCAACTGGG|660|
|CCGACGAGAA|AGTCCTTGAA|GCGCGTAACA|TCGGACTTTG|CAGCACAAAG|CTGAGTGAAG|720|
|GTAGGACAGG|AAAATTGTCG|ATAATGAGGA|AGAAGGAGTT|GAAGCCCGGG|TCGCGGGTTT|780|
|ATTTCTCCGT|AGGATCGACA|CTTTATCCAG|AACACAGAGC|CAGCTTGCAG|AGCTGGCATC|840|
|TTCCATCGGT|GTTCCACTTG|AATGGAAAGC|AGTCGTACAC|TTGCCGCTGT|GATACAGTGG|900|
|TGAGTTGCGA|AGGCTACGTA|GTGAAGAAAA|TCACCATCAG|TCCCGGGATC|ACGGGAGAAA|960|
|CCGTGGGATA|CGCGGTTACA|CACAATAGCG|AGGGCTTCTT|GCTATGCAAA|GTTACTGACA|1020|
|CAGTAAAAGG|AGAACGGGTA|TCGTTCCCTG|TGTGCACGTA|CATCCCGGCC|ACCATATGCG|1080|
|ATCAGATGAC|TGGTATAATG|GCCACGGATA|TATCACCTGA|CGATGCACAA|AAACTTCTGG|1140|
|TTGGGCTCAA|CCAGCGAATT|GTCATTAACG|GTAGGACTAA|CAGGAACACC|AACACCATGC|1200|
|AAAATTACCT|TCTGCCGATC|ATAGCACAAG|GGTTCAGCAA|ATGGGCTAAG|GAGCGCAAGG|1260|
|ATGATCTTGA|TAACGAGAAA|ATGCTGGGTA|CTAGAGAACG|CAAGCTTACG|TATGGCTGCT|1320|
|TGTGGGCGTT|TCGCACTAAG|AAAGTACATT|CGTTTTATCG|CCCACCTGGA|ACGCAGACCT|1380|
|GCGTAAAAGT|CCCAGCCTCT|TTTAGCGCTT|TTCCCATGTC|GTCCGTATGG|ACGACCTCTT|1440|
|TGCCCATGTC|GCTGAGGCAG|AAATTGAAAC|TGGCATTGCA|ACCAAAGAAG|GAGGAAAAAC|1500|
|TGCTGCAGGT|CTCGGAGGAA|TTAGTCATGG|AGGCCAAGGC|TGCTTTTGAG|GATGCTCAGG|1560|
|AGGAAGCCAG|AGCGGAGAAG|CTCCGAGAAG|CACTTCCACC|ATTAGTGGCA|GACAAAGGCA|1620|
|TCGAGGCAGC|CGCAGAAGTT|GTCTGCGAAG|TGGAGGGGCT|CCAGGCGGAC|ATCGGAGCAG|1680|
|CATTAGTTGA|AACCCCGCGC|GGTCACGTAA|GGATAATACC|TCAAGCAAAT|GACCGTATGA|1740|
|TCGACAGTA|TATCGTTGTC|TCGCCAAACT|CTGTGCTGAA|GAATGCCAAA|CTCGCACCAG|1800|
|CGCACCCGCT|AGCAGATCAG|GTTAAGATCA|TAACACACTC|CGGAAGATCA|GGAAGGTACG|1860|
|CGGTCGAACC|ATACGACGCT|AAAGTACTGA|TGCCAGCAGG|AGGTGCCGTA|CCATGGCCAG|1920|
|AATTCCTAGC|ACTGAGTGAG|AGCGCCACGT|TAGTGTACAA|CGAAAGAGAG|TTTGTGAACC|1980|
|GCAAACTATA|CCACATTGCC|ATGCATGGCC|CCGCCAAGAA|TACAGAAGAG|GAGCAGTACA|2040|
|AGGTTACAAA|GGCAGAGCTT|GCAGAAACAG|AGTACGTGTT|TGACGTGGAC|AAGAAGCGTT|2100|
|GCGTTAAGAA|GGAAGAAGCC|TCAGGTCTGG|TCCTCTCGGG|AGAACTGACC|AACCCTCCCT|2160|
|ATCATGAGCT|AGCTCTGGAG|GGACTGAAGA|CCCGACCTGC|GGTCCCGTAC|AAGGTCGAAA|2220|
|CAATAGGAGT|GATAGGCACA|CCGGGGTCGG|GCAAGTCAGC|TATTATCAAG|TCAACTGTCA|2280|
|CGGCACGAGA|TCTTGTTACC|AGCGGAAAGA|AAGAAAATTG|TCGCGAAATT|GAGGCCGACG|2340|
|TGCTAAGACT|GAGGGGTATG|CAGATTACGT|CGAAGACAGT|AGATTCGGTT|ATGCTCAACG|2400|
|GATGCCACAA|AGCCGTAGAA|GTGCTGTACG|TTGACGAAGC|GTTCGCGTGC|CACGCAGGAG|2460|
|CACTACTTGC|CTTGATTGCT|ATCGTCAGGC|CCCGCAAGAA|GGTAGTACTA|TGCGGAGACC|2520|

FIG. 8A

```
CCATGCAATG CGGATTCTTC AACATGATGC AACTAAAGGT ACATTTCAAT CACCCTGAAA    2580
AAGACATATG CACCAAGACA TTCTACAAGT ATATCTCCCG GCGTTGCACA CAGCCAGTTA    2640
CAGCTATTGT ATCGACACTG CATTACGATG GAAAGATGAA AACCACGAAC CCGTGCAAGA    2700
AGAACATTGA AATCGATATT ACAGGGCCA CAAAGCCGAA GCCAGGGGAT ATCATCCTGA     2760
CATGTTTCCG CGGGTGGGTT AAGCAATTGC AAATCGACTA TCCCGGACAT GAAGTAATGA    2820
CAGCCGCGGC CTCACAAGGG CTAACCAGAA AAGGAGTGTA TGCCGTCCGG CAAAAAGTCA    2880
ATGAAAACCC ACTGTACGCG ATCACATCAG AGCATGTGAA CGTGTTGCTC ACCCGCACTG    2940
AGGACAGGCT AGTGTGGAAA ACCTTGCAGG GCGACCCATG GATTAAGCAG CCCACTAACA    3000
TACCTAAAGG AAACTTTCAG GCTACTATAG AGGACTGGGA AGCTGAACAC AAGGGAATAA    3060
TTGCTGCAAT AAACAGCCCC ACTCCCCGTG CCAATCCGTT CAGCTGCAAG ACCAACGTTT    3120
GCTGGGCGAA AGCATTGGAA CCGATACTAG CCACGGCCGG TATCGTACTT ACCGGTTGCC    3180
AGTGGAGCGA ACTGTTCCCA CAGTTTGCGG ATGACAAACC ACATTCGGCC ATTTACGCCT    3240
TAGACGTAAT TTGCATTAAG TTTTTCGGCA TGGACTTGAC AAGCGGACTG TTTTCTAAAC    3300
AGAGCATCCC ACTAACGTAC CATCCCGCCG ATTCAGCGAG GCCGGTAGCT CATTGGACA    3360
ACAGCCCAGG AACCCGCAAG TATGGGTACG ATCACGCCAT TGCCGCCGAA CTCTCCCGTA    3420
GATTTCCGGT GTTCCAGCTA GCTGGGAAGG GCACACAACT TGATTTGCAG ACGGGGAGAA    3480
CCAGAGTTAT CTCTGCACAG CATAACCTGG TCCCGGTGAA CCGCAATCTT CCTCACGCCT    3540
TAGTCCCCGA GTACAAGGAG AAGCAACCCG GCCCGGTCAA AAAATTCTTG AACCAGTTCA    3600
AACACCACTC AGTACTTGTG GTATCAGAGG AAAAAATTGA AGCTCCCCGT AAGAGAATCG    3660
AATGGATCGC CCCGATTGCC ATAGCCGGTG CAGATAAGAA CTACAACCTG GCTTTCGGGT    3720
TTCCGCCGCA GGCACGGTAC GACCTGGTGT TCATCAACAT TGGAACTAAA TACAGAAACC    3780
ACCACTTTCA GCAGTGCGAA GACCATGCGG CGACCTTAAA AACCCTTTCG CGTTCGCCC    3840
TGAATTGCCT TAACCCAGGA GGCACCCTCG TGGTGAAGTC CTATGGCTAC GCCGACCGCA    3900
ACAGTGAGGA CGTAGTCACC GCTCTTGCCA GAAAGTTTGT CAGGGTGTCT GCAGCGAGAC    3960
CAGATTGTGT CTCAAGCAAT ACAGAAATGT ACCTGATTTT CCGACAACTA GACAACAGCC    4020
GTACACGGCA ATTCACCCCG CACCATCTGA ATTGCGTGAT TTCGTCCGTG TATGAGGGTA    4080
CAAGAGATGG AGTTGGAGCC GCGCCGTCAT ACCGCACCAA AAGGGAGAAT ATTGCTGACT    4140
GTCAAGAGGA AGCAGTTGTC AACGCAGCCA ATCCGCTGGG TAGACCAGGC GAAGGAGTCT    4200
GCCGTGCCAT CTATAAACGT TGGCCGACCA GTTTTACCGA TTCAGCCACG GAGACAGGCA    4260
CCGCAAGAAT GACTGTGTGC CTAGGAAAGA AAGTGATCCA CGCGGTCGGC CCTGATTTCC    4320
GGAAGCACCC AGAAGCAGAA GCCTTGAAAT TGCTACAAAA CGCCTACCAT GCAGTGGCAG    4380
ACTTAGTAAA TGAACATAAC ATCAAGTCTG TCGCCATTCC ACTGCTATCT ACAGGCATTT    4440
ACGCAGCCGG AAAAGACCGC CTTGAAGTAT CACTTAACTG CTTGACAACC GCGCTAGACA    4500
GAACTGACGC GGACGTAACC ATCTATTGCC TGGATAAGAA GTGGAAGGAA AGAATCGACG    4560
CGGCACTCCA ACTTAAGGAG TCTGTAACAG AGCTGAAGGA TGAAGATATG GAGATCGACG    4620
ATGAGTTAGT ATGGATCCAT CCAGACAGTT GCTTGAAGGG AAGAAAGGGA TTCAGTACTA    4680
CAAAAGGAAA ATTGTATTCG TACTTCGAAG GCACCAAATT CCATCAAGCA GCAAAAGACA    4740
TGGCGGAGAT AAAGGTCCTG TTCCCTAATG ACCAGGAAAG TAATGAACAA CTGTGTGCCT    4800
ACATATTGGG TGAGACCATG GAAGCAATCC GCGAAAAGTG CCCGGTCGAC CATAACCCGT    4860
CGTCTAGCCC GCCCAAAACG TTGCCGTGCC TTTGCATGTA TGCCATGACG CCAGAAAGGG    4920
TCCACAGACT TAGAAGCAAT AACGTCAAAG AAGTTACAGT ATGCTCCTCC ACCCCCCTTC    4980
CTAAGCACAA AATTAAGAAT GTTCAGAAGG TTCAGTGCAC GAAAGTAGTC CTGTTTAATC    5040
```

FIG. 8B

```
CGCACACTCC CGCATTCGTT CCCGCCCGTA AGTACATAGA AGTGCCAGAA CAGCCTACCG    5100
CTCCTCCTGC ACAGGCCGAG GAGGCCCCCG AAGTTGTAGC GACACCGTCA CCATCTACAG    5160
CTGATAACAC CTCGCTTGAT GTCACAGACA TCTCACTGGA TATGGATGAC AGTAGCGAAG    5220
GCTCACTTTT TTCGAGCTTT AGCGGATCGG ACAACTCTAT TACTAGTATG GACAGTTGGT    5280
CGTCAGGACC TAGTTCACTA GAGATAGTAG ACCGAAGGCA GGTGGTGGTG GCTGACGTTC    5340
ATGCCGTCCA AGAGCCTGCC CCTATTCCAC CGCCAAGGCT AAAGAAGATG GCCCGCCTGG    5400
CAGCGGCAAG AAAAGAGCCC ACTCCACCGG CAAGCAATAG CTCTGAGTCC CTCCACCTCT    5460
CTTTTGGTGG GGTATCCATG TCCCTCGGAT CAATTTTCGA CGGAGAGACG GCCCGCCAGG    5520
CAGCGGTACA ACCCCTGGCA ACAGGCCCCA CGGATGTGCC TATGTCTTTC GGATCGTTTT    5580
CCGACGGAGA GATTGATGAG CTGAGCCGCA GAGTAACTGA GTCCGAACCC GTCCTGTTTG    5640
GATCATTTGA ACCGGCGAA GTGAACTCAA TTATATCGTC CCGATCAGCC GTATCTTTTC     5700
CACTACGCAA GCAGAGACGT AGACGCAGGA GCAGGAGGAC TGAATACTGA CTAACCGGGG    5760
TAGGTGGGTA CATATTTTCG ACGGACACAG GCCCTGGGCA CTTGCAAAAG AAGTCCGTTC    5820
TGCAGAACCA GCTTACAGAA CCGACCTTGG AGCGCAATGT CCTGGAAAGA ATTCATGCCC    5880
CGGTGCTCGA CACGTCGAAA GAGGAACAAC TCAAACTCAG GTACCAGATG ATGCCCACCG    5940
AAGCCAACAA AAGTAGGTAC CAGTCTCGTA AAGTAGAAAA TCAGAAAGCC ATAACCACTG    6000
AGCGACTACT GTCAGGACTA CGACTGTATA ACTCTGCCAC AGATCAGCCA GAATGCTATA    6060
AGATCACCTA TCCGAAACCA TTGTACTCCA GTAGCGTACC GGCGAACTAC TCCGATCCAC    6120
AGTTCGCTGT AGCTGTCTGT AACAACTATC TGCATGAGAA CTATCCGACA GTAGCATCTT    6180
ATCAGATTAC TGACGAGTAC GATGCTTACT TGGATATGGT AGACGGGACA GTCGCCTGCC    6240
TGGATACTGC AACCTTCTGC CCCGCTAAGC TTAGAAGTTA CCCGAAAAAA CATGAGTATA    6300
GAGCCCCGAA TATCCGCAGT GCGGTTCCAT CAGCGATGCA GAACACGCTA CAAAATGTGC    6360
TCATTGCCGC AACTAAAAGA AATTGCAACG TCACGCAGAT GCGTGAACTG CCAACACTGG    6420
ACTCAGCGAC ATTCAATGTC GAATGCTTTC GAAAATATGC ATGTAATGAC GAGTATTGGG    6480
AGGAGTTCGC TCGAAGCCA ATTAGGATTA CCACTGAGTT TGTCACCGCA TATGTAGCTA     6540
GACTGAAAGG CCCTAAGGCC GCCGCACTAT TTGCAAAGAC GTATAATTTG GTCCCATTGC    6600
AAGAAGTGCC TATGGATAGA TTCGTCATGG ACATGAAAAG AGACGTGAAA GTTACACCAG    6660
GCACGAAACA CACAGAAGAA AGACCGAAAG TACAAGTGAT ACAAGCCGCA GAACCCCTGG    6720
CGACTGCTTA CTTATGCGGG ATTCACCGGG AATTAGTGCG TAGGCTTACG GCCGTCTTGC    6780
TTCCAAACAT TCACACGCTT TTTGACATGT CGGCGGAGGA TTTTGATGCA ATCATAGCAG    6840
AACACTTCAA GCAAGGCGAC CCGGTACTGG AGACGGATAT CGCATCATTC GACAAAAGCC    6900
AAGACGACGC TATGGCGTTA ACCGGTCTGA TGATCTTGGA GGACCTGGGT GTGGATCAAC    6960
CACTACTCGA CTTGATCGAG TGCGCCTTTG GAGAAATATC ATCCACCCAT CTACCTACGG    7020
GTACTCGTTT TAAATTCGGG GCGATGATGA AATCCGGAAT GTTCCTCACA CTTTTTGTCA    7080
ACACAGTTTT GAATGTCGTT ATCGCCAGCA GAGTACTAGA AGAGCGGCTT AAAACGTCCA    7140
GATGTGCAGC GTTCATTGGC GACGACAACA TCATACATGG AGTAGTATCT GACAAAGAAA    7200
TGGCTGAGAG GTGCGCCACC TGGCTCAACA TGGAGGTTAA GATCATCGAC GCAGTCATCG    7260
GTGAGAGACC ACCTTACTTC TGCGGCGGAT TTATCTTGCA AGATTCGGTT ACTTCCACAG    7320
CGTGCCGCGT GGCGGATCCC CTGAAAAGGC TGTTTAAGTT GGGTAAACCG CTCCCAGCCG    7380
ACGACGAGCA AGACGAAGAC AGAAGACGCG CTCGCTAGA TGAAACAAAG GCGTGGTTTA      7440
GAGTAGGTAT AACAGGCACT TTAGCAGTGG CCGTGACGAC CCGGTATGAG GTAGACAATA    7500
TTACACCTGT CCTACTGGCA TTGAGAACTT TTGCCCAGAG CAAAAGAGCA TTCCAAGCCA    7560
```

FIG. 8C

```
TCAGAGGGGA AATAAAGCAT CTCTACGGTG GTCCTAAATA GTCAGCATAG TACATTTCAT    7620
CTGACTAATA CTACAACACC ACCACCATGA ATAGAGGATT CTTTAACATG CTCGGCCGCC    7680
GCCCCTTCCC GGCCCCCACT GCCATGTGGA GGCCGCGGAG AAGGAGGCAG GCGGCCCCGA    7740
TGCCTGCCCG CAACGGGCTG GCTTCTCAAA TCCAGCAACT GACCACAGCC GTCAGTGCCC    7800
TAGTCATTGG ACAGGCAACT AGACCTCAAC CCCCACGTCC ACGCCCGCCA CCGCGCCAGA    7860
AGAAGCAGGC GCCCAAGCAA CCACCGAAGC CGAAGAAACC AAAAACGCAG GAGAAGAAGA    7920
AGAAGCAACC TGCAAAACCC AAACCCGGAA AGAGACAGCG CATGGCACTT AAGTTGGAGG    7980
CCGACAGATT GTTCGACGTC AAGAACGAGG ACGGAGATGT CATCGGGCAC GCACTGGCCA    8040
TGGAAGGAAA GGTAATGAAA CCTCTGCACG TGAAAGGAAC CATCGACCAC CCTGTGCTAT    8100
CAAAGCTCAA ATTTACCAAG TCGTCAGCAT ACGACATGGA GTTCGCACAG TTGCCAGTCA    8160
ACATGAGAAG TGAGGCATTC ACCTACACCA GTGAACACCC CGAAGGATTC TATAACTGGC    8220
ACCACGGAGC GGTGCAGTAT AGTGGAGGTA GATTTACCAT CCCTCGCGGA GTAGGAGGCA    8280
GAGGAGACAG CGGTCGTCCG ATCATGGATA ACTCCGGTCG GGTTGTCGCG ATAGTCCTCG    8340
GTGGCGCTGA TGAAGGAACA CGAACTGCCC TTTCGGTCGT CACCTGGAAT AGTAAAGGGA    8400
AGACAATTAA GACGACCCCG GAAGGGACAG AAGAGTGGTC CGCAGCACCA CTGGTCACGG    8460
CAATGTGTTT GCTCGGAAAT GTGAGCTTCC CATGCGACCG CCCGCCCACA TGCTATACCC    8520
GCGAACCTTC CAGAGCCCTC GACATCCTTG AAGAGAACGT GAACCATGAG GCCTACGATA    8580
CCCTGCTCAA TGCCATATTG CGGTGCGGAT CGTCTGGCAG AAGCAAAAGA AGCGTCATTG    8640
ACGACTTTAC CCTGACCAGC CCCTACTTGG GCACATGCTC GTACTGCCAC CATACTGTAC    8700
CGTGCTTCAG CCCTGTTAAG ATCGAGCAGG TCTGGACGA AGCGGACGAT AACACCATAC    8760
GCATACAGAC TTCCGCCCAG TTTGGATACG ACCAAAGCGG AGCAGCAAGC GCAAACAAGT    8820
ACCGCTACAT GTCGCTTAAG CAGGATCACA CCGTTAAAGA AGGCACCATG GATGACATCA    8880
AGATTAGCAC CTCAGGACCG TGTAGAAGGC TTAGCTACAA AGGATACTTT CTCCTCGCAA    8940
AATGCCCTCC AGGGACAGC GTAACGGTTA GCATAGTGAG TAGCAACTCA GCAACGTCAT    9000
GTACACTGGC CCGCAAGATA AAACCAAAAT TCGTGGGACG GAAAAATATA GATCTACCTC    9060
CCGTTCACGG TAAAAAAATT CCTTGCACAG TGTACGACCG TCTGAAAGAA ACAACTGCAG    9120
GCTACATCAC TATGCACAGG CCGAGACCGC ACGCTTATAC ATCCTACCTG GAAGAATCAT    9180
CAGGGAAAGT TTACGCAAAG CCGCCATCTG GAAGAACAT TACGTATGAG TGCAAGTGCG    9240
GCGACTACAA GACCGGAACC GTTTCGACCC GCACCGAAAT CACTGGTTGC ACCGCCATCA    9300
AGCAGTGCGT CGCCTATAAG AGCGACCAAA CGAAGTGGGT CTTCAACTCA CCGGACTTGA    9360
TCAGACATGA CGACCACACG GCCCAAGGGA AATTGCATTT GCCTTTCAAG TTGATCCCGA    9420
GTACCTGCAT GGTCCCTGTT GCCCACGCGC CGAATGTAAT ACATGGCTTT AAACACATCA    9480
GCCTCCAATT AGATACAGAC CACTTGACAT TGCTCACCAC CAGGAGACTA GGGCAAACC    9540
CGGAACCAAC CACTGAATGG ATCGTCGGAA AGACGGTCAG AAACTTCACC GTCGACCGAG    9600
ATGGCCTGGA ATACATATGG GGAAATCATG AGCCAGTGAG GGTCTATGCC CAAGAGTCAG    9660
CACCAGGAGA CCCTCACGGA TGGCCACACG AAATAGTACA GCATTACTAC CATCGCCATC    9720
CTGTGTACAC CATCTTAGCC GTCGCATCAG CTACCGTGGC GATGATGATT GGCGTAACTG    9780
TTGCAGTGTT ATGTGCCTGT AAAGCGCGCC GTGAGTGCCT GACGCCATAC GCCCTGGCCC    9840
CAAACGCCGT AATCCCAACT TCGCTGGCAC TCTTGTGCTG CGTTAGGTCG GCCAATGCTG    9900
AAACGTTCAC CGAGACCATG AGTTACTTGT GGTCGAACAG TCAGCCGTTC TTCTGGGTCC    9960
AGTTGTGCAT ACCTTTGGCC GCTTTCATCG TTCTAATGCG CTGCTGCTCC TGCTGCCTGC   10020
CTTTTTTAGT GGTTGCCGGC GCCTACCTGG CGAAGGTAGA CGCCTACGAA CATGCGACCA   10080
```

FIG. 8D

```
CTGTTCCAAA TGTGCCACAG ATACCGTATA AGGCACTTGT TGAAAGGGCA GGGTATGCCC    10140
CGCTCAATTT GGAGATCACT GTCATGTCCT CGGAGGTTTT GCCTTCCACC AACCAAGAGT    10200
ACATTACCTG CAAATTCACC ACTGTGGTCC CCTCCCCAAA AATCAAATGC TGCGGCTCCT    10260
TGGAATGTCA GCCGGCCGCT CATGCAGACT ATACCTGCAA GGTCTTCGGA GGGGTCTACC    10320
CCTTTATGTG GGGAGGAGCG CAATGTTTTT GCGACAGTGA GAACAGCCAG ATGAGTGAGG    10380
CGTACGTCGA ATTGTCAGCA GATTGCGCGT CTGACCACGC GCAGGCGATT AAGGTGCACA    10440
CTGCCGCGAT GAAAGTAGGA CTGCGTATTG TGTACGGGAA CACTACCAGT TTCCTAGATG    10500
TGTACGTGAA CGGAGTCACA CCAGGAACGT CTAAAGACTT GAAAGTCATA GCTGGACCAA    10560
TTTCAGCATC GTTTACGCCA TTCGATCATA AGGTCGTTAT CCATCGCGGC CTGGTGTACA    10620
ACTATGACTT CCCGGAATAT GGAGCGATGA AACCAGGAGC GTTTGGAGAC ATTCAAGCTA    10680
CCTCCTTGAC TAGCAAGGAT CTCATCGCCA GCACAGACAT TAGGCTACTC AAGCCTTCCG    10740
CCAAGAACGT GCATGTCCCG TACACGCAGG CCTCATCAGG ATTTGAGATG TGGAAAAACA    10800
ACTCAGGCCG CCCACTGCAG GAAACCGCAC CTTTCGGGTG TAAGATTGCA GTAAATCCGC    10860
TCCGAGCGGT GGACTGTTCA TACGGAACA TTCCCATTTC TATTGACATC CCGAACGCTG    10920
CCTTTATCAG GACATCAGAT GCACCACTGG TCTCAACAGT CAAATGTGAA GTCAGTGAGT    10980
GCACTTATTC AGCAGACTTC GGCGGGATGG CCACCCTGCA GTATGTATCC GACGCGAAG     11040
GTCAATGCCC CGTACATTCG CATTCGAGCA CAGCAACTCT CCAAGAGTCG ACAGTACATG    11100
TCCTGGAGAA AGGAGCGGTG ACAGTACACT TTAGCACCGC GAGTCCACAG GCGAACTTTA    11160
TCGTATCGCT GTGTGGGAAG AAGACAACAT GCAATGCAGA ATGTAAACCA CCAGCTGACC    11220
ATATCGTGAG CACCCCGCAC AAAAATGACC AAGAATTTCA AGCCGCCATC TCAAAAACAT    11280
CATGGAGTTG GCTGTTTGCC CTTTTCGGCG GCGCCTCGTC GCTATTAATT ATAGGACTTA    11340
TGATTTTTGC TTGCAGCATG ATGCTGACTA GCACACGAAG ATGACCGCTA CGCCCAATG    11400
ATCCGACCAG CAAAACTCGA TGTACTTCCG AGGAACTGAT GTGCATAATG CATCAGGCTG    11460
GTACATTAGA TCCCCGCTTA CCGCGGGCAA TATAGCAACA CTAAAAACTC GATGTACTTC    11520
CGAGGAAGCG CAGTGCATAA TGCTGCGCAG TGTTGCCACA TAACCACTAT ATTAACCATT    11580
TATCTAGCGG ACGCCAAAAA CTCAATGTAT TTCTGAGGAA GCGTGGTGCA TAATGCCACG    11640
CAGCGTCTGC ATAACTTTTA TTATTTCTTT TATTAATCAA CAAAATTTTG TTTTTAACAT    11700
TTCAAAAAAA AAAAAAAAAA AAAAAAAAAA AAAAAAAAA                          11740
```

FIG. 8E

Mapping the mutations that reduce or eliminate cytopathogenecity in Sindbis virus vectors

| | neoR phenotype | | |
|---|---|---|---|
| | SIN1 | S1 | S2 |
| | + | − | + |

FIG. 8H nsP-Induced Expression of Alphavirus Structural Proteins in Stable Packaging Cell Lines
Transfected with Eukaryotic Layered Vector Initiation System (ELVS™) Plasmid DNAs

FIG. 16

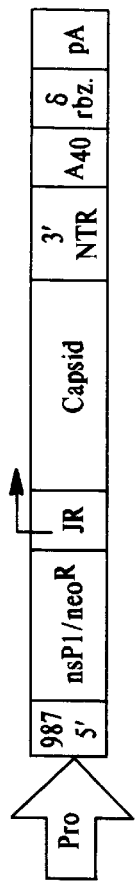
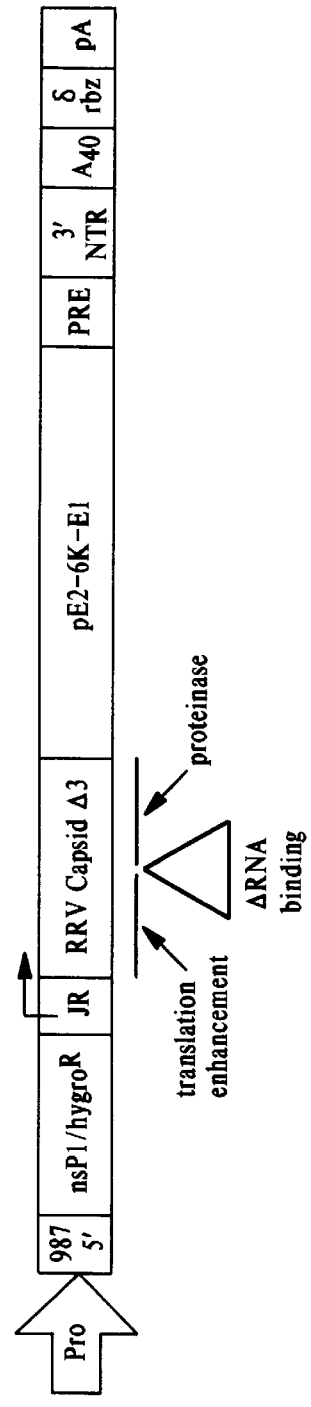
FIG. 21B

Identification of Cell Lines That Inducibly Express An Alphavirus Capsid Protein

FIG. 21D

| Data-replicon (vector) | helper(all tRNA 5') | inf units/ml | pfu/ml |
|---|---|---|---|
| 1. SINrep/LacZ | DHBBCrrvSin-gps | 5x10^8 | 1.5x10^6 pinpoint |
| 2. " " | DHBBCsin + DHBB(CdeletedRRVSin-gps) | 5-10x10^9 | 1.5x10^7 tiny |
| 3. Sinrep/capsid | DHBB(CdeletedRRVSin-gps) | | 6x10^7 normal size | the latter (as well as gels) show that only the Sindbis virus capsid gets incorporated into extracellular particles when both are present in the transfected cell.

III constructs

A Toto1101 – sites for the insertion of the RRV capsid gene

B RRV – sites used for cloning of the RRV capsid gene

C chimeras 1) complete RRV capsid gene
2) RRV capsid gene nts 7835-7888 deleted.

FIG. 26A

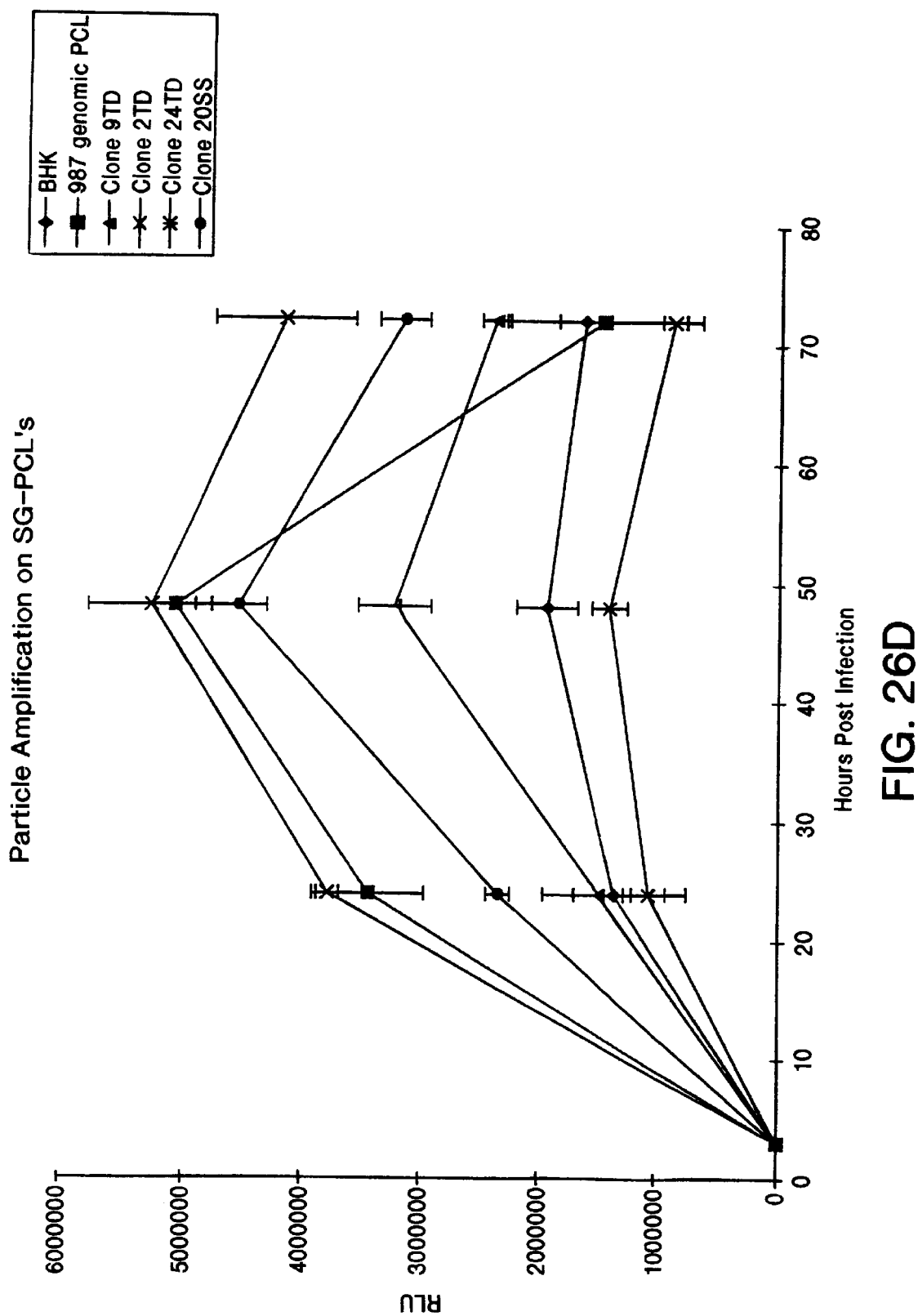

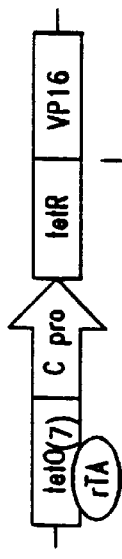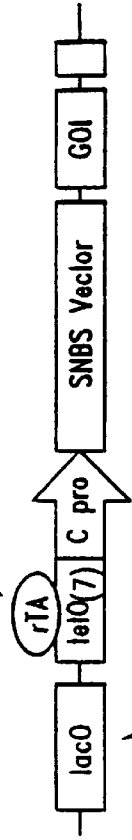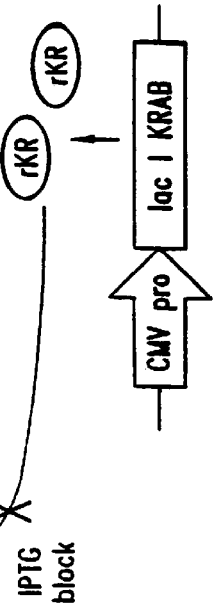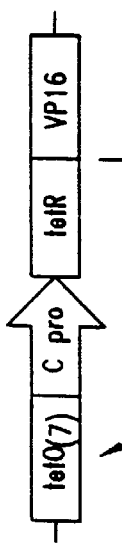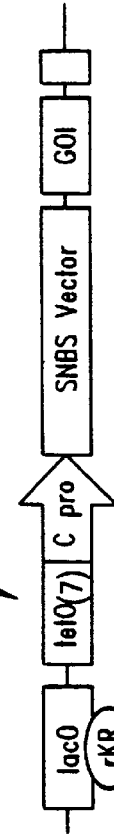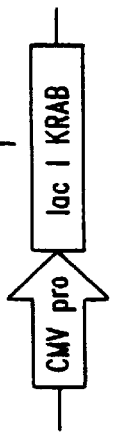
FIG. 30

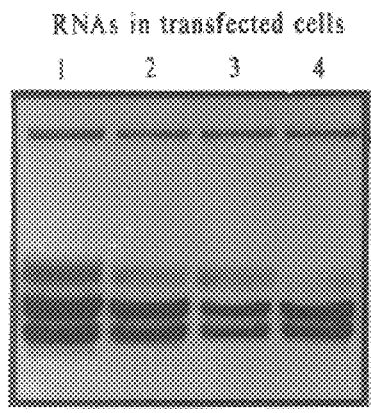
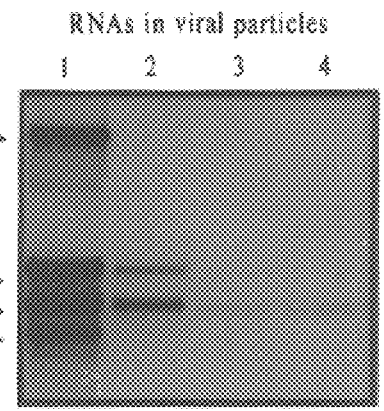
FIG. 31A     FIG. 31B
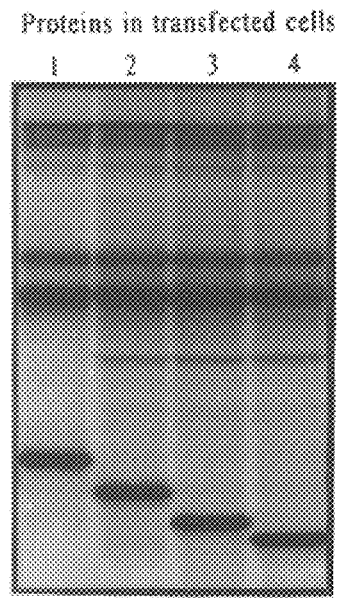
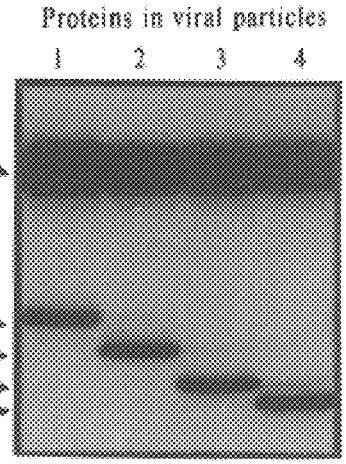
FIG. 32A     FIG. 32B

```
                      ++ + +   +
Crrv       MNYIPTQTFYGRRVRPRPAFRPVQVSMQPTPTMVTPMLQAPDLQAQQMQQLISAVSALTT 60
CrrvΔ1     MNYIPTQTFYGRRWRPRPAFRPVQVSMQPTPTMVTPMLQAPDLQAQQMQQLISAVSALTT
CrrvΔ2     MNYIPTQTFYGRRVRPRPAFRPVQVSMQPTPTMVTPMLQAPDLQAQQMQQLISAVSALTT
CrrvΔ3     MNYIPTQTFYGRRVRPRPAFRPVQVSMQPTPTMVTPMLQAPDLQAQQMQQLISAVSALTT +   +  +    ++  + + ++   +++   +++   + +   ++++  ++ +
Crrv       KQNVKAPKGQRQKKQQKPKEKKENQKKKPTQKKKQQQKPKPQAKKKKPGRRERMCMKIEN 120
CrrvΔ1     KQNVKAPKGQRQKKQQKPKEKKENQKKKPTLK-----------------RRERMCMKIEN
CrrvΔ2     KQNVKAPKGQRQKKQLK--------------------------------RRERMCMKIEN
CrrvΔ3     KQNLK--------------------------------------------RRERMCMKIEN
```

CΔ1rrv - del 8 Lys
CΔ2rrv - del 15 Lys
CΔ3rrv - del 19 Lys

SEQUENCE LISTING (1) GENERAL INFORMATION:

(iii) NUMBER OF SEQUENCES: 125

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:1:

ATCTCTACGG TGGTCCTAAA TAGT                                              24

(2) INFORMATION FOR SEQ ID NO:2:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:2:

GGTGGAGCTC TAATACGACT CACTATAGAT TGACGGCGTA GTACACAC                    48

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:

AATTTCTGCC TCAGC                                                        15

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

TATGCAAAGT TACTGAC                                                      17

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

CTGTCATTAC TTCATGTC                                                     18

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO:6:

GCGTGGATCA CTTTC                                                        15

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:7:

ATTGCGTGAT TTCGTCCGT                                                    19

(2) INFORMATION FOR SEQ ID NO:8:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:8:

TAAATTTGAG CTTTG                                                        15

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:9:

GGCATATGGC ATTAGTTG                                                     18

(2) INFORMATION FOR SEQ ID NO:10:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:10:

CTGGCCATGG AAGGAAAGG                                                    19

(2) INFORMATION FOR SEQ ID NO:11:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (xi) SEQUENCE DESCRIPTION: SEQ ID NO:11:

CCCCTCGAGG GTTTTTTTTT TTTTTTTTTT TTGAAATGTT AAAAACAAAA TTTTGTTG         58

(2) INFORMATION FOR SEQ ID NO:12:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO:12:

TATATGGGCC CGATTTAGGT GACACTATAG ATTGACGGCG TAGTACAC                48

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

CTGGCAACCG GTAAGTACGA TAC                                          23

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

ATACTAGCCA CGGCCGGTAT C                                            21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

TCCTCTTTCG ACGTGTCGAG C                                            21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

ACCTTGGAGC GCAATGTCCT G                                            21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:17:

CCTTTTCAGG GGATCCGCCA C                                            21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

GTGGCGGATC CCCTGAAAAG G                                                            21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

TGGGCCGTGT GGTCGTCATG                                                              20

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

TGGGTCTTCA ACTCACCGGA C                                                            21

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

CAATTCGACG TACGCCTCAC TC                                                           22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:22:

GAGTGAGGCG TACGTCGAAT TG                                                           22

(2) INFORMATION FOR SEQ ID NO:23:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:23:

TATATTCTAG ATTTTTTTTT TTTTTTTTTT TTTTTTTTTT TTTTTTGAAA TG                          52

(2) INFORMATION FOR SEQ ID NO:24:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:24:

ATATATCTAG AGCCATGGGC CACACACGGA GGCAG    35

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:25:

ATATAGGATC CCTGTTATAC AGGGCGTACA CTTTC    35

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:26:

ATATACTCGA GACCATGATT GAACAAGATG GATTG    35

(2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:27:

TATATAGCGG CCGCTCAGAA GAACTCGTCA AGAAG    35

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:28:

CTGTAGATGG TGACGGTGTC G    21

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:29:

GAAGTGCCAG AACAGCCTAC CG    22

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:30:

```
TATATCTCGA GGGTGGTGTT GTAGTATTAG TCAG                                34
```

(2) INFORMATION FOR SEQ ID NO:31:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:31:

```
TATATATATA TGCGGCCGCC GCTACGCCCC AATGATCCGA C                         41
```

(2) INFORMATION FOR SEQ ID NO:32:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:32:

```
CTATAGAGCT CGTTTAAACT TTTTTTTTTT TTTTTTTTTT TTTTTTTTTT TTTTTTTTTG     60

AAATG                                                                65
```

(2) INFORMATION FOR SEQ ID NO:33:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:33:

```
TCGATCCTAG GA                                                        12
```

(2) INFORMATION FOR SEQ ID NO:34:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:34:

```
AGGATCCTAG T                                                         11
```

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

```
CTCGATCCTA GGATCGAGGC                                                20
```

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

GAGCTAGGAT CCTAGCTCCG                                              20

(2) INFORMATION FOR SEQ ID NO:37:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:37:

TATATATGAG CTCTAATAAA ATGAGGAAAT TGCATCGCAT TGTC                   44

(2) INFORMATION FOR SEQ ID NO:38:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:38:

TATATGAATT CATAGAATGA CACCTACTCA GACAATGCGA TGC                    43

(2) INFORMATION FOR SEQ ID NO:39:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:39:

AAAAAAAAAA GGGTCGGCAT GGCATCTCCA CCTCCTCGCG GTCCGACCTG GGCATC      56

(2) INFORMATION FOR SEQ ID NO:40:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:40:

TATATGAGCT CCTCCCTTAG CCATCCGAGT GGACGTGCGT CCTCCTTCGG ATGCCCAGGT  60

CGGACCGCG                                                         69

(2) INFORMATION FOR SEQ ID NO:41:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:41:

TATATATAGA TCTTTGACAT TGATTATTGA CTAG                              34

(2) INFORMATION FOR SEQ ID NO:42:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:42:

CCGTCAATAC GGTTCACTAA ACGAGCTCTG CTTATATAGA CC             42

(2) INFORMATION FOR SEQ ID NO:43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:43:

GCTCGTTTAG TGAACCGTAT TGACGGCGTA GTACACAC                  38

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:44:

CTGGCAACCG GTAAGTACGA TAC                                  23

(2) INFORMATION FOR SEQ ID NO:45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:45:

GGTAACAAGA TCTCGTGCCG TG                                   22

(2) INFORMATION FOR SEQ ID NO:46:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:46:

CCTATGCGGC CGCGTGGAAC CTTTGTGGCT CCTC                      34

(2) INFORMATION FOR SEQ ID NO:47:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:47:

CCTATTGGCC AGCAGACCAA TTTATGCCTA C                         31

(2) INFORMATION FOR SEQ ID NO:48:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:48:

CCTATGCGGC CGCTAGACTG GACAGCCAAT GACG                                34

(2) INFORMATION FOR SEQ ID NO:49:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:49:

CCTATTGGCC AGCCAAGACA TCATCCGGGC AG                                 32

(2) INFORMATION FOR SEQ ID NO:50:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:50:

TATATATCCG GAAAGCTCTA AGGTAAATAT AAAATTTTT                           39

(2) INFORMATION FOR SEQ ID NO:51:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:51:

TATATAGGAT CCTAGGTTAG GTTGGAATCT AAAATACACA AAC                      43

(2) INFORMATION FOR SEQ ID NO:52:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:52:

TCGATCCTAG GA                                                       12

(2) INFORMATION FOR SEQ ID NO:53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:53:

GCTCTTAATT AAGAGC                                                   16

(2) INFORMATION FOR SEQ ID NO:54:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:54:

-continued

CTGTTTAAAC AGATCTTATC TCGAGTATGC GGCCGCTATG AATTCGTTTA AACGA        55

(2) INFORMATION FOR SEQ ID NO:55:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:55:

TCGTTTAAAC GAATTCATAG CGGCCGCATA CTCGAGATAA GATCTGTTTA AACAG        55

(2) INFORMATION FOR SEQ ID NO:56:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:56:

ATATATCCGG AGTCCGGCCG CTTGGGTGGA GAGGCTA        37

(2) INFORMATION FOR SEQ ID NO:57:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:57:

ATATAGGATC CTCAGAAGAA CTCGTCAAGA AGGCGA        36

(2) INFORMATION FOR SEQ ID NO:58:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:58:

TATATATGAG CTCTTACAAA TAAAGCAATA GCATCACAAA TTTC        44

(2) INFORMATION FOR SEQ ID NO:59:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:59:

TATATGAATT CGTTTGGACA AACCACAACT AGAATG        36

(2) INFORMATION FOR SEQ ID NO:60:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:60:

TATATAGATC TAGTCTTATG CAATACTCTT GTAGT        35

(2) INFORMATION FOR SEQ ID NO:61:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:61:

GGGATACTCA CCACTATATC TCGACGGTAT CGAGGTAGGG CACT                44

(2) INFORMATION FOR SEQ ID NO:62:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:62:

GATATAGTGG TGAGTATCCC CG                                    22

(2) INFORMATION FOR SEQ ID NO:63:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:63:

TATATGGATC CCGGAGATCC TTAATCTTCT CATG                          34

(2) INFORMATION FOR SEQ ID NO:64:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:64:

TATATATGCA TCCCCCCCCC CCCCAACG                              28

(2) INFORMATION FOR SEQ ID NO:65:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:65:

CATGCGAAAC GATCCTCATC CTTACAATCG TGGTTTTCAA AGG                 43

(2) INFORMATION FOR SEQ ID NO:66:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:66:

GATGAGGATC GTTTCGCATG ATTGA                                25

(2) INFORMATION FOR SEQ ID NO:67:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:67:

TATATATGCA TTCAGAAGAA CTCGTCAAGA AGGCGA                      36

(2) INFORMATION FOR SEQ ID NO:68:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:68:

ATATACTCGA GACCACCACC ATGAATAGAG GATTC                       35

(2) INFORMATION FOR SEQ ID NO:69:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:69:

TATATGCGGC CGCTATTACC ACTCTTCTGT CCCTTCCGGG GT               42

(2) INFORMATION FOR SEQ ID NO:70:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:70:

ATATACTCGA GAGCAATGTC CGCAGCACCA CTGGTCACGG CA               42

(2) INFORMATION FOR SEQ ID NO:71:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:71:

ATATAGGCGG CCGCTCATCT TCGTGTGCTA GTCAGCATC                   39

(2) INFORMATION FOR SEQ ID NO:72:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:72:

ACACATTAAT TAACGATGCC GCCGGAAGCG AGAA                        34

(2) INFORMATION FOR SEQ ID NO:73:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:73:

```
ACACATTAAT TAAGTATTGG CCCCAATGGG GTCT                             34
```

(2) INFORMATION FOR SEQ ID NO:74:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:74:

```
CCACGAATTC GGTCCTAAAT AGATGC                                      26
```

(2) INFORMATION FOR SEQ ID NO:75:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:75:

```
CCACAAGCTT CCGGGCGAGG CCGCC                                       25
```

(2) INFORMATION FOR SEQ ID NO:76:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:76:

```
CCACGGATCC CGGCGTTCCG TCC                                         23
```

(2) INFORMATION FOR SEQ ID NO:77:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:77:

```
CCACAAGCTT GTGCACTGGG ATCTG                                       25
```

(2) INFORMATION FOR SEQ ID NO:78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:78:

```
CCACGGATCC GTGCACATGA AGTCC                                       25
```

(2) INFORMATION FOR SEQ ID NO:79:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:79:

CCACAAGCTT CCGGAGTTAC CCGAGTGACC                                          30

(2) INFORMATION FOR SEQ ID NO:80:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:80:

CCACCTTAAG CGTCGGCTTT TTCTTC                                              26

(2) INFORMATION FOR SEQ ID NO:81:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:81:

CCACCTTAAG AGAAGAGAAA GAATG                                               25

(2) INFORMATION FOR SEQ ID NO:82:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:82:

CCACAAGCTT GGACCACCGT AGAG                                                24

(2) INFORMATION FOR SEQ ID NO:83:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:83:

CCGCGTGGCG GATCCCCTG                                                      19

(2) INFORMATION FOR SEQ ID NO:84:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:84:

CCACGGATCC GGAAGGGACA GAAG                                                24

(2) INFORMATION FOR SEQ ID NO:85:

```
       (i) SEQUENCE CHARACTERISTICS:
           (A) LENGTH: 16 base pairs
           (B) TYPE: nucleic acid
           (C) STRANDEDNESS: single
           (D) TOPOLOGY: linear (xi) SEQUENCE DESCRIPTION: SEQ ID NO:85:

CACGGTCCTG AGGTGC                                                    16

(2) INFORMATION FOR SEQ ID NO:86:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (xi) SEQUENCE DESCRIPTION: SEQ ID NO:86:

TATATATATC TCGAGACCGC CAAGATGTTC CCGTTCCAGC CA                        42

(2) INFORMATION FOR SEQ ID NO:87:

(i) SEQUENCE CHARACTERISTICS:
           (A) LENGTH: 38 base pairs
           (B) TYPE: nucleic acid
           (C) STRANDEDNESS: single
           (D) TOPOLOGY: linear (xi) SEQUENCE DESCRIPTION: SEQ ID NO:87:

TATATATATG CGGCCGCTCA ATTATGTTTC TGGTTGGT                             38

(2) INFORMATION FOR SEQ ID NO:88:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (xi) SEQUENCE DESCRIPTION: SEQ ID NO:88:

TATATAGATC TGGCGCGCCT TTACCACTCC TATCAGTGAT AG                        42

(2) INFORMATION FOR SEQ ID NO:89:

(i) SEQUENCE CHARACTERISTICS:
           (A) LENGTH: 35 base pairs
           (B) TYPE: nucleic acid
           (C) STRANDEDNESS: single
           (D) TOPOLOGY: linear (xi) SEQUENCE DESCRIPTION: SEQ ID NO:89:

TACGCCGTCA ATACGGTTCA CTAAACGAGC TCTGC                                35

(2) INFORMATION FOR SEQ ID NO:90:

(i) SEQUENCE CHARACTERISTICS:
           (A) LENGTH: 35 base pairs
           (B) TYPE: nucleic acid
           (C) STRANDEDNESS: single
           (D) TOPOLOGY: linear (xi) SEQUENCE DESCRIPTION: SEQ ID NO:90:

TAGTGAACCG TATTGACGGC GTAGTACACA CTATT                                35

(2) INFORMATION FOR SEQ ID NO:91:

(i) SEQUENCE CHARACTERISTICS:
```

(A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:91:

CGTTGAGCAT AACCGAATCT AC                                              22

(2) INFORMATION FOR SEQ ID NO:92:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:92:

ATATAGAGCT CTTAATTAAT CTTTGTGAAG GAACCTTACT TC                         42

(2) INFORMATION FOR SEQ ID NO:93:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:93:

ATATAGAGCT CAGGCGTTGA AAAGATTAGC GACCG                                 35

(2) INFORMATION FOR SEQ ID NO:94:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:94:

TATATATTAA TTAAATAGAA TGACACCTAC TCAGACAATG CGATGC                     46

(2) INFORMATION FOR SEQ ID NO:95:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:95:

ATATACTCGA GTAGCAATGG TGAAACCAGT AACGTTATAC                            40

(2) INFORMATION FOR SEQ ID NO:96:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:96:

GCCCTTTCTC TTCTTTTTTG GCTGCCCGCT TTCCAGTCGG GAAAC                      45

(2) INFORMATION FOR SEQ ID NO:97:

(i) SEQUENCE CHARACTERISTICS:
        (A) LENGTH: 39 base pairs (B) TYPE: nucleic acid
        (C) STRANDEDNESS: single
        (D) TOPOLOGY: linear (xi) SEQUENCE DESCRIPTION: SEQ ID NO:97:

CCAAAAAAGA AGAGAAAGGG CGGTGGTGCT TTGTCTCCT                                      39

(2) INFORMATION FOR SEQ ID NO:98:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:98:

ATATAGAGCT CTTAAACTGA TGATTTGATT TCAAATGC                                       38

(2) INFORMATION FOR SEQ ID NO:99:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:99:

CGCGCCGAAT TGTGAGCGCT CACAATTCGG                                                30

(2) INFORMATION FOR SEQ ID NO:100:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:100:

Pro Lys Lys Lys Lys Arg Lys
1               5

(2) INFORMATION FOR SEQ ID NO:101:

(i) SEQUENCE CHARACTERISTICS:
        (A) LENGTH: 8000 base pairs
        (B) TYPE: nucleic acid
        (C) STRANDEDNESS: single
        (D) TOPOLOGY: linear (xi) SEQUENCE DESCRIPTION: SEQ ID NO:101:

ATTGACGGCG TAGTACACAC TATTGAATCA AACAGCCGAC CAATCGCACT ACCATCACAA               60

TGGAGAAGCC AGTAGTAAAC GTAGACGTAG ACCCCCAGAG TCCGTTTGTC GTGCAACTGA              120

AAAAAAGCTT CCCGCAATTT GAGGTAGTAG CACAGCAGGT CACTCCAAAT GACCATGCTA              180

ATGCCAGAGC ATTTTCGCAT CTGGCCAGTA AACTAATCGA GCTGGAGGTT CCTACCACAG              240

CGACGATCTT GGACATAGGC AGCGCACCGG CTCGTAGAAT GTTTTCCGAG CACCAGTATC              300

ATTGTGTCTG CCCCATGCGT AGTCCAGAAG ACCCGGACCG CATGATGAAA TACGCCAGTA              360

AACTGGCGGA AAAAGCGTGC AAGATTACAA ACAAGAACTT GCATGAGAAG ATTAAGGATC              420

TCCGGACCGT ACTTGATACG CCGGATGCTG AAACACCATC GCTCTGCTTT CACAACGATG              480

TTACCTGCAA CATGCGTGCC GAATATTCCG TCATGCAGGA CGTGTATATC AACGCTCCCG              540

GAACTATCTA TCATCAGGCT ATGAAAGGCG TGCGGACCCT GTACTGGATT GGCTTCGACA              600

-continued

| | | | | |
|---|---|---|---|---|
| CCACCCAGTT | CATGTTCTCG | GCTATGGCAG | GTTCGTACCC | TGCGTACAAC ACCAACTGGG | 660 |
| CCGACGAGAA | AGTCCTTGAA | GCGCGTAACA | TCGGACTTTG | CAGCACAAAG CTGAGTGAAG | 720 |
| GTAGGACAGG | AAAATTGTCG | ATAATGAGGA | AGAAGGAGTT | GAAGCCCGGG TCGCGGGTTT | 780 |
| ATTTCTCCGT | AGGATCGACA | CTTTATCCAG | AACACAGAGC | CAGCTTGCAG AGCTGGCATC | 840 |
| TTCCATCGGT | GTTCCACTTG | AATGGAAAGC | AGTCGTACAC | TTGCCGCTGT GATACAGTGG | 900 |
| TGAGTTGCGA | AGGCTACGTA | GTGAAGAAAA | TCACCATCAG | TCCCGGGATC ACGGGAGAAA | 960 |
| CCGTGGGATA | CGCGGTTACA | CACAATAGCG | AGGGCTTCTT | GCTATGCAAA GTTACTGACA | 1020 |
| CAGTAAAAGG | AGAACGGGTA | TCGTTCCCTG | TGTGCACGTA | CATCCCGGCC ACCATATGCG | 1080 |
| ATCAGATGAC | TGGTATAATG | CCACGGATA | TATCACCTGA | CGATGCACAA AAACTTCTGG | 1140 |
| TTGGGCTCAA | CCAGCGAATT | GTCATTAACG | GTAGGACTAA | CAGGAACACC AACACCATGC | 1200 |
| AAAATTACCT | TCTGCCGATC | ATAGCACAAG | GGTTCAGCAA | ATGGGCTAAG GAGCGCAAGG | 1260 |
| ATGATCTTGA | TAACGAGAAA | ATGCTGGGTA | CTAGAGAACG | CAAGCTTACG TATGGCTGCT | 1320 |
| TGTGGGCGTT | TCGCACTAAG | AAAGTACATT | CGTTTTATCG | CCCACCTGGA ACGCAGACCT | 1380 |
| GCGTAAAAGT | CCCAGCCTCT | TTTAGCGCTT | TTCCCATGTC | GTCCGTATGG ACGACCTCTT | 1440 |
| TGCCCATGTC | GCTGAGGCAG | AAATTGAAAC | TGGCATTGCA | ACCAAAGAAG GAGGAAAAAC | 1500 |
| TGCTGCAGGT | CTCGGAGGAA | TTAGTCATGG | AGGCCAAGGC | TGCTTTTGAG GATGCTCAGG | 1560 |
| AGGAAGCCAG | AGCGGAGAAG | CTCCGAGAAG | CACTTCCACC | ATTAGTGGCA GACAAAGGCA | 1620 |
| TCGAGGCAGC | CGCAGAAGTT | GTCTGCGAAG | TGGAGGGGCT | CCAGGCGGAC ATCGGAGCAG | 1680 |
| CATTAGTTGA | AACCCCGCGC | GGTCACGTAA | GGATAATACC | TCAAGCAAAT GACCGTATGA | 1740 |
| TCGGACAGTA | TATCGTTGTC | TCGCCAAACT | CTGTACTGAA | GAATGCCAAA CTCGCACCAG | 1800 |
| CGCACCCGCT | AGCAGATCAG | GTTAAGATCA | TAACACACTC | CGGAAGATCA GGAAGGTACG | 1860 |
| CGGTCGAACC | ATACGACGCT | AAAGTACTGA | TGCCAGCAGG | AGGTGCCGTA CCATGGCCAG | 1920 |
| AATTCCTAGC | ACTGAGTGAG | AGCGCCACGT | TAGTGTACAA | CGAAAGAGAG CTTGTGAACC | 1980 |
| GCAAACTATA | CCACATTGCC | ATGCATGGCC | CCGCCAAGAA | TACAGAAGAG GAGCAGTACA | 2040 |
| AGGTTACAAA | GGCAGAGCTT | GCAGAAACAG | AGTACGTGTT | TGACGTGGAC AAGAAGCGTT | 2100 |
| GCGTTAAGAA | GGAAGAAGCC | TCAGGTCTGG | TCCTCTCGGG | AGAACTGACC AACCCTCCCT | 2160 |
| ATCATGAGCT | AGCTCTGGAG | GGACTGAAGA | CCCGACCTGC | GGTCCCGTAC AAGGTCGAAA | 2220 |
| CAATAGGAGT | GATAGGCACA | CCGGGGTCGG | GCAAGTCAGC | TATTATCAAG TCAACTGTCA | 2280 |
| CGGCACGAGA | TCTTGTTACC | AGCGGAAAGA | AAGAAAATTG | TCGCGAAATT GAGGCCGACG | 2340 |
| TGCTAAGACT | GAGGGGTATG | CAGATTACGT | CGAAGACAGT | AGATTCGGTT ATGCTCAACG | 2400 |
| GATGCCACAA | AGCCGTAGAA | GTGCTGTACG | TTGACGAAGC | GTTCGCGTGC CACGCAGGAG | 2460 |
| CACTACTTGC | CTTGATTGCT | ATCGTCAGGC | CCCGCAAGAA | GGTAGTACTA TGCGGAGACC | 2520 |
| CCATGCAATG | CGGATTCTTC | AACATGATGC | AACTAAAGGT | ACATTTCAAT CACCCTGAAA | 2580 |
| AGACATATG | CACCAAGACA | TTCTACAAGT | ATATCTCCCG | CGCGTTGCACA CAGCCAGTTA | 2640 |
| CAGCTATTGT | ATCGACACTG | CATTACGATG | GAAAGATGAA | AACCACGAAC CCGTGCAAGA | 2700 |
| AGAACATTGA | AATCGATATT | ACAGGGGCCA | CAAAGCCGAA | GCCAGGGGAT ATCATCCTGA | 2760 |
| CATGTTTCCG | CGGGTGGGTT | AAGCAATTGC | AAATCGACTA | TCCCGGACAT GAAGTAATGA | 2820 |
| CAGCCGCGGC | CTCACAAGGG | CTAACCGAAA | AGGAGTGTA | TGCCGTCCGG CAAAAAGTCA | 2880 |
| ATGAAAACCC | ACTGTACGCG | ATCACATCAG | AGCATGTGAA | CGTGTTGCTC ACCCGCACTG | 2940 |
| AGGACAGGCT | AGTGTGGAAA | ACCTTGCAGG | GCGACCCATG | GATTAAGCAG CTCACTAACA | 3000 |

-continued

```
TACCTAAAGG AAACTTTCAG GCTACTATAG AGGACTGGGA AGCTGAACAC AAGGGAATAA    3060
TTGCTGCAAT AAACAGCCCC ACTCCCCGTG CCAATCCGTT CAGCTGCAAG ACCAACGTTT    3120
GCTGGGCGAA AGCATTGGAA CCGATACTAG CCACGGCCGG TATCGTACTT ACCGGTTGCC    3180
AGTGGAGCGA ACTGTTCCCA CAGTTTGCGG ATGACAAACC ACATTCGGCC ATTTACGCCT    3240
TAGACGTAAT TTGCATTAAG TTTTTCGGCA TGGACTTGAC AAGCGGACTG TTTTCTAAAC    3300
AGAGCATCCC ACTAACGTAC CATCCCGCCG ATTCAGCGAG GCCGGTAGCT CATTGGGACA    3360
ACAGCCCAGG AACCCGCAAG TATGGGTACG ATCACGCCAT TGCCGCCGAA CTCTCCCGTA    3420
GATTTCCGGT GTTCCAGCTA GCTGGGAAGG GCACACAACT TGATTTGCAG ACGGGGAGAA    3480
CCAGAGTTAT CTCTGCACAG CATAACCTGG TCCCGGTGAA CCGCAATCTT CCTCACGCCT    3540
TAGTCCCCGA GTACAAGGAG AAGCAACCCG GCCCGGTCGA AAAATTCTTG AACCAGTTCA    3600
AACACCACTC AGTACTTGTG GTATCAGAGG AAAAAATTGA AGCTCCCCGT AAGAGAATCG    3660
AATGGATCGC CCCGATTGGC ATAGCCGGTG CAGATAAGAA CTACAACCTG GCTTTCGGGT    3720
TTCCGCCGCA GGCACGGTAC GACCTGGTGT TCATCAACAT TGGAACTAAA TACAGAAACC    3780
ACCACTTTCA GCAGTGCGAA GACCATGCGG CGACCTTAAA AACCCTTTCG CGTTCGGCCC    3840
TGAATTGCCT TAACTCAGGA GGCACTCTCG TGGTGAAGTC CTATGGCTAC GCCGACCGCA    3900
ACAGTGAGGA CGTAGTCACC GCTCTTGCCA GAAAGTTTGT CAGGGTGTCT GCAGCGAGAC    3960
CAGATTGTGT CTCAAGCAAT ACAGAAATGT ACCTGATTTT CCGACAACTA GACAACAGCC    4020
GTACACGGCA ATTCACCCCG CACCATCTGA ATTGCGTGAT TTCGTCCGTG TATGAGGGTA    4080
CAAGAGATGG AGTTGGAGCC GCGCCGTCAT ACCGCACCAA AAGGGAGAAT ATTGCTGACT    4140
GTCAAGAGGA AGCAGTTGTC AACGCAGCCA ATCCGCTGGG TAGACCAGGC GAAGGAGTCT    4200
GCCGTGCCAT CTATAAACGT TGGCCGACCA GTTTTACCGA TTCAGCCACG GAGACAGGCA    4260
CCGCAAGAAT GACTGTGTGC CTAGGAAAGA AAGTGATCCA CGCGGTCGGC CCTGATTTCC    4320
GGAAGCACCC AGAAGCAGTA GCCTTGAAAT TGCTACAAAA CGCCTACCAT GCAGTGGCAG    4380
ACTTAGTAAA TGAACATAAC ATCAAGTCTG TCGCCATTCC ACTGCTATCT ACAGGCATTT    4440
ACGCAGCCGG AAAAGACCGC CTTGAAGTAT CACTTAACTG CTTGACAACC GCGCTAGACA    4500
GAACTGACGC GGACGTAACC ATCTATTGCC TGGATAAGAA GTGGAAGGAA AGAATCGACG    4560
CGGCACTCCA ACTTAAGGAG TCTGTAACAG AGCTGAAGGA TGAAGATATG GAGATCGACG    4620
ATGAGTTAGT ATGGATCCAT CCAGACAGTT GCTTGAAGGG AAGAAAGGGA TTCAGTACTA    4680
CAAAAGGAAA ATTGTATTCG TACTTCGAAG GCACCAAATT CCATCAAGCA GCAAAAGACA    4740
TGGCGGAGAT AAAGGTCCTG TTCCCTAATG ACCAGGAAAG TAATGAACAA CTGTGTGCCT    4800
ACATATTGGG TGAGACCATG GAAGCAATCC GCGAAAAGTG CCCGGTCGAC ATAACCCGT    4860
CGTTTAGCCC GCCCAAAACG TTGCCGTGCC TTTGCATGTA TGCCATGACG CCAGAAAGGG    4920
TCCACAGACT TAGAAGCAAT AACGTCAAAG AAGTTACAGT ATGCTCCTCC ACCCCCCTTC    4980
CTAAGCACAA AATTAAGAAT GTTCAGAAGG TTCAGTGCAC GAAAGTAGTC CTGTTTAATC    5040
CGCACACTCC CGCATTCGTT CCCGCCCGTA AGTACATAGA AGTGCCAGAA CAGCCTACCG    5100
CTCCTCCTGC ACAGGCCGAG GAGGCCCCCG AAGTTGTAGC GACACCGTCA CCATCTACAG    5160
CTGATAACAC CTCGCTTGAT GTCACAGACA TCTCACTGGA TATGGATGAC AGTAGCGAAG    5220
GCTCACTTTT TTCGAGCTTT AGCGGATCGG ACAACTCTAT TACTAGTATG GACAGTTGGT    5280
CGTCAGGACC TAGTTCACTA GAGATAGTAG ACCGAAGGCA GGTGGTGGTG GCTGACGTTC    5340
```

-continued

| | | | | |
|---|---|---|---|---|
|ATGCCGTCCA|AGAGCCTGCC|CCTATTCCAC|CGCCAAGGCT|AAAGAAGATG GCCCGCCTGG 5400|
|CAGCGGCAAG|AAAAGAGCCC|ACTCCACCGG|CAAGCAATAG|CTCTGAGTCC CTCCACCTCT 5460|
|CTTTTGGTGG|GGTATCCATG|TCCCTCGGAT|CAATTTTCGA|CGGAGAGACG GCCCGCCAGG 5520|
|CAGCGGTACA|ACCCCTGGCA|ACAGGCCCCA|CGGATGTGCC|TATGTCTTTC GGATCGTTTT 5580|
|CCGACGGAGA|GATTGATGAG|CTGAGCCGCA|GAGTAACTGA|GTCCGAACCC GTCCTGTTTG 5640|
|GATCATTTGA|ACCGGCGAA|GTGAACTCAA|TTATATCGTC|CCGATCAGCC GTATCTTTTC 5700|
|CTCTACGCAA|GCAGAGACGT|AGACGCAGGA|GCAGGAGGAC|TGAATACTGA CTAACCGGGG 5760|
|TAGGTGGGTA|CATATTTTCG|ACGGACACAG|GCCCTGGGCA|CTTGCAAAAG AAGTCCGTTC 5820|
|TGCAGAACCA|GCTTACAGAA|CCGACCTTGG|AGCACAATGT|CCTGGAAAGA ATTCATGCCC 5880|
|CGGTGCTCGA|CACGTCGAAA|GAGGAACAAC|TCAAACTCAG|GTACCAGATG ATGCCCACCG 5940|
|AAGCCAACAA|AAGTAGGTAC|CAGTCTCGTA|AGTAGAAAA|TCAGAAAGCC ATAACCACTG 6000|
|AGCGACTACT|GTCAGGACTA|CGACTGTATA|ACTCTGCCAC|AGATCAGCCA GAATGCTATA 6060|
|AGATCACCTA|TCCGAAACCA|TTGTACTCCA|GTAGCGTACC|GGCGAACTAC TCCGATCCAC 6120|
|AGTTCGCTGT|AGCTGTCTGT|AACAACTATC|TGCATGAGAA|CTATCCGACA GTAGCATCTT 6180|
|ATCAGATTAC|TGACGAGTAC|GATGCTTACT|TGGATATGGT|AGACGGGACA GTCGCCTGCC 6240|
|TGGATACTGC|AACCTTCTGC|CCCGCTAAGC|TTAGAAGTTA|CCCGAAAAAA CATGAGTATA 6300|
|GAGCCCCGAA|TATCCGCAGT|GCGGTTCCAT|CAGCGATGCA|GAACACGCTA CAAAATGTGC 6360|
|TCATTGCCGC|AACTAAAAGA|AATTGCAACG|TCACGCAGAT|GCGTGAACTG CCAACACTGG 6420|
|ACTCAGCGAC|ATTCAATGTC|GAATGCTTTC|GAAAATATGC|ATGTAATGAC GAGTATTGGG 6480|
|AGGAGTTCGC|TCGGAAGCCA|ATTAGGATTA|CCACTGAGTT|TGTCACCGCA TATGTAGCTA 6540|
|GACTGAAAGG|CCCTAAGGCC|GCCGCACTAT|TTGCAAAGAC|GTATAATTTG GTCCCATTGC 6600|
|AAGAAGTGCC|TATGGATAGA|TTCGTCATGG|ACATGAAAAG|AGACGTGAAA GTTACACCAG 6660|
|GCACGAAACA|CACAGAAGAA|AGACCGAAAG|TACAAGTGAT|ACAAGCCGCA GAACCCCTGG 6720|
|CGACTGCTTA|CTTATGCGGG|ATTCACCGGG|AATTAGTGCG|TAGGCTTACG GCCGTCTTGC 6780|
|TTCCAAACAT|TCACACGCTT|TTTGACATGT|CGGCGGAGGA|TTTTGATGCA ATCATAGCAG 6840|
|AACACTTCAA|GCAAGGCGAC|CCGGTACTGG|AGACGGATAT|CGCATCATTC GACAAAAGCC 6900|
|AAGACGACGC|TATGGCGTTA|ACCGGTCTGA|TGATCTTGGA|GGACCTGGGT GTGGATCAAC 6960|
|CACTACTCGA|CTTGATCGAG|TGCGCCTTTG|GAGAAATATC|ATCCACCCAT CTACCTACGG 7020|
|GTACTCGTTT|TAAATTCGGG|GCGATGATGA|AATCCGGAAT|GTTCCTCACA CTTTTTGTCA 7080|
|ACACAGTTTT|GAATGTCGTT|ATCGCCAGCA|GAGTACTAGA|AGAGCGGCTT AAAACGTCCA 7140|
|GATGTGCAGC|GTTCATTGGC|GACGACAACA|TCATACATGG|AGTAGTATCT GACAAAGAAA 7200|
|TGGCTGAGAG|GTGCGCCACC|TGGCTCAACA|TGGAGGTTAA|GATCATCGAC GCAGTCATCG 7260|
|GTGAGAGACC|ACCTTACTTC|TGCGGCGGAT|TTATCTTGCA|AGATTCGGTT ACTTCCACAG 7320|
|CGTGCCGCGT|GGCGGATCCC|CTGAAAAGGC|TGTTTAAGTT|GGGTAAACCG CTCCCAGCCG 7380|
|ACGACGAGCA|AGACGAAGAC|AGAAGACGCG|CTCTGCTAGA|TGAAACAAAG GCGTGGTTTA 7440|
|GAGTAGGTAT|AACAGGCACT|TTAGCAGTGG|CCGTGACGAC|CCGGTATGAG GTAGACAATA 7500|
|TTACACCTGT|CCTACTGGCA|TTGAGAACTT|TTGCCCAGAG|CAAAAGAGCA TTCCAAGCCA 7560|
|TCAGAGGGGA|AATAAAGCAT|CTCTACGGTG|TCCTAAATA|GTCAGCATAG TTCATTTCAT 7620|
|CTGACTAATA|CTACAACACC|ACCACCATGA|ATAGAGGATT|CTTTAACATG CTCGGCCGCC 7680|
|GCCCCTTCCC|GGCCCCCACT|GCCATGTGGA|GGCCGCGGAG|AAGGAGGCAG GCGGCCCCGA 7740|

| | | |
|---|---|---|
| TGCCTGCCCG CAACGGGCTG GCTTCTCAAA TCCAGCAACT GACCACAGCC GTCAGTGCCC | 7800 |
| TAGTCATTGG ACAGGCAACT AGACCTCAAC CCCCATGTCC ACGCCCGCCA CCGCGCCAGA | 7860 |
| AGAAGCAGGC GCCCAAGCAA CCACCGAAGC CGAAGAAACC AAAAACGCAG GAGAAGAAGA | 7920 |
| AGAAGCAACC TGCAAAACCC AAACCCGGAA AGAGACAGCG CATGGCACTT AAGTTGGAGG | 7980 |
| CCGACAGATT GTTCGACGTC | 8000 |

(2) INFORMATION FOR SEQ ID NO:102:

(i) SEQUENCE CHARACTERISTICS:
        (A) LENGTH: 8000 base pairs
        (B) TYPE: nucleic acid
        (C) STRANDEDNESS: single
        (D) TOPOLOGY: linear (xi) SEQUENCE DESCRIPTION: SEQ ID NO:102:

| | | |
|---|---|---|
| ATTGACGGCG TAGTACACAC TATTGAATCA AACAGCCGAC CAATTGCACT ACCATCACAA | 60 |
| TGGAGAAGCC AGTAGTAAAC GTAGACGTAG ACCCCCAGAG TCCGTTTGTC GTGCAACTGC | 120 |
| AAAAAAGCTT CCCGCAATTT GAGGTAGTAG CACAGCAGGT CACTCCAAAT GACCATGCTA | 180 |
| ATGCCAGAGC ATTTTCGCAT CTGGCCAGTA AACTAATCGA GCTGGAGGTT CCTACCACAG | 240 |
| CGACGATCTT GGACATAGGC AGCGCACCGG CTCGTAGAAT GTTTTCCGAG CACCAGTATC | 300 |
| ATTGTGTCTG CCCCATGCGT AGTCCAGAAG ACCCGGACCG CATGATGAAA TACGCCAGTA | 360 |
| AACTGGCGGA AAAAGCGTGC AAGATTACAA ACAAGAACTT GCATGAGAAG ATTAAGGATC | 420 |
| TCCGGACCGT ACTTGATACG CCGGATGCTG AAACACCATC GCTCTGCTTT CACAACGATG | 480 |
| TTACCTGCAA CATGCGTGCC GAATATTCCG TCATGCAGGA CGTGTATATC AACGCTCCCG | 540 |
| GAACTATCTA TCATCAGGCT ATGAAAGGCG TGCGGACCCT GTACTGGATT GGCTTCGACA | 600 |
| CCACCCAGTT CATGTTCTCG GCTATGGCAG GTTCGTACCC TGCGTACAAC ACCAACTGGG | 660 |
| CCGACGAGAA AGTCCTTGAA GCGCGTAACA TCGGACTTTG CAGCACAAAG CTGAGTGAAG | 720 |
| GTAGGACAGG AAAATTGTCG ATAATGAGGA AGAAGGAGTT GAAGCCCGGG TCGCGGGTTT | 780 |
| ATTTCTCCGT AGGATCGACA CTTTATCCAG AACACAGAGC CAGCTTGCAG AGCTGGCATC | 840 |
| TTCCATCGGT GTTCCACTTG AATGGAAAGC AGTCGTACAC TTGCCGCTGT GATACAGTGG | 900 |
| TGAGTTGCGA AGGCTACGTA GTGAAGAAAA TCACCATCAG TCCCGGGATC ACGGGAGAAA | 960 |
| CCGTGGGATA CGCGGTTACA CACAATAGCG AGGGCTTCTT GCTATGCAAA GTTACTGACA | 1020 |
| CAGTAAAAGG AGAACGGGTA TCGTTCCCTG TGTGCACGTA CATCCCGGCC ACCATATGCG | 1080 |
| ATCAGATGAC TGGTATAATG GCCACGGATA TATCACCTGA CGATGCACAA AAACTTCTGG | 1140 |
| TTGGGCTCAA CCAGCGAATT GTCATTAACG GTAGGACTAA CAGGAACACC AACACCATGC | 1200 |
| AAAATTACCT TCTGCCGATC ATAGCACAAG GGTTCAGCAA ATGGGCTAAG GAGCGCAAGG | 1260 |
| ATGATCTTGA TAACGAGAAA ATGCTGGGTA CTAGAGAACG CAAGCTTACG TATGGCTGCT | 1320 |
| TGTGGGCGTT TCGCACTAAG AAAGTACATT CGTTTTATCG CCCACCTGGA ACGCAGACCT | 1380 |
| GCGTAAAAGT CCCAGCCTCT TTTAGCGCTT TTCCCATGTC GTCCGTATGG ACGACCTCTT | 1440 |
| TGCCCATGTC GCTGAGGCAG AAATTGAAAC TGGCATTGCA ACCAAAGAAG GAGGAAAAAC | 1500 |
| TGCTGCAGGT CTCGGAGGAA TTAGTCATGG AGGCCAAGGC TGCTTTTGAG GATGCTCAGG | 1560 |
| AGGAAGCCAG AGCGGAGAAG CTCCGAGAAG CACTTCCACC ATTAGTGGCA GACAAAGGCA | 1620 |
| TCGAGGCAGC CGCAGAAGTT GTCTGCGAAG TGGAGGGGCT CCAGGCGGAC ATCGGAGCAG | 1680 |
| CATTAGTTGA AACCCCGCGC GGTCACGTAA GGATAATACC TCAAGCAAAT GACCGTATGA | 1740 |

-continued

```
TCGGACAGTA TATCGTTGTC TCGCCAAACT CTGTGCTGAA GAATGCCAAA CTCGCACCAG   1800

CGCACCCGCT AGCAGATCAG GTTAAGATCA TAACACACTC CGGAAGATCA GGAAGGTACG   1860

CGGTCGAACC ATACGACGCT AAAGTACTGA TGCCAGCAGG AGGTGCCGTA CCATGGCCAG   1920

AATTCCTAGC ACTGAGTGAG AGCGCCACGT TAGTGTACAA CGAAAGAGAG TTTGTGAACC   1980

GCAAACTATA CCACATTGCC ATGCATGGCC CCGCCAAGAA TACAGAAGAG GAGCAGTACA   2040

AGGTTACAAA GGCAGAGCTT GCAGAAACAG AGTACGTGTT TGACGTGGAC AAGAAGCGTT   2100

GCGTTAAGAA GGAAGAAGCC TCAGGTCTGG TCCTCTCGGG AGAACTGACC AACCCTCCCT   2160

ATCATGAGCT AGCTCTGGAG GGACTGAAGA CCCGACCTGC GGTCCCGTAC AAGGTCGAAA   2220

CAATAGGAGT GATAGGCACA CCGGGGTCGG GCAAGTCAGC TATTATCAAG TCAACTGTCA   2280

CGGCACGAGA TCTTGTTACC AGCGGAAAGA AGAAAATTG TCGCGAAATT GAGGCCGACG   2340

TGCTAAGACT GAGGGGTATG CAGATTACGT CGAAGACAGT AGATTCGGTT ATGCTCAACG   2400

GATGCCACAA AGCCGTAGAA GTGCTGTACG TTGACGAAGC GTTCGCGTGC CACGCAGGAG   2460

CACTACTTGC CTTGATTGCT ATCGTCAGGC CCCGCAAGAA GGTAGTACTA TGCGGAGACC   2520

CCATGCAATG CGGATTCTTC AACATGATGC AACTAAAGGT ACATTTCAAT CACCCTGAAA   2580

AAGACATATG CACCAAGACA TTCTACAAGT ATATCTCCCG GCGTTGCACA CAGCCAGTTA   2640

CAGCTATTGT ATCGACACTG CATTACGATG GAAAGATGAA AACCACGAAC CCGTGCAAGA   2700

AGAACATTGA AATCGATATT ACAGGGGCCA CAAAGCCGAA GCCAGGGGAT ATCATCCTGA   2760

CATGTTTCCG CGGGTGGGTT AAGCAATTGC AAATCGACTA TCCCGGACAT GAAGTAATGA   2820

CAGCCGCGGC CTCACAAGGG CTAACCAGAA AAGGAGTGTA TGCCGTCCGG CAAAAAGTCA   2880

ATGAAAACCC ACTGTACGCG ATCACATCAG AGCATGTGAA CGTGTTGCTC ACCCGCACTG   2940

AGGACAGGCT AGTGTGGAAA ACCTTGCAGG GCGACCCATG GATTAAGCAG CCCACTAACA   3000

TACCTAAAGG AAACTTTCAG GCTACTATAG AGGACTGGGA AGCTGAACAC AAGGGAATAA   3060

TTGCTGCAAT AAACAGCCCC ACTCCCCGTG CCAATCCGTT CAGCTGCAAG ACCAACGTTT   3120

GCTGGGCGAA AGCATTGGAA CCGATACTAG CCACGGCCGG TATCGTACTT ACCGGTTGCC   3180

AGTGGAGCGA ACTGTTCCCA CAGTTTGCGG ATGACAAACC ACATTCGGCC ATTTACGCCT   3240

TAGACGTAAT TTGCATTAAG TTTTTCGGCA TGGACTTGAC AAGCGGACTG TTTTCTAAAC   3300

AGAGCATCCC ACTAACGTAC CATCCCGCCG ATTCAGCGAG GCCGGTAGCT CATTGGGACA   3360

ACAGCCCAGG AACCCGCAAG TATGGGTACG ATCACGCCAT TGCCGCCGAA CTCTCCCGTA   3420

GATTTCCGGT GTTCCAGCTA GCTGGGAAGG GCACACAACT TGATTTGCAG ACGGGGAGAA   3480

CCAGAGTTAT CTCTGCACAG CATAACCTGG TCCCGGTGAA CCGCAATCTT CCTCACGCCT   3540

TAGTCCCCGA GTACAAGGAG AAGCAACCCG GCCCGGTCAA AAAATTCTTG AACCAGTTCA   3600

AACACCACTC AGTACTTGTG GTATCAGAGG AAAAAATTGA AGCTCCCCGT AAGAGAATCG   3660

AATGGATCGC CCCGATTGGC ATAGCCGGTG CAGATAAGAA CTACAACCTG GCTTTCGGGT   3720

TTCCGCCGCA GGCACGGTAC GACCTGGTGT TCATCAACAT TGGAACTAAA TACAGAAACC   3780

ACCACTTTCA GCAGTGCGAA GACCATGCGG CGACCTTAAA AACCCTTTCG CGTTCGGCCC   3840

TGAATTGCCT TAACCCAGGA GGCACCCTCG TGGTGAAGTC CTATGGCTAC GCCGACCGCA   3900

ACAGTGAGGA CGTAGTCACC GCTCTTGCCA GAAAGTTTGT CAGGGTGTCT GCAGCGAGAC   3960

CAGATTGTGT CTCAAGCAAT ACAGAAATGT ACCTGATTTT CCGACAACTA GACAACAGCC   4020

GTACACGGCA ATTCACCCCG CACCATCTGA ATTGCGTGAT TTCGTCCGTG TATGAGGGTA   4080
```

```
CAAGAGATGG AGTTGGAGCC GCGCCGTCAT ACCGCACCAA AAGGGAGAAT ATTGCTGACT   4140

GTCAAGAGGA AGCAGTTGTC AACGCAGCCA ATCCGCTGGG TAGACCAGGC GAAGGAGTCT   4200

GCCGTGCCAT CTATAAACGT TGGCCGACCA GTTTTACCGA TTCAGCCACG GAGACAGGCA   4260

CCGCAAGAAT GACTGTGTGC CTAGGAAAGA AAGTGATCCA CGCGGTCGGC CCTGATTTCC   4320

GGAAGCACCC AGAAGCAGAA GCCTTGAAAT TGCTACAAAA CGCCTACCAT GCAGTGGCAG   4380

ACTTAGTAAA TGAACATAAC ATCAAGTCTG TCGCCATTCC ACTGCTATCT ACAGGCATTT   4440

ACGCAGCCGG AAAAGACCGC CTTGAAGTAT CACTTAACTG CTTGACAACC GCGCTAGACA   4500

GAACTGACGC GGACGTAACC ATCTATTGCC TGGATAAGAA GTGGAAGGAA AGAATCGACG   4560

CGGCACTCCA ACTTAAGGAG TCTGTAACAG AGCTGAAGGA TGAAGATATG GAGATCGACG   4620

ATGAGTTAGT ATGGATCCAT CCAGACAGTT GCTTGAAGGG AAGAAAGGGA TTCAGTACTA   4680

CAAAAGGAAA ATTGTATTCG TACTTCGAAG GCACCAAATT CCATCAAGCA GCAAAAGACA   4740

TGGCGGAGAT AAAGGTCCTG TTCCCTAATG ACCAGGAAAG TAATGAACAA CTGTGTGCCT   4800

ACATATTGGG TGAGACCATG GAAGCAATCC GCGAAAAGTG CCCGGTCGAC CATAACCCGT   4860

CGTCTAGCCC GCCCAAAACG TTGCCGTGCC TTTGCATGTA TGCCATGACG CCAGAAAGGG   4920

TCCACAGACT TAGAAGCAAT AACGTCAAAG AAGTTACAGT ATGCTCCTCC ACCCCCCTTC   4980

CTAAGCACAA AATTAAGAAT GTTCAGAAGG TTCAGTGCAC GAAAGTAGTC CTGTTTAATC   5040

CGCACACTCC CGCATTCGTT CCCGCCCGTA AGTACATAGA AGTGCCAGAA CAGCCTACCG   5100

CTCCTCCTGC ACAGGCCGAG GAGGCCCCCG AAGTTGTAGC GACACCGTCA CCATCTACAG   5160

CTGATAACAC CTCGCTTGAT GTCACAGACA TCTCACTGGA TATGGATGAC AGTAGCGAAG   5220

GCTCACTTTT TTCGAGCTTT AGCGGATCGG ACAACTCTAT TACTAGTATG GACAGTTGGT   5280

CGTCAGGACC TAGTTCACTA GAGATAGTAG ACCGAAGGCA GGTGGTGGTG GCTGACGTTC   5340

ATGCCGTCCA AGAGCCTGCC CCTATTCCAC CGCCAAGGCT AAAGAAGATG GCCCGCCTGG   5400

CAGCGGCAAG AAAAGAGCCC ACTCCACCGG CAAGCAATAG CTCTGAGTCC CTCCACCTCT   5460

CTTTTGGTGG GGTATCCATG TCCCTCGGAT CAATTTTCGA CGGAGAGACG GCCCGCCAGG   5520

CAGCGGTACA ACCCCTGGCA ACAGGCCCCA CGGATGTGCC TATGTCTTTC GGATCGTTTT   5580

CCGACGGAGA GATTGATGAG CTGAGCCGCA GAGTAACTGA GTCCGAACCC GTCCTGTTTG   5640

GATCATTTGA ACCGGGCGAA GTGAACTCAA TTATATCGTC CCGATCAGCC GTATCTTTTC   5700

CACTACGCAA GCAGAGACGT AGACGCAGGA GCAGGAGGAC TGAATACTGA CTAACCGGGG   5760

TAGGTGGGTA CATATTTTCG ACGGACACAG GCCCTGGGCA CTTGCAAAAG AAGTCCGTTC   5820

TGCAGAACCA GCTTACAGAA CCGACCTTGG AGCGCAATGT CCTGGAAAGA ATTCATGCCC   5880

CGGTGCTCGA CACGTCGAAA GAGGAACAAC TCAAACTCAG GTACCAGATG ATGCCCACCG   5940

AAGCCAACAA AAGTAGGTAC CAGTCTCGTA AGTAGAAAA TCAGAAAGCC ATAACCACTG    6000

AGCGACTACT GTCAGGACTA CGACTGTATA ACTCTGCCAC AGATCAGCCA GAATGCTATA   6060

AGATCACCTA TCCGAAACCA TTGTACTCCA GTAGCGTACC GGCGAACTAC TCCGATCCAC   6120

AGTTCGCTGT AGCTGTCTGT AACAACTATC TGCATGAGAA CTATCCGACA GTAGCATCTT   6180

ATCAGATTAC TGACGAGTAC GATGCTTACT GGATATGGT AGACGGGACA GTCGCCTGCC    6240

TGGATACTGC AACCTTCTGC CCCGCTAAGC TTAGAAGTTA CCCGAAAAAA CATGAGTATA   6300

GAGCCCCGAA TATCCGCAGT GCGGTTCCAT CAGCGATGCA GAACACGCTA CAAAATGTGC   6360

TCATTGCCGC AACTAAAAGA AATTGCAACG TCACGCAGAT GCGTGAACTG CCAACACTGG   6420

ACTCAGCGAC ATTCAATGTC GAATGCTTTC GAAAATATGC ATGTAATGAC GAGTATTGGG   6480
```

```
AGGAGTTCGC TCGGAAGCCA ATTAGGATTA CCACTGAGTT TGTCACCGCA TATGTAGCTA    6540

GACTGAAAGG CCCTAAGGCC GCCGCACTAT TTGCAAAGAC GTATAATTTG GTCCCATTGC    6600

AAGAAGTGCC TATGGATAGA TTCGTCATGG ACATGAAAAG AGACGTGAAA GTTACACCAG    6660

GCACGAAACA CACAGAAGAA AGACCGAAAG TACAAGTGAT ACAAGCCGCA GAACCCCTGG    6720

CGACTGCTTA CTTATGCGGG ATTCACCGGG AATTAGTGCG TAGGCTTACG GCCGTCTTGC    6780

TTCCAAACAT TCACACGCTT TTTGACATGT CGGCGGAGGA TTTTGATGCA ATCATAGCAG    6840

AACACTTCAA GCAAGGCGAC CCGGTACTGG AGACGGATAT CGCATCATTC GACAAAAGCC    6900

AAGACGACGC TATGGCGTTA ACCGGTCTGA TGATCTTGGA GGACCTGGGT GTGGATCAAC    6960

CACTACTCGA CTTGATCGAG TGCGCCTTTG GAGAAATATC ATCCACCCAT CTACCTACGG    7020

GTACTCGTTT TAAATTCGGG GCGATGATGA ATCCGGAAT GTTCCTCACA CTTTTTGTCA    7080

ACACAGTTTT GAATGTCGTT ATCGCCAGCA GAGTACTAGA AGAGCGGCTT AAAACGTCCA    7140

GATGTGCAGC GTTCATTGGC GACGACAACA TCATACATGG AGTAGTATCT GACAAAGAAA    7200

TGGCTGAGAG GTGCGCCACC TGGCTCAACA TGGAGGTTAA GATCATCGAC GCAGTCATCG    7260

GTGAGAGACC ACCTTACTTC TGCGGCGGAT TTATCTTGCA AGATTCGGTT ACTTCCACAG    7320

CGTGCCGCGT GGCGGATCCC CTGAAAAGGC TGTTTAAGTT GGGTAAACCG CTCCCAGCCG    7380

ACGACGAGCA AGACGAAGAC AGAAGACGCG CTCTGCTAGA TGAAACAAAG GCGTGGTTTA    7440

GAGTAGGTAT AACAGGCACT TTAGCAGTGG CCGTGACGAC CCGGTATGAG GTAGACAATA    7500

TTACACCTGT CCTACTGGCA TTGAGAACTT TTGCCCAGAG CAAAAGAGCA TTCCAAGCCA    7560

TCAGAGGGGA AATAAAGCAT CTCTACGGTG GTCCTAAATA GTCAGCATAG TACATTTCAT    7620

CTGACTAATA CTACAACACC ACCACCATGA ATAGAGGATT CTTTAACATG CTCGGCCGCC    7680

GCCCCTTCCC GGCCCCCACT GCCATGTGGA GGCCGCGGAG AAGGAGGCAG GCGGCCCCGA    7740

TGCCTGCCCG CAACGGGCTG GCTTCTCAAA TCCAGCAACT GACCACAGCC GTCAGTGCCC    7800

TAGTCATTGG ACAGGCAACT AGACCTCAAC CCCCACGTCC ACGCCCGCCA CCGCGCCAGA    7860

AGAAGCAGGC GCCCAAGCAA CCACCGAAGC CGAAGAAACC AAAAACGCAG GAGAAGAAGA    7920

AGAAGCAACC TGCAAAACCC AAACCCGGAA AGAGACAGCG CATGGCACTT AAGTTGGAGG    7980

CCGACAGATT GTTCGACGTC                                              8000
```

(2) INFORMATION FOR SEQ ID NO:103:

(i) SEQUENCE CHARACTERISTICS:
        (A) LENGTH: 11740 base pairs
        (B) TYPE: nucleic acid
        (C) STRANDEDNESS: single
        (D) TOPOLOGY: linear (xi) SEQUENCE DESCRIPTION: SEQ ID NO:103:

```
ATTGACGGCG TAGTACACAC TATTGAATCA AACAGCCGAC CAATTGCACT ACCATCACAA      60

TGGAGAAGCC AGTAGTAAAC GTAGACGTAG ACCCCCAGAG TCCGTTTGTC GTGCAACTGC     120

AAAAAAGCTT CCCGCAATTT GAGGTAGTAG CACAGCAGGT CACTCCAAAT GACCATGCTA     180

ATGCCAGAGC ATTTTCGCAT CTGGCCAGTA AACTAATCGA GCTGGAGGTT CCTACCACAG     240

CGACGATCTT GGACATAGGC AGCGCACCGG CTCGTAGAAT GTTTTCCGAG CACCAGTATC     300

ATTGTGTCTG CCCCATGCGT AGTCCAGAAG ACCCGGACCG CATGATGAAA TACGCCAGTA     360

AACTGGCGGA AAAAGCGTGC AAGATTACAA ACAAGAACTT GCATGAGAAG ATTAAGGATC     420

TCCGGACCGT ACTTGATACG CCGGATGCTG AAACACCATC GCTCTGCTTT CACAACGATG     480
```

```
TTACCTGCAA CATGCGTGCC GAATATTCCG TCATGCAGGA CGTGTATATC AACGCTCCCG    540

GAACTATCTA TCATCAGGCT ATGAAAGGCG TGCGGACCCT GTACTGGATT GGCTTCGACA    600

CCACCCAGTT CATGTTCTCG GCTATGGCAG GTTCGTACCC TGCGTACAAC ACCAACTGGG    660

CCGACGAGAA AGTCCTTGAA GCGCGTAACA TCGGACTTTG CAGCACAAAG CTGAGTGAAG    720

GTAGGACAGG AAAATTGTCG ATAATGAGGA AGAAGGAGTT GAAGCCCGGG TCGCGGGTTT    780

ATTTCTCCGT AGGATCGACA CTTTATCCAG AACACAGAGC CAGCTTGCAG AGCTGGCATC    840

TTCCATCGGT GTTCCACTTG AATGGAAAGC AGTCGTACAC TTGCCGCTGT GATACAGTGG    900

TGAGTTGCGA AGGCTACGTA GTGAAGAAAA TCACCATCAG TCCCGGGATC ACGGGAGAAA    960

CCGTGGGATA CGCGGTTACA CACAATAGCG AGGGCTTCTT GCTATGCAAA GTTACTGACA   1020

CAGTAAAAGG AGAACGGGTA TCGTTCCCTG TGTGCACGTA CATCCCGGCC ACCATATGCG   1080

ATCAGATGAC TGGTATAATG GCCACGGATA TATCACCTGA CGATGCACAA AAACTTCTGG   1140

TTGGGCTCAA CCAGCGAATT GTCATTAACG GTAGGACTAA CAGGAACACC AACACCATGC   1200

AAAATTACCT TCTGCCGATC ATAGCACAAG GGTTCAGCAA ATGGGCTAAG GAGCGCAAGG   1260

ATGATCTTGA TAACGAGAAA ATGCTGGGTA CTAGAGAACG CAAGCTTACG TATGGCTGCT   1320

TGTGGGCGTT TCGCACTAAG AAAGTACATT CGTTTTATCG CCCACCTGGA ACGCAGACCT   1380

GCGTAAAAGT CCCAGCCTCT TTTAGCGCTT TTCCCATGTC GTCCGTATGG ACGACCTCTT   1440

TGCCCATGTC GCTGAGGCAG AAATTGAAAC TGGCATTGCA ACCAAAGAAG GAGGAAAAAC   1500

TGCTGCAGGT CTCGGAGGAA TTAGTCATGG AGGCCAAGGC TGCTTTTGAG GATGCTCAGG   1560

AGGAAGCCAG AGCGGAGAAG CTCCGAGAAG CACTTCCACC ATTAGTGGCA GACAAAGGCA   1620

TCGAGGCAGC CGCAGAAGTT GTCTGCGAAG TGGAGGGGCT CCAGGCGGAC ATCGGAGCAG   1680

CATTAGTTGA AACCCCGCGC GGTCACGTAA GGATAATACC TCAAGCAAAT GACCGTATGA   1740

TCGGACAGTA TATCGTTGTC TCGCCAAACT CTGTGCTGAA GAATGCCAAA CTCGCACCAG   1800

CGCACCCGCT AGCAGATCAG GTTAAGATCA TAACACACTC CGGAAGATCA GGAAGGTACG   1860

CGGTCGAACC ATACGACGCT AAAGTACTGA TGCCAGCAGG AGGTGCCGTA CCATGGCCAG   1920

AATTCCTAGC ACTGAGTGAG AGCGCCACGT TAGTGTACAA CGAAAGAGAG TTTGTGAACC   1980

GCAAACTATA CCACATTGCC ATGCATGGCC CCGCCAAGAA TACAGAAGAG GAGCAGTACA   2040

AGGTTACAAA GGCAGAGCTT GCAGAAACAG AGTACGTGTT TGACGTGGAC AAGAAGCGTT   2100

GCGTTAAGAA GGAAGAAGCC TCAGGTCTGG TCCTCTCGGG AGAACTGACC AACCCTCCCT   2160

ATCATGAGCT AGCTCTGGAG GGACTGAAGA CCCGACCTGC GGTCCCGTAC AAGGTCGAAA   2220

CAATAGGAGT GATAGGCACA CCGGGGTCGG GCAAGTCAGC TATTATCAAG TCAACTGTCA   2280

CGGCACGAGA TCTTGTTACC AGCGGAAAGA AAGAAAATTG TCGCGAAATT GAGGCCGACG   2340

TGCTAAGACT GAGGGGTATG CAGATTACGT CGAAGACAGT AGATTCGGTT ATGCTCAACG   2400

GATGCCACAA AGCCGTAGAA GTGCTGTACG TTGACGAAGC GTTCGCGTGC CACGCAGGAG   2460

CACTACTTGC CTTGATTGCT ATCGTCAGGC CCCGCAAGAA GGTAGTACTA TGCGGAGACC   2520

CCATGCAATG CGGATTCTTC AACATGATGC AACTAAAGGT ACATTTCAAT CACCCTGAAA   2580

AAGACATATG CACCAAGACA TTCTACAAGT ATATCTCCCG GCGTTGCACA CAGCCAGTTA   2640

CAGCTATTGT ATCGACACTG CATTACGATG GAAAGATGAA AACCACGAAC CCGTGCAAGA   2700

AGAACATTGA AATCGATATT ACAGGGGCCA CAAAGCCGAA GCCAGGGGAT ATCATCCTGA   2760

CATGTTTCCG CGGGTGGGTT AAGCAATTGC AAATCGACTA TCCCGGACAT GAAGTAATGA   2820
```

-continued

```
CAGCCGCGGC CTCACAAGGG CTAACCAGAA AAGGAGTGTA TGCCGTCCGG CAAAAAGTCA    2880

ATGAAAACCC ACTGTACGCG ATCACATCAG AGCATGTGAA CGTGTTGCTC ACCCGCACTG    2940

AGGACAGGCT AGTGTGGAAA ACCTTGCAGG GCGACCCATG GATTAAGCAG CCCACTAACA    3000

TACCTAAAGG AAACTTTCAG GCTACTATAG AGGACTGGGA AGCTGAACAC AAGGGAATAA    3060

TTGCTGCAAT AAACAGCCCC ACTCCCCGTG CCAATCCGTT CAGCTGCAAG ACCAACGTTT    3120

GCTGGGCGAA AGCATTGGAA CCGATACTAG CCACGGCCGG TATCGTACTT ACCGGTTGCC    3180

AGTGGAGCGA ACTGTTCCCA CAGTTTGCGG ATGACAAACC ACATTCGGCC ATTTACGCCT    3240

TAGACGTAAT TTGCATTAAG TTTTTCGGCA TGGACTTGAC AAGCGGACTG TTTTCTAAAC    3300

AGAGCATCCC ACTAACGTAC CATCCCGCCG ATTCAGCGAG GCCGGTAGCT CATTGGGACA    3360

ACAGCCCAGG AACCCGCAAG TATGGGTACG ATCACGCCAT TGCCGCCGAA CTCTCCCGTA    3420

GATTTCCGGT GTTCCAGCTA GCTGGGAAGG GCACACAACT TGATTTGCAG ACGGGGAGAA    3480

CCAGAGTTAT CTCTGCACAG CATAACCTGG TCCCGGTGAA CCGCAATCTT CCTCACGCCT    3540

TAGTCCCCGA GTACAAGGAG AAGCAACCCG GCCCGGTCAA AAAATTCTTG AACCAGTTCA    3600

AACACCACTC AGTACTTGTG GTATCAGAGG AAAAAATTGA AGCTCCCCGT AAGAGAATCG    3660

AATGGATCGC CCCGATTGGC ATAGCCGGTG CAGATAAGAA CTACAACCTG GCTTTCGGGT    3720

TTCCGCCGCA GGCACGGTAC GACCTGGTGT TCATCAACAT TGGAACTAAA TACAGAAACC    3780

ACCACTTTCA GCAGTGCGAA GACCATGCGG CGACCTTAAA AACCCTTTCG CGTTCGGCCC    3840

TGAATTGCCT TAACCCAGGA GGCACCCTCG TGGTGAAGTC CTATGGCTAC GCCGACCGCA    3900

ACAGTGAGGA CGTAGTCACC GCTCTTGCCA GAAAGTTTGT CAGGGTGTCT GCAGCGAGAC    3960

CAGATTGTGT CTCAAGCAAT ACAGAAATGT ACCTGATTTT CCGACAACTA GACAACAGCC    4020

GTACACGGCA ATTCACCCCG CACCATCTGA ATTGCGTGAT TCGTCCGTG TATGAGGGTA    4080

CAAGAGATGG AGTTGGAGCC GCGCCGTCAT ACCGCACCAA AAGGGAGAAT ATTGCTGACT    4140

GTCAAGAGGA AGCAGTTGTC AACGCAGCCA ATCCGCTGGG TAGACCAGGC GAAGGAGTCT    4200

GCCGTGCCAT CTATAAACGT TGGCCGACCA GTTTTACCGA TTCAGCCACG GAGACAGGCA    4260

CCGCAAGAAT GACTGTGTGC CTAGGAAAGA AAGTGATCCA CGCGGTCGGC CCTGATTTCC    4320

GGAAGCACCC AGAAGCAGAA GCCTTGAAAT TGCTACAAAA CGCCTACCAT GCAGTGGCAG    4380

ACTTAGTAAA TGAACATAAC ATCAAGTCTG TCGCCATTCC ACTGCTATCT ACAGGCATTT    4440

ACGCAGCCGG AAAAGACCGC CTTGAAGTAT CACTTAACTG CTTGACAACC GCGCTAGACA    4500

GAACTGACGC GGACGTAACC ATCTATTGCC TGGATAAGAA GTGGAAGGAA AGAATCGACG    4560

CGGCACTCCA ACTTAAGGAG TCTGTAACAG AGCTGAAGGA TGAAGATATG GAGATCGACG    4620

ATGAGTTAGT ATGGATCCAT CCAGACAGTT GCTTGAAGGG AAGAAAGGGA TTCAGTACTA    4680

CAAAAGGAAA ATTGTATTCG TACTTCGAAG GCACCAAATT CCATCAAGCA GCAAAAGACA    4740

TGGCGGAGAT AAAGGTCCTG TTCCCTAATG ACCAGGAAAG TAATGAACAA CTGTGTGCCT    4800

ACATATTGGG TGAGACCATG GAAGCAATCC GCGAAAAGTG CCCGGTCGAC CATAACCCGT    4860

CGTCTAGCCC GCCCAAAACG TTGCCGTGCC TTTGCATGTA TGCCATGACG CCAGAAAGGG    4920

TCCACAGACT TAGAAGCAAT AACGTCAAAG AAGTTACAGT ATGCTCCTCC ACCCCCCTTC    4980

CTAAGCACAA AATTAAGAAT GTTCAGAAGG TTCAGTGCAC GAAAGTAGTC CTGTTTAATC    5040

CGCACACTCC CGCATTCGTT CCCGCCCGTA AGTACATAGA AGTGCCAGAA CAGCCTACCG    5100

CTCCTCCTGC ACAGGCCGAG GAGGCCCCCG AAGTTGTAGC GACACCGTCA CCATCTACAG    5160

CTGATAACAC CTCGCTTGAT GTCACAGACA TCTCACTGGA TATGGATGAC AGTAGCGAAG    5220
```

```
GCTCACTTTT TTCGAGCTTT AGCGGATCGG ACAACTCTAT TACTAGTATG GACAGTTGGT   5280

CGTCAGGACC TAGTTCACTA GAGATAGTAG ACCGAAGGCA GGTGGTGGTG GCTGACGTTC   5340

ATGCCGTCCA AGAGCCTGCC CCTATTCCAC CGCCAAGGCT AAAGAAGATG GCCCGCCTGG   5400

CAGCGGCAAG AAAAGAGCCC ACTCCACCGG CAAGCAATAG CTCTGAGTCC CTCCACCTCT   5460

CTTTTGGTGG GGTATCCATG TCCCTCGGAT CAATTTTCGA CGGAGAGACG GCCCGCCAGG   5520

CAGCGGTACA ACCCCTGGCA ACAGGCCCCA CGGATGTGCC TATGTCTTTC GGATCGTTTT   5580

CCGACGGAGA GATTGATGAG CTGAGCCGCA GAGTAACTGA GTCCGAACCC GTCCTGTTTG   5640

GATCATTTGA ACCGGGCGAA GTGAACTCAA TTATATCGTC CCGATCAGCC GTATCTTTTC   5700

CACTACGCAA GCAGAGACGT AGACGCAGGA GCAGGAGGAC TGAATACTGA CTAACCGGGG   5760

TAGGTGGGTA CATATTTTCG ACGGACACAG GCCCTGGGCA CTTGCAAAAG AAGTCCGTTC   5820

TGCAGAACCA GCTTACAGAA CCGACCTTGG AGCGCAATGT CCTGGAAAGA ATTCATGCCC   5880

CGGTGCTCGA CACGTCGAAA GAGGAACAAC TCAAACTCAG GTACCAGATG ATGCCCACCG   5940

AAGCCAACAA AAGTAGGTAC CAGTCTCGTA AAGTAGAAAA TCAGAAAGCC ATAACCACTG   6000

AGCGACTACT GTCAGGACTA CGACTGTATA ACTCTGCCAC AGATCAGCCA GAATGCTATA   6060

AGATCACCTA TCCGAAACCA TTGTACTCCA GTAGCGTACC GGCGAACTAC TCCGATCCAC   6120

AGTTCGCTGT AGCTGTCTGT AACAACTATC TGCATGAGAA CTATCCGACA GTAGCATCTT   6180

ATCAGATTAC TGACGAGTAC GATGCTTACT GGATATGGT AGACGGGACA GTCGCCTGCC   6240

TGGATACTGC AACCTTCTGC CCCGCTAAGC TTAGAAGTTA CCCGAAAAAA CATGAGTATA   6300

GAGCCCCGAA TATCCGCAGT GCGGTTCCAT CAGCGATGCA GAACACGCTA CAAAATGTGC   6360

TCATTGCCGC AACTAAAAGA AATTGCAACG TCACGCAGAT GCGTGAACTG CCAACACTGG   6420

ACTCAGCGAC ATTCAATGTC GAATGCTTTC GAAAATATGC ATGTAATGAC GAGTATTGGG   6480

AGGAGTTCGC TCGGAAGCCA ATTAGGATTA CCACTGAGTT TGTCACCGCA TATGTAGCTA   6540

GACTGAAAGG CCCTAAGGCC GCCGCACTAT TTGCAAAGAC GTATAATTTG GTCCCATTGC   6600

AAGAAGTGCC TATGGATAGA TTCGTCATGG ACATGAAAAG AGACGTGAAA GTTACACCAG   6660

GCACGAAACA CACAGAAGAA AGACCGAAAG TACAAGTGAT ACAAGCCGCA GAACCCCTGG   6720

CGACTGCTTA CTTATGCGGG ATTCACCGGG AATTAGTGCG TAGGCTTACG GCCGTCTTGC   6780

TTCCAAACAT TCACACGCTT TTTGACATGT CGGCGGAGGA TTTTGATGCA ATCATAGCAG   6840

AACACTTCAA GCAAGGCGAC CCGGTACTGG AGACGGATAT CGCATCATTC GACAAAAGCC   6900

AAGACGACGC TATGGCGTTA ACCGGTCTGA TGATCTTGGA GGACCTGGGT GTGGATCAAC   6960

CACTACTCGA CTTGATCGAG TGCGCCTTTG GAGAAATATC ATCCACCCAT CTACCTACGG   7020

GTACTCGTTT TAAATTCGGG GCGATGATGA AATCCGGAAT GTTCCTCACA CTTTTTGTCA   7080

ACACAGTTTT GAATGTCGTT ATCGCCAGCA GAGTACTAGA AGAGCGGCTT AAAACGTCCA   7140

GATGTGCAGC GTTCATTGGC GACGACAACA TCATACATGG AGTAGTATCT GACAAAGAAA   7200

TGGCTGAGAG GTGCGCCACC TGGCTCAACA TGGAGGTTAA GATCATCGAC GCAGTCATCG   7260

GTGAGAGACC ACCTTACTTC TGCGGCGGAT TTATCTTGCA AGATTCGGTT ACTTCCACAG   7320

CGTGCCGCGT GGCGGATCCC CTGAAAAGGC TGTTTAAGTT GGGTAAACCG CTCCCAGCCG   7380

ACGACGAGCA AGACGAAGAC AGAAGACGCG CTCTGCTAGA TGAAACAAAG GCGTGGTTTA   7440

GAGTAGGTAT AACAGGCACT TTAGCAGTGG CCGTGACGAC CCGGTATGAG GTAGACAATA   7500

TTACACCTGT CCTACTGGCA TTGAGAACTT TTGCCCAGAG CAAAAGAGCA TTCCAAGCCA   7560
```

-continued

```
TCAGAGGGGA AATAAAGCAT CTCTACGGTG GTCCTAAATA GTCAGCATAG TACATTTCAT    7620

CTGACTAATA CTACAACACC ACCACCATGA ATAGAGGATT CTTTAACATG CTCGGCCGCC    7680

GCCCCTTCCC GGCCCCCACT GCCATGTGGA GGCCGCGGAG AAGGAGGCAG GCGGCCCCGA    7740

TGCCTGCCCG CAACGGGCTG GCTTCTCAAA TCCAGCAACT GACCACAGCC GTCAGTGCCC    7800

TAGTCATTGG ACAGGCAACT AGACCTCAAC CCCCACGTCC ACGCCCGCCA CCGCGCCAGA    7860

AGAAGCAGGC GCCCAAGCAA CCACCGAAGC CGAAGAAACC AAAAACGCAG GAGAAGAAGA    7920

AGAAGCAACC TGCAAAACCC AAACCCGGAA AGAGACAGCG CATGGCACTT AAGTTGGAGG    7980

CCGACAGATT GTTCGACGTC AAGAACGAGG ACGGAGATGT CATCGGGCAC GCACTGGCCA    8040

TGGAAGGAAA GGTAATGAAA CCTCTGCACG TGAAAGGAAC CATCGACCAC CCTGTGCTAT    8100

CAAAGCTCAA ATTTACCAAG TCGTCAGCAT ACGACATGGA GTTCGCACAG TTGCCAGTCA    8160

ACATGAGAAG TGAGGCATTC ACCTACACCA GTGAACACCC CGAAGGATTC TATAACTGGC    8220

ACCACGGAGC GGTGCAGTAT AGTGGAGGTA GATTTACCAT CCCTCGCGGA GTAGGAGGCA    8280

GAGGAGACAG CGGTCGTCCG ATCATGGATA ACTCCGGTCG GGTTGTCGCG ATAGTCCTCG    8340

GTGGCGCTGA TGAAGGAACA CGAACTGCCC TTTCGGTCGT CACCTGGAAT AGTAAAGGGA    8400

AGACAATTAA GACGACCCCG GAAGGGACAG AAGAGTGGTC CGCAGCACCA CTGGTCACGG    8460

CAATGTGTTT GCTCGGAAAT GTGAGCTTCC CATGCGACCG CCCGCCCACA TGCTATACCC    8520

GCGAACCTTC CAGAGCCCTC GACATCCTTG AAGAGAACGT GAACCATGAG GCCTACGATA    8580

CCCTGCTCAA TGCCATATTG CGGTGCGGAT CGTCTGGCAG AAGCAAAAGA AGCGTCATTG    8640

ACGACTTTAC CCTGACCAGC CCCTACTTGG GCACATGCTC GTACTGCCAC CATACTGTAC    8700

CGTGCTTCAG CCCTGTTAAG ATCGAGCAGG TCTGGGACGA AGCGGACGAT AACACCATAC    8760

GCATACAGAC TTCCGCCCAG TTTGGATACG ACCAAAGCGG AGCAGCAAGC GCAAACAAGT    8820

ACCGCTACAT GTCGCTTAAG CAGGATCACA CCGTTAAAGA AGGCACCATG GATGACATCA    8880

AGATTAGCAC CTCAGGACCG TGTAGAAGGC TTAGCTACAA AGGATACTTT CTCCTCGCAA    8940

AATGCCCTCC AGGGGACAGC GTAACGGTTA GCATAGTGAG TAGCAACTCA GCAACGTCAT    9000

GTACACTGGC CCGCAAGATA AAACCAAAAT TCGTGGGACG GGAAAAATAT GATCTACCTC    9060

CCGTTCACGG TAAAAAAATT CCTTGCACAG TGTACGACCG TCTGAAAGAA CAACTGCAG    9120

GCTACATCAC TATGCACAGG CCGAGACCGC ACGCTTATAC ATCCTACCTG GAAGAATCAT    9180

CAGGGAAAGT TTACGCAAAG CCGCCATCTG GAAGAACAT TACGTATGAG TGCAAGTGCG    9240

GCGACTACAA GACCGGAACC GTTTCGACCC GCACCGAAAT CACTGGTTGC ACCGCCATCA    9300

AGCAGTGCGT CGCCTATAAG AGCGACCAAA CGAAGTGGGT CTTCAACTCA CCGGACTTGA    9360

TCAGACATGA CGACCACACG GCCCAAGGGA AATTGCATTT GCCTTTCAAG TTGATCCCGA    9420

GTACCTGCAT GGTCCCTGTT GCCCACGCGC CGAATGTAAT ACATGGCTTT AAACACATCA    9480

GCCTCCAATT AGATACAGAC CACTTGACAT TGCTCACCAC CAGGAGACTA GGGCAAACC    9540

CGGAACCAAC CACTGAATGG ATCGTCGGAA AGACGGTCAG AAACTTCACC GTCGACCGAG    9600

ATGGCCTGGA ATACATATGG GGAAATCATG AGCCAGTGAG GGTCTATGCC CAAGAGTCAG    9660

CACCAGGAGA CCCTCACGGA TGGCCACACG AAATAGTACA GCATTACTAC CATCGCCATC    9720

CTGTGTACAC CATCTTAGCC GTCGCATCAG CTACCGTGGC GATGATGATT GGCGTAACTG    9780

TTGCAGTGTT ATGTGCCTGT AAAGCGCGCC GTGAGTGCCT GACGCCATAC GCCCTGGCCC    9840

CAAACGCCGT AATCCCAACT TCGCTGGCAC TCTTGTGCTG CGTTAGGTCG GCCAATGCTG    9900

AAACGTTCAC CGAGACCATG AGTTACTTGT GGTCGAACAG TCAGCCGTTC TTCTGGGTCC    9960
```

```
AGTTGTGCAT ACCTTTGGCC GCTTTCATCG TTCTAATGCG CTGCTGCTCC TGCTGCCTGC    10020

CTTTTTTAGT GGTTGCCGGC GCCTACCTGG CGAAGGTAGA CGCCTACGAA CATGCGACCA    10080

CTGTTCCAAA TGTGCCACAG ATACCGTATA AGGCACTTGT TGAAAGGGCA GGGTATGCCC    10140

CGCTCAATTT GGAGATCACT GTCATGTCCT CGGAGGTTTT GCCTTCCACC AACCAAGAGT    10200

ACATTACCTG CAAATTCACC ACTGTGGTCC CCTCCCCAAA AATCAAATGC TGCGGCTCCT    10260

TGGAATGTCA GCCGGCCGCT CATGCAGACT ATACCTGCAA GGTCTTCGGA GGGGTCTACC    10320

CCTTTATGTG GGGAGGAGCG CAATGTTTTT GCGACAGTGA AACAGCCAG ATGAGTGAGG     10380

CGTACGTCGA ATTGTCAGCA GATTGCGCGT CTGACCACGC GCAGGCGATT AAGGTGCACA    10440

CTGCCGCGAT GAAAGTAGGA CTGCGTATTG TGTACGGGAA CACTACCAGT TTCCTAGATG    10500

TGTACGTGAA CGGAGTCACA CCAGGAACGT CTAAAGACTT GAAAGTCATA GCTGGACCAA    10560

TTTCAGCATC GTTTACGCCA TTCGATCATA AGGTCGTTAT CCATCGCGGC CTGGTGTACA    10620

ACTATGACTT CCCGGAATAT GGAGCGATGA AACCAGGAGC GTTTGGAGAC ATTCAAGCTA    10680

CCTCCTTGAC TAGCAAGGAT CTCATCGCCA GCACAGACAT TAGGCTACTC AAGCCTTCCG    10740

CCAAGAACGT GCATGTCCCG TACACGCAGG CCTCATCAGG ATTTGAGATG TGGAAAAACA    10800

ACTCAGGCCG CCCACTGCAG GAAACCGCAC CTTTCGGGTG TAAGATTGCA GTAAATCCGC    10860

TCCGAGCGGT GGACTGTTCA TACGGGAACA TTCCCATTTC TATTGACATC CCGAACGCTG    10920

CCTTTATCAG GACATCAGAT GCACCACTGG TCTCAACAGT CAAATGTGAA GTCAGTGAGT    10980

GCACTTATTC AGCAGACTTC GGCGGGATGG CCACCCTGCA GTATGTATCC GACCGCGAAG    11040

GTCAATGCCC CGTACATTCG CATTCGAGCA CAGCAACTCT CCAAGAGTCG ACAGTACATG    11100

TCCTGGAGAA AGGAGCGGTG ACAGTACACT TTAGCACCGC GAGTCCACAG GCGAACTTTA    11160

TCGTATCGCT GTGTGGGAAG AAGACAACAT GCAATGCAGA ATGTAAACCA CCAGCTGACC    11220

ATATCGTGAG CACCCCGCAC AAAAATGACC AAGAATTTCA AGCCGCCATC TCAAAAACAT    11280

CATGGAGTTG GCTGTTTGCC CTTTTCGGCG GCGCCTCGTC GCTATTAATT ATAGGACTTA    11340

TGATTTTTGC TTGCAGCATG ATGCTGACTA GCACACGAAG ATGACCGCTA CGCCCCAATG    11400

ATCCGACCAG CAAAACTCGA TGTACTTCCG AGGAACTGAT GTGCATAATG CATCAGGCTG    11460

GTACATTAGA TCCCCGCTTA CCGCGGGCAA TATAGCAACA CTAAAAACTC GATGTACTTC    11520

CGAGGAAGCG CAGTGCATAA TGCTGCGCAG TGTTGCCACA TAACCACTAT ATTAACCATT    11580

TATCTAGCGG ACGCCAAAAA CTCAATGTAT TTCTGAGGAA GCGTGGTGCA TAATGCCACG    11640

CAGCGTCTGC ATAACTTTTA TTATTTCTTT TATTAATCAA CAAAATTTTG TTTTTAACAT    11700

TTCAAAAAAA AAAAAAAAA AAAAAAAAAA AAAAAAAAA                           11740
```

(2) INFORMATION FOR SEQ ID NO:104:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:104:

Ser Ile Leu Gly Ser Arg
1               5

(2) INFORMATION FOR SEQ ID NO:105:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:105:

GTCCGTTTGT CGTGCAACTG C                                              21

(2) INFORMATION FOR SEQ ID NO:106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:106:

GTCCGTTTGT CGTGCAACTG A                                              21

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:107:

CAATCTTCCT CACGCCTTAG C                                              21

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:108:

CAATCTTCCT CACGCCTTAG T                                              21

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:109:

TCCTAAATAG TCAGCATAGT A                                              21

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:110:

TCCTAAATAG TCAGCATAGT T                                              21

(2) INFORMATION FOR SEQ ID NO:111:

(i) SEQUENCE CHARACTERISTICS:
        (A) LENGTH: 34 base pairs (B) TYPE: nucleic acid
            (C) STRANDEDNESS: single
            (D) TOPOLOGY: linear (xi) SEQUENCE DESCRIPTION: SEQ ID NO:111:

TATATCTCGA GGGTGGTGTT GTAGTATTAG TCAG                                34

(2) INFORMATION FOR SEQ ID NO:112:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:112:

TATATGATAT CAAAAAGCCT GAACTCACCG CGACG                               35

(2) INFORMATION FOR SEQ ID NO:113:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:113:

ATATAGGATC CTCAGTTAGC CTCCCCCATC TCCCG                               35

(2) INFORMATION FOR SEQ ID NO:114:

(i) SEQUENCE CHARACTERISTICS:
            (A) LENGTH: 120 amino acids
            (B) TYPE: amino acid
            (C) STRANDEDNESS:
            (D) TOPOLOGY: linear (xi) SEQUENCE DESCRIPTION: SEQ ID NO:114:

Met Asn Tyr Ile Pro Thr Gln Thr Phe Tyr Gly Arg Arg Trp Arg Pro
1               5                  10                  15

Arg Pro Ala Phe Arg Pro Trp Gln Val Ser Met Gln Pro Thr Pro Thr
            20                  25                  30

Met Val Thr Pro Met Leu Gln Ala Pro Asp Leu Gln Ala Gln Met
        35                  40                  45

Gln Gln Leu Ile Ser Ala Val Ser Ala Leu Thr Thr Lys Gln Asn Val
    50                  55                  60

Lys Ala Pro Lys Gly Gln Arg Gln Lys Gln Gln Lys Pro Lys Glu
65                  70                  75                  80

Lys Lys Glu Asn Gln Lys Lys Pro Thr Gln Lys Lys Gln Gln
                85                  90                  95

Gln Lys Pro Lys Pro Gln Ala Lys Lys Lys Pro Gly Arg Arg Glu
            100                 105                 110

Arg Met Cys Met Lys Ile Glu Asn
        115                 120

(2) INFORMATION FOR SEQ ID NO:115:

(i) SEQUENCE CHARACTERISTICS:
            (A) LENGTH: 103 amino acids
            (B) TYPE: amino acid
            (C) STRANDEDNESS:
            (D) TOPOLOGY: linear (xi) SEQUENCE DESCRIPTION: SEQ ID NO:115:

```
Met Asn Tyr Ile Pro Thr Gln Thr Phe Tyr Gly Arg Arg Trp Arg Pro
1               5                   10                  15

Arg Pro Ala Phe Arg Pro Trp Gln Val Ser Met Gln Pro Thr Pro Thr
            20                  25                  30

Met Val Thr Pro Met Leu Gln Ala Pro Asp Leu Gln Ala Gln Gln Met
            35                  40                  45

Gln Gln Leu Ile Ser Ala Val Ser Ala Leu Thr Thr Lys Gln Asn Val
        50                  55                  60

Lys Ala Pro Lys Gly Gln Arg Gln Lys Lys Gln Gln Lys Pro Lys Glu
65                  70                  75                  80

Lys Lys Glu Asn Gln Lys Lys Pro Thr Leu Lys Arg Arg Glu Arg
                85                  90                  95

Met Cys Met Lys Ile Glu Asn
            100
```

(2) INFORMATION FOR SEQ ID NO:116:

(i) SEQUENCE CHARACTERISTICS:
        (A) LENGTH: 88 amino acids
        (B) TYPE: amino acid
        (C) STRANDEDNESS:
        (D) TOPOLOGY: linear (xi) SEQUENCE DESCRIPTION: SEQ ID NO:116:

```
Met Asn Tyr Ile Pro Thr Gln Thr Phe Tyr Gly Arg Arg Trp Arg Pro
1               5                   10                  15

Arg Pro Ala Phe Arg Pro Trp Gln Val Ser Met Gln Pro Thr Pro Thr
            20                  25                  30

Met Val Thr Pro Met Leu Gln Ala Pro Asp Leu Gln Ala Gln Gln Met
            35                  40                  45

Gln Gln Leu Ile Ser Ala Val Ser Ala Leu Thr Thr Lys Gln Asn Val
        50                  55                  60

Lys Ala Pro Lys Gly Gln Arg Gln Lys Lys Gln Leu Lys Arg Arg Glu
65                  70                  75                  80

Arg Met Cys Met Lys Ile Glu Asn
            85
```

(2) INFORMATION FOR SEQ ID NO:117:

(i) SEQUENCE CHARACTERISTICS:
        (A) LENGTH: 76 amino acids
        (B) TYPE: amino acid
        (C) STRANDEDNESS:
        (D) TOPOLOGY: linear (xi) SEQUENCE DESCRIPTION: SEQ ID NO:117:

```
Met Asn Tyr Ile Pro Thr Gln Thr Phe Tyr Gly Arg Arg Trp Arg Pro
1               5                   10                  15

Arg Pro Ala Phe Arg Pro Trp Gln Val Ser Met Gln Pro Thr Pro Thr
            20                  25                  30

Met Val Thr Pro Met Leu Gln Ala Pro Asp Leu Gln Ala Gln Gln Met
            35                  40                  45

Gln Gln Leu Ile Ser Ala Val Ser Ala Leu Thr Thr Lys Gln Asn Leu
        50                  55                  60

Lys Arg Arg Glu Arg Met Cys Met Lys Ile Glu Asn
65                  70                  75
```

(2) INFORMATION FOR SEQ ID NO:118:

```
    (i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:118:

ATATAGGATC CTTCGCATGA TTGAACAAGA TGGATTGC                              38

(2) INFORMATION FOR SEQ ID NO:119:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:119:

Leu Xaa Pro Gly Gly
1               5

(2) INFORMATION FOR SEQ ID NO:120:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:120:

Leu Asn Pro Gly Gly Thr
1               5

(2) INFORMATION FOR SEQ ID NO:121:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:121:

Leu Lys Pro Gly Gly Thr
1               5

(2) INFORMATION FOR SEQ ID NO:122:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:122:

Leu Lys Pro Gly Gly Ile
1               5

(2) INFORMATION FOR SEQ ID NO:123:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:123:

Leu Xaa Pro Gly Gly Ser
```

-continued

```
1               5

(2) INFORMATION FOR SEQ ID NO:124:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:124:

Leu Asn Thr Gly Gly Thr
1               5

(2) INFORMATION FOR SEQ ID NO:125:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:125:

Leu Xaa Pro Gly Gly
1               5
```

RECOMBINANT ALPHAVIRUS-BASED VECTORS WITH REDUCED INHIBITION OF CELLULAR MACROMOLECULAR SYNTHESIS

CROSS-REFERENCE TO RELATED APPLICATION

This application is a divisional of U.S. application Ser. No. 08/944,645 filed Oct. 6, 1997 which is a continuation-in-part of U.S. patent application Ser. No. 08/833,148 filed Apr. 4, 1997, which application is now abandoned; which is a continuation-in-part of U.S. patent application Ser. No. 08/679,640, filed Jul. 12, 1996, which application is now abandoned; which is a continuation-in-part of U.S. patent application Ser. No. 08/668,953, filed Jun. 24, 1996, which application is now abandoned; which is a continuation-in-part of U.S. patent application Ser. No. 08/628,594, filed Apr. 5, 1996, which application is now abandoned; all of which applications are incorporated by reference herein in their entirety.

STATEMENT OF GOVERNMENT INTEREST

This invention has been made in part with government support under grant number AI 11377, awarded by the National Institutes of Health. The government may have certain rights in the invention.

TABLE OF CONTENTS

A. Sources of Wild-Type Alphavirus

B. Selection of Alphaviruses with a Desired Phenotype
1. Biological Selection of Virus Variants
   a. Selection from Virus Stocks Containing DI Particles
   b. Selection from Virus Stocks Not Containing DI Particles
2. Genetic Selection of Virus Variants
3. Genetic Selection of Variants Using Virus-Derived Vectors
4. Use of Viral Variants C. Alphavirus Vector Constructs and Alphavirus RNA Vector Replicons
1. 5' Promoters Which Initiate Synthesis of Viral RNA
2. Sequences Which Initiate Transcription
3. Alphavirus Nonstructural Proteins
   a. nsP1
   b. nsP2
   c. nsP3
   d. nsP4
4. Viral Junction Regions
5. Alphavirus RNA Polymerase Recognition Sequence, and Poly(A) Tract D. Eukaryotic Layered Vector Initiation Systems E. Recombinant Alphavirus Particles, and Generation and Use of 'Empty' Togavirus Particles or Togaviruses Particles Containing Non-Homologous Viral RNA F. Heterologous Sequences
1. Lymphokines
2. Toxins
3. Prodrug Converting Enzymes
4. Antisense Sequences
5. Ribozymes
6. Proteins and Other Cellular Constituents
   a. Altered Cellular Components
   b. Antigens from Foreign Organisms or Other Pathogens
7. Sources for Heterologous Sequences
G. Alphavirus Packaging/Producer Cell Lines
H. Pharmaceutical Compositions
I. Methods for Utilizing Gene Delivery Vehicles
1. Immunostimulation
2. Blocking Agents
3. Expression of Palliatives
a. Inhibitor Palliatives
b. Conditional Toxic Palliatives
4. Expression of Markers
5. Immune Down-Regulation
6. Replacement or Augmentation Gene Therapy
7. Lymphokines and Lymphokine Receptors
8. Suicide Vectors
9. Gene Delivery Vehicles to Prevent the Spread of Metastatic Tumors
10. Administration of Gene Delivery Vehicles
11. Modulation of Transcription Factor Activity
12. Production of Recombinant Proteins
J. Deposit Information

EXAMPLES

Example 1

Isolation and Characterization of SIN-1
A. Isolation, Plaque Purification, and Characterization of SIN-1 from a Wild-Type Sindbis Virus Stock
B. Molecular Cloning of SIN-1
C. Sequence of the SIN-1 Phenotype
D. Characterization and Genetic Mapping of the SIN-1 Phenotype with Molecular Clones Example 2

Isolation and Characterization of Positive Strand RNA Viruses Which Exhibit Reduced Inhibition of Host Macromolecular Synthesis
A. Biological Selection of Virus Variants
B. Genetic Selection of Virus Variants
C. Genetic Selection of Variants Using Virus-Derived Vectors
1 Vectors Expressing an Immunogenic Protein
2. Vectors Expressing a Selectable Marker Example 3

Preparation of SIN1-Based RNA Vector Replicons
A. Construction of the SIN-1 Basic Vector Example 4

Preparation of SIN1-Based DNA Vectors
A. Construction of Plasmid DNA SIN-1 Derived Expression Vectors
B. Expression of Heterologous Proteins in Cells Transfected with PBG/SIN-1 ELVS 1.5-SEAP, PBG/SIN-1 ELVS 1.5-LUC OR PBG/SIN-1 ELVS 1.5-B-Gal Expression Vectors Example 5

Modifications of Plasmid DNA SIN-1Derived Expression Vectors

Example 6

Construction of Alphavirus Packaging Cell Lines
A. Construction of Vector-Inducible Alphavirus PCL
B. Construction of PCL with Operably-Linked Selection Marker
C. Construction of "Split Structural Gene" PCL Configurations
D. Construction of PCL with "Hybrid" Structural Proteins
E. Production of Packaged Alphavirus Vectors from PCL Example 7

Construction of Alphavirus Producer Cell Lines
A. Alphavirus DNA Vectors with Single Level Regulation
B. Alphavirus DNA Vectors with Two Level Regulation Example 8

Methods for the Generation of Alphavirus Derived Empty or Chimeric Viral Particles

TECHNICAL FIELD OF THE INVENTION

The present invention relates generally to recombinant DNA technology; and more specifically, to the development of recombinant vectors useful for directing the expression of one or more heterologous gene products.

BACKGROUND OF THE INVENTION

Alphaviruses comprise a set of genetically, structurally, and serologically related arthropod-borne viruses of the Togaviridae family. These viruses are distributed worldwide, and persist in nature through a mosquito to vertebrate cycle. Birds, rodents, horses, primates, and humans are among the defined alphavirus vertebrate reservoir/hosts.

Twenty-six known viruses and virus subtypes have been classified within the alphavirus genus utilizing the hemagglutination inhibition (HI) assay. This assay segregates the 26 alphaviruses into three major complexes: the Venezuelan equine encephalitis (VEE) complex, the Semliki Forest (SF) complex, and the western equine encephalitis (WEE) complex. In addition, four other viruses, eastern equine encephalitis (EEE), Barmah Forest, Middelburg, and Ndumu, receive individual classification based on the HI serological assay.

Members of the alphavirus genus also are classified based on their relative clinical features in humans: alphaviruses associated primarily with encephalitis, and alphaviruses associated primarily with fever, rash, and polyarthritis. Included in the former group are the VEE and WEE complexes, and EEE. In general, infection with this group can result in permanent sequelae, including behavior changes and learning disabilities, or death. In the latter group is the SF complex, comprised of the individual alphaviruses Semliki Forests Sindbis, Ross River, Chikungunya, O'nyong-nyong, and Mayaro. With respect to this group, although serious epidemics have been reported, infection is in general self-limiting, without permanent sequelae.

Sindbis virus is the prototype member of the Alphavirus genus of the Togaviridae family. Its replication strategy after infection of cells (see FIG. 1) has been well characterized in chicken embryo fibroblasts (CEF) and baby hamster kidney (BHK) cells, where Sindbis virus grows rapidly and to high titer, and serves as a model for other alphaviruses. Briefly, the genome from Sindbis virus (like other alphaviruses) is an approximately 12 kb single-stranded positive-sense RNA molecule which is capped and polyadenylated, and contained within a virus-encoded capsid protein shell. The nucleocapsid is further surrounded by a host-derived lipid envelope into which two viral-specific glycoproteins, E1 and E2, are inserted and anchored to the nucleocapsid. Certain alphaviruses (e.g., SF) also maintain an additional protein, E3, which is a cleavage product of the E2 precursor protein, PE2. After virus particle absorption to target cells, penetration, and uncoating of the nucleocapsid to release viral genomic RNA into the cytoplasm, the replicative process is initiated by translation of the nonstructural proteins (nsPs) from the 5' two-thirds of the viral genome. The four nsPs (nsP1–nsP4) are translated directly from the genomic RNA template as one of two polyproteins (nsP123 or nsP1234), and processed post-translationally into monomeric units by an active protease in the C-terminal domain nsP2. A leaky opal (UGA) codon present between nsP3 and nsP4 of most alphaviruses accounts for a 10 to 20% abundance of the nsP1234 polyprotein, as compared to the nsP123 polyprotein. Both of the nonstructural polyproteins and their derived monomeric units may participate in the RNA replicative process, which involves binding to the conserved nucleotide sequence elements (CSEs) present at the 5' and 3' ends, and a junction region subgenomic promoter located internally in the genome (discussed further below).

The positive strand genomic RNA serves as template for the nsP-catalyzed synthesis of a full-length complementary negative strand. Synthesis of the complementary negative strand is catalyzed after binding of the nsP complex to the 3' terminal CSE of the positive strand genomic RNA. The negative strand, in turn, serves as template for the synthesis of additional positive strand genomic RNA and an abundantly expressed 26S subgenomic RNA, initiated internally at the junction region promoter. Synthesis of additional positive strand genomic RNA occurs after binding of the nsP complex to the 3' terminal CSE of the complementary negative strand genomic RNA template. Synthesis of the subgenomic mRNA from the negative strand genomic RNA template, is initiated from the junction region promoter. Thus, the 5' end and junction region CSEs of the positive strand genomic RNA are functional only after they are transcribed into the negative strand genomic RNA complement (i.e., the 5' end CSE is functional when it is the 3' end of the genomic negative stranded complement). The structural proteins (sPs) are translated from the subgenomic 26S RNA, which represents the 3' one-third of the genome, and like the nsPs, are processed post-translationally into the individual proteins.

Several groups have suggested utilizing certain members of the alphavirus genus as an expression vector, including, for example, Sindbis virus (Xiong et al., *Science* 243:1188–1191, 1989; Hahn et al., *Proc. Natl. Acad. Sci. USA* 89:2679–2683, 1992; Dubensky et al., *J. Virol.* 70:508–519, 1996), Semliki Forest virus (Liljestrom, *Bio/Technology* 9:1356–1361, 1991), and Venezuelan Equine Encephalitis virus (Davis et al., *J. Cell. Biochem. Suppl.* 19A:10, 1995). In addition, one group has suggested using alphavirus-derived vectors for the delivery of therapeutic genes in vivo. One difficulty, however, with the above-referenced vectors is that inhibition of host cell-directed macromolecular synthesis (i.e., protein or RNA synthesis) begins within a few hours after infection and cytopathic effects (CPE) occur within 12 to 16 hours post infection (hpi). Inhibition and shutoff of host cell protein synthesis begins within 2 hpi in BHK cells infected with recombinant viral particles, in the presence or absence of structural protein expression, suggesting that the early events after virus infection (e.g., synthesis of nsPs and minus strand RNA) may directly influence the inhibition of host cell protein synthesis and subsequent development of CPE and cell death.

SIN-1 is a variant strain derived from wild-type Sindbis, and was isolated from a culture of BHK cells persistently infected with Sindbis virus over a period of one month (Weiss et al. *J. Virol.* 33: 463–474, 1980). A pure SIN-1 virus stock obtained by expansion from a single plaque does not kill the BHK cells which it infects. Importantly, virus yields (>$10^3$ PFU/cell) are the same in BHK cells infected with wild-type Sindbis virus or the variant SIN-1 virus. Thus, the principle phenotype of SIN-1 in infected BHK cells is characterized by production of wild-type levels of infectious virus in the absence of virus-induced cell death.

The present invention provides recombinant vectors with selected desirable phenotypes for use in a variety of applications, including for example, gene therapy and recombinant protein production, and further provides other related advantages.

SUMMARY OF THE INVENTION

Briefly stated, the present invention provides RNA vector replicons, alphavirus vector constructs, eukaryotic layered vector initiation systems and recombinant alphavirus particles which exhibit reduced, delayed, or no inhibition of cellular macromolecular synthesis (e.g., protein or RNA synthesis), thereby permitting the use of these vectors for protein expression, gene therapy and the like, with reduced, delayed, or no development of CPE or cell death. Such vectors may be constructed from a wide variety of alphaviruses (e.g., Semliki Forest virus, Ross River virus, Venezuelan equine encephalitis virus or Sindbis virus), and designed to express numerous heterologous sequences (e.g., a sequence corresponding to protein, a sequence corresponding to antisense RNA, a sequence corresponding to non-coding sense RNA, or a sequence corresponding to ribozyme).

Within one aspect of the invention, isolated nucleic acid molecules are provided comprising an altered alphavirus nonstructural protein gene which, when operably incorporated into a recombinant alphavirus, increases the time required to reach 50% inhibition of host-cell directed macromolecular synthesis following expression in mammalian cells, as compared to a wild-type alphavirus. As utilized within the context of the present invention, "altered alphavirus nonstructural protein gene" refers to a gene which, when operably incorporated into an alphavirus RNA vector replicon, recombinant alphavirus particle, or eukaryotic layered vector initiation system, produces the desired phenotype (e.g., reduced, delayed or no inhibition of cellular macromolecular synthesis). Such altered alphavirus nonstructural protein genes will have one or more nucleotide substitutions deletions, or insertions, which alter the nucleotide sequence from that of the wild-type alphavirus gene. The gene may be derived either artificially (e.g., from directed selection procedures; see Example 2 below), or from naturally occurring viral variants (see Example 1 below). In addition, it should be understood that when the isolated nucleic acid molecules of the present invention are incorporated into an alphavirus RNA vector replicon, recombinant alphavirus particle, or eukaryotic layered vector initiation system as discussed above, that they may, within certain embodiments, substantially increase the time required to reach 50% inhibition of host-cell directed macromolecular synthesis, up to and including substantially no detectable inhibition of host-cell directed macromolecular synthesis (over any period of time). Assays suitable for detecting percent inhibition of host-cell directed macromolecular synthesis include, for example, that described within Example 1.

Within other aspects of the invention, isolated nucleic acid molecules are provided comprising an altered alphavirus nonstructural protein gene which, when operably incorporated into a recombinant alphavirus particle, eukaryotic layered vector initiation system, or RNA vector replicon, results in a reduced level (e.g., 2-fold, 5-fold, 10-fold, 50-fold or more than 100-fold) of vector-specific RNA synthesis as compared to the wild-type, and the same or greater level of protein encoded by RNA transcribed from the viral junction region promoter, as compared to a wild-type recombinant alphavirus particle, wild-type eukaryotic layered vector initiation system, or wild-type RNA vector replicon. Representative assays for quantitating RNA levels include [$^3$H] uridine incorporation as described in Example 1, or RNA accumulation as detected by Northern Blot analysis (see Example 4). Representative assays for quantitating protein levels include scanning densitometry (see Example 4) and various enzymatic assays (see Examples 3–5).

Within one embodiment of the above, the isolated nucleic acid molecule encodes nonstructural protein 2 (nsP2). Within a further embodiment, the isolated nucleic acid molecule has a mutation in the LXPGG motiff of nsP2.

Within another aspect of the invention, expression vectors are provided comprising a promoter operably linked to one of the above-described nucleic acid molecules. Within one embodiment, the expression vector further comprises a polyadenylation sequence or transcription termination sequence 3' to the nucleic acid molecule.

Within yet another aspect of the present invention, alphavirus vector constructs are provided, comprising a 5' promoter which initiates synthesis of viral RNA in vitro from cDNA, a 5' sequence which initiates transcription of alphavirus RNA, a nucleic acid molecule which operably encodes all four alphaviral nonstructural. proteins including an isolated nucleic acid molecule as described above, an alphavirfus viral junction region promoter, an alphavirus RNA polymerase recognition sequence and a 3' polyadenylate tract.

Within a related aspect, such constructs further comprise a selected heterologous sequence downstream of and operably linked to a viral junction region. Within a related aspect, alphavirus vector constructs are provided comprising a 5' promoter which initiates synthesis of viral RNA in vitro from cDNA, a 5' sequence which initiates transcription of alphavirus RNA, a nucleic acid molecule which operably encodes all four alphavirus non-structural proteins, an alphavirus viral junction region promoter, an alphavirus RNA polymerase recognition sequence, and a 3' polyadenylate tract, wherein said in vitro synthesized RNA, upon packaging into an alphavirus particle and introduction of the particle into a mammalian host cell, increases the time required to reach 50% inhibition of host-cell directed macromolecular synthesis following expression in mammalian cells, as compared to a wild-type alphavirus particle.

Within a further aspect, alphavirus vector constructs are provided comprising a 5' promoter which initiates synthesis of viral RNA in vitro from cDNA, a 5' sequence which initiates transcription of alphavirus RNA, a nucleic acid molecule which operably encodes all four alphavirus nonstructural proteins, an alphavirus viral junction region promoter, an alphavirus RNA polymerase recognition sequence, and a 3' polyadenylate tract, wherein said in vitro synthesized RNA, upon packaging into an alphavirus particle and introduction of the particle into a mammalian host cell, has a reduced level of vector-specific RNA synthesis as compared to wild-type alphavirus particle, and the same or greater level of protein encoded by RNA transcribed from the viral junction region promoter, as compared to a wild-type alphavirus particle.

Within yet other aspects of the present invention, RNA vector replicons capable of translation in a eukaryotic system are provided, comprising a 5' sequence which initiates transcription of alphavirus RNA, a nucleic acid molecule which operably encodes all four alphaviral nonstructural proteins, including the isolated nucleic acid molecules discussed above, an alphavirus viral junction region, an alphavirus RNA polymerase recognition sequence and a 3' polyadenylate tract.

Within a related aspect, alphavirus RNA vector replicons capable of translation in a eukaryotic system are provided, comprising a 5' sequence which initiates transcription of alphavirus RNA, a nucleic acid molecule which operably encodes all four alphaviral nonstructural proteins, an alphavirus viral junction region promoter, an alphavirus polymerase recognition sequence and a 3' polyadenylate tract, wherein said alphavirus RNA, upon packaging into an alphavirus particle and introduction of the particle into a mammalian host cell, increases the time required to reach 50% inhibition of host-cell directed macromolecular synthesis following expression in mammalian cells, as compared to a wild-type alphavirus particle.

Within other aspects, alphavirus RNA vector replicons capable of translation in a eukaryotic system are provided comprising a 5' sequence which initiates transcription of alphavirus RNA, a nucleic acid molecule which operably encodes all four alphaviral nonstructural proteins, an alphavirus viral junction region promoter, an alphavirus polymerase recognition sequence and a 3' polyadenylate tract, wherein said alphavirus RNA, upon packaging into an alphavirus particle and introduction of the particle into a mammalian host cell, has a reduced level of vector-specific RNA synthesis as compared to wild-type alphavirus particle, and the same or greater level of protein encoded by RNA transcribed from the viral junction region promoter, as compared to a wild-type alphavirus particle.

Within another embodiment, such RNA vector replicons further comprise a selected heterologous sequence downstream of and operably linked to a viral junction region. Within further aspects of the invention, host cells are provided which contain one of the RNA vector replicons described herein. Within additional aspects of the invention, pharmaceutical compositions are provided comprising RNA vector replicons as described above and a pharmaceutically acceptable carrier or diluent.

Within other aspects of the invention, recombinant alphavirus particles are provided, comprising one or more alphavirus structural proteins, a lipid envelope, and an RNA vector replicon as described herein. Within one embodiment, one or more of the alphavirus structural proteins are derived from a different alphavirus than the alphavirus from which the RNA vector replicon was derived. Within other embodiments, the alphavirus structural protein and lipid envelopes are derived from different species. Within further aspects, pharmaceutical compositions are provided comprising a recombinant alphavirus particle as disclosed above and a pharmaceutically acceptable carrier or diluent. Further, mammalian cells infected with such recombinant alphavirus particles are also provided.

Within certain embodiments of the invention, the above described vectors or particles may further comprise a resistance marker which has been fused, in-frame, with the heterologous sequence. Representative examples of such resistance markers include hygromycin phosphotransferase and neomycin phosphotransferase.

Within other aspects of the present invention, methods are provided for selecting alphavirus or recombinant alphavirus vector variants which exhibit the phenotype described herein of reduced, delayed, or, no inhibition of host cell directed macromolecular synthesis. Representative examples of such methods include the use of selectable drug or antigenic markers and are provided in more detail below in Example 2.

Within other aspects of the present invention, Togavirus capsid particles are provided which contain substantially no genomic (i.e., wild-type virus genome) or RNA vector replicon nucleic acids. Representative examples of Togaviruses include, for example alphaviruses and rubiviruses (e.g., rubella). Within certain embodiments, the capsid particles further comprise a lipid envelope containing one or more alphavirus glycoproteins. Within other embodiments, the capsid particle further comprises an alphavirus envelope (i.e., the lipid bilayer and the glycoprotein complement). Within related aspects of the present invention, pharmaceutical compositions are provided comprising the above noted capsid particles (with or without a lipid bilayer (e.g., viral envelope containing alphavirus glycoproteins)) along with a pharmaceutically acceptable carrier or diluent. Within further aspects, such capsid particles (with or without a lipid bilayer (e.g., viral envelope containing alphavirus glycoproteins)) or pharmaceutical compositions may be utilized as a vaccinating agent in order to induce an immune response against a desired togavirus.

Within further aspects of the invention, inducible promoters are provided comprising a core RNA polymerase promoter sequence, an operably linked nucleic acid sequence that directs the DNA binding of a protein that activates transcription from the core promoter sequence, and an operably linked nucleic acid sequence that directs the DNA binding of a protein that represses transcription from the core promoter sequence. Such promoters may be utilized in the gene delivery vehicles described herein, as well as a wide variety of other vectors known to those skilled in the art.

Within other aspects, alphavirus structural protein expression cassettes are provided comprising a 5' promoter which initiates synthesis of viral RNA from DNA, a nucleic acid molecule which encodes one or more functional alphavirus structural proteins, a selectable marker operably linked to transcription of the expression cassette, and optionally, a 3' sequence which controls transcription termination. Within one embodiment, such expression cassettes further comprise a 5' sequence which initiates transcription of alphavirus RNA, a viral junction region promoter, and an alphavirus RNA polymerase recognition sequence. Within another embodiment, the expression cassette further comprises a catalytic ribozyme processing sequence, post-translational transcriptional regulatory elements which facilitate RNA export from the nucleus, and/or elements which permit translation of multicistronic mRNA, selected from the group consisting of Internal Ribosome Entry Site elements, elements promoting ribosomal read through and BiP sequence.

Within other embodiments, the selectable marker is operably linked to a 5' promoter capable of initiating synthesis of alphavirus RNA from cDNA. Within further embodiments, the selectable marker is positioned downstream from a junction region promoter and from the nucleic acid molecule which encodes alphavirus structural proteins. Within yet other embodiments, the 5' promoter is an inducible promoter as described herein. Within another embodiment, the alphavirus structural protein expression cassette further comprises an alphavirus capsid protein gene or other sequence (e.g., a tobacco etch virus or "TEV" leader) which is capable of enhancing translation of one or more functional alphavirus structural protein genes located 3' to the enhancer sequence. Preferably, the capsid protein gene sequence is derived from a different alphavirus than that from which the sequence encoding the alphavirus structural genes is obtained.

Within yet other aspects of the invention, alphavirus packaging cell lines are provided comprising a cell containing an alphavirus structural protein expression cassette as described above. In certain embodiments, the alphavirus packaging cell lines are stably transformed with the alphavirus structural protein expression cassettes provided herein. Within related aspects, alphavirus producer cell lines are provided comprising a cell which contains a stably transformed alphavirus structural protein expression cassette, and a vector selected from the group consisting of RNA vector replicons, alphavirus vector constructs and eukaryotic layered vector initiation systems.

Within yet other aspects of the present invention, eukaryotic layered vector initiation systems are provided, comprising a 5' promoter capable of initiating in vivo the 5' synthesis of RNA from cDNA, a sequence which initiates transcription of alphavirus RNA following the 5' promoter; a nucleic acid molecule which operably encodes all four alphaviral nonstructural proteins, including an isolated nucleic acid molecule as discussed above, an alphavirus RNA polymerase recognition sequence, and a 3' polyadenylate tract.

Also provided are eukaryotic layered vector initiation systems comprising a 5' promoter capable of initiating in vivo the 5' synthesis of alphavirus RNA from cDNA, a sequence which initiates transcription of alphavirus RNA following the 5' promoter, a nucleic acid molecule which operably encodes all four alphaviral nonstructural proteins, an alphavirus RNA polymerase recognition sequence, and a 3 polyadenylate tract, wherein the in vivo synthesized RENA, upon packaging into an alphavirus particle and introduction of the particle into a mammalian host cell, increases the time required to reach 50% inhibition of host-cell directed macromolecular synthesis following expression in mammalian cells, as compared to a wild-type alphavirus particle.

Related eukaryotic layered vector initiation system are also provided which comprise a 5' promoter capable of initiating in vivo the 5' synthesis of alphavirus RNA from cDNA, a sequence which initiates transcription of alphavirus RNA following the 5' promoter, a nucleic acid molecule which operably encodes all four alphaviral nonstructural proteins, an alphavirus RNA polymerase recognition sequence, and a 3' polyadenylate tract, wherein said in vivo synthesized RNA, upon packaging into an alphavirus particle and introduction of the particle into a mammalian host cell, has a reduced level of vector-specific RNA synthesis as compared to wild-type alphavirus particle, and the same or greater level of protein encoded by RNA transcribed from the viral junction region promoter, as compared to a wild-type alphavirus particle.

Representative examples of suitable 5' promoters for eukaryotic layered vector initiation systems include RNA polymerase I promoters, RNA polymerase II promoters, RNA polymerase III promoters, the HSV-TK promoter. RSV promoter, tetracycline inducible promoter, MoMLV promoter, a SV40 promoter and a CMV promoter. Within preferred embodiments, the 5' promoter is an inducible promoter as described herein.

Within certain embodiments, eukaryotic layered vector initiation systems are provided which further comprise a heterologous sequence operably linked to a viral junction region, and/or a post-transcriptional regulatory element which facilitates RNA export from the nucleus. Within further embodiments, the eukaryotic layered vector initiation systems provided herein may further comprise a transcription termination signal.

Within related aspects, the present invention also provides host cells (e.g., vertebrate or insect) containing a stably transformed eukaryotic layered vector initiation system as described above. Within further aspects of the present invention, methods for delivering a selected heterologous sequence to a vertebrate or insect are provided, comprising the step of administering to a vertebrate or insect an alphavirus vector construct, RNA vector replicon, recombinant alphavirus particle, or a eukaryotic layered vector initiation system as described herein. Within certain embodiments, the alphavirus vector construct, RNA vector replicon, recombinant alphavirus particle or eukaryotic layered vector initiation system is administered to cells of the vertebrate ex vivo, followed by administration of the vector or particle-containing cells to a warm-blooded animal.

Within other aspects, pharmaceutical compositions are provided comprising a eukaryotic layered vector initiation system as discussed above, and a pharmaceutically acceptable carrier or diluent. Within certain embodiments, the pharmaceutical composition is provided as a liposomal formulation.

Within further aspects, methods of making recombinant alphavirus particles are provided, comprising the steps of (a) introducing a vector such as a eukaryotic layered vector initiation system, RNA vector replicon, or alphavirus vector particle as described above into a population of packaging cells under conditions and for a time sufficient to permit production of recombinant alphavirus particles, and (b) harvesting recombinant alphavirus particles. Within related aspects, methods of making a selected protein are provided, comprising the steps of (a) introducing a vector which encodes a selected heterologous protein, such as a eukaryotic layered vector initiation system, RNA vector replicon or alphavirus vector particle described above, into a population of packaging cells, or other cells under conditions and for a time sufficient to permit production of the selected protein, and (b) harvesting protein produced by the vector containing cells. Within yet other aspects, methods of making a selected protein are provided, comprising the step of introducing a eukaryotic layered vector initiation system which is capable of producing a selected heterologous protein into a host cell, under conditions and for a time sufficient to permit expression of the selected protein. Within further aspects, host cell lines are provided which contain a RNA vector replicon as described herein.

Within yet other aspects of the present invention, alphavirus vaccines are provided, comprising one of the above-described alphavirus vector constructs, RNA vector replicons, eukaryotic vector initiation systems, or recombinant alphavirus particles, which may or may not express one of the heterologous sequences provided herein (e.g., they may be utilized solely as a vaccine for treating or preventing alphaviral diseases). For example, within one embodiment of the invention, recombinant togavirus particles are provided which have substantially no nucleic acid or RNA vector replicon nucleic acid. Within a further embodiment, recombinant togavirus particles are provided which contain heterologous viral nucleic acids (i.e., from a different virus than the togavirus particle). Within yet another embodiment, the recombinant togavirus particle is T=3 or greater.

Within further aspects of the invention, recombinant chimeric togavirus particles (either empty, or containing nucleic acids) are provided wherein the viral particle has viral structural components obtained or derived from different Togaviridae (e.g., the capsid protein and glycoprotein is obtained from different alphavirus sources).

Within other aspects of the invention, methods for stimulating an immune response within a vertebrate are provided, comprising the step of administering to a vertebrate an alphavirus vector construct, an alphavirus RNA vector replicon according, a recombinant alphavirus particle, or a eukaryotic layered vector initiation system, wherein the alphavirus vector construct, RNA vector replicon, particle, or eukaryotic layered vector initiation system expresses an antigen which stimulates an immune response within said vertebrate (see, e.g., U.S. Ser. No. 08/404,796 for suitable antigens). Within related aspects, methods are provided for inhibiting a pathogenic agent within a vertebrate, comprising the step of administering to a vertebrate an alphavirus vector construct, an alphavirus RNA vector replicon, a recombinant alphavirus particle, or a eukaryotic layered vector initiation system according, wherein said alphavirus vector construct, RNA vector replicon, particle, or eukaryotic layered vector initiation system expresses an palliative which is capable of inhibiting a pathogenic agent (see, e.g., U.S. Ser. No. 08/404,796 for suitable palliatives).

These and other aspects and embodiments of the invention will become evident upon reference to the following detailed description and attached figures. In addition, various references are set forth herein that describe in more detail certain procedures or compositions (e.g., plasmids, sequences, etc.), and are therefore incorporated by reference in their entirety as if each were individually noted for incorporation.

BRIEF DESCRIPTION OF THE FIGURES

FIGS. 6A–6D is the cDNA sequence of 8000 bases of SIN-1 virus (SEQ. ID NO. 101).

FIGS. 7A–7D is the cDNA sequence of 8000 bases of SINCG virus (SEQ. ID NO. 102).

FIG. 8F is a schematic illustration depicting selection of vectors expressing the desired phenotype using a selectable marker.

FIG. 8G is a northern blot analysis of RNAs isolated from G418-resistant BHK-21 cell pools stably transformed with a variant Sindbis virus vector or Semliki Forest virus vector expressing neomycin phosphotransferase.

FIG. 8H is a schematic illustration of the genetic determinants responsible for the desired phenotype in variant Sindbis virus vectors.

FIG. 9A is a northern blot analysis of RNAs isolated from BHK-21 cells that were transfected with pBG/SIN-1 ELVS 1.5-SEAP or pBG/wt ELVS 1.5-SEAP plasmid DNAs, and hybridized with a radiolabeled viral RNA probe.

FIG. 9B is a graph depicting a 7 day timecourse of alkaline phosphatase expression in BHK cells transfected with pBG/SIN-1 ELVS 1.5-SEAP or pBG/wt ELVS 1.5-SEAP plasmid DNAs.

FIG. 10 is a graph depicting a 4 day timecourse of luciferase expression in BHK cells transfected with pBG/SIN-1 ELVS 1.5-luc or pBG/wt ELVS 1.5-luc plasmid DNAs.

FIG. 11A is a northern blot analysis of RNAs isolated from BHK-21 cells that were transfected with pBG/SIN-1 ELVS-1.5-β-gal or pBG/wt ELVS 1.5-β-gal plasmid DNAs, and hybridized with a radiolabeled viral RNA probe.

FIG. 11B is a western blot analysis detecting β-gal expression in BHK-21 cells transfected with either pBG/SIN-1 ELVS-1.5-β-gal or pBG/wt ELVS 1.5-β-gal plasmid DNAs.

FIG. 11C is a graph depicting a 5 day timecourse of alkaline phosphatase expression in BHK cells transfected with pBG/SIN-1 ELVS-1.5-β-gal or pBG/wt ELVS 1.5-β-gal plasmid DNAs.

FIGS. 12A & B are graphs depicting β-gal expression in HT1080 and BHK-21 cells transfected with ELVS β-gal vectors with or without HBV PRE sequences, as measured by RLU (relative light units).

FIG. 13 is a schematic illustration of RNA amplification, structural protein expression, and vector packaging by vector inducible alphavirus packaging cell lines.

FIG. 14 is a schematic illustration of vector inducible structural protein expression cassettes used in the generation of alphavirus packaging cell lines.

FIG. 15 is a graph depicting luciferase vector packaging (transfer of expression) by different alphavirus packaging cell lines.

FIG. 16 is a western blot analysis demonstrating induction of structural protein expression by an alphavirus packaging cell line following transfection and subsequent expression with an alphavirus vector (ELVS-βgal), but not a conventional plasmid DNA expression vector (pCMV-βgal).

FIG. 17A is a graph depicting luciferase vector packaging by C6/36 mosquito cells containing the pDCMV-intSINrbz structural protein expression cassette.

FIG. 21B is a schematic illustration depicting the structural protein expression cassettes in which the capsid protein and glycoproteins are separated, used to derive stable split structural gene packaging cell lines.

FIG. 21D is a western blot analysis demonstrating induction of alphavirus capsid protein synthesis by several clonal cell lines following transfection and subsequent expression with an alphavirus expression vector (ELVS-βgal).

FIG. 24 is a schematic illustration of vector packaging by "split" structural protein gene expression cassettes which contain a Ross River virus capsid protein gene sequence upstream of the Sindbis virus glycoprotein genes.

FIG. 25 is a schematic illustration of vector packaging by "split" structural protein gene expression cassettes which contain a Ross River virus capsid protein gene sequence upstream of the Sindbis virus glycoprotein genes on one cassette, and the Sindbis virus capsid protein gene in a separate cassette.

FIG. 26A is a table showing the results of vector particle packaging using the above "split" structural protein gene expression cassettes.

FIG. 26B is two graphs which depict the packaging activity of 25 clonal cell lines from drug-resistant cell pools derived by stable transfection with the split structural protein gene expression cassettes illustrated in FIG. 21B, relative to a genomic structural protein gene PCL (987 dlneo).

FIG. 26C is a western blot analysis demonstrating induction of structural protein expression by three split structural gene alphavirus packaging cell lines following transfection and subsequent expression with an alphavirus vector (ELVS-βgal), but not a conventional plasmid DNA expression vector (pCI-βgal).

FIG. 26D is a graph depicting the amplification and production of β-gal protein over time in several split structural gene alphavirus packaging cell lines (Clone 9TD, Clone 2TD, Clone 24TD, Clone 20SS), relative to a genomic structural protein gene PCL (987 genomic PCL).

FIG. 27 is a schematic illustration of the use of alphavirus packaging cell lines for the amplification of packaged vector particle preparations and the large scale production of recombinant protein.

FIG. 28 is a graph depicting the amplification and production of β-gal protein over time using alphavirus packaging cell lines.

FIG. 29 is a schematic illustration of the use of a tetracycline regulated promoter system to control expression of alphavirus vector RNA from cDNA in vivo.

FIG. 30 is a schematic illustration of the use of a linked transcriptional repressor and a transcriptional inducer/activator regulated promoter system to control expression of alphavirus vector RNA from cDNA in vivo.

FIGS. 31A & B are autoradiographs of [$^{3}H$]uridine-labeled RNAs electrophoresed on denaturing glyoxal gels that were isolated from BHK cell electroporated with SINrep/LacZ replicon and DH RNAs from various RRV capsid containing DH constructs, and from the vector particles present in the culture fluids at 18 hours post electroporation.

FIGS. 32A & B are protein gel autoradiographs depicting $^{35}S$ methionine-labelled proteins from BHK cells electroporated with SINrep/LacZ replicon and DH RNAs from various RRV capsid containing DH constructs, and from the vector particles present in the culture fluids at 18 hours post electroporation.

FIGS. 33A–D are Kyte-Doolittle hydrophobicity plots of various Ross River virus (RRV) capsid proteins, expressed from the wild-type gene (A) and three deletion mutants CΔ1rrv, CΔ2rrv, and CΔ3rrv (B–D, respectively).

FIG. 34 is a schematic that illustrates the amino-terminus RRV capsid proteins expressed from the wild-type gene (SEQ. ID NO. 114), and three deletion mutants CΔ1rrv (SEQ. ID NO. 115), CΔ2rrv (SEQ. ID NO. 116), and CΔ3rrv (SEQ. ID NO. 117). The lysine residues deleted in the RRV capsid gene mutants are indicated.

FIG. 35 is a graph that illustrates the relative levels of [$^{35}S$]methionine and [$^{3}H$]uridine incorporated into virus particles in BHK cells infected at high MOI with Toto1101 wild-type virus.

FIG. 36 is a graph that illustrates the relative levels of [$^{35}S$]methionine and [$^{3}H$]uridine incorporated into virus particles in BHK cells electroporated with SINrep/lacZ and DH-BB (5' tRNA) Crrv DH RNAs.

FIG. 37 is a graph that illustrates the relative levels of [$^{35}S$]methionine and [$^{3}H$]uridine incorporated into virus particles in BHK cells electroporated with SINrep/lacZ and RRV capsid deletion mutant DH-BB (5' tRNA) CΔ3rrv DH RNAs.

FIG. 38 is a graph which compiles the results shown in FIGS. 35–37, depicting the relative levels of [$^{35}S$] methionine and [$^{3}H$]uridine incorporated into virus particles in BHK cells electroporated with SINrep/lacZ and DH RNAs, or infected with Toto1101 wild-type virus.

FIG. 39 is a graph which illustrates luciferase vector packaging by BHK cells stably transformed with pBGSVCMVdlhyg.

DEFINITION OF TERMS

The following terms are used throughout the specification. Unless otherwise indicated, these terms are defined as follows:

Figure 1:
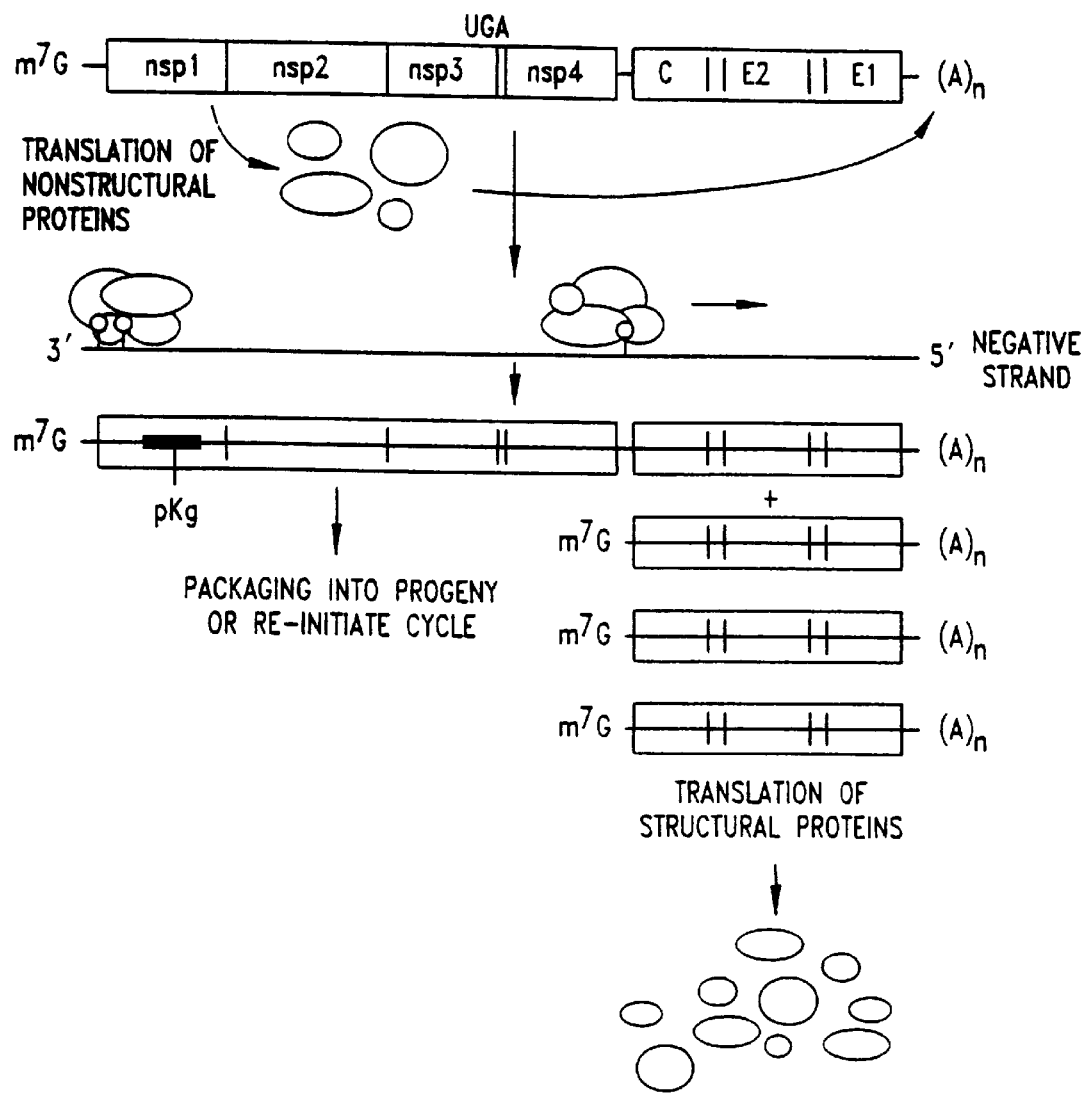
FIG. 1 is a schematic illustration of Sindbis virus and general alphavirus genomic organization and replication strategy.

"Genomic RNA" refers to RNA which contains all of the genetic information required to direct its own amplification or self-replication in vivo, within a target cell. To direct its own replication, the RNA molecule may: 1) encode one or more polymerase, replicase, or other proteins which may interact with viral or host cell-derived proteins, nucleic acids or ribonucleoproteins to catalyze the RNA amplification process; and 2) contain cis RNA sequences required for replication, which may be bound during the process of replication by its self-encoded proteins, or non-self-encoded cell-derived proteins, nucleic acids or ribonucleoproteins, or complexes between any of these components. An alphavirus-derived genomic RNA molecule should contain the following ordered elements: 5' viral or defective-interfering RNA sequence(s) required in cis for replication, sequences which, when expressed, code for biologically active alphavirus nonstructural proteins (e.g., nsP1, nsP2, nsP3, nsP4), 3' viral sequences required in cis for replication, and a polyadenylate tract. The alphavirus-derived genomic RNA vector replicon also may contain a viral subgenomic "junction region" promoter which may, in certain embodiments, be modified in order to prevent, increase, or reduce viral transcription of the subgenomic fragment, and sequences which, when expressed, code for biologically active alphavirus structural proteins (e.g., C, E3, E2, 6K, E1). Generally, the term genomic RNA refers to a molecule of positive polarity, or "message" sense, and the genomic RNA may be of length different from that of any known, naturally-occurring alphavirus. In preferred embodiments, the genomic RNA does not contain the sequences which encode any alphaviral structural protein(s); rather those sequences are substituted with heterologous sequences. In those instances where the genomic RNA is to be packaged into a recombinant alphavirus particle, it must contain one or more sequences which serve to initiate interactions with alphavirus structural proteins that lead to particle formation, and preferably is of a length which is packaged efficiently by the packaging system being employed.

"Subgenomic RNA", or "26S" RNA, refers to a RNA molecule of a length or size which is smaller than the genomic RNA from which it was derived. The subgenomic RNA should be transcribed from an internal promoter whose sequences reside within the genomic RNA or its complement. Transcription of the subgenomic RNA may be mediated by viral-encoded polymerase(s), host cell-encoded polymerase(s), transcription factor(s), ribonucleoprotein(s), or a combination thereof. In preferred embodiments, the subgenomic RNA is produced from a vector according to the invention, and encodes or expresses the gene(s) or sequence(s) of interest. The subgenomic RNA need not necessarily have a sedimentation coefficient of 26.

"Alphavirus vector construct" refers to an assembly which is capable of directing the expression of a sequence(s) or gene(s) of interest. Such vector constructs are comprised of a 5' sequence which is capable of initiating transcription of an alphavirus RNA (also referred to as 5' CSE, in background), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE, in background). In addition, the vector construct should include a viral subgenomic "junction region" promoter which may, in certain embodiments, be modified in order to prevent, increase, or reduce viral transcription of the subgenomic fragment, and also a polyadenylate tract. The vector also may include sequences from one or more structural protein genes or portions thereof, extraneous nucleic acid molecule(s) which are of a size sufficient to allow production of viable virus, a 5' promoter which is capable of initiating the synthesis of viral RNA in vitro from cDNA, a heterologous sequence to be expressed, as well as one or more restriction sites for insertion of heterologous sequences.

"Alphavirus RNA vector replicon", "RNA vector replicon" and "replicon" refers to a RNA molecule which is capable of directing its own amplification or self-replication in vivo, within a target cell. To direct its own amplification, the RNA molecule may: 1) encode one or more polymerase, replicase, or other proteins which may interact with viral or host cell-derived proteins, nucleic acids or ribonucleoproteins to catalyze RNA amplification; and 2) contain cis RNA sequences required for replication which may be bound by its self-encoded proteins, or non-self-encoded cell-derived proteins, nucleic acids or ribonucleoproteins, or complexes between any of these components. In certain embodiments, the amplification also may occur in vitro. An alphavirus-derived RNA vector replicon molecule should contain the following ordered elements: 5' viral sequences required in cis for replication (also referred to as 5' CSE, in background), sequences which, when expressed, code for biologically active alphavirus nonstructural proteins (e.g., nsP1, nsP2, nsP3, nsP4), 3' viral sequences required in cis for replication (also referred to as 3' CSE, in background), and a polyadenylate tract. The alphavirus-derived RNA vector replicon also may contain a viral subgenomic "junction region" promoter which may, in certain embodiments, be modified in order to prevent, increase, or reduce viral transcription of the subgenomic fragment, sequences from one or more structural protein genes or portions thereof, extraneous nucleic acid molecule(s) which are of a size sufficient to allow production of viable virus, as well as heterologous sequence(s) to be expressed. The source of RNA vector replicons in a cell may be from infection with a virus or recombinant alphavirus particle, or transfection of plasmid DNA or in vitro transcribed RNA.

"Recombinant Alphavirus Particle" refers to a virion unit containing an alphavirus RNA vector replicon. Generally, the recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which alphaviral-encoded envelope glycoproteins are embedded. The particle may also contain other components (e.g., targeting elements such as biotin, other viral structural proteins, or other receptor binding ligands) which direct the tropism of the particle from which the alphavirus was derived, or other RNA molecules.

"Structural protein expression cassette" refers to a nucleic acid molecule which is capable of directing the synthesis of one or more alphavirus structural proteins. The expression cassette should include a 5' promoter which is capable of initiating in vivo the synthesis of RNA from cDNA, as well as sequences which, when expressed, code for one or more biologically active alphavirus structural proteins (e.g., C, E3, E2, 6K, E1), and a 3' sequence which controls transcription termination. The expression cassette also may include a 5' sequence which is capable of initiating transcription of an alphavirus RNA (also referred to as 5' CSE, in background), a viral subgenomic "junction region" promoter, and an alphavirus RNA polymerase recognition sequence (also referred to as 3' CSE, in background). In certain embodiments, the expression cassette also may include splice recognition sequences, a catalytic ribozyme processing sequence, a sequence encoding a selectable marker, a nuclear export signal, as well as a polyadenylation sequence. In addition, expression of the alphavirus structural protein(s) may, in certain embodiments, be regulated by the use of an inducible promoter.

"Stable Transformation" refers to the introduction of a nucleic acid molecule into a living cell, and long-term or permanent maintenance of that nucleic acid molecule in progeny cells through successive cycles of cell division. The nucleic acid molecule may be maintained in any cellular compartment, including, but not limited to, the nucleus, mitochondria, or cytoplasm. In preferred embodiments, the nucleic acid molecule is maintained in the nucleus. Maintenance may be intrachromosomal (integrated) or extrachromosomal, as an episomal event.

"Alphavirus packaging cell line" refers to a cell which contains an alphavirus structural protein expression cassette and which produces recombinant alphavirus particles after introduction of an alphavirus vector construct, RNA vector replicon, eukaryotic layered vector initiation system, or recombinant alphavirus particle. The parental cell may be of mammalian or non-mammalian origin. Within preferred embodiments, the packaging cell line is stably transformed with the structural protein expression cassette.

"Alphavirus producer cell line" refers to a cell line which is capable of producing recombinant alphavirus particles, comprising an alphavirus packaging cell line which also contains an alphavirus vector construct, RNA vector replicon, eukaryotic layered vector initiation system, or recombinant alphavirus particle. Preferably, the alphavirus vector construct is eukaryotic layered vector initiation system, and the producer cell line is stably transformed with the vector construct. In preferred embodiments, transcription of the alphavirus vector construct and subsequent production of recombinant alphavirus particles occurs only in response to one or more factors, or the differentiation state of the alphavirus producer cell line.

"Defective helper construct" refers to an assembly which is capable of RNA amplification or replication, and expression of one or more alphavirus structural proteins in response to biologically active alphavirus nonstructural proteins supplied in trans. The defective helper construct should contain the following ordered elements: 5' viral or defective-interfering RNA sequences required in cis for replication, a viral subgenomic junction region promoter, sequences which, when expressed, code for one or more biologically active alphavirus structural proteins (e.g., C, E3, E2, 6K, E1), 3' viral sequences required in cis for replication, and a polyadenylate tract. The defective helper construct also may contain a 5' promoter which is capable of initiating the synthesis of viral RNA from cDNA, a 3' sequence which controls transcription termination, splice recognition sequences, a catalytic ribozyme processing sequence, a sequence encoding a selectable marker, and a nuclear export signal.

"Eukaryotic Layered Vector Initiation System" refers to an assembly which is capable of directing the expression of a sequence(s) or gene(s) of interest. The eukaryotic layered vector initiation system should contain a 5' promoter which is capable of initiating in vivo (i.e. within a cell) the synthesis of RNA from cDNA, and a nucleic acid vector sequence which is capable of directing its own replication in a eukaryotic cell and also expressing a heterologous sequence. The nucleic acid sequence which is capable of directing its own amplification may be of viral or non-viral origin. In certain embodiments, the nucleic acid vector sequence is an alphavirus-derived sequence and is comprised of a 5' sequence which is capable of initiating transcription of an alphavirus RNA (also referred to as 5' CSE, in background), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE, in background). In addition, the vector sequence may include a viral subgenomic "junction region" promoter which may, in certain embodiments, be modified in order to prevent, increase, or reduce viral transcription of the subgenomic fragment, sequences from one or more structural protein genes or portions thereof, extraneous nucleic acid molecule(s) which are of a size sufficient to allow optimal amplification, a heterologous sequence to be expressed, one or more restriction sites for insertion of heterologous sequences, as well as a polyadenylation sequence. The eukaryotic layered vector initiation system may also contain splice recognition sequences, a catalytic ribozyme processing sequence, a nuclear export signal, and a transcription termination sequence. In certain embodiments, in vivo synthesis of the vector nucleic acid sequence from cDNA may be regulated by the use of an inducible promoter.

"Alphavirus cDNA vector construct" refers to an assembly which is capable of directing the expression of a sequence(s) or gene(s) of interest. The vector construct is comprised of a 5' sequence which is capable of initiating transcription of an alphavirus RNA (also referred to as 5' CSE), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE, in background). In addition, the vector construct should include a 5' promoter which is capable of initiating in vivo the synthesis of viral RNA from cDNA, and a 3' sequence which controls transcription termination. Within certain embodiments, the vector construct may further comprise a viral subgenomic "junction region" promoter which may, in certain embodiments, be modified in order to prevent, increase, or reduce viral transcription of the subgenomic fragment The vector also may include sequences from one or more structural protein genes or portions thereof, extraneous nucleic acid molecule(s) which are of a size sufficient to allow production of viable virus, a heterologous sequence to be expressed, one or more restriction sites for insertion of heterologous sequences, splice recognition sequences, a catalytic ribozyme processing sequence, a nuclear export signal, as well as a polyadenylation sequence. In certain embodiments, in vivo synthesis of viral RNA from cDNA may be regulated by the use of an inducible promoter.

"Gene delivery vehicle" refers to a construct which can be utilized to deliver a gene or sequence of interest. Representative examples include alphavirus RNA vector replicons, alphavirus vector constructs, eukaryotic layered vector initiation systems and recombinant alphavirus particles.

Numerous aspects and advantages of the invention will be apparent to those skilled in the art upon consideration of the following detailed description which provides illumination of the practice of the invention.

DETAILED DESCRIPTION OF THE INVENTION

As noted above, the present invention provides novel gene delivery vehicles including for example, RNA vector replicons, alphavirus vector constructs, eukaryotic layered vector initiation systems and recombinant alphavirus particles. Briefly, introduction of plasmid DNA-, in vitro transcribed RNA-, or particle-based vectors of the present invention into a cell, results in levels of heterologous gene expression that are equivalent, or higher, as compared to expression levels of wild-type derived alphaviral vectors. Unexpectedly however, the level of vector-specific RNA synthesized is at least about 5 to 10-fold lower in cultured cells which contain a gene delivery vehicle of the present invention, as compared to wild-type derived vectors. Furthermore, such gene delivery vehicles exhibit reduced, delayed, or no inhibition of host cell-directed macromolecular synthesis following introduction into a host cell, as compared to wild-type derived vectors.

As discussed in more detail below, the present invention provides: (A) sources of wild-type alphaviruses suitable for constructing the gene delivery vehicles of the present invention; (B) methods for selecting alphaviruses with a desired phenotype; (C) construction of alphavirus vector constructs and alphavirus RNA vector replicons; (D) construction of Eukaryotic Layered Vector Initiation Systems; (E) construction of recombinant alphavirus particles; (F) heterologous sequences which may be expressed by the gene delivery vehicles of the present invention; (G) construction of alphavirus packaging or producer cell lines; (H) pharmaceutical compositions; and (I) methods for utilizing alphavirus-based vectors.

A. Sources of Wild-Type Alphavirus

As noted above, the present invention provides a wide variety of alphavirus-based vectors (e.g., RNA vector replicons, alphavirus vector constructs, eukaryotic layered vector initiation systems and recombinant alphavirus particles), as well as methods for utilizing such vector constructs and particles. Briefly, sequences encoding wild-type alphaviruses suitable for use in preparing the above-described vectors can be readily obtained given the disclosure provided herein from naturally-occurring sources, or from depositories (e.g., the American Type Culture Collection, Rockville, Md.). In addition, wild-type alphaviruses may be utilized for comparing the level of host-cell directed macromolecular synthesis in cells infected with the wild-type alphavirus, with the level of host-cell directed macromolecular synthesis in cells containing the gene delivery vehicles of the present invention.

Representative examples of suitable alphaviruses include Aura virus (ATCC VR-368), Bebaru virus (ATCC VR-600, ATCC VR-1240), Cabassou virus (ATCC VR-922), Chikungunya virus (ATCC VR-64, ATCC VR-1241), Eastern equine encephalomyelitis virus (ATCC VR-65, ATCC VR-1242), Fort Morgan virus (ATCC VR-924), Getah virus (ATCC VR-369, ATCC VR-1243), Kyzylagach virus (ATCC VR-927), Mayaro virus (ATCC VR-66, ATCC VR-1277), Middleburg virus (ATCC VR-370), Mucambo virus (ATCC VR-580, ATCC VR-1244), Ndumu virus (ATCC VR-371), Pixuna virus (ATCC VR-372, ATCC VR-1245), Ross River virus (ATCC VR-373, ATCC VR-1246), Semliki Forest virus (ATCC VR-67, ATCC VR-1247), Sindbis virus (ATCC VR-68, ATCC VR-1248, see also CMCC #4640, described below), Tonate virus (ATCC VR-925), Triniti virus (ATCC VR469), Una virus (ATCC VR-374), Venezuelan equine encephalomyelitis virus (ATCC VR-69, ATCC VR-923, ATCC VR-1250, ATCC VR-1249, ATCC VR-532), Western equine encephalomyelitis virus (ATCC VR-70, ATCC VR-1251, ATCC VR-622, ATCC VR-1252), Whataroa virus (ATCC VR-926), and Y-62-33 virus (ATCC VR-375).

For purposes of comparing levels of cellular macromolecular synthesis, the following plasmids may also be utilized as a standard source of wild-type alphavirus stocks. These plasmids include: for Semliki Forest Virus, pSP6-SFV4 (Liljestrom et al., *J. Virol.* 65:4107–4113, 1991); for Venezuelan equine encephalitis virus, pV2000 Davis et al., *Vir.* 183:20–31, 1991); for Ross River virus, pRR64 (Kuhn et al., *Vir.* 82:430–441, 1991). Briefly, for these plasmids, virus can be obtained from BHK cells transfected with in vitro transcribed genomic RNA from the plasmids. For Sindbis virus, infectious virus may be isolated directly from BHK cells transfected with pVGELVIS (ATCC No. 75891) plasmid DNA, or alternatively, obtained as a wild-type virus stock (see deposit information provided below regarding ATCC No. VR-2526).

B. Selection of Alphaviruses with a Desired Phenotype

The duration of in vivo heterologous gene expression from alphavirus-based vectors is affected by several mechanisms, including inhibition of host cell-directed macromolecular synthesis. However, prior to the present invention, there had been no obvious method to select for or identify coding or non-coding vector viral-specific sequence changes that result in a non-cytopathic phenotype. Therefore, within one aspect of the present invention methods are provided for isolating and/or constructing alphavirus-derived gene delivery vehicles with reduced or no inhibition of host cell directed macromolecular synthesis.

1. Biological Selection of Virus Variants a. Selection from Virus Stocks Containing DI Particles One approach for isolating non-cytopathic alphavirus variants exploits the presence of defective interfering (DI) particles in wild-type virus preparations. Briefly, although certain RNA viruses, for example rhabdoviruses (e.g., vesicular stomatitis virus) and alphaviruses (e.g., Sindbis virus and Semliki Forest virus), are highly cytopathic, they can nevertheless establish long-term persistent infection in cultured cells in the presence of DI particles. DI particles, by definition, are derived from wild-type virus and contain one or more mutations (e.g., deletions, rearrangements, nucleotide substitutions, etc.) from the wild-type genome which prevent autonomous replication by the DI. In general, the genome of DI particles is smaller and of a lower complexity compared to wild-type virus, and is deleted of protein-encoding regions while maintaining regions required in cis for replication. Such cis sequences often are duplicated and/or rearranged. In the case of certain alphaviruses e.g., Sindbis virus), the sequence and organization of DI RNA genomes have been analyzed and found to contain a minimum of 50 nt from the extreme 3'-end of the wild-type virus genome, and at their 5'-ends, either a wild-type sequence or a cellular tRNA (e.g., tRNA$^{Asp}$) sequence, in addition to the viral sequence. In all cases, the propagation and maintenance of the mutated DI genomes requires the co-existence of parental helper virus in the infected cell. However, as a result of their genetic structure, DI genome replication is vastly superior and comparatively abundant to its wild-type counterpart. This characteristic results in interference of wild-type genome replication, the absence or low level production of infectious virus, and the establishment of long-term persistent infection of cells.

Therefore, as described below in Examples 1 and 2, the ability to establish long-term persistent infection in permissive cells (e.g., mammalian cells, including cells of human origin) by infecting with a mixed alphavirus stock containing a population of DI particles provides a mechanism to isolate, over time, fully intact virus variants that are able to establish persistent infection, even in the absence of DI particles. Such infectious virus variants can be isolated from long-term persistently infected cultures by multiple rounds of plaque purification and have been found to initiate productive, persistent, and non-cytopathic infection in the host cells. Furthermore, the level of variant virus produced from such a productive, persistent, and non-cytopathic infection is indistinguishable from wild-type virus infection. This observation is in distinct contrast to the previous requirement for establishment of persistent infections with virus stocks containing a mixture of DI particles.

b. Selection from Virus Stocks not Containing DI Particles

In addition to selection from virus stocks that contain defective-interfering particles, virus variants suitable for use within the present invention may be obtained from purified virus stocks (without DI particles) which are either subjected to random mutagenesis prior to infection of susceptible cultured cells or allowed to generate non-specific mutations during RNA replication with the cultured cells. Briefly, the initial virus stock may be obtained as a natural isolate or biological variant derived therefrom, or may be generated by transfecting cultured cells with an infectious nucleic acid molecule comprising a genomic cDNA clone or in vitro transcribed RNA. If desired, the virus stock may then subjected to physical or chemical mutagenesis (although preferred, such mutagenesis is not required). In the case of chemical mutagenesis, preferred embodiments utilize a readily available mutagenic agent, for example nitrous acid, 5-azacytidine, N-methyl-N'-nitro-N-nitrosoguanidine, or ethylmethane sulfonate (Sigma, St. Louis, Mo.), prior to virus infection. Following random mutagenesis, specific selection procedures are applied to isolate virus variants possessing the desired phenotype, as described in more detail below in Example 2.

2. Genetic Selection of Virus Variants

In a related approach, mutations may be obtained not using a virus stock, but rather, using cloned genomic cDNA of the virus that can be used subsequently to transcribe infectious viral RNA in vitro (for example, Sindbis virus (Rice et al., *J. Virol.* 61:3809–3819, 1987; Dubensky et al., *J. Virol.* 70:508–519, 1996, SFV (Liljeström et al., *J. Virol.* 65:4107–4113, 1991, VEE (Davis et al., *Virology* 183:20–31, 1991), Ross River virus (Kuhn et al., *Virology* 182:430–441, 1991), poliovirus (Van Der Werf et al., *Proc. Natl. Acad. Sci. USA* 83:2330–2334, 1986)) or in vivo (Sindbis virus (Dubensky et al., ibid.), poliovirus (Racaniello and Baltimore, *Science* 214:916–919, 1981)). Briefly, the infectious nucleic acid is introduced into susceptible cultured cells (e.g., mammalian cells, including cells of human origin) either directly or following mutagenesis performed using one of the above-referenced methods. Alternatively, vector nucleic acid may be packaged into particles initially, and the particles used to deliver vector into the target cell population for selection. Subsequently, specific selection procedures to isolate virus variants possessing the desired phenotype are applied, and are described below.

In certain embodiments, random mutagenesis may be performed initially by propagation of the plasmid containing viral cDNA in the XL1-Red strain of *E. coli* (Stratagene, San Diego, Calif.), which is deficient in three of the primary DNA repair pathways, resulting from mutS, mutD, and mutT mutations. However, other mutagenesis procedures including, but not limited to, linker-scanning mutagenesis (Haltiner et al., *Nucleic Acids Res.* 13:1015, 1985; Barany, *Proc. Natl. Acad. Sci. USA* 82:4202, 1985), random oligonucleotide-directed mutagenesis (Kunkel et al., *Methods Enzymol.* 155:166, 1987; Zoller and Smith, *Methods Enzymol.* 154:329, 1987; Hill et al., *Methods Enzymol.* 155:558, 1987; Hermes et al., *Gene* 84:143, 1989) and PCR mutagenesis (Herlitze and Koenen, *Gene* 91:143, 1990), can be readily substituted utilizing published protocols. The resulting mixed population of mutated cDNA clones is introduced into susceptible cultured cells directly, or after transcription in vitro. Enrichment for transfected cells which contain mutated virus of the desired phenotype is accomplished based on increased survival time over wild-type virus infected cells, as described below.

3. Genetic Selection of Variants Using Virus-Derived Vectors

In another approach, mutations may be generated in any region a virus-derived expression vector, including the regulatory, untranslated regions, or protein-encoding gene regions. For example, within one aspect of the invention methods are provided for selecting viral variants with reduced or no inhibition of host-cell directed macromolecular synthesis, comprising the steps of: (a) introducing into a cell a eukaryotic layered vector initiation system, RNA vector replicon, or recombinant alphavirus particle which directs the expression of a immunogenic cell surface protein (suitable for detection of vector containing cells), or alternatively, a selectable marker (either a drug or non-drug marker wherein non-vector containing cells are killed upon addition of, for example, a drug such as neomycin, hygromycin, phleomycin, gpt, puromycin, or histidinol); (b) incubation or culturing the cells under conditions and for a time sufficient to select vector containing cells which exhibit the desired phenotype; followed by (c) isolating cells which contain the vector of the desired phenotype and (d) analysis of the vector for the causal mutation.

As noted above, the viral vectors of the present invention may be derived from a wide variety of viruses (e.g., Sindbis virus (Xiong et al., *Science* 243:1188–1191, 1989; Hahn et al., *Proc. Natl. Acad. Sci. USA* 89:2679–2683, 1992; Schlesinger, *Trends Biotechnol.* 11:18–22, 1993; Dubensky et al., ibid), Semliki Forest virus (Liljestrom and Garoff, *Bio/Technology* 9:1356–1361, 1991). Venezuelan equine encephalitis virus (Davis et al., *J. Cell. Biochem. Suppl.* 19A:310, 1995), poliovirus (Choi et al., *J. Virol.* 65:2875–2883, 1991; Ansardi et al., *Cancer Res.* 54:6359–6364, 1994; and Andino et al., *Science* 265:1448–1451, 1994). Representative examples of the above-described methods are discussed-in more detail below within Example 2.

4. Use of Viral Variants

As discussed in more detail herein, viral variants which have been selected or generated utilizing the methods provided herein may be utilized to construct a wide variety of recombinant gene delivery vehicles which exhibit the desired phenotype. Within certain embodiments, the gene delivery vehicle contains a mutation within the Leu-Xaa-Pro-Gly-Gly ("LXPGG") (SEQ ID NO:119) motif of the nsP2 gene. Briefly, for alphaviruses wherein published sequence of the nsP2 gene is available, a highly conserved amino acid motif -Leu-Xaa-Pro-Gly-Gly- ("LXPGG") (SEQ ID NO:119) is observed. As predicted by standard protein modelling algorithms (Chou and Fasman, *Adv. Enzym.* 47:45–148, 1978), the residues of this motif possibly comprise a β turn in the structure. Proline 726 of nsP2 in Sindbis virus is the central residue of this motif. The corresponding motif in other alphaviruses is illustrated in the table below (SEQ ID NO:120–123).

| Alphavirus Strain* | Pro-Gly-Gly Region | nsP2 a.a.'s (P-G-G) |
|---|---|---|
| 1. Sindbis virus | Leu-Asn-Pro-Gly-Gly-Thr | a.a. = 726–728 |
| 2. S.A.AR86 virus | Leu-Asn-Pro-Gly-Gly-Thr | a.a. = 726–728 |
| 3. Ockelbo virus | Leu-Asn-Pro-Gly-Gly-Thr | a.a. = 726–728 |
| 4. Aura virus | Leu-Lys-Pro-Gly-Gly-Thr | a.a. = 725–727 |
| 5. Semliki Forest virus | Leu-Lys-Pro-Gly-Gly-Ile | a.a. = 718–720 |
| 6. VEE virus | Leu-Asn-Pro-Gly-Gly-Thr | a.a. = 713–715 |
| 7. Ross River virus | Leu-Xaa-Pro-Gly-Gly-Ser | a.a. = 717–719 |

*Alphavirus strains with published nsP2 sequences: (1) Strauss et al., Virology 133: 92–110, 1984; (2) Simpson et al., Virology 222: 464–469 1996; (3) Shirako et al., Virology 182: 753–764, 1991; (4) Rumenapf et al., Virology 208: 621–633, 1995; (5) Takkinen, Nucleic Acids Res. 14: 5667–5682, 1986; (6) Kinney et al., Virology 170: 19–30, 1989; and (7) Faragher et al, Virology 163: 509–526, 1988.

Hence, within various embodiments of the present invention, gene delivery vehicles are provided wherein the gene delivery vehicle contains an nsP2 gene with a mutation in the LXPGG (SEQ ID NO:119) motiff. Within one embodiment, the Leu codon is mutated to another amino acid selected from the group consisting of Ala, Arg, Asn, Asp, Asx, Cys, Gln, Glu, Glx, Gly, His, Ile, Lys, Met, Phe, Pro, Ser, Thr, Trp, Tyr, Val, or another rare or non-protein amino acid (see, e.g., Lehninger, Biochemistry, Worth Publishers. Inc., N.Y. N.Y., 1975). Within another embodiment, the Pro codon is mutated to another amino acid selected from the group consisting of Ala, Arg, Asn, Asp, Asx, Cys, Gln, Glu, Glx, Gly, His, Ile, Leu, Lys, Met, Phe, Ser, Thr, Trp, Tyr, Val, or another rare or non-protein amino acid. Within other embodiments, either or both of the Gly codons may be mutated to another amino acid selected from the group consisting of Ala, Arg, Asn, Asp, Asx, Cys, Gln, Glu, Glx, His, Ile, Leu, Lys, Met, Phe, Pro, Ser, Thr, Trp, Tyr, Val, or another rare or non-protein amino acid. Within yet other embodiments, the Xaa amino acid, or amino acids between 1 and 3 residues upstream or downstream of the LXPGG (SEQ ID NO:119) motiff may be mutated from the wild-type amino acid in order to effect the phenotype of the resultant gene delivery vehicle. Within certain embodiments of the invention, the LXPGG (SEQ ID NO:119) motiff may be mutated to contain more than one codon alteration, or alternatively, one or more codon insertions or deletions.

C. Alphavirus Vector Constructs and Alphavirus RNA Vector Replicons

As noted above, the present invention provides both DNA and RNA constructs which are derived from alphaviruses. Briefly, within one aspect of the present invention alphavirus vector constructs are provided, comprising a 5' promoter which initiates synthesis of viral RNA in vitro from cDNA, a 5' sequence which initiates transcription of alphavirus RNA, a nucleic acid molecule which operably encodes all four alphaviral nonstructural proteins including an isolated nucleic acid molecule as described above, an alphavirus RNA polymerase recognition sequence and a 3' polyadenylate tract. Within other aspects, RNA vector replicons are provided, comprising a 5' sequence which initiates transcription of alphavirus RNA, a nucleic acid molecule which operably encodes all four alphaviral nonstructural proteins, including the isolated nucleic acid molecules discussed above, an alphavirus RNA polymerase recognition sequence and a 3' polyadenylate tract. Within preferred embodiments of the above, the above constructs further comprise a viral junction region. Each of these aspects are discussed in more detail below.

5' Promoters Which Initiate Synthesis of Viral RNA

As noted above, within certain embodiments of the invention, alphavirus vector constructs are provided which contain 5' promoters which (e.g., DNA dependent RNA polymerase promoters) initiate synthesis of viral RNA from cDNA by a process of in vitro transcription. Within preferred embodiments such promoters include, for example, the bacteriophage T7, T3, and SP6 RNA polymerase promoters. Similarly, eukarytoic layered vector initiation systems are provided (e.g., DNA dependent RNA polymerase promoters) which contain 5' promoters which initiate synthesis of viral RNA from cDNA in vivo (i.e., within a cell). Within certain embodiments, such RNA polymerase promoters (for either alphavirus vector constructs or eukaryotic layered vector initiation systems) may be derived from both prokaryotic and eukaryotic organisms, and include, for example, the bacterial β-galactosidase and trpE promoters, and the eukaryotic viral simian virus 40 (SV40) (e.g., early or late), cytomegalovirus (CMV) (e.g., immediate early), Moloney murine leukemia virus (MoMLV) or Rous sarcoma virus (RSV) LTR, and herpes simplex virus (HSV) (thymidine kinase) promoters.

2. Sequences Which Initiate Transcription

As noted above, within preferred embodiments the alphavirus vector constructs and RNA vector replicons of the present invention contain a 5' sequence which is capable of initiating transcription of an alphavirus RNA (also referred to as 5'-end CSE, or 5' cis replication sequence). Representative examples of such sequences include nucleotides 1–60, and to a lesser extent nucleotides through bases 150–210, of the wild-type Sindbis virus, nucleotides 10–75 for tRNA$^{Asp}$ (aspartic acid, Schlesinger et al., U.S. Pat. No. 5,091,309), and 5' sequences from other alphaviruses which initiate transcription. It is the complement of these sequences, which corresponds to the 3' end of the of the minus-strand genomic copy, which are bound by the nsP replicase complex, and possibly additional host cell factors, from which transcription of the positive-strand genomic RNA is initiated.

3. Alphavirus Nonstructural Proteins

The alphavirus vector constructs and RNA vector replicons provided herein also require sequences encoding all four alphaviral nonstructural proteins, including a sequence which provides the desired phenotype discussed above. Briefly, a wide variety of sequences which encode alphavirus nonstructural proteins, in addition to those explicitly provided herein, may be utilized in the present invention, and are therefore deemed to fall within the scope of the phrase "alphavirus nonstructural proteins." For example, due to the degeneracy of the genetic code, more than one codon may code for a given amino acid. Therefore, a wide variety of nucleic acid sequences which encode alphavirus nonstructural proteins may be generated. Furthermore, amino acid substitutions, additions, or deletions at any of numerous positions may still provide functional or biologically active nonstructural proteins. Within the context of the present invention, alphavirus nonstructural proteins are deemed to be biologically active if they promote self-replication of the vector construct, i.e., replication of viral nucleic acids and not necessarily the production of infectious virus, and may be readily determined by metabolic labeling or RNase protection assays performed over a time course. Methods for making such derivatives are readily accomplished by one of ordinary skill in the art given the disclosure provided herein.

Alphaviruses express four nonstructural proteins, designated nsp1, nsp2, nsp3, and nsp4. Vectors of the present invention derived from alphaviruses should contain sequences encoding the four nonstructural proteins. In wild-type Sindbis virus, nonstructural proteins 1–3 are encoded by nucleotides 60 to 5747, while nsP4 is encoded by nucleotides 5769 to 7598 (see FIG. 1). The nonstructural proteins are translated from the genomic positive strand RNA as one of two large polyproteins, known as P123 or P1234, respectively, depending upon (i) whether there is an opal termination codon between the coding regions of nsP3 and nsP4 and (ii) if there is such an opal codon present, whether there is translation termination of the nascent polypeptide at that point or readthrough and hence production of P1234. The opal termination codon is present at the nsP3/nsP4 junction of the alphaviruses SIN (strain AR339 and the SIN-1 strain described herein), AURA, WEE, EEE, VEE, and RR, and thus the P123 and P1234 species are expressed in cells infected with these viruses. In contrast, no termination codon is present at the nsP3/nsP4 junction of the alphaviruses SIN (strain AR86, SF, and ONN), and thus only the P1234 species is expressed in cells infected with these viruses. Both the polyprotein and processed monomeric forms of the nonstructural proteins function in the replication of the alphavirus RNA genome. Experiments examining growth characteristics of alphavirus nonstructural protein cleavage mutants have indicated that the polyproteins are involved in the synthesis of the genomic negative stranded RNA, while the individual monomeric proteins catalyze the synthesis of the genomic and subgenomic positive stranded RNA species (Shirako and Strauss, *J. Virol.* 68:1874–1885, 1974). Translational readthrough generally occurs about 10%–20% of the time in cells infected with wild type Sindbis virus containing the opal termination codon at the nsP3/nsP4 junction. Processing of P123 and P1234 is by a proteinase activity encoded by the one of the nonstructural proteins, and is discussed further below. The order of processing, whether in cis or in trans, depends on various factors, including the stage of infection. For example, Sindbis virus and SFV produce P123 and nsp4 early in infection, and P12 and P34 later in infection. Further processing then releases the individual nonstructural proteins. Each nonstructural protein has several functions, some of which are described below.

a. nsP1

Nonstructural protein 1 is required for the initiation of (or continuation of) minus-strand RNA synthesis. It also plays a role in capping the 5' terminus of genomic and subgenomic alphavirus RNAs during transcription, as nsP1 possesses both methyltransferase (Mi and Stollar, *Vir.* 184:423–427, 1991) and guanyltransferase activity (Strauss and Strauss, *Microbiol. Rev.* 58(3):491–562. 1994). NsP1 also modulates the proteinase activity of nsP2, as polyproteins containing nsP1 inefficiently cleave between nsP2 and nsP3 (de Groot et al., *EMBO J.* 9:2631–2638, 1990).

b. nsP2

Nonstructural protein 2 is a multifunctional protein, involved in the replication of the viral RNA and processing of the nonstructural polyprotein. The N-terminal domain of the protein (spanning about the first 460 amino acids) is believed to be a helicase which is active in duplex unwinding during RNA replication and transcription. Synthesis of 26S subgenomic mRNA, which, in vectors according to the present invention, encodes the gene(s) of interest, requires functional nsP2. The C-terminal domain of nsP2, between amino acid residues 460–807 of Sindbis virus, proteolytically cleaves in trans and in cis the nonstructural polyprotein between the nsP1/nsP2, nsP2/nsP3, and nsP3/nsP4 junctions. Alignment of the primary sequences of the alphavirus nsP2 C-terminal domains suggests that nsP2 is a papain-like proteinase (Hardy and Strauss, *J. Virol.* 63:4653–4664, 1988).

Other observed characteristics of nsP2 have not, as yet, been assigned a function directly related to the propagation of alphaviruses. For example, it has been shown that nsP2 is closely associated with ribosomes in SFV-infected cells, and can be cross-linked to rRNA by UV irradiation (Ranki et al., *FEBS Lett.* 108:299–302, 1979). Further, 50% of nsP2 is localized in the nuclear matrix, particularly in the area of the nucleoli of SFV-infected BHK cells (Peränen et al., *J. Virol.* 64:1888–1896, 1990). Localization of nsP2 to the nuclei presumably proceeds by active transport, as it exceeds the size of small proteins and metabolites (about 20–60 kD), which can enter the nucleus by diffusion through nuclear core complexes (Paine et al., *Nature* 254:109–114, 1975). Putative NLS sequences have been identified in the alphaviruses SFV, SIN, RR, ONN, OCK, and VEE (Rikkonen et al., *Vir.* 189:462–473, 1992).

c. nsP3

Nonstructural protein nsP3 contains two distinct domains, although their precise roles in viral replication are not well understood. The N-terminal domain ranges in length from 322 to 329 residues in different alphaviruses and exhibits a minimum of 51% amino acid sequence identity among any two alphaviruses. The C-terminal domain, however, is not conserved among known alphaviruses in length or in sequence, and multiple changes are tolerated (Li et al., *Virology*, 179:416–427). The protein is found associated with replication complexes in a heavily phosphorylated state. In alphaviruses whose genomes contain an opal termination codon between the nsP3/nsP4 junction, two different proteins are produced depending upon whether or not there is readthrough of the opal termination signal. Readthrough results in an nsP3 protein which contains 7 additional carboxy terminal amino acids after cleavage of the polyprotein. It is clear that nsP3 is required in some capacity for viral RNA synthesis, as particular mutants of this protein are RNA negative, and the P123 polyprotein is required for minus-strand RNA synthesis.

d. nsP4

NsP4 is the virus-encoded RNA polymerase and contains the GDD motif characteristic of such enzymes (Kamer and Argos, *Nucleic Acids Res.* 12:7269–7282, 1984). Thus, nsP4 is indispensable for alphavirus RNA replication. The concentration of nsP4 is tightly regulated in infected cells. In most alphaviruses, translation of nsP4 requires readthrough of an opal codon between the nsP3 and nsP4 coding regions, resulting in lower intracellular levels as compared to other nonstructural proteins. Additionally, the bulk of nsP4 is metabolically unstable, through degradation by the N-end rule pathway (Gonda et al., *J. Biol. Chem.* 264:16700–16712, 1989). However, some nsP4 is stable, due to its association with replication complexes which conceal degradation signals. Thus, stabilization of the enzyme by altering the amino terminal residue may prove useful in promoting more long term expression of proteins encoded by the vectors described herein. Stabilizing amino terminal residues include methionine, alanine, and tyrosine.

4. Viral Junction Regions

The alphavirus viral junction region normally controls transcription initiation of the subgenomic mRNA; thus, this element is also referred to as the subgenomic mRNA promoter. In the case of Sindbis virus, the normal viral junction region typically begins at approximately nucleotide number 7579 and continues through at least nucleotide number 7612 (and possibly beyond). At a minimum, nucleotides 7579 to 7602 (5'-ATC TCT ACG GTG GTC CTA AAT AGT-SEQ. ID NO. 1) are believed necessary for transcription of the subgenomic fragment. This region (nucleotides 7579 to 7602) is hereinafter referred to as the "minimal junction region core."

Within certain aspects of the invention, the viral junction region is inactivated in order to prevent synthesis of the subgenomic fragment. As utilized within the context of the present invention, "inactivated" means that the species corresponding to subgenomic mRNA is not observed in autoradiograms from denaturing gels of electrophoresed RNA purified from cells containing these vectors and treated with 1 µg/ml dactinomycin and labeled with [$^3$H]-uridine, as described (Frolov and Schlesinger, *J. Virol.* 68:1721–1727, 1994).

Within one embodiment of the invention, gene delivery vehicles may be constructed by the placement of signals promoting either ribosome readthrough or internal ribosome entry immediately downstream of the disabled junction region promoter. In this vector configuration, synthesis of subgenomic message cannot occur; however, the heterologous proteins are expressed from genomic length mRNA by either ribosomal readthrough (scanning) or internal ribosome entry.

In certain applications of the gene delivery vehicles described herein, the expression of more than one heterologous gene is desired. For example, in order to treat metabolic disorders such as Gaucher's syndrome, multiple administrations of gene delivery vehicles or particles may be required, since duration of the therapeutic palliative may be limited. Therefore, within certain embodiments of the invention it may be desirable to co-express in a target cell the Adenovirus 2 E3 gene, along with a therapeutic palliative, such as the glucocerebrosidase gene. In wild-type virus, the structural protein (sP) polycistronic message is translated into a single polyprotein which is processed subsequently into individual proteins in part by the sP capsid proteinase. Thus, expression of multiple heterologous genes from a polycistronic message requires a mechanism different from the wild-type virus, since the protease activity of the capsid sP, or the peptides recognized for cleavage, are not present in the replacement region of the alphavirus vectors. Therefore, within further embodiments of the invention, functional elements which permit translation of multiple independent heterologous sequences, including ribosomal readthrough, cap-independent translation, internal ribosome entry, or minimal junction region core sequences, can be utilized.

5. Alphavirus RNA Polymerase Recognition Sequence, and Poly(A) Tract

As noted above, alphavirus vector constructs or RNA vector replicons of the present invention also should include an alphavirus RNA polymerase recognition sequence (also termed "alphavirus replicase recognition sequence", "3' terminal CSE", or "3' cis replication sequence"). Briefly, the alphavirus RNA polymerase recognition sequence, which is located at the 3' end region of positive stranded genomic RNA, provides a recognition site at which the virus begins replication by synthesis of the negative strand. A wide variety of sequences may be utilized as an alphavirus RNA polymerase recognition sequence. For example, within one embodiment, Sindbis virus vector constructs in which the polymerase recognition is truncated to the smallest region that can still function as a recognition sequence (e.g., nucleotides 11,684 to 11,703) can be utilized. Within another embodiment of the invention, Sindbis virus vector constructs in which the entire nontranslated region downstream from the E1 sP gene to the 3' end of the viral genome including the polymerase recognition site (e.g., nucleotides 11,382 to 11,703), can be utilized.

Within preferred embodiments of the invention, the alphavirus vector construct or RNA vector replicon may additionally contain a poly(A) tract, which increases dramatically the observed level of heterologous gene expression in cells transfected with alphavirus-derived vectors (see e.g., Dubensky et al, supra). Briefly, the poly(A) tract may be of any size which is sufficient to promote stability in the cytoplasm, thereby increasing the efficiency of initiating the viral life cycle. Within various embodiments of the invention, the poly(A) sequence comprises at least 10 adenosine nucleotides, and most preferably, at least 25 adenosine nucleotides. Within one embodiment, the poly(A) sequence is attached directly to Sindbis virus nucleotide 11,703.

D. Eukaryotic Layered Vector Initiation Systems

Due to the size of a full-length genomic alphavirus cDNA clone, in vitro transcription of full-length, capped RNA molecules is rather inefficient. This results in a lowered transfection efficiency, in terms of infectious centers of virus (as measured by plaque formation), relative to the amount of in vitro transcribed RNA transfected. Such inefficiency is also relevant to the in vitro transcription of alphavirus expression vectors. Testing of candidate cDNA clones and other alphavirus cDNA expression vectors for their ability to initiate an infectious cycle or to direct the expression of a heterologous sequence can thus be greatly facilitated if a cDNA clone is transfected into susceptible cells as a DNA molecule, which then directs the synthesis of viral RNA in vivo.

Therefore, within one aspect of the present invention DNA-based vectors (referred to as "Eukaryotic Layered Vector Initiation Systems") are provided that are capable of directing the synthesis of viral RNA (genomic or vector) in vivo. Generally, eukaryotic layered vector initiation systems comprise a 5' promoter that is capable of initiating in vivo (i.e., within a cell) the 5' synthesis of RNA from cDNA, a construct that is capable of directing its own replication in a cell, the construct also being capable of expressing a heterologous nucleic acid sequence, and a 3' sequence that controls transcription termination (e.g., a polyadenylate tract). Such eukaryotic layered vector initiation systems provide a two-stage or "layered" mechanism that controls expression of heterologous nucleotide sequences. Briefly, the first layer initiates transcription of the second layer and comprises a promoter that is capable of initiating in vivo the 5' to 3' synthesis of RNA from cDNA (e.g., a 5' eukaryotic promoter), and may further comprise other elements, including a 3' transcription termination/polyadenylation site, one or more splice sites, as well as other RNA nuclear export elements, including, for example, the hepatitis B virus posttranscriptional regulatory element (PRE) (Huang et al., *Mol. Cell. Biol.* 13:7476, 1993; Huang et al., *J. Virol.* 68:3193, 1994; Huang et al., *Mol. Cell. Biol.*, 15:3864–3869, 1995), the Mason-Pfizer monkey virus constitutive transport element (CTE) (Bray et al., *Proc. Natl. Acad. Sci. USA* 91:1256–1260, 1994), the HIV Rev responsive element (Malim et al., *Nature* 338:254–257, 1989; Cullen et al., *Trends Biochem. Sci.* 16:346, 1991). and other similar elements; if desired. Representative promoters suitable for use within the present invention include both eukaryotic (e.g., pol I, II, or III) and prokaryotic promoters, and inducible or non-inducible (i.e., constitutive) promoters, such as, for example, Moloney murine leukemia virus promoters, metallothionein promoters, the glucocorticoid promoter, Drosophila actin 5C distal promoter, SV40 promoter, heat shock protein 65 promoter, heat shock protein 70 promoter, immunoglobulin promoters, mouse polyoma virus promoter (Py), Rous sarcoma Virus (RSV), herpes simplex virus (HSV) promoter, BK virus and JC virus promoters, mouse mammary tumor virus (MMTV) promoter, alphavirus junction region, CMV promoter, Adenovirus E1 or VA1RNA promoters, rRNA promoters, tRNA methionine promoter, CaMV 35S promoter, nopaline synthetase promoter, tetracycline responsive promoter, and the lac promoter.

Within yet other embodiments of the invention, inducible promoters may be utilized. For example, within one embodiment inducible promoters are provided which initiate the synthesis of RNA from DNA, comprising a core RNA polymerase promoter sequence, and an operably linked nucleic acid sequence that directs the DNA binding of a transcriptional activator protein, and an operably linked nucleic acid sequence that directs the DNA binding of a transcriptional repressor protein. Within a further embodiment, the nucleic acid sequence that directs the DNA binding of a transcriptional activator protein is a sequence that binds a tetracycline repressor/VP16 transactivator fusion protein. Within yet another embodiment, the nucleic acid sequence that directs the DNA binding of a transcription repressor protein is a sequence that binds a lactose repressor/Kruppel domain fusion protein.

The second layer comprises an autocatalytic vector construct which is capable of expressing one or more heterologous nucleotide sequences and of directing its own replication in a cell, either autonomously or in response to one or more factors (e.g. is inducible). The second layer may be of viral or non-viral origin. Within one. embodiment of the invention, the second layer construct may be an alphavirus vector construct as described above.

A wide variety of vector systems may be utilized as the first layer of the eukaryotic layered vector initiation system, including for example, viral vector, constructs developed from DNA viruses such as those classified in the Poxviridae, including for example canary pox virus or vaccinia virus (e.g., Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330 and 5,017,487; WO 89/01973); Papoviridae such as BKV, JCV or SV40 (e.g., Mulligan et al., *Nature* 277:108–114, 1979); Adenoviridae, such as adenovirus (e.g., Berkner, *Biotechniques* 6:616–627, 1988; Rosenfeld et al., *Science* 252:431–434, 1991); Parvoviridae, such as adeno-associated virus (e.g., Samulski et al., *J. Vir.* 63:3822–3828, 1989; Mendelson et al., *Virol.* 166:154–165, 1988; PA 7/222,684); Herpesviridae, such as Herpes Simplex Virus (e.g., Kit, *Adv. Exp. Med. Biol.* 215:219–236, 1989); and Hepadnaviridae (e.g., HBV), as well as certain RNA viruses which replicate through a DNA intermediate, such as the Retroviridae (see, e.g., U.S. Pat. No. 4,777,127, GB 2,200,651, EP 0,345,242 and WO91/02805; Retroviridae include leukemia in viruses such as MoMLV and immunodeficiency viruses such as HIV, e.g., Poznansky, *J. Virol.* 65:532–536, 1991).

Similarly, a wide variety of vector systems may be utilized as second layer of the eukaryotic layered vector initiation system, including for example, vector systems derived from viruses of the following families: Picornaviridae (e.g., poliovirus, rhinovirus, coxsackieviruses), Caliciviridae, Togaviridae (e.g., alphavirus, rubella), Flaviviridae (e.g., yellow fever, HCV), Coronaviridae (e.g., HCV, TGEV, IBV, MHV, BCV), Bunyaviridae, Arenaviridae, Retroviridae (e.g., RSV, MoMLV, HIT, HTLV), hepatitis delta virus and Astrovirus. In addition, non-mammalian RNA viruses (as well as components derived therefrom) may also be utilized, including for example, bacterial and bacteriophage replicases, as well as components derived from plant viruses, such as potexviruses (e.g., PVX), carlaviruses (e.g., PVM), tobraviruses (e.g., TRV, PEBV, PRV), Tobamoviruses (e.g., TMV, ToMV, PPMV), luteoviruses (e.g., PLRV), potyviruses (e.g., TEV, PPV, PVY), tombusviruses (e.g., CyRSV), nepoviruses (e.g., GFLV), bromoviruses (e.g., BMV), and topamoviruses.

The replication competency of the autocatalytic vector construct, contained within the second layer of the eukaryotic vector initiation system, may be measured by a variety of assays known to one of skill in the art including, for example, ribonuclease protection assays which measure increases of both positive-sense and negative-sense RNA in transfected cells over time, in the presence of an inhibitor of cellular RNA synthesis, such as dactinomycin, and also assays which measure the synthesis of a subgenomic RNA or expression of a heterologous reporter gene in transfected cells.

Within particularly preferred embodiments of the invention, eukaryotic layered vector initiation systems are provided that comprise a 5' promoter which is capable of initiating in vivo the synthesis of alphavirus RNA from cDNA (i.e., a DNA promoter of RNA synthesis), followed by a 5' sequence which is capable of initiating transcription of an alphavirus RNA, a nucleic acid sequence which operably encodes all four alphaviral nonstructural proteins (including a nucleic acid molecule as described above which, when operably incorporated into a recombinant alphavirus particle, results in the desired phenotype), an alphavirus RNA polymerase recognition sequence, and a 3' sequence which controls transcription termination/polyadenylation. In addition, a viral junction region which is operably linked to a heterologous sequence to be expressed may be included. Within various embodiments the viral junction region may be modified, such that viral transcription of the subgenomic fragment is increased. reduced, or inactivated. Within other embodiments, a second viral junction region may be inserted following the first inactivated viral junction region, the second viral junction region being either active or modified such that viral transcription of the subgenomic fragment is increased or reduced.

Following in vivo transcription of the eukaryotic layered vector initiation system, the resulting alphavirus RNA vector replicon molecule is comprised of a 5' sequence which is capable of initiating transcription of an alphavirus RNA, a nucleotide sequence encoding biologically active alphavirus nonstructural proteins, a viral junction region, a heterologous nucleotide sequence, an alphavirus RNA polymerase recognition sequence, and a polyadenylate sequence.

Various aspects of the alphavirus cDNA vector constructs have been discussed above, including the 5' sequence which is capable of initiating transcription of an alphavirus, the nucleotide sequence encoding alphavirus nonstructural proteins, the viral junction region, including junction regions which have been inactivated such that viral transcription of the subgenomic fragment is prevented, and the alphavirus RNA polymerase recognition sequence. In addition, modified junction regions and tandem junction regions have also been discussed above.

In another embodiment of the invention, the eukaryotic layered vector initiation system is derived from an alphavirus vector, such as a Sindbis vector construct, which has been adapted to replicate in one or more cell lines from a particular eukaryotic species, especially a mammalian species, such as humans. For instance, if the gene encoding the recombinant protein to be expressed is of human origin and the protein is intended for human therapeutic use, production in a suitable human cell line may be preferred in order that the protein be post-translationally modified as would be expected to occur in humans. This approach may be useful in further enhancing recombinant protein production (as discussed in more detail below). Given the overall plasticity of an alphaviral genome due to the infidelity of the viral replicase, variant strains with an enhanced ability to establish high titer productive infection in selected eukaryotic cells (e.g., human, murine, canine, feline, etc.) can be isolated. Additionally, variant alphaviral strains having an enhanced ability to establish high titer persistent infection in eukaryotic cells may also be isolated using this approach. Alphavirus expression vectors can then be constructed from cDNA clones of these variant strains according to procedures provided herein.

Within another embodiment of the invention, the eukaryotic layered vector initiation system comprises a promoter for initial alphaviral vector transcription that is transcriptionally active only in a differentiated cell type. Briefly, it is well established that alphaviral infection of mammalian cells in culture, such as those derived from hamster (e.g., baby hamster kidney cells) or chicken (e.g., chicken embryo fibroblasts), typically results in cytoxicity. Thus, to produce a stably transformed or transfected host cell line, the eukaryotic layered vector initiation system may be introduced into a host cell wherein the promoter which enables the initial vector amplification is a transcriptionally inactive, but inducible, promoter. In a particularly preferred embodiment, such a promoter is differentiation state dependent. In this configuration, activation of the promoter and subsequent activation of the alphavirus DNA vector coincides with induction of cell differentiation. Upon growth to a certain cell number of such a stably transformed or transfected host cell line, the appropriate differentiation stimulus is provided, thereby initiating transcription of the vector construct and amplified expression of the desired gene and encoded polypeptide(s). Many such differentiation state-dependent promoters are known to those in the art, as are cell lines which can be induced to differentiate by application of a specific stimulus. Representative examples include cell lines F9 and P19, HL60, and Freund erythroleukemic cell lines and HEL, which are activated by retinoic acid, horse serum, and DMSO, respectively.

In a preferred embodiment, such promoters can be regulated by two separate components. For example, as described in Example 7, binding sites for both a transcriptional activator and a transcriptional repressor are positioned adjacent to a "core" promoter, in an operably-dependent manner. In this configuration, the uninduced state is maintained by blocking the ability of the transcriptional activator to find its recognition site, while allowing the transcriptional repressor to be constitutively expressed and bound to its recognition site. Induction is permitted by blocking the transcriptional repressor and removing the transactivator block. For example, a tetracycline-responsive promoter system (Gossen and Bujard, *Proc. Natl. Acad Sci.* 89:5547–5551, 1992) may be utilized for inducible transcription of an alphavirus vector RNA. In this system, the expression of a tetracycline repressor and HSV-VP16 transactivator domain, as a "fusion" protein (rTA), stimulates in vivo transcription of the alphavirus vector RNA by binding specifically to a tetracycline operator sequence (tetO) located immediately adjacent to a minimal "core" promoter (for example, CMV). The binding and transactivation event is reversibly blocked by the presence of tetracycline, and may be "turned on" by removing tetracycline from the culture media. As uninduced basal levels of transcription will vary among different cell types, other different minimal core promoters (for example HSV-tk) may be linked to the tetracycline operator sequences, provided the transcription start site is known, to allow juxtaposition at or in the immediate proximity of alphavirus vector nucleotide 1.

The rTA transactivator can be provided by an additional expression cassette also stably transformed into the same cell line; and in certain embodiments, the rTA expression cassette may itself be autoregulatory. The use of an autoregulatory rTA expression cassette circumvents potential toxicity problems associated with constitutive high level expression of rTA by linking expression to transcriptional control by the same tetO-linked promoter to which rTA itself binds. This type of system creates a negative feedback cycle that ensures very little rTA is produced in the presence of tetracycline, but becomes highly active when the tetracycline is removed. Such an autoregulatory rTA expression cassette is provided in plasmid pTet-tTAk (Shockett et al., *Proc. Natl. Acad. Sci. USA* 92:6522–6526, 1995).

For transcriptional repression, the KRAB repression domain of a certain zinc finger proteins can also be utilized. Briefly, KRAB (Krüppel-associated box) domains are highly conserved sequences present in the amino-terminal regions of more than one-third of all Krüppel-class $Cys_2His_2$ zinc finger proteins. The domains contain two predicted amphipathic α-helicies and have been shown to function as DNA binding-dependent RNA polymerase II transcriptional repressors (for example, Licht et al., *Nature* 346: 76–79, 1990). Like other transcription factors, the active repression domain and the DNA-binding domain are distinct and separable. Therefore, the repression domain can be linked as a fusion protein to any sequence specific DNA binding protein for targeting. Thus, the DNA binding protein component can be reversibly prevented from binding in a regulatable fashion, thereby turning "off" the transcriptional silencing. For example, the KRAB domain from human Kox1 (Thiesen, *New Biol.* 2:363–374, 1990) can be fused to the DNA-binding lactose (lac) repressor protein, forming a hybrid transcriptional silencer with reversible, sequence-specific binding to a lac operator sequence engineered immediately adjacent to the tet-responsive promoter. In this configuration, constitutive expression of the lac repressor/ KRAB domain fusion (rKR) will result in binding to the lac operator sequence and the elimination of any "leaky" basal transcription from the uninduced tet-responsive promoter. When vector expression is desired and tetracycline is removed from the system, IPTG is added to prevent rKR-mediated transcriptional silencing.

In addition, KRAB domains from other zinc finger proteins, for example, ZNF133 (Tommerup et al., *Hum. Mol. Genet.* 2:1571–1575, 1993), ZNF91 (Bellefroid et al., *EMBO J.* 12:1363–1374, 1993), ZNF2 (Rosati et al., *Nucleic Acids Res.* 19:5661–5667, 1991), as well as other transferable repressor domains, for example, Drosophila en or eve genes (Jaynes and O'Farrell, *EMBO J.* 10:1427–1433, 1991; Han and Manley, *Genes Dev.* 7:491–503, 1993), human zinc finger protein YY1 (Shi et al., *Cell* 67:377–388, 1991), Wilms' tumor suppressor protein WT1 (Madden et al., *Science* 253:1550–1553, 1991), thyroid hormone receptor (Baniahmad et al., *EMBO J.* 11:1015–1023, 1992), retinoic acid receptor (Baniahmad et al., ibid), Kid-1 (Witzgall et al., *Proc. Natl. Acad. Sci. USA* 91:4514–4518, 1994), can likewise be readily used in the gene delivery vehicles provided herein. Furthermore, the lac repressor/lac operator component of this system may be substituted by any number of other regulatable systems derived from other sources, for example, the tryptophan and maltose operons, or GAL4.

E. Recombinant Alphavirus Particles, and Generation and Use of 'Empty' Togavirus Particles or Togaviruses Particles Containing Non-homologous Viral RNA Within another aspect of the present invention, the generation of recombinant alphavirus particles containing RNA alphavirus vectors, which are capable of infection of eukaryotic target cells, are described. Briefly, such recombinant alphavirus particles generally comprise one or more alphavirus structural proteins, a lipid envelope, and an RNA vector replicon as described herein.

Methods for generating recombinant alphavirus vector particles may be readily accomplished by, for example, co-transfection of complementing vector and defective helper (DH) molecules derived from in vitro transcribed RNA, or, alternatively, plasmid DNA, or by coinfection with virus (see Xiong et al., Science 25 243:1188–1191, 1989, Bredenbeek et al., J. Virol. 67:6439–6446, 1993, Dubensky et al., J. Virol 70:508–519, 1996 and Dubensky et al., W/O 95/07994).

Within other aspects, methods for generating recombinant alphavirus vector particles from alphavirus-derived packaging or producer cell lines are provided. Briefly, such PCL and their stably transformed structural protein expression cassettes can be derived using methods described within W/O 95/07994, or using novel methods described within this invention. For example, the production of recombinant alphavirus vector particles by PCL can be accomplished following introduction of alphavirus-based vector molecules with desirable properties into the PCL (see Example 6), the vectors being derived from in vitro transcribed RNA, plasmid DNA, or previously obtained recombinant alphavirus particles. In yet a further example, production of recombinant particles from alphavirus vector producer cell lines is described (see Example 7).

Within other embodiments, methods are provided for producing high-titer stable togavirus capsid particles that do not contain any genomic RNA (i.e., contain substantially no viral RNA) or RNA Vector Replicons. As utilized within the present invention, it should be understood that "substantially no" genomic or RNA Vector Replicon nucleic acids refers to ratios of greater than 10:1, and preferably greater than 15:1 of $^{35}S$ methionine versus $^3H$ uridine incorporation into virus particles (as compared to wild-type) (see, e.g., Example 8 and FIG. 38). For example, within one embodiment empty capsid particles (preferably with the lipid bilayer and lycoprotein complement) are constructed from a selected pathogenic virus from the togavirus family (such as an Alphavirus or Rubivirus), and used as immunogens to establish protective immunity against infection with the wild-type togavirus. The empty viral particles are a desirable immunogenic alternative, as they are unable to replicate and produce virus, yet are able to generate both cellular and humoral immune responses. Thus, utilizing the methods which are described in more detail in Example 8, empty capsid particles derived from togaviruses (with or without a lipid bilayer and glycoprotein complement) can be generated from a wide variety of togaviruses, including, but not limited to, alphaviruses (such as Sindbis Virus (e.g., SIN-1 or wild-type Sindbis virus), Venezuelan Equine Encephalitis virus, Ross River virus, Eastern Equine Encephalitis virus, Western Equine Encephalitis virus, and rubiviruses (e.g., rubella), In a second embodiment, sequences from heterologous viruses which encode peptides that bind to genomic viral RNA can be inserted into a defective helper (DH) expression cassette in the amino terminal region of the alphavirus capsid gene, which has been deleted of the sequences which encode the region of the protein that binds to the homologous alphavirus genomic RNA. For example, BHK cells can be electroporated with an alphavirus replicon RNA, a DH RNA containing a sequence that encodes a heterologous virus genomic RNA binding peptide and a replicon derived from the same heterologous virus. Thus, the alphavirus particles produced contain a genomic RNA from a heterologous virus, and possess the host-range tropism of the alphavirus. As one possible example, gag sequences encoding proteins required for retrovirus RNA binding are included in the DH expression cassette construct. In this configuration, the resulting alphavirus particles would contain retrovirus vector RNA.

F. Heterologous Sequences

As noted above, a wide variety of nucleotide sequences may be carried and expressed by the gene delivery vehicles of the present invention. Preferably, the nucleotide sequences should be of a size sufficient to allow production of viable virus. Within the context of the present invention, the production of any measurable titer by recombinant alphavirus particles, for example, by plaque assay, luciferase assay, or β-galactosidase assay of infectious virus on appropriate susceptible monolayers, or the expression of detectable levels of the heterologous gene product by RNA or DNA vectors, is considered to be "production of viable virus." This may be, at a minimum. an alphavirus vector construct which does not contain any additional heterologous sequence. However, within other embodiments, the vector construct may contain additional heterologous or foreign sequences. Within preferred embodiments, the heterologous sequence can comprise a heterologous sequence of at least about 1.00 bases, 2 kb, 3.5 kb, 5 kb, 7 kb, or even a heterologous sequence of at least about 8 kb.

As will be evident to one of ordinary skill in the art given the disclosure provided herein, the efficiency of recombinant alphavirus particle packaging and hence, viral titer, is to some degree dependent upon the size of the sequence to be packaged. Thus, in order to increase the efficiency of packaging and the production of viable virus, additional noncoding sequences may be added to the vector construct. Moreover, within certain embodiments of the invention it may be desired to increase or decrease viral titer. This increase or decrease may be accomplished by increasing or decreasing the size of the heterologous sequence, and hence the efficiency of packaging.

As briefly noted above, a wide variety of heterologous sequences may be included within the gene delivery vehicles described herein including, for example, sequences which encode palliatives such as lymphokines or cytokines, toxins, prodrug converting enzyme, antigens which stimulate an immune response, ribozymes, proteins for therapeutic application such as growth or regulatory factors, and proteins which assist or inhibit an immune response, as well as antisense sequences (or sense sequences for "antisense applications"). In addition, as discussed above, the gene delivery vehicles provided herein may contain (and express, within certain embodiments) two or more heterologous sequences.

1. Lymphokines

Within one embodiment of the invention, the heterologous sequence encodes a lymphokine. Briefly, lymphokines act to proliferate, activate, or differentiate immune effectors cells. Representative examples of lymphokines include gamma interferon, tumor necrosis factor, IL-1, IL-2, IL-3, IL4, IL-5, IL-6, IL-7, IL-8, IL-9, IL-10, IL-11, IL-12, IL-13, IL-14, IL-15, GM-CSF, CSF-1 and G-CSF.

Within related embodiments of the invention the heterologous sequence encodes an immunomodulatory cofactor. Briefly, as utilized within the context of the present invention, "immunomodulatory cofactor" refers to factors which, when manufactured by one or more of the cells involved in an immune response, or when added exogenously to the cells, causes the immune response to be different in quality or potency from that which would have occurred in the absence of the cofactor. The quality or potency of a response may be measured by a variety of assays known to one of skill in the art including, for example, in vitro assays which measure cellular proliferation (e.g., $^3$H thymidine uptake), and in vitro cytotoxic assays (e.g., which measure $^{51}$Cr release) (see Warner et al., *AIDS Res. and Human Retroviruses* 7:645–655, 1991).

Representative examples of immunomodulatory co-factors include alpha interferon (Finter et al., *Drugs* 42(5):749–765, 1991; U.S. Pat. Nos. 4,892,743; 4,966,843; WO 85/02862; Nagata et al., *Nature* 284:316–320, 1980; Familletti et al., *Methods in Enz.* 78:387–394, 1981 Twu et al., *Proc. Natl. Acad. Sci. USA* 86:2046–2050, 1989; Faktor et al., *Oncogene* 5:867–872, 1990), beta interferon (Seif et al., *J. Virol.* 65:664–671, 1991), gamma interferons (Radford et al., *American Society of Hepatology:*2008–2015, 1991; Watanabe et al., *PNAS* 86:9456–9460, 1989; Gansbacher et al., *Cancer Research* 50:7820–7825, 1990; Maio et al., *Can. Immunol. Immunother* 30:3442, 1989; U.S. Pat. Nos. 4,762,791 and 4,727,138), G-CSF (U.S. Pat. Nos. 4,999,291 and 4,810,643), GM-CSF (WO 85/04188), TNFs (Jayaraman et al., *J. Immunology* 144:942–951, 1990), Interleukin-2 (IL-2) (Karupiah et al., *J. Immunology* 144:290–298, 1990; Weber et al., *J. Exp. Med.* 166:1716–1733, 1987; Gansbacher et al., *J. Exp. Med.* 172:1217–1224, 1990; U.S. Pat. No. 4,738,927), IL4 (Tepper et al., *Cell* 57:503–512, 1989; Golumbek et al., *Science* 254:713–716, 1991; U.S. Pat. No. 5,017,691), IL-6 (Brakenhof et al., *J. Immunol.* 139:4116–4121, 1987; WO 90/06370), IL-12, IL-15 (Grabstein et al., *Science* 264:965–968, 1994; Genbank-EMBL Accession No. V03099), ICAM-1 (Altman et al., *Nature* 338:512–514, 1989), ICAM-2, LFA-1. LFA-3, MHC class I molecules, MHC class II molecules, $_2$-microglobulin. chaperones, CD3. B7/BB1, MHC linked transporter proteins or analogues thereof.

The choice of which immunomodulatory cofactor to include within a alphavirus vector construct may be based upon known therapeutic effects of the cofactor, or experimentally determined. For example, in chronic hepatitis B infections alpha interferon has been found to be efficacious in compensating a patient's immunological deficit and thereby assisting recovery from the disease. Alternatively, a suitable immunomodulatory cofactor may be experimentally determined. Briefly, blood samples are first taken from patients with a hepatic disease. Peripheral blood lymphocytes (PBLs) are restimulated in vitro with autologous or HLA-matched cells (e.g., EBV transformed cells), and transduced with an alphavirus vector construct which directs the expression of an immunogenic portion of a hepatitis antigen and the immunomodulatory cofactor. Stimulated PBLs are used as effectors in a CTL assay with the HLA-matched transduced cells as targets. An increase in CTL response over that seen in the same assay performed using HLA-matched stimulator and target cells transduced with a vector encoding the antigen alone, indicates a useful immunomodulatory cofactor. Within one embodiment of the invention, the immunomodulatory cofactor gamma interferon is particularly preferred.

Another example of an immunomodulatory cofactor is the B7/BB1 costimulatory factor. Briefly, activation of the full functional activity of T cells requires two signals. One signal is provided by interaction of the antigen-specific T cell receptor with peptides which are bound to major histocompatibility complex (MHC) molecules, and the second signal, referred to as costimulation is delivered to the T cell by antigen-presenting cells. The second signal is required for interleukin-2 (IL-2) production by T cells and appears to involve interaction of the B7/BB1 molecule on antigen-presenting cells with CD28 and CTLA-4 receptors on T lymphocytes (Linsley et al., *J. Exp. Aced.* 173:721–730, 1991a, and *J. Exp. Med.* 174:561–570, 1991). Within one embodiment of the invention, B7/BB1 may be introduced into tumor cells in order to cause costimulation of CD8$^+$ T cells, such that the CD8$^+$ T cells produce enough IL-2 to expand and become fully activated. These CD8$^+$ T cells can kill tumor cells that are not expressing B7 because costimulation is no longer required for further CTL function. Vectors that express both the costimulatory B7/BB1 factor and, for example, an immunogenic HBV core protein, may be made utilizing methods which are described herein. Cells transduced with these vectors will become more effective antigen-presenting cells. The HBV core-specific CTL response will be augmented from the fully activated CD8$^+$ T cell via the costimulatory ligand B7/BB 1.

2. Toxins

Within another embodiment of the invention, the heterologous sequence encodes a toxin. Briefly, toxins act to directly inhibit the growth of a cell. Representative examples of toxins include ricin (Lamb et al., *Eur. J. Biochem.* 148:265–270, 1985), abrin (Wood et al., *Eur. J. Biochem.* 198:723–732, 1991; Evensen et al., *J. of Biol. Chem.* 266:6848–6852, 1991; Collins et al., *J. of Biol. Chem.* 265:8665–8669, 1990; Chen et al., *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez and Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), antiviral protein (Barbieri et al., *Biochem. J.* 203:55–59, 1982; Irvin et al., *Arch. Biochem. & Biophys.* 200:418–425, 1980; Irvin, *Arch. Biochem. & Biophys.* 169:522–528, 1975), tritin, Shigella toxin (Calderwood et al., *PNAS* 84:43644368, 1987; Jackson et al., *Microb. Path.* 2:147–153, 1987), Pseudomonas exotoxin A (Carroll and Collier, *J. Biol. Chem.* 262:8707–8711, 1987), herpes simplex virus thymidine kinase (HSVTK) (Field et al., *J. Gen. Virol.* 49:115–124, 1980), and *E. coli,* guanine phosphoribosyl transferase.

3. Prodrug Converting Enzymes

Within other embodiments of the invention, the heterologous sequence encodes a prodrug converting enzyme. Briefly, as utilized within the context of the present invention, a prodrug converting enzyme refers to a gene product that activates a compound with little or no cytotoxicity into a toxic product (the prodrug). Representative examples of such gene products include HSVTK and VZVTK (as well as analogues and derivatives thereof), which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAU, FIAC, DHPG) to HSVTK phosphorylates the drug into its corresponding active nucleotide triphosphate form.

Representative examples of other prodrug converting enzymes which can also be utilized within the context of the present invention include: *E. coli* guanine phosphoribosyl transferase which converts thioxanthine into toxic thioxanthine monophosphate (Besnard et al., *Mol. Cell. Biol.* 7:4139–4141, 1987); alkaline phosphatase, which converts inactive phosphorylated compounds such as mitomycin phosphate and doxorubicin-phosphate into toxic dephosphorylated compounds; fungal (e.g., *Fusarium oxysporum*) or bacterial cytosine deaminase, which converts 5-fluorocytosine to the toxic compound 5-fluorouracil (Mullen, *PNAS* 89:33, 1992); carboxypeptidase G2, which cleaves the glutamic acid from para-N-bis (2-chloroethyl) aminobenzoyl glutamic acid, thereby creating a toxic benzoic acid mustard; and Penicillin-V amidase, which converts phenoxyacetabide derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990).

4. Antisense Sequences

Within another embodiment of the invention, the heterologous sequence is an antisense sequence. Briefly, antisense sequences are designed to bind to RNA transcripts, and thereby prevent cellular synthesis of a particular protein or prevent use of that RNA sequence by the cell. Representative examples of such sequences include antisense thymidine kinase, antisense dihydrofolate reductase (Maher and Dolnick, *Arch. Biochem. & Biophys.* 253:214–220, 1987; Bzik et al., *PNAS* 84:8360–8364, 1987), antisense HER2 (Coussens et al., *Science* 230:1132–1139, 1985), antisense ABL (Fainstein et al., *Oncogene* 4:1477–1481, 1989), antisense Myc (Stanton et al., *Nature* 310:423–425, 1984) and antisense ras, as well as antisense sequences which block any of the cell cycle signaling components (e.g., cyclins, cyclin-dependent kinases, cyclin-dependent kinase inhibitors) or enzymes in the nucleotide biosynthetic pathway. In addition, within other embodiments of the invention antisense sequences to interferon and 2 microglobulin may be utilized in order to decrease immune response.

In addition, within a further embodiment of the invention, antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon) due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

5. Ribozymes

Within other aspects of the present invention, gene delivery vehicles are provided which produce ribozymes upon infection of a host cell. Briefly, ribozymes are used to cleave specific RNAs and are designed such that it can only affect one specific RNA sequence. Generally, the substrate binding sequence of a ribozyme is between 10 and 20 nucleotides long. The length of this sequence is sufficient to allow a hybridization with target RNA and disassociation of the ribozyme from the cleaved RNA.

A wide variety of ribozymes may be utilized within the context of the present invention, including for example, Group I intron ribozymes (Cech et al., U.S. Pat. No. 4,987,071); hairpin ribozymes (Hampel et al., *Nucl. Acids Res.* 18:299–304, 1990, U.S. Pat. No. 5,254,678 and European Patent Publication No. 0 360 257), hammerhead ribozymes (Rossi, J. J. et al., *Pharmac. Ther.* 50:245–254, 1991; Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988), hepatitis delta virus ribozymes (Perrotta and Been, *Biochem.* 31:16, 1992); RNase P ribozymes (Takada et al., *Cell* 35:849, 1983); as well as other types of ribozymes (see e.g., WO 95/29241. and WO 95/31551). Further examples of ribozymes include those described in U.S. Pat. Nos. 5,116, 742, 5,225,337 and 5,246,921.

6. Proteins and Other Cellular Constituents

Within other aspects of the present invention, a wide variety of proteins or other cellular constituents may be carried and/or expressed by the gene delivery vehicles provided herein. Representative examples of such proteins include native or altered cellular components, as well as foreign proteins or cellular constituents, found in for example, viruses, bacteria, parasites or fungus.

a. Altered Cellular Components

Within one embodiment, gene delivery vehicles are provided which direct the expression of an immunogenic, non-tumorigenic, altered cellular component (see, e.g., WO 93/10814). As utilized herein, the term "immunogenic" refers to altered cellular components which are capable, under the appropriate conditions, of causing an immune response. This response must be cell-mediated, and may also include a humoral response. The term "non-tumorigenic" refers to altered cellular components which will not cause cellular transformation or induce tumor formation in nude mice. The phrase "altered cellular component" refers to proteins and other cellular constituents which are either associated with rendering a cell tumorigenic, or are associated with tumorigenic cells in general, but are not required or essential for rendering the cell tumorigenic.

Briefly, before alteration, the cellular components may be essential to normal cell growth and regulation and include, for example, proteins which regulate intracellular protein degradation, transcriptional regulation, cell-cycle control, and cell-cell interaction. After alteration, the cellular components no longer perform their regulatory functions and, hence, the cell may experience uncontrolled growth. Representative examples of altered cellular components include ras*, p53*, Rb*, altered protein encoded by the Wilms' tumor gene, ubiquitin*, mucin*, protein encoded by the DCC, APC, and MCC genes, the breast cancer gene BRCA1*, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Once a sequence encoding the altered cellular component has been obtained, it is necessary to ensure that the sequence encodes a non-tumorigenic protein. Various assays which assess the tumorigenicity of a particular cellular component are known and may easily be accomplished. Representative assays include a rat fibroblast assay, tumor formation in nude mice or rats, colony formation in soft agar, and preparation of transgenic animals, such as transgenic mice.

Tumor formation in nude mice or rats is a particularly important and sensitive method for determining the tumorigenicity of a particular cellular component. Nude mice lack a functional cellular immune system (i.e., do not possess CTLs), and therefore provide a useful in vivo model in which to test the tumorigenic potential of cells. Normal non-tumorigenic cells do not display uncontrolled growth properties if infected into nude mice. However, transformed cells will rapidly proliferate and generate tumors in nude mice. Briefly, in one embodiment an alphavirus vector construct is administered to syngeneic murine cells, followed by injection into nude mice. The mice are visually examined for a period of 2 to 8 weeks after injection in order to determine tumor growth. The mice may also be sacrificed and autopsied in order to determine whether tumors are present. (Giovanella et al., *J. Natl. Cancer Inst.* 48:1531–1533, 1972; Furesz et al., *Abnormal Cells, New Products and Risk,* Hopps and Petricciani (eds.), Tissue Culture Association, 1985; and Levenbook et al., *J. Biol. Std.* 13:135–141, 1985.)

Tumorigenicity may also be assessed by visualizing colony formation in soft agar (Macpherson and Montagnier, *Virol.* 23:291–294, 1964). Briefly, one property of normal non-tumorigenic cells is "contact inhibition" (i.e., cells will stop proliferating when they touch neighboring cells). If cells are plated in a semi-solid agar support medium, normal cells rapidly become contact inhibited and stop proliferating, whereas tumorigenic cells will continue to proliferate and form colonies in soft agar.

If the altered cellular component is associated with making the cell tumorigenic, then it is necessary to make the altered cellular component non-tumorigenic. For example, within one embodiment the sequence or gene of interest which encodes the altered cellular component is truncated in order to render the gene product non-tumorigenic. The gene encoding the altered cellular component may be truncated to a variety of sizes, although it is preferable to retain as much as possible of the altered cellular component. In addition, it is necessary that any truncation leave intact at least some of the immunogenic sequences of the altered cellular component Alternatively, multiple translational termination codons may be introduced downstream of the immunogenic region. Insertion of termination codons will prematurely terminate protein expression, thus preventing expression of the transforming portion of the protein.

As noted above, in order to generate an appropriate immune response, the altered cellular component must also be immunogenic. Immunogenicity of a particular sequence is often difficult to predict, although T cell epitopes often possess an immunogenic amphipathic alpha-helix component. In general, however, it is preferable to determine immunogenicity in an assay. Representative assays include an ELISA, which detects the presence of antibodies against the newly introduced vector, as well as assays which test for T helper cells such as gamma-interferon assays, IL-2 production assays, and proliferation assays.

As noted above, within another aspect of the present invention, several different altered cellular components may be co-expressed in order to form a general anti-cancer therapeutic. Generally, it will be evident to one of ordinary skill in the art that a variety of combinations can be made. Within preferred embodiments, this therapeutic may be targeted to a particular type of cancer. For example, nearly all colon cancers possess mutations in ras, p53, DCC APC or MCC genes. An alphavirus vector construct which co-expresses a number of these altered cellular components may be administered to a patient with colon cancer in order to treat all possible mutations. This methodology may also be utilized to treat other cancers. Thus, an alphavirus vector construct which co-expresses mucin*, ras*, neu, BRCA1* and p53* may be utilized to treat breast cancer.

b. Antigens from Foreign Organisms or Other Pathogens

Within other aspects of the present invention. vectors are provided which direct the expression of immunogenic portions of antigens from foreign organisms or other pathogens. Representative examples of such antigens include bacterial antigens (e.g., *E. coli,* streptococcal, staphylococcal, mycobacterial, etc.), fungal antigens, parasitic antigens, and viral antigens (e.g., influenza virus, Feline Leukemia Virus ("FeLV"), immunodeficiency viruses such as Feline Immunodeficiency Virus ("FIV") or Human Immunodeficiency Virus ("HIV"), Hepatitis A, B and C Virus ("HAV", "HBV" and "HCV", respectively), Respiratory Syncytial Virus, Human Papiloma Virus ("HPV"), Epstein-Barr Virus ("EBV"), Herpes Simplex Virus ("HSV"), Hantavirus, HTLV I, HTLV II and Cytomegalovirus ("CMV"). As utilized within the context of the present invention, "immunogenic portion" refers to a portion of the respective antigen which is capable, under the appropriate conditions, of causing an immune response (i.e., cell-mediated or humoral). "Portions" may be of variable size, but are preferably at least 9 amino acids long, and may include the entire antigen. Cell-mediated immune responses may be mediated through Major Histocompatability Complex ("MHC") class I presentation, MHC Class II presentation, or both.

Within one aspect of the invention, alphavirus vector constructs are provided which direct the expression of immunogenic portions of Hepatitis B antigens (see, e.g., WO 93/15207). The Hepatitis B virus presents several different antigens, including among others, three HB "S" antigens (HBsAgs), an HBc antigen (HBcAg), an HBe antigen (HBeAg), and an HBx antigen (HBxAg) (see Blum et al., *TIG* 5(5):154–158, 1989). Briefly, the HBeAg results from proteolytic cleavage of a P22 pre-core intermediate and is secreted from the cell. HBeAg is found in serum as a 17 kD protein. The HBcAg is a protein of 183 amino acids, and the HBxAg is a protein of 145 to 154 amino acids, depending on subtype.

The HBsAgs (designated "large," "middle" and "small") are encoded by three regions of the Hepatitis B genome: S, pre-S2 and pre-S1. The large protein, which has a length varying from 389 to 400 amino acids, is encoded by pre-S1, pre-S2, and S regions, and is found in glycosylated and non-glycosylated forms. The middle protein is 281 amino acids long and is encoded by the pre-S2 and S regions. The small protein is 226 amino acids long and is encoded by the S region. It exists in two forms, glycosylated (GP $27^s$) and non-glycosylated (P$24^s$). If each of these regions are expressed separately, the pre-S1 region will code for a protein of approximately 119 amino acids, the pre-S2 region will code for a protein of approximately 55 amino acids, and the S region will code for a protein of approximately 226 amino acids.

As will be evident to one of ordinary skill in the art, various immunogenic portions of the above-described S antigens may be combined in order to induce an immune response when administered by one of the alphavirus vector constructs described herein. In addition, due to the large immunological variability that is found in different geographic regions for the S open reading frame of HBV, particular combinations of antigens may be preferred for administration in particular geographic regions.

Also presented by HBV are pol ("HBV pol"), ORF 5, and ORF 6 antigens. Briefly, the polymerase open reading frame of HBV encodes reverse transcriptase activity found in virions and core-like particles in infected livers. The polymerase protein consists of at least two domains: the amino terminal domain which encodes the protein that primes reverse transcription, and the carboxyl terminal domain which encodes reverse transcriptase and RNase H activity. Immunogenic portions of HBV pol may be determined utilizing methods described herein, utilizing alphavirus vector constructs described below, and administered in order to generate an immune response within a warm-blooded animal. Similarly, other HBV antigens, such as ORF 5 and ORF 6 (Miller et al., *Hepatology* 9:322–327, 1989) may be expressed utilizing alphavirus vector constructs as described herein.

As noted above, at least one immunogenic portion of an antigen from a foreign organism is incorporated into a gene delivery vehicle. The immunogenic portion(s) which are incorporated into the gene delivery vehicles may be of varying length, although it is generally preferred that the portions be at least 9 amino acids long and may include the entire antigen. Immunogenicity of a particular sequence is often difficult to predict, although T cell epitopes may be predicted utilizing computer algorithms such as TSITES (MedImmune, Maryland), in order to scan coding regions for potential T-helper sites and CTL sites. From this analysis, peptides are synthesized and used as targets in an in vitro cytotoxic assay. Other assays, however, may also be utilized, including, for example, ELISA, which detects the presence of antibodies against the newly introduced vector, as well as assays which test for T helper cells. such as gamma-interferon assays, IL-2 production assays and proliferation assays.

Immunogenic portions may also be selected by other methods. For example, the HLA A2.1 transgenic mouse has been shown to be useful as a model for human T-cell recognition of viral antigens. Briefly, in the influenza and hepatitis B viral systems, the murine T cell receptor repertoire recognizes the same antigenic determinants recognized by human T cells. In both systems, the CTL response generated in the HLA A2.1 transgenic mouse is directed toward virtually the same epitope as those recognized by human CTLs of the HLA A2.1 haplotype (Vitiello et al., *J. Exp. Med.* 173:1007–1015, 1991; Vitiello et al., *Abstract of Molecular Biology of Hepatitis B Virus Symposia*, 1992).

As noted above, more than one immunogenic portion may be incorporated into the gene delivery vehicles. For example, a gene delivery vehicle may express (either separately or as one construct) all or immunogenic portions of HBcAg, HBeAg, HBsAgs, HBxAg, as well as immunogenic portions of the HCV antigens C, E1, E2, NS3, NS4, or NS5.

7. Sources for Heterologous Sequences

Sequences which encode the above-described proteins may be readily obtained from a variety of sources, including for example, depositories such as the American Type Culture Collection (ATCC, Rockville, Md.), or from commercial sources such as British Bio-Technology Limited (Cowley, Oxford, England). Representative examples include BBG 12 (containing the GM-CSF gene coding for the mature protein of 127 amino acids); BBG 6 (which contains sequences encoding gamma interferon), ATCC No. 39656 (which contains sequences encoding TNF), ATCC No. 20663 (which contain sequences encoding alpha interferon), ATCC Nos. 31902, 31902 and 39517 (which contains sequences encoding beta interferon), ATCC No 67024 (which contain a sequence which encodes Interleukin-1b); ATCC Nos. 39405, 39452, 39516, 39626 and 39673 (which contains sequences encoding Interleukin-2); ATCC Nos. 59399, 59398, and 67326 (which contain sequences encoding Interleukin-3); ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Sequences which encode altered cellular components as described above may be readily obtained from a variety of sources. For example, plasmids which contain sequences that encode altered cellular products may be obtained from a depository such as the American Type Culture Collection (ATCC, Rockville, Md.), or from commercial sources such as Advanced Biotechnologies (Columbia, Md.). Representative examples of plasmids containing some of the above-described sequences include ATCC No. 41000 (containing a G to T mutation in the 12th codon of ras), and ATCC No. 41049 (containing a G to A mutation in the 12th codon).

Alternatively, plasmids which encode normal cellular components may also be obtained from depositories such as the ATCC (see, for example, ATCC No. 41001, which contains a sequence which encodes the normal ras protein; ATCC No. 57103, which encodes abl; and ATCC Nos. 59120 or 59121, which encode the bcr locus) and mutated to form the altered cellular component. Methods for mutagenizing particular sites may readily be accomplished using methods known in the art (see Sambrook et al., supra., 15.3 et seq.). In particular, point mutations of normal cellular components such as ras may readily be accomplished by site-directed mutagenesis of the particular codon, for example, codons 12, 13 or 61.

Figure 3:
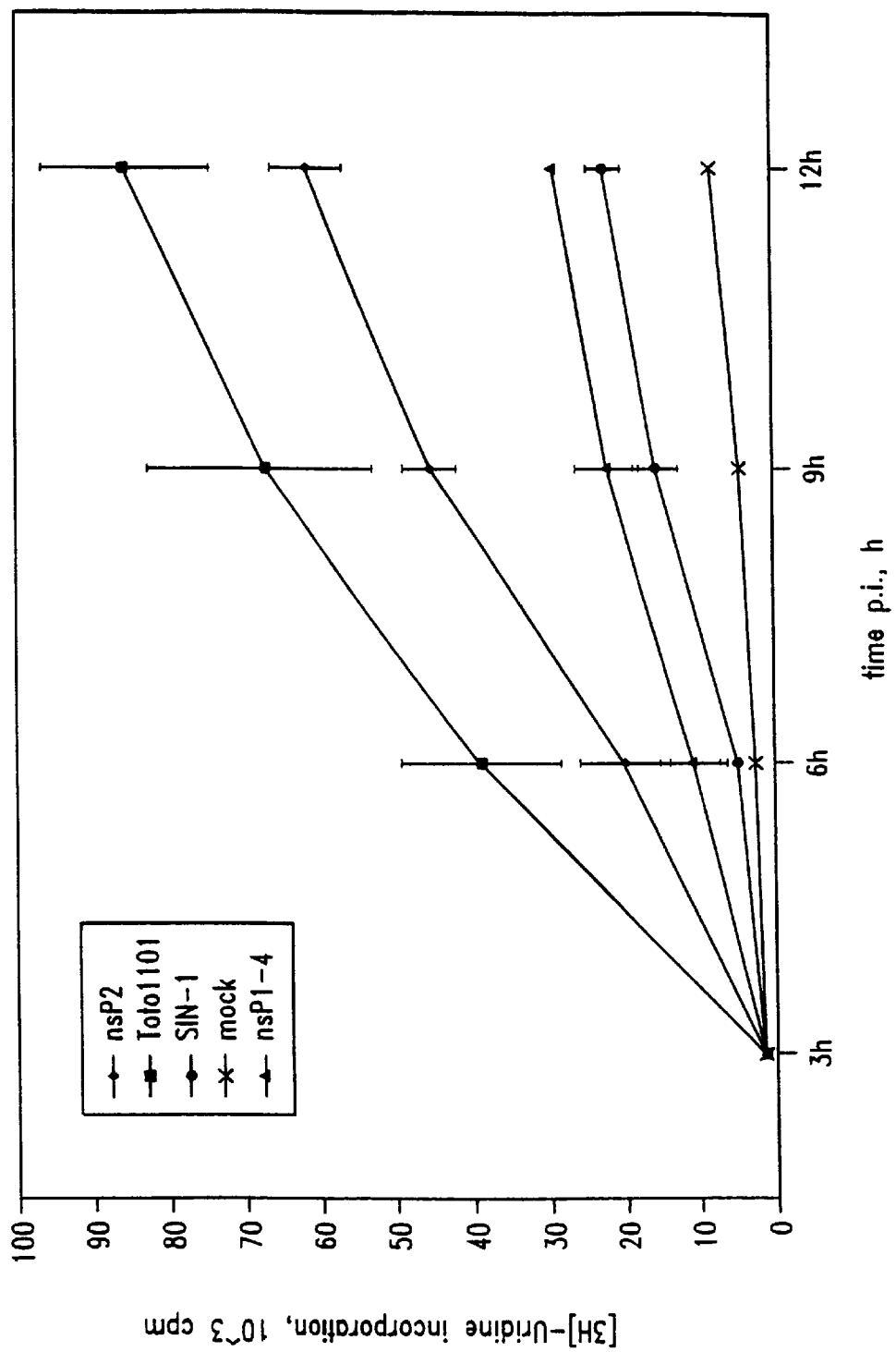
FIG. 3 is a graph depicting viral RNA synthesis in BHK cells following infection by Toto 1101, SIN-1/nsP2, SIN-1/nsP1–4, or SIN-1 virus. Cells were infected at an MOI 10 and at 1 hour post-infection, actinomycin D and $^3$H-uridine were added. At 3, 6, 9, and 12 hpi the amount of $^3$H-uridine incorporation was determined.

Sequences which encode the above-described viral antigens may likewise be obtained from a variety of sources. For example, molecularly viral cloned genes may be obtained from sources such as the American Type Culture Collection (ATCC, Rockville, Md.). For example, ATCC No. 45020 contains the total genomic DNA of hepatitis B (extracted from purified Dane particles) (see FIG. 3 of Blum et al., *TIG* 5(5):154–158, 1989) in the Bam HI site of pBR322 (Moriarty et al., *Proc. Natl. Acad. Sci. USA* 78:2606–2610, 1981).

Alternatively, cDNA sequences which encode the above-described heterologous sequences may be obtained from cells which express or contain the sequences. Briefly, within one embodiment, mRNA from a cell which expresses the gene of interest is reverse transcribed with reverse transcriptase using oligonucleotide dT or random primers. The single stranded cDNA may then be amplified by PCR (see U.S. Pat. Nos. 4,683,202; 4,683,195 and 4,800,159. See also *PCR Technology: Principles and Applications for DNA Amplification*, Erlich (ed.), Stockton Press, 1989) utilizing oligonucleotide primers complementary to sequences on either side of desired sequences. In particular, a double-stranded DNA is denatured by heating in the presence of heat stable Taq polymerase, sequence-specific DNA primers, dATP, dCTP, dGTP and dTTP. Double-stranded DNA is produced when synthesis is complete. This cycle may be repeated many times, resulting in a factorial amplification of the desired DNA.

Sequences which encode the above-described proteins may also be synthesized, for example, on an Applied Biosystems Inc. DNA synthesizer (e.g., APB DNA synthesizer model 392 (Foster City. Calif.)).

G. Alphavirus Packaging/Producer Cell Lines

Within further aspects of the invention, alphavirus packaging and producer cell lines are provided. In particular, within one aspect of the present invention, alphavirus packaging cell lines are provided wherein the viral structural proteins are supplied in trans from one or more stably transformed expression vectors, and are able to encapsidate transfected, transduced, or intracellularly produced vector RNA transcripts in the cytoplasm and release infectious packaged vector particles through the cell membrane. In preferred embodiments, the structural proteins necessary for packaging are synthesized at high levels only after induction by the RNA vector replicon itself or some other provided stimulus, and the transcripts encoding these structural proteins are capable of cytoplasmic amplification in a manner that will allow expression levels sufficient to mimic that of a natural viral infection. Furthermore, in other embodiments, expression of a selectable marker is operably linked to the structural protein expression cassette. Such a linked selectable marker allows efficient generation of functional, stably transformed PCL.

For example, alphavirus RNA vector replicon molecules of the desired phenotype to be packaged, which are themselves capable of autocatalytic replication in the cell cytoplasm, can be introduced into the packaging cells as in vitro transcribed RNA, recombinant alphavirus particles, or as alphavirus cDNA vector constructs. The RNA vector transcripts then replicate to high levels, stimulate amplification of the structural protein gene transcript(s) and subsequent protein expression, and are subsequently packaged by the viral structural proteins, yielding infectious vector particles. The intracellular expression of alphavirus proteins and/or vector RNA above certain levels may result in cytotoxic effects in packaging or producer cell lines. Therefore, within certain embodiments of the invention, it may be desirable for these elements to be derived from virus variants selected for reduced cytotoxicity of their expressed structural proteins, reduced inhibition of host macromolecular synthesis, and/or the ability to establish persistent infection.

To optimize vector packaging cell line performance and final vector titer, successive cycles of gene transfer and vector packaging may be performed. For example, supernatants containing infectious packaged vector particles derived from vector transfection of the packaging cell lines, can be used to infect or "transduce" a fresh monolayer or suspension culture of alphavirus packaging cells. Successive transductions with packaged vector particles and fresh packaging cells may be preferred over nucleic acid transfection because of its higher RNA transfer efficiency into cells, optimized biological placement of the vector in the cell, and ability to "scale-up" the process for vector production from increasingly larger numbers of packaging cells. This leads to higher expression and higher titer of packaged infectious recombinant alphavirus vector.

Within other aspects of the invention, a stably integrated or episomally maintained DNA expression vector can be used to produce the alphavirus vector RNA molecule within the cell. Briefly, such a DNA expression vector can be configured, in preferred embodiments, to be inducible, such that trancription of the alphavirus vector RNA occurs only when cells have been propagated to a desired density, and are subsequently induced. Once transcribed, the alphavirus vector maintains the ability to self-replicate autocatalytically and triggers a cascade of events that culminate in packaged vector particle production. This approach allows for continued vector expression over extended periods of culturing because the integrated DNA vector expression system is maintained through a drug or other selection marker and the DNA system, once induced, will constitutively express unaltered RNA vector replicons which cannot be diluted out by defective RNA copies. Production of larger-scale, high titer packaged alphavirus vector is possible in this alphavirus "producer cell line" configuration, the DNA-based alphavirus vector is introduced initially into the packaging cell line by transfection, since size restrictions could prevent packaging of the expression vector into a viral vector particle for transduction.

H. Pharmaceutical Compositions

As noted above, the present invention also provides pharmaceutical compositions comprising the gene delivery vehicles described herein in combination with a pharmaceutically acceptable carrier, diluent, or recipient. For example, within one embodiment, RNA or DNA vector constructs of the present invention can be lyophilized for long term storage and transport, and may be reconstituted prior to administration using a variety of substances, but are preferably reconstituted using water. In certain instances, dilute salt solutions which bring the final formulation to isotonicity may also be used. In addition, it may be advantageous to use aqueous solutions containing components which enhance the activity or physically protect the reconstituted nucleic acid preparation. Such components include cytokines, such as IL-2, polycations, such as protamine sulfate, lipid formulations, or other components. Lyophilized or dehydrated recombinant vectors may be reconstituted with any convenient volume of water or the reconstituting agents noted above that allow substantial, and preferably total solubilization of the lyophilized or dehydrated sample.

Recombinant alphavirus particles or infectious recombinant virus (both referred to as virus below) may be preserved either in crude or purified forms. In order to produce virus in a crude form, producing cells may first be cultivated in a bioreactor or flat stock culture, wherein viral particles are released from the cells into the culture media. Virus may then be preserved in crude form by first adding a sufficient amount of a formulation buffer to the culture media containing the recombinant virus to form an aqueous suspension. Within certain preferred embodiments, the formulation buffer is an aqueous solution that contains a saccharide, a high molecular weight structural additive, and a buffering component in water. The aqueous solution may also contain one or more amino acids.

The recombinant virus can also be preserved in a purified form. More specifically, prior to the addition of the formulation buffer, the crude recombinant virus described above may be clarified by passing it through a filter and then concentrated, such as by a cross flow concentrating system (Filtron Technology Corp., Nortborough, Mass.). Within one embodiment, DNase is added to the concentrate to digest exogenous DNA. The digest is then diafiltrated in order to remove excess media components and to establish the recombinant virus in a more desirable buffered solution. The diafiltrate is then passed over a Sephadex S-500 gel column and a purified recombinant virus is eluted. A sufficient amount of formulation buffer is then added to this eluate in order to reach a desired final concentration of the constituents and to minimally dilute the recombinant virus. The aqueous suspension may then be stored, preferably at −70° C., or immediately dried. As above, the formulation buffer may be an aqueous solution that contains a saccharide, a high molecular weight structural additive, and a buffering component in water. The aqueous-solution may also contain one or more amino acids.

Crude recombinant virus may also be purified by ion exchange column chromatography. Briefly, crude recombinant virus may be clarified by first passing it through a filter, followed by loading the filtrate onto a column containing a highly sulfonated cellulose matrix. The recombinant virus may then be eluted from the column in purified form by using a high salt buffer, and the high salt buffer exchanged for a more desirable buffer by passing the eluate over a molecular exclusion column. A sufficient amount of formulation buffer is then added, as discussed above, to the purified recombinant virus and the aqueous suspension is either dried immediately or stored, preferably at −70° C.

The aqueous suspension in crude or purified form can be dried by lyophilization or evaporation at ambient temperature. Briefly, lyophilization involves the steps of cooling the aqueous suspension below the gas transition temperature or below the eutectic point temperature of the aqueous suspension, and removing water from the cooled suspension by sublimation to form a lyophilized virus. Within one embodiment, aliquots of the formulated recombinant virus are placed into an Edwards Refrigerated Chamber (3 shelf RC3S unit) attached to a freeze dryer (Supermodulyo 12K). A multistep freeze drying procedure as described by Phillips et al. (*Cryobiology* 18:414, 1981) is used to lyophilize the formulated recombinant virus, preferably from a temperature of −40° C. to −45° C. The resulting composition contains less than 10% water by weight of the lyophilized virus. Once lyophilized, the recombinant virus is stable and may be stored at −20° C. to 25° C., as discussed in more detail below.

Within the evaporative method, water is removed from the aqueous suspension at ambient temperature by evaporation. Within one embodiment, water is removed through spray-drying (EP 520,748). Within the spray-drying process, the aqueous suspension is delivered into a flow of preheated gas, usually air, whereupon water rapidly evaporates from droplets of the suspension. Spray-drying apparatus are available from a number of manufacturers (e.g., Drytec, Ltd., Tonbridge, England; Lab-Plant, Ltd., Huddersfield, England). Once dehydrated, the recombinant virus is stable and may be stored at −20° C. to 25° C. Within the methods described herein, the resulting moisture content of the dried or lyophilized virus may be determined through use of a Karl-Fischer apparatus (EM Science Aquastar VIB volumetric titrator, Cherry Hill, N.J.), or through a gravimetric method.

The aqueous solutions used for formulation, as previously described, are preferably composed of a saccharide, high molecular weight structural additive, a buffering component, and water. The solution may also include one or more amino acids. The combination of these components act to preserve the activity of the recombinant virus upon freezing and lyophilization or drying through evaporation. Although one saccharide that can be utilized is lactose, other saccharides may likewise be utilized including, for example, sucrose, mannitol, glucose, trehalose, inositol, fructose, maltose or galactose. In addition, combinations of saccharides can be used, for example, lactose and mannitol, or sucrose and mannitol. A particularly preferred concentration of lactose is 3%–4% by weight. Preferably, the concentration of the saccharide ranges from 1% to 12% by weight.

The high molecular weight structural additive aids in preventing viral aggregation during freezing and provides structural support in the lyophilized or dried state. Within the context of the present invention. structural additives are considered to be of "high molecular weight" if they are greater than 5000 m.w. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight. Preferably, the concentration of the high molecular weight structural additive ranges from 0.1% to 10% by weight.

The amino acids, if present, function to further preserve viral infectivity upon cooling and thawing of the aqueous suspension. In addition, amino acids function to further preserve viral infectivity during sublimation of the cooled aqueous suspension and while in the lyophilized state. A preferred amino acid is arginine, but other amino acids such as lysine, ornithine, serine, glycine, glutamine, asparagine, glutamic acid or aspartic acid can also be used. A particularly preferred arginine concentration is 0.1% by weight. Preferably, the amino acid concentration ranges from 0.1% to 10% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. A particularly preferred pH of the recombinant virus formulation is 7.4, and a preferred buffer is tromethamine.

In addition, it is preferable that the aqueous solution contain a neutral salt which is used to adjust the final formulated recombinant alphavirus to an appropriate iso-osmotic salt concentration. Suitable neutral salts include sodium chloride, potassium chloride or magnesium chloride. A preferred salt is sodium chloride.

Aqueous solutions containing the desired concentration of the components described above may be prepared as concentrated stock solutions.

It will be evident to those skilled in the art, given the disclosure provided herein, that it may be preferable to utilize certain saccharides within the aqueous solution when the lyophilized virus is intended for storage at room temperature. More specifically, it is preferable to utilize disaccharides, such as lactose or trehalose, particularly for storage at room temperature.

The lyophilized or dehydrated viruses of the subject invention may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted virus. Such components include cytokines, such as IL-2, polycations, such as protamine sulfate, or other components which enhance the transduction efficiency of the reconstituted virus. Lyophilized or dehydrated recombinant virus may be reconstituted with any convenient volume of water or the reconstituting agents noted above that allow substantial, and preferably total solubilization of the lyophilized or dehydrated sample.

1. Methods for Utilizing Gene Delivery Vehicles

As noted above, the present invention also provides methods for delivering a selected heterologous sequence to a vertebrate (e.g., a mammal such as a human or other warm-blooded animal such as a horse, cow, pig, sheep, dog, cat, rat or mouse) or insect, comprising the step of administering to a vertebrate or insect a gene delivery vehicle as described herein which is capable of expressing the selected heterologous sequence. Such gene delivery vehicles may be administered either directly (e.g., intravenously, intramuscularly. intraperitoneally, subcutaneously, orally, rectally, intraocularly, intranasally), or by various physical methods such as lipofection (Felgner et al., *Proc. Natl. Acad. Sci. USA* 84:7413–7417, 1989), direct DNA injection (Fung et al., *Proc. Natl. Acad. Sci. USA* 80:353–357, 1983; Seeger et al., *Proc. Natl. Acad. Sci USA* 81:5849–5852; Acsadi et al., *Nature* 352:815–818, 1991); microprojectile bombardment (Williams et al., *PNAS* 88:2726–2730, 1991); liposomes of several types (see., e.g., Wang et al., *PNAS* 84:7851–7855, 1987); CaPO$_4$ (Dubensky et al., *PNAS* 81:7529–7533, 1984); DNA ligand (Wu et al, *J. Biol. Chem.* 264:16985–16987, 1989); administration of nucleic acids alone (WO 90/11092); or administration of DNA linked to killed adenovirus (Curiel et al., *Hum. Gene Ther.* 3:147–154, 1992); via polycation compounds such as polylysine. utilizing receptor specific ligands; as well as with psoralen inactivated viruses such as Sendai or Adenovirus. In addition, the gene delivery vehicles may either be administered directly (i.e., in vivo), or to cells which have been removed (ex vivo), and subsequently returned.

As discussed in more detail below, gene delivery vehicles may be administered to a vertebrate or insect for a wide variety of therapeutic and/or other productive purposes, including for example. for the purpose of stimulating a specific immune response; inhibiting the interaction of an agent with a host cell receptor; to express a toxic palliative, including for example, conditional toxic palliatives; to immunologically regulate the immune system: to prevent cell division, to express markers, for replacement gene therapy, to promote wound healing and/or to produce a recombinant protein. These and other uses are discussed in more detail below.

1. Immunostimulation

Within one aspect of the present invention, compositions and methods are provided for administering a gene delivery vehicle which is capable of preventing, inhibiting, stabilizing or reversing infectious, cancerous, auto-immune or immune diseases. Representative examples of such diseases include viral infections such as HIV, HBV, HCV, HTLV I, HTLV II, CMV, EBV and HPV, melanomas, diabetes, graft vs. host disease, Alzheimer's disease and heart disease. More specifically, within one aspect of the present invention, compositions and methods are provided for stimulating an immune response (either humoral or cell-mediated) to a pathogenic agent, such that the pathogenic agent is either killed or inhibited. Representative examples of pathogenic agents include bacteria, fungi, parasites. viruses and cancer cells.

Within one embodiment of the invention the pathogenic agent is a virus, and methods are provided for stimulating a specific immune response and inhibiting viral spread by using a gene delivery vehicle that directs the expression of an antigen or modified form thereof to susceptible target cells capable of either (1) initiating an immune response to the viral antigen or (2) preventing the viral spread by occupying cellular receptors required for viral interactions. Expression of the vector nucleic acid encoded protein may be transient or stable with time. Where an immune response is to be stimulated to a pathogenic antigen, the gene delivery vehicle is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogues thereof (e.g., Altmann et al., *Nature* 338:512, 1989). Cells infected with gene delivery vehicles are expected to do this efficiently because they closely mimic genuine viral infection and because they: (a) are able to infect non-replicating cells, (b) do not integrate into the host cell genome, (c) are not associated with any life threatening diseases, and (d) express high levels of heterologous protein. Because of these differences, gene delivery vehicles can easily be thought of as safe viral vectors which can be used on healthy individuals for vaccine use.

This aspect of the invention has a further advantage over other systems that might be expected to function in a similar manner, in that the presenter cells are fully viable and healthy, and low levels of viral antigens, relative to heterologous genes, are expressed. This presents a distinct advantage since the antigenic epitopes expressed can be altered by selective cloning of sub-fragments of the gene for the antigen into the recombinant alphavirus, leading to responses against immunogenic epitopes which may otherwise be overshadowed by immunodominant epitopes. Such an approach may be extended to the expression of a peptide having multiple epitopes. one or more of the epitopes being derived from different proteins. Further, this aspect of the invention allows efficient stimulation of cytotoxic T lymphocytes (CTL) directed against antigenic epitopes, and peptide fragments of antigens encoded by sub-fragments of genes, through intracellular synthesis and association of these peptide fragments with MHC Class I molecules. This approach may be utilized to map major immunodominant epitopes for CTL induction.

An immune response may also be achieved by transferring to an appropriate immune cell (such as a T lymphocyte) the gene for the specific T cell receptor which recognizes the antigen of interest (in the context of an appropriate MHC molecule if necessary). for an immunoglobulin which recognizes the antigen of interest, or for a hybrid of the two which provides a CTL response in the absence of the MHC context. Thus, the gene delivery vehicle cells may be used as an immunostimulant, immunomodulator, or vaccine.

In another embodiment of the invention, methods are provided for producing inhibitor palliatives wherein gene delivery vehicles deliver and express defective interfering viral structural proteins, which inhibit viral assembly. Such gene delivery vehicles may encode defective gag, pol, env or other viral particle proteins or peptides and these would inhibit in a dominant fashion the assembly of viral particles. This occurs because the interaction of normal subunits of the viral particle is disturbed by interaction with the defective subunits.

In another embodiment of the invention, methods are provided for the expression of inhibiting peptides or proteins specific for viral protease. Briefly viral protease cleaves the viral gag and gag, pol proteins into a number of smaller peptides. Failure of this cleavage in all cases leads to complete inhibition of production of infectious retroviral particles. As an example, the HIV protease is known to be an aspartyl protease and these are known to be inhibited by peptides made from amino acids from protein or analogues. Gene delivery vehicles to inhibit HIV will express one or multiple fused copies of such peptide inhibitors.

Another embodiment involves the delivery of suppressor genes which when deleted. mutated, or not expressed in a cell type, lead to tumorigenesis in that cell type. Reintroduction of the deleted gene by means of a gene delivery vehicle leads to regression of the tumor phenotype in these cells. Examples of such cancers are retinoblastoma and Wilms Tumor. Since malignancy can be considered to be an inhibition of cellular terminal differentiation compared with cell growth, the alphavirus vector delivery and expression of gene products which lead to differentiation of a tumor should also. in general, lead to regression.

In yet another embodiment, the gene delivery vehicle provides a therapeutic effect by transcribing a ribozyme (an RNA enzyme) (Haseloff and Gerlach. *Nature* 334:585, 1989) which will cleave and hence inactivate RNA molecules corresponding to a pathogenic function. Since ribozymes function by recognizing a specific sequence in the target RNA and this sequence is normally 12 to 17 bp, this allows specific recognition of a particular RNA species such as a RNA or a retroviral genome. Additional specificity may be achieved in some cases by making this a conditional toxic palliative (see below).

One way of increasing the effectiveness of inhibitory palliatives is to express viral inhibitory genes in conjunction with the expression of genes which increase the probability of infection of the resistant cell by the virus in question. The result is a nonproductive "dead-end" event which would compete for productive infection events. In the specific case of HIV, gene delivery vehicles may be delivered which inhibit HIV replication (by expressing anti-sense tat. etc., as described above) and also overexpress proteins required for infection, such as CD4. In this way, a relatively small number of vector-infected HIV-resistant cells act as a "sink" or "magnet" for multiple nonproductive fusion events with free virus or virally infected cells.

2. Blocking Agents

Many infectious diseases, cancers, autoimmune diseases, and other diseases involve the interaction of viral particles with cells, cells with cells, or cells with factors produced by themselves or other cells. In viral infections, viruses commonly enter cells via receptors on the surface of susceptible cells. In cancers or other proliferative conditions (e.g., restenosis), cells may respond inappropriately or not at all to signals from other cells or factors, or specific factors may be mutated, overexpressed, or underexpressed. resulting in loss of appropriate cell cycle control. In autoimmune disease, there is inappropriate recognition of "self" markers. Within the present invention, such interactions may be blocked by producing, in vivo, an analogue to either of the partners in an interaction. Alternatively, cell cycle control may be restored by preventing the transition from one phase to another (e.g., G1 to S phase) using a blocking factor which is absent or underexpressed. This blocking action may occur intracellularly, on the cell membrane, or extracellularly, and the action of an alphavirus vector carrying a gene for a blocking agent, can be mediated either from inside a susceptible cell or by secreting a version of the blocking protein to locally block the pathogenic interaction.

In the case of HIV, the two agents of interaction are the gp 120/gp 41 envelope protein and the CD4 receptor molecule. Thus, an appropriate blocker would be a gene delivery vehicle expressing either an HIV env analogue that blocks HIV entry without causing pathogenic effects, or a CD4 receptor analogue. The CD4 analogue would be secreted and would function to protect neighboring cells, while the gp 120/gp 41 is secreted or produced only intracellularly so as to protect only the vector-containing cell. It may be advantageous to add human immunoglobulin heavy chains or other components to CD4 in order to enhance stability or complement lysis. Administration of a gene delivery vehicle encoding such a hybrid-soluble CD4 to a host results in a continuous supply of a stable hybrid molecule. Efficacy of treatment can be assayed by measuring the usual indicators of disease progression, including antibody level, viral antigen production, infectious HIV levels, or levels of nonspecific infections.

In the case of uncontrolled proliferative states, such as cancer or restenosis, cell cycle progression may be halted by the expression of a number of different factors that affect signaling by cyclins or cyclin-dependent kinases (CDK). For example, the cyclin-dependent kinase inhibitors, p16, p21, and p27 each regulate cyclin:CDK mediated cell cycle signaling. Overexpression of these factors within a cell by a gene delivery vehicle results in a cytostatic suppression of cell proliferation. Other factors that may be used therapeutically, as blocking agents or targets to disrupt cell proliferation, include, for example, wild-type or mutant Rb, p53, Myc, Fos, Jun, PCNA, GAX, lentiviral vpr and p15. Within related embodiments, cardiovascular diseases such as restenosis or atherosclerosis may be treated or prevented with vectors that express products which promote re-endothelialization, or vascular remodeling (e.g., VEGF, TFPI, SOD).

3. Expression of Palliatives

Techniques similar to those described above can be used to produce gene delivery vehicles which direct the expression of an agent (or "palliative") which is capable of inhibiting a function of a pathogenic agent or gene. Within the present invention, "capable of inhibiting a function" means that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for a cancerous cell, cancer-promoting growth factor, or uncontrolled proliferative condition (e.g., restenosis) include viability, cell replication, altered susceptibility to external signals (e.g., contact inhibition), and lack of production or production of mutated forms of anti-oncogene proteins.

a. Inhibitor Palliatives

In one aspect of the present invention, the gene delivery vehicle directs the expression of a gene which can interfere with a function of a pathogenic agent, for instance in viral or malignant diseases. Such expression may either be essentially continuous or in response to the presence in the cell of another agent associated either with the pathogenic condition or with a specific cell type (an "identifying agent"). In addition, vector delivery may be controlled by targeting vector entry specifically to the desired cell type (for instance, a virally infected or malignant cell) as discussed above.

One method of administration is leukophoresis, in which about 20% of an individual's PBLs are removed at any one time and manipulated in vitro. Thus, approximately $2 \times 10^9$ cells may be treated and replaced. Repeat treatments may also be performed. Alternatively, bone marrow may be treated and allowed to amplify the effect as described above. In addition, packaging cell lines producing a vector may be directly injected into a subject, allowing continuous production of recombinant virions.

In one embodiment. gene delivery vehicles which express RNA complementary to key pathogenic gene transcripts (for example, a viral gene product or an activated cellular oncogene) can be used to inhibit translation of that transcript into protein, such as the inhibition of translation of the HIV tat protein. Since expression of this protein is essential for viral replication, cells containing the gene delivery vehicle would be resistant to HIV replication.

In a second embodiment, where the pathogenic agent is a single-stranded virus having a packaging signal, RNA complementary to the viral packaging signal (e.g., an HIV packaging signal when the palliative is directed against HIV) is expressed, so that the association of these molecules with the viral packaging signal will, in the case of retroviruses, inhibit stem loop formation or tRNA primer binding required for proper encapsidation or replication of the alphavirus RNA genome.

In a third embodiment. a gene delivery vehicle may be introduced which expresses a palliative capable of selectively inhibiting the expression of a pathogenic gene, or a palliative capable of inhibiting the activity of a protein produced by the pathogenic agent. In the case of HIV. one example is a mutant tat protein which lacks the ability to transactivate expression from the HIV LTR and interferes (in a transdominant manner) with the normal functioning of tat protein. Such a mutant has been identified for HTLV II tat protein ("XII Leu$^5$" mutant; see Wachsman et al., *Science* 235:674, 1987). A mutant transrepressor tat should inhibit replication much as has been shown for an analogous mutant repressor in HSV-1 (Friedmann et al., *Nature* 335:452, 1988).

Such a transcriptional repressor protein can be selected for in tissue culture using any viral-specific transcriptional promoter whose expression is stimulated by a virus-specific transactivating protein (as described above). In the specific case of HIV, a cell line expressing HIV tat protein and the HSVTK gene driven by the HIV promoter will die in the presence of ACV. However, if a series of mutated tat genes are introduced to the system. a mutant with the appropriate properties (i.e., represses transcription from the HIV promoter in the presence of wild-type tat) will grow and be selected. The mutant gene can then be reisolated from these cells. A cell line containing multiple copies of the conditionally lethal vector/tat system may be used to assure that surviving cell clones are not caused by endogenous mutations in these genes. A battery of randomly mutagenized tat genes are then introduced into these cells using a "rescuable" alphavirus vector (i.e., one that expresses the mutant tat protein and contains a bacterial origin of replication and drug resistance marker for growth and selection in bacteria). This allows a large number of random mutations to be evaluated and permits facile subsequent molecular cloning of the desired mutant cell line. This procedure may be used to identify and utilize mutations in a variety of viral transcriptional activator/viral promoter systems for potential antiviral therapies.

b. Conditional Toxic Palliatives

Another approach for inhibiting a pathogenic agent is to express a palliative which is toxic for the cell expressing the pathogenic condition. In this case, expression of the palliative from the gene delivery vehicle should be limited by the presence of an entity associated with the pathogenic agent, such as a specific viral RNA sequence identifying the pathogenic state, in order to avoid destruction of nonpathogenic cells.

In one embodiment of this method, a gene delivery vehicle can be utilized to express a toxic gene (as discussed above) from a cell-specific responsive vector. In this manner, rapidly replicating cells, which contain the RNA sequences capable of activating the cell-specific responsive vectors, are preferentially destroyed by the cytotoxic agent produced by the gene delivery vehicle.

In a similar manner to the preceding embodiment, the gene delivery vehicle can carry a gene for phosphorylation, phosphoribosylation, ribosylation, or other metabolism of a purine- or pyrimidine-based drug. This gene may have no equivalent in mammalian cells and might come from organisms such as a virus. bacterium, fungus, or protozoan. An example of this would be the *E. coli* guanine phosphoribosyl transferase gene product, which is lethal in the presence of thioxanthine (see Besnard et al., *Mol. Cell. Biol.* 7:4139–4141, 1987). Conditionally lethal gene products of this type (also referred to as "prodrugs converting enzymes" above) have application to many presently known purine- or pyrimidine-based anticancer drugs. which often require intracellular ribosylation or phosphorylation in order to become effective cytotoxic agents. The conditionally lethal gene product could also metabolize a nontoxic drug which is not a purine or pyrimidine analogue to a cytotoxic form (see Searle et al., *Brit. J. Cancer* 53:377–384, 1986).

Mammalian viruses in general tend to have "immediate early" genes which are necessary for subsequent transcriptional activation from other viral promoter elements. RNA sequences of this nature are excellent candidates for activating alphavirus vectors intracellular signals (or "identifying agents") of viral infection. Thus, conditionally lethal genes expressed from alphavirus cell-specific vectors responsive to these viral "immediate early" gene products could specifically kill cells infected with any particular virus. Additionally, since the human and interferon promoter elements are transcriptionally activated in response to infection by a wide variety of nonrelated viruses, the introduction of vectors expressing a conditionally lethal gene product like HSVTK, for example. in response to interferon production could result in the destruction of cells infected with a variety of different viruses.

In another aspect of the present invention gene delivery vehicles are provided which direct the expression of a gene product capable of activating an otherwise inactive precursor into an active inhibitor of the pathogenic agent. For example, the HSVTK gene product may be used to more effectively metabolize potentially antiviral nucleoside analogues such as AZT or ddC. The HSVTK gene may be expressed under the control of a cell-specific responsive vector and introduced into these cell types. AZT (and other nucleoside antivirals) must be metabolized by cellular mechanisms to the nucleotide triphosphate form in order to specifically inhibit retroviral reverse transcriptase, and thus, HIV replication (Furmam et al., *Proc. Natl. Acad. Sci. USA* 83:8333–8337, 1986). Constitutive expression of HSVTK (a nucleoside and nucleoside kinase with very broad substrate specificity) results in more effective metabolism of these drugs to their biologically active nucleotide triphosphate form. AZT or ddC therapy will thereby be more effective allowing lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, will be made more efficacious.

Administration of these gene delivery vehicles to human T cell and macrophage/monocyte cell lines can increase their resistance to HIV in the presence of AZT and ddC compared to the same cells without retroviral vector treatment. Treatment with AZT would be at lower than normal levels to avoid toxic side effects but still efficiently inhibit the spread of HIV. The course of treatment would be as described for the blocker.

In one embodiment, the gene delivery vehicle carries a gene specifying a product which is not in itself toxic but, when processed or modified by a protein such as a protease specific to a viral or other pathogen. is converted into a toxic form. For example, the gene delivery vehicle could carry a gene encoding a proprotein for ricin A chain, which becomes toxic upon processing by the HIV protease. More specifically, a synthetic inactive proprotein form of the toxin ricin or diphtheria A chains could be cleaved to the active form by arranging for the HIV virally encoded protease to recognize and cleave off an appropriate "pro" element.

In another embodiment, the gene delivery vehicle may express a "reporting product" on the surface of the target cells in response to the presence of an identifying agent in the cells (such as expression of a viral gene). This surface protein can be recognized by a cytotoxic agent, such as antibodies for the reporting protein, or by cytotoxic T cells. In a similar manner, such a system can be used as a detection system (see below) to simply identify those cells having a particular gene which expresses an identifying protein.

Similarly, in another embodiment, a surface protein could be expressed which would itself be therapeutically beneficial. In the particular case of HIV, expression of the human CD4 protein specifically in HIV-infected cells may be beneficial in two ways:

1. Binding of CD4 to HIV env intracellularly could inhibit the formation of viable viral particles, much as soluble CD4 has been shown to do for free virus, but without the problem of systematic clearance and possible immunogenicity, since the protein will remain membrane bound and is structurally identical to endogenous CD4 (to which the patient should be immunologically tolerant).

2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monocytes and macrophages, which act as a reservoir for virus production as a result of their relative refractility to HIV-induced cytotoxicity (which. in turn, is apparently due to the relative lack of CD4 on their cell surfaces).

In another embodiment, the gene delivery vehicle can provide a ribozyme which will cleave and inactivate RNA molecules essential for viability of the vector infected cell. By making ribozyme production dependent on a specific RNA sequence corresponding to the pathogenic state, such as HIV tat, toxicity is specific to the pathogenic state.

4. Expression of Markers

The above-described technique of expressing a palliative in a cell in response to a specific RNA sequence can also be modified to enable detection of a particular gene in a cell which expresses an identifying protein (for example, a gene carried by a particular virus), and hence enable detection of cells carrying that virus. In addition, this technique enables the detection of viruses (such as HIV) in a clinical sample of cells carrying an identifying protein associated with the virus.

This modification can be accomplished by providing a genome coding for a product, the presence of which can be readily identified (the "marker product"), in a gene delivery vehicle which responds to the presence of the identifying protein in the infected cells. For example, HIV, when it infects suitable cells, makes tat and rev. The indicator cells can thus be provided with a genome (such as by infection with an appropriate recombinant alphavirus) which codes for a marker gene, such as the alkaline phosphatase gene, β-galactosidase gene, or the luciferase gene which is expressed by the recombinant alphavirus upon activation by the tat and/or rev RNA transcript. In the case of β-galactosidase or alkaline phosphatase, exposing the cells to substrate analogues results in a color or fluorescence change if the sample is positive for HIV. In the case of luciferase, exposing the sample to luciferin will result in luminescence if the sample is positive for HIV. For intracellular enzymes such as β-galactosidase, the viral titre can be measured directly by counting colored or fluorescent cells, or by making cell extracts and performing a suitable assay. For the membrane bond form of alkaline phosphatase, virus titre can also be measured by performing enzyme assays on the cell surface using a fluorescent substrate. For secreted enzymes, such as an engineered form of alkaline phosphatase, small samples of culture supernatant are assayed for activity, allowing continuous monitoring of a single culture over time. Thus, different forms of this marker system can be used for different purposes. These include counting active virus, or sensitively and simply measuring viral spread in a culture and the inhibition of this spread by various drugs.

Further specificity can be incorporated into the preceding system by testing for the presence of the virus either with or without neutralizing antibodies to that virus. For example, in one portion of the clinical sample being tested, neutralizing antibodies to HIV may be present; whereas in another portion there would be no neutralizing antibodies. If the tests were negative in the system where there were antibodies and positive where there were no antibodies, this would assist in confirming the presence of HIV.

Within an analogous system for an in vitro assay, the presence of a particular gene, such as a viral gene, may be determined in a cell sample. In this case, the cells of the sample are infected with a suitable gene delivery vehicle which carries the reporter gene which is only expressed in the presence of the appropriate viral RNA transcript. The reporter gene, after entering the sample cells, will express its reporting product (such as β-galactosidase or luciferase) only if the host cell expresses the appropriate viral proteins.

These assays are more rapid and sensitive, since the reporter gene can express a greater amount of reporting product than identifying agent present, which results in an amplification effect.

5. Immune Down-Regulation

As described above, the present invention also provides gene delivery vehicles capable of suppressing one or more elements of the immune system in target cells infected with the alphavirus. Briefly, specific down-regulation of inappropriate or unwanted immune responses, such as in chronic hepatitis or in transplants of heterologous tissue such as bone marrow, can be engineered using immune-suppressive viral gene products which suppress surface expression of transplantation (MHC) antigen. Group C adenoviruses Ad2 and Ad5 possess a 19 kd glycoprotein (gp 19) encoded in the E3 region of the virus. This gp 19 molecule binds to class I MHC molecules in the endoplasmic reticulum of cells, and prevents terminal glycosylation and translocation of class I MHC to the cell surface. For example, prior to bone marrow transplantation, donor bone marrow cells may be infected with a gp 19-encoding gene delivery vehicle which, upon expression of the gp 19, inhibit the surface expression of MHC class I transplantation antigens. These donor cells may be transplanted with low risk of graft rejection and may require a minimal immunosuppressive regimen for the transplant patient. This may allow an acceptable donor-recipient chimeric state to exist with fewer complications. Similar treatments may be used to treat the range of so-called autoimmune diseases, including lupus erythromiatis, multiple sclerosis, humanoid arthritis or chronic hepatitis B infection.

An alternative method involves the use of anti-sense message, ribozyme, or other specific gene expression inhibitor specific for T cell clones which are autoreactive in nature. These block the expression of the T cell receptor of particular unwanted clones responsible for an autoimmune response. The anti-sense, ribozyme, or other gene may be introduced using the viral vector delivery system.

6. Replacement or Augmentation Gene Therapy

One further aspect of the present invention relates to transforming cells of a vertebrate or insect with a gene delivery vehicle which supplies genetic sequences capable of expressing a therapeutic protein. Within one embodiment of the present invention, the gene delivery vehicle is designed to express a therapeutic protein capable of preventing, inhibiting, stabilizing or reversing an inherited or noninherited genetic defect in metabolism, immune regulation, hormonal regulation. enzymatic or membrane associated structural function. This embodiment also describes the gene delivery vehicle capable of transducing individual cells, whereby the therapeutic protein is able to be expressed systemically or locally from a specific cell or tissue, whereby the therapeutic protein is capable of (a) the replacement of an absent or defective cellular protein or enzyme, or (b) supplement production of a defective of low expressed cellular protein or enzyme. Such diseases may include cystic fibrosis, Parkinson's disease, hypercholesterolemia, adenosine deaminase deficiency, β-globin disorders, Hemophilia A & B, Gaucher's disease, diabetes and leukemia.

As an example of the present invention, a gene delivery vehicle can be constructed and utilized to treat Gaucher disease. Briefly Gaucher disease is a genetic disorder that is characterized by the deficiency of the enzyme glucocerebrosidase. This type of therapy is an example of a single gene replacement therapy by providing a functional cellular enzyme. This enzyme deficiency leads to the accumulation of glucocerebrosidase in the lysosomes of all cells in the body. However, the disease phenotype is manifested only in the macrophages, except in the very rare neuronpathic forms of the disease. The disease usually leads to enlargement of the liver and spleen and lesions in the bones. (For a review, see *Science* 256:794, 1992, and *The Metabolic Basis of Inherited Disease*, 6th ed.; Scriver et al., vol. 2, p. 1677).

Gene delivery vehicles can similarly be utilized to deliver a wide variety of therapeutic proteins in order to treat, cure, prevent a disease or disease process. Representative examples of such genes include, but are not limited to, insulin (see U.S. Pat. No. 4,431,740 and BE 885196A), hemoglobin (Lawn et al., *Cell* 21:647–51, 1980), erythropoietin (EPO; see U.S. Pat. No. 4,703,008), megakaryocyte growth and differentiation factor (MGDF), stem cell factor (SCF), G-CSF (Nagata et al., *Nature* 319:415–418, 1986), GM-CSF, M-CSF (see WO 8706954), the flt3 ligand (Lyman et al. (1993), *Cell* 75:1157–1167), EGF, acidic and basic FGF, PDGF, members of the interleukin or interferon families, supra, neurotropic factors (e.g., BDNF; Rosenthal et al., *Endocrinology* 129:1289–1294, 1991, NT-3; see WO 9103569, CNTF; see WO 9104316, NGF; see WO 9310150), coagulation factors (e.g., factors VIII and IX), thrombolytic factors such as t-PA (see EP 292009, AU 8653302 and EP 174835) and streptokinase (see EP 407942), human growth hormone (see JP 94030582 and U.S. Pat. No. 4,745,069) and other animal somatotropins, integrins and other cell adhesion molecules, such as ICAM-1 and ELAM (see also other "heterologous sequences" discussed above), and other growth factors, such as IGF-I and IGF-II, TGF-β, osteogenic protein-1 (Ozkaynak et al., *EMBO J.* 9:2085–2093, 1990), and other bone morphogenetic proteins (e.g., BMP-4, Nakase et al, *J. Bone Miner. Res.* 9:651–659, 1994).

7. Lymphokines and Lymphokine Receptors

As noted above, the present invention also provides gene delivery vehicles which can, among other functions, direct the expression of one or more cytokines or cytokine receptors. Briefly, in addition to their role as cancer therapeutics, cytokines can have negative effects resulting in certain pathological conditions. For example, most resting T-cells, B cells, large granular lymphocytes and monocytes do not express IL-2R (receptor). In contrast to the lack of IL-2R expression on normal resting cells. IL-2R is expressed by abnormal cells in patients with certain leukemias (ATL, Hairy-cell, Hodgkins, acute and chronic granulocytic), autoimmune diseases, and is associated with allograft rejection. Interestingly, in most of these patients the serum concentration of a soluble form of IL-2R is elevated. Therefore, with certain embodiments of the invention therapy may be effected by increasing the serum concentration of the soluble form of the cytokine receptor. For example, in the case of IL-2R, a gene delivery vehicle can be engineered to produce both soluble IL-2R and IL-2R, creating a high affinity soluble receptor. In this configuration, serum IL-2 levels would decrease, inhibiting the paracrine loop. This same strategy also may be effective against autoimmune diseases. In particular, because some autoimmune diseases (e.g., Rheumatoid arthritis, SLE) also are associated with abnormal expression of IL-2, blocking the action of IL-2 by increasing the serum level of receptor may also be utilized in order to treat such autoimmune diseases.

In other cases inhibiting the levels of IL-1 may be beneficial. Briefly, IL-1 consists of two polypeptides, IL-1 and IL-1. each of which has plieotropic effects. IL-1 is primarily synthesized by mononuclear phagocytes, in response to stimulation by microbial products or inflammation. There is a naturally occurring antagonist of the IL-1R. referred to as the IL-1 Receptor antagonist ("IL-1Ra"). This IL-1R antagonist has the same molecular size as mature IL-1 and is structurally related to it. However. binding of IL-1Ra to the IL-1R does not initiate any receptor signaling. Thus, this molecule has a different mechanism of action than a soluble receptor, which complexes with the cytokine and thus prevents interaction with the receptor. IL-1 does not seem to play an important role in normal homeostasis. In animals, antibodies to IL-1 receptors reduce inflammation and anorexia due to endotoxins and other inflammation inducing agents.

In the case of septic shock, IL-1 induces secondary compounds which are potent vasodilators. In animals, exogenously supplied IL-1 decreases mean arterial pressure and induces leukopenia. Neutralizing antibody to IL-1 reduced endotoxin-induced fever in animals. In a study of patients with septic shock who were treated with a constant infusion of IL-1R for three days, the 28 day mortality was 16% compared to 44% in patients who received placebo infusions. In the case of autoimmune disease, reducing the activity of IL-1 reduces inflammation. Similarly, blocking the activity of IL-1 with recombinant receptors can result in increased allograft survival in animals, again presumably by decreasing inflammation.

These diseases provide further examples where gene delivery vehicles may be engineered to produce a soluble receptor or more specifically the IL-1Ra molecule. For example, in patients undergoing septic shock, a single injection of IL-1Ra producing vector particles could replace the current approach requiring a constant infusion of recombinant IL-1R.

Cytokine responses, or more specifically, incorrect cytokine responses may also be involved in the failure to control or resolve infectious diseases. Perhaps the best studied example is non-healing forms of leishmaniasis in mice and humans which have strong, but counterproductive $T_H2$-dominated responses. Similarly, lepromotomatous leprosy is associated with a dominant, but inappropriate $T_H2$ response. In these conditions. gene delivery vehicles may be useful for increasing circulating levels of IFN gamma, as opposed to the site-directed approach proposed for solid tumor therapy. IFN gamma is produced by $T_H$-1 T-cells. and functions as a negative regulator of $T_H$-2 subtype proliferation. IFN gamma also antagonizes many of the IL-4 mediated effects on B-cells, including isotype switching to IgE.

IgE, mast cells and eosinophils are involved in mediating allergic reaction. IL-4 acts on differentiating T-cells to stimulate $T_H$-2 development, while inhibiting $T_H$-1 responses. Thus, alphavirus-based gene therapy may also be accomplished in conjunction with traditional allergy therapeutics. One possibility is to deliver a gene delivery vehicle which produces IL4R with small amounts of the offending allergen (i.e., traditional allergy shots). Soluble IL-4R would prevent the activity of IL-4, and thus prevent the induction of a strong $T_H$-2 response.

8. Suicide Vectors

One further aspect of the present invention relates to the use of gene delivery vehicle suicide vectors to limit the spread of wild-type alphavirus in the packaging/producer cell lines. Briefly, within one embodiment the gene delivery vehicle is comprised of an antisense or ribozyme sequence specific for the wild-type alphavirus sequence generated from an RNA recombination event between the 3' sequences of the junction region of the vector, and the 5' alphavirus structural sequences of the packaging cell line expression vector. The antisense or ribozyme molecule would only be thermostable in the presence of the specific recombination sequence and would not have any other effect in the alphavirus packaging/producer cell line. Alternatively, a toxic molecule (such as those disclosed herein), may also be expressed in the context of a vector that would only express in the presence of wild-type alphavirus.

9. Gene Delivery Vehicles to Prevent the Spread of Metastatic Tumors

One further aspect of the present invention relates to the use of gene delivery vehicles for inhibiting or reducing the invasiveness of malignant neoplasms. Briefly, the extent of malignancy typically relates to vascularization of the tumor. One cause for tumor vascularization is the production of soluble tumor angiogenesis factors (TAF) (Paweletz et al., *Crit. Rev. Oncol. Hematol.* 9:197, 1989) expressed by some tumors. Within one aspect of the present invention, tumor vascularization may be slowed utilizing gene delivery vehicles to express antisense or ribozyme RNA molecules specific for TAF. Alternatively, anti-angiogenesis factors (Moses et al., *Science* 248:1408, 1990; Shapiro et al., *PNAS* 84:2238, 1987) may be expressed either alone or in combination with the above-described ribozymes or antisense sequences in order to slow or inhibit tumor vascularization. Alternatively, gene delivery vehicles can also be used to express an antibody specific for the TAF receptors on surrounding tissues.

10. Administration of Gene Delivery Vehicles

Within other aspects of the present invention, methods are provided for administering a gene delivery vehicle to a vertebrate or insect. Briefly, the final mode of gene delivery vehicle administration usually relies on the specific therapeutic application, the best mode of increasing vector potency, and the most convenient route of administration. Generally, this embodiment includes gene delivery vehicles which can be designed to be delivered by, for example, (1) direct injection into the blood stream; (2) direct injection into a specific tissue or tumor; (3) oral administration; (4) nasal inhalation; (5) direct application to mucosal tissues; or (6) ex vivo administration of transduced autologous cells into the vertebrate or insect. Within certain embodiments of the invention, for ex vivo applications cells can be first removed from a host, positively and/or negatively selected in order to yield a population of cells which is at least partially purified (e.g., CD34$^+$ stem cells, T cells, or the like), transduced, transfected, or, infected with one of the gene delivery vehicles of the present invention, and reintroduced into either the same host or another individual.

Thus, the therapeutic gene delivery vehicle can be administered in such a fashion such that the vector can (a) transduce a normal healthy cell and transform the cell into a producer of a therapeutic protein or agent which is secreted systemically or locally, (b) transform an abnormal or defective cell, transforming the cell into a normal functioning phenotype, (c) transform an abnormal cell so that it is destroyed, and/or (d) transduce cells to manipulate the immune response.

11. Modulation of Transcription Factor Activity

In yet another embodiment, gene delivery vehicles may be utilized in order to regulate the growth control activity of transcription factors in the infected cell. Briefly, transcription factors directly influence the pattern of gene expression through sequence-specific trans-activation or repression (Karin, *New Biologist* 21:126–131, 1990). Thus, it is not surprising that mutated transcription factors represent a family of oncogenes. Gene delivery vehicles can be used, for example, to return control to tumor cells whose unregulated growth is activated by oncogenic transcription factors, and proteins which promote or inhibit the binding cooperatively in the formation of homo-and heterodimer trans-activating or repressing transcription factor complexes.

One method for reversing cell proliferation would be to inhibit the trans-activating potential of the c-myc/Max heterodimer transcription factor complex. Briefly, the nuclear oncogene c-myc is expressed by proliferating cells and can be activated by several distinct mechanisms, including retroviral insertion, amplification, and chromosomal translocation. The Max protein is expressed in quiescent cells and, independently of c-myc, either alone or in conjunction with an unidentified factor, functions to repress expression of the same genes activated by the myc/Max heterodimer (Cole, *Cell* 65:715–716, 1991).

Inhibition of c-myc or c-myc/Max proliferation of tumor cells may be accomplished by the overexpression of Max in target cells controlled by gene delivery vehicles. The Max protein is only 160 amino acids (corresponding to 480 nucleotide RNA length) and is easily incorporated into a gene delivery vehicle either independently, or in combination with other genes and/or antisense/ribozyme moieties targeted to factors which release growth control of the cell.

Modulation of homo/hetero-complex association is another approach to control transcription factor activated gene expression. For example, transport from the cytoplasm to the nucleus of the trans-activating transcription factor NF-B is prevented while in a heterodimer complex with the inhibitor protein IB. Upon induction by a variety of agents, including certain cytokines, IB becomes phosphorylated and NF-B is released and transported to the nucleus, where it can exert its sequence-specific trans-activating function (Baeuerle and Baltimore, *Science* 242:540–546, 1988). The dissociation of the NF-B/IB complex can be prevented by masking with an antibody the phosphorylation site of IB. This approach would effectively inhibit the trans-activation activity of the NF-IB transcription factor by preventing its transport to the nucleus. Expression of the IB phosphorylation site specific antibody or protein in target cells may be accomplished with an alphavirus gene transfer vector. An approach similar to the one described here could be used to prevent the formation of the trans-activating transcription heterodimer factor AP-1 (Turner and Tijan, *Science* 243:1689–1694, 1989), by inhibiting the association between the jun and fos proteins.

12. Production of Recombinant Proteins

In another aspect of the present invention, togavirus (including alphavirus) gene delivery vehicles can be utilized to direct the expression of one or more recombinant proteins in eukaryotic cells (ex vivo, in vivo, or established cell lines). As used herein, a "recombinant protein" refers to a protein, polypeptide, enzyme, or fragment thereof. Using this approach, proteins having therapeutic or other commercial application can be more cost-effectively produced. Furthermore, proteins produced in eukaryotic cells may be more authentically modified post-translationally (e.g., glycosylated, sulfated, acetylated, etc.), as compared to proteins produced in prokaryotic cells. In addition, such systems may be employed in the in vivo production of various chemical compounds, e.g., fine or specialty chemicals.

Within this aspect, the gene delivery vehicle encoding the desired protein, enzyme, or enzymatic pathway (as may be required for the production of a desired chemical) is transformed, transfected, transduced or otherwise introduced into a suitable eukaryotic cell. Representative examples of proteins which can be produced using such a system include, but are not limited to, insulin (see U.S. Pat. No. 4,431,740 and BE 885196A), hemoglobin (Lawn et al., Cell 21:647–51, 1980), erythropoietin (EPO; see U.S. Pat. No. 4,703,008), megakaryocyte growth and differentiation factor (MGDF), stem cell factor (SCF), G-CSF (Nagata et al., Nature 319:415–418, 1986), GM-CSF, M-CSF (see WO 8706954), the flt3 ligand (Lyman et al. (1993), Cell 75:1157–1167), EGF, acidic and basic FGF, PDGF, members of the interleukin or interferon families, supra, neurotropic factors (e.g., BDNF; Rosenthal et al., Endocrinology 129:1289–1294, 1991, NT-3; see WO 9103569, CNTF; see WO 9104316. NGF; see WO 9310150), coagulation factors (e.g., factors VIII and IX), thrombolytic factors such as t-PA (see EP 292009, AU 8653302 and EP 174835) and streptokinase (see EP 407942), human growth hormone (see JP 94030582 and U.S. Pat. No. 4,745,069) and other animal somatotropins, integrins and other cell adhesion molecules, such as ICAM-1 and ELAM (see also other "heterologous sequences" discussed above), and other growth factors, such as VEGF, IGF-I and IGF-II, TGF-$\beta$, osteogenic protein-1 (Ozkaynak et al., EMBO J. 9:2085–2093, 1990), and other bone or cartilage morphogenetic proteins (e.g., BMP-4, Nakase et al, J. Bone Miner. Res. 9:651–659, 1994). As those in the art will appreciate, once characterized, any gene can be readily cloned into gene delivery vehicles according to the present invention, followed by introduction into a suitable host cell and expression of the desired gene. In addition, such vectors may be delivered directly in vivo, either locally or systemically to promote the desired therapeutic effect (e.g., wound healing applications).

Methods for producing recombinant proteins using the vectors and alphavirus packaging cell lines described herein are provided (see examples 6 and 7). Briefly, gene delivery vehicles, in the form of in vitro transcribed RNA, plasmid DNA, or recombinant vector particles, which encode recombinant proteins, may be introduced (via transfection or infection) into alphavirus packaging cell lines (PCLs) such that only a small fraction of the cultured cells ($\leq 1\%$) contain vector molecules. Vector replicons are packaged by the sPs, supplied in trans by the PCL, following vector RNA amplification, which proceeds according to the Sindbis virus replication strategy. In turn, the produced recombinant vector particles infect the remaining cells of the culture. Thus, a bloom of recombinant protein expression results over time as recombinant vector particles are produced and subsequently infect all cells in the PCL culture. Similarly, amplification of vector particles with PCL may be used to generate large, high titer particle stocks for other applications. In yet another aspect of this invention, recombinant protein expression from producer cell lines is described (see Example 7). Briefly, cell lines are derived which contain all of the genetic elements, including vector replicon and defective helper expression cassettes, from which the production of vector particles can be induced, via addition of an extracellular stimulus to the culture. Thus, expression of vector-encoded recombinant protein occurs as a result of induction of alphavirus vector particle producer cell lines. In yet a still further aspect of this invention, recombinant protein expression from cell lines stably transformed with eukaryotic layered vector initiation systems are described (see Example 7). Briefly, cell lines are derived which are stably transformed with an inducible eukaryotic layered vector initiation system cassette that encodes a recombinant protein of interest. Thus, expression of vector-encoded recombinant protein occurs as a result of induction of the eukaryotic layered vector initiation system cassette.

As should be readily understood given the disclosure provided herein, protein production utilizing RNA vectors replicons, eukaryotic layered vector initiation systems, or recombinant vector particles may also be accomplished by methods other than introduction into packaging or producer cell lines. For example, such vectors may be introduced into a wide variety of other eukaryotic host cell lines (e.g., COS, BHK CHO, 293, or HeLa cells), as well as direct administration in vivo or to ex vivo cells, in order to produce the desired protein.

J. Deposit Information

The following materials have been deposited with the American Type Culture Collection:

| Deposit | Designation | Deposit Date | Accession No. |
| --- | --- | --- | --- |
| Wild type Sindbis virus | CMCC #4639 | Apr. 2, 1996 | VR-2526 |
| SIN-1 Sindbis virus | CMCC #4640 | Apr. 2 1996 | VR-2527 |
| pBG-SIN1 ELVS1.5 SEAP | CMCC #4641 | Apr. 2, 1996 | 97502 |

The above materials were deposited by Chiron Corporation with the American Type Culture Collection (ATCC), 12301 Parklawn Drive, Rockville, Md. under the terms of the Budapest Treaty on the International Recognition of the Deposit of Microorganisms for purposes of Patent Procedure. The accession number is available from the ATCC at telephone number (301) 881-2600.

These deposits are provided as convenience to those of skill in the art, and are not an admission that a deposit is required under 35 U.S.C. §112. The nucleic acid sequence of these deposits, as well as the amino acid sequence of the polypeptides encoded thereby, are incorporated herein by reference and should be referred to in the event of an error in the sequence described therein. A license may be required to make, use, or sell the deposited materials, and no such license is granted hereby.

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example, "Molecular Cloning," Second Edition (Sambrook et al., Cold Spring Harbor Laboratory Press, 1987) and "current Protocols in Molecular Biology" (Ausubel et al., eds. Greene Associates/Wiley Interscience, NY, 1990).

EXAMPLES

Example 1

Isolation and Characterization of Sin1

Below, the identification and molecular characterization of a positive strand RNA virus which exhibits reduced inhibition of host macromolecular synthesis and is capable of establishing persistent infection in vertebrate cells, as compared to lytic, cytopathogenic wild type strains of the same virus, is described. For example, Sindbis virus is used as a prototype representative of the Alphavirus genus.

A. Isolation, Plaque Purification, and Characterization of SIN-1 from a Wild-Type Sindbis Virus Stock The isolation, molecular cloning, and characterization of a Sindbis virus variant strain is described. This strain is able to establish productive persistent infection in the absence of cytopathicity, but produce levels of virus equivalent to that of wild-type virus.

A high-titered (>$10^8$ PFU/ml) wild-type stock obtained by infection of BHK cells (ATCC No. CCL-10) with Sindbis virus (CMCC #4639) at low MOI ($\leq 0.1$). To facilitate infection, the virus inoculum was contained in a volume just sufficient to cover the monolayer when added to the cells. BHK cells were maintained, and all virus dilutions were performed, in Eagle minimal essential medium supplemented with 10% fetal calf serum. Cells were cultured at 37° C. in a 5% $CO_2$ atmosphere. Extensive CPE, as demonstrated by "rounding up", loss of adhesion, and increased light refraction of individual cells within the monolayer, and additionally, the decreased overall cell density of the monolayer, was observed within 48 hours post infection (hpi). The cell culture fluids were collected. cell debris was removed by low speed centrifugation (4,000 rpm for 10 min at room temperature), and the virus stock was aliquoted and stored at −70° C. The titer of the Sindbis virus stock was determined by plaque assay as described previously (Strauss et al., *Virology* 74:154–168, 1976). Briefly, chicken embryo fibroblasts (CEF) monolayers were infected with various dilutions of the virus stock and the monolayer overlayed with media supplemented with 0.75% agarose. At 24–48 hpi plaques due to cell lysis were visualized and quantitated either directly or, alternatively, by staining with crystal violet after removing the agarose overlay. The virus titer was determined from samples infected with virus dilutions in which the plaques were accurately quantitated.

A Sindbis virus stock enriched for DI particles was obtained by repeated high MOI passage ($\geq 5$) on BHK cells. BHK monolayers were infected initially with the Sindbis virus seed stock at an MOI=5. The culture medium was collected and clarified by low speed centrifugation after complete cell lysis of the infected culture was observed (usually within 24 hpi). The clarified medium collected from the infected culture was then used to infect a fresh BHK monolayer. For example, 2 ml of the virus inoculum was added to a fresh BHK monolayer in a 10 cm petri dish. At 1 hpi, 8 ml of fresh medium was added to the virus-infected culture. As described above, the culture medium was collected and clarified after observation of complete cell lysis of the culture. This process was repeated until the rate at which cytopathogenicity in the BHK monolayer developed after infection was delayed until at least 4 days. The delay in the onset of cytopathogenicity after infection signifies the presence of a high level of DI particles in the virus preparation.

The presence of a high level of DI particles in the virus preparation derived from multiple serial undiluted passages of infected cell medium was determined by an interference assay or by RNA analysis of BHK infected cells. In the first method, a homologous interference assay was performed as a measure of the presence of DI particles. Briefly, BHK cells were infected alone at an MOI=10 with the high-titered (>$10^8$ PFU/ml) wild-type stock prepared as described above At 16 hpi, the virus yield was determined by plaque assay, as described above. The virus yield from this experiment was typically $1\times10^9$ to $1\times10^{10}$ PFU/ml. In another experimental group, BHK cells were simultaneously coinfected with the wild-type stock (MOI=10) and the virus stock prepared from multiple serial undiluted passages of infected cell medium (MOI=5). As before, the virus yield was determined at 16 hpi by plaque assay. If the virus stock from the second experimental group contains a high level of DI particles, the virus yield will be at least 2–3 orders of magnitude lower than the first experiment (e.g. $\leq 1\times10^7$ PFU/ml).

As a more definitive method for demonstrating the presence of DI articles in the virus preparation,virus-specific RNA in BHK infected cells at 16 hpi was analyzed. Briefly, BHK cells were infected (MOI=10) with the high-titered (>$10^8$ PFU/ml) wild-type stock or with the virus stock containing DI particles. Mock-infected controls and infected cells were treated with dactinomycin (1 mg/ml) and labeled with [$^3$H]uridine (20 mCi/ml) from 1 to 16 hpi. RNA was isolated from infected and control cells by using RNAzol B. as described by the manufacturer (Tel-Test, Inc., Friendswood, Tex.). Alternatively, RNA was isolated with Tri-Reagent (Molecular Research Center, Inc., Cincinnati, Ohio), or by conventional methods using phenol extraction of cells lysed in a buffer (0.05 M Tris, 0.1 M NaCl, 0.001 M EDTA, pH 7.5) containing 0.5% Triton and 0.5% recrystallized naphthalene disulfonate, as described by Weiss et al. (*J. Virol.* 14:1189–1198, 1974). The RNAs were denatured with glyoxal and electrophoresed through 1.1% horizontal agarose gels prepared in 0.01M sodium phosphate buffer (pH 7.0), at 5V/cm (McMaster and Carmichael. *Proc Natl. Acad. Sci. USA*, 74:4835–4838, 1977). Alternatively, RNA can be electrophoresed through formaldehyde gels. Following electrophoresis, all moisture was removed from the gels under vacuum with a gel dryer, and the dried gels were treated for fluorography and exposed to film. Two RNAs, corresponding to the genomic and subgenomic species (42S and 26S, respectively), were observed in samples from BHK cells infected with the wild-type virus stock. In contrast, a large number of RNA species that are distinct from the standard viral 42S and 26S RNAs were observed in samples from BHK cells infected with the virus stock containing DI particles. Multiple RNAs corresponding to DI RNAs migrated predominantly at molecular weights smaller than the 26S RNA species from wild-type virus. An example of multiple RNAs in addition to the 42S and 26S species observed in BHK cells infected with a virus stock containing DI particles may be seen in FIG. 3, lane 3, of Weiss et al. (*J. Virol.* 33:463–474, 1980).

A Sindbis virus variant strain which is able to establish productive persistent infection with decreased cytopathogenicity was isolated and molecularly cloned from a virus stock enriched for DI particles. BHK cells were infected at high multiplicity (MOI=5) with the Sindbis virus stock enriched for DI particles. Cytopathogenicity developed slowly compared to infection of BHK cells with wild-type virus; however, most cells were eventually lysed and detached from the plate. Cell debris and non-adherent cells were removed every two days by medium changes. Within two weeks after initial infection, separate and distinct colonies were observed. These colonies were thriving and demonstrated no morphological evidence of CPE, compared to uninfected BHK cell controls. Within 3–4 weeks, the cell colonies were large and discernible to the naked eye. The colonies were isolated with cloning rings, and the cells were dispersed with either 3 mM EDTA or trypsin. Dispersed cells from each colony were replated without dilution. Thereafter, cells were subcultured at a 1:10 dilution upon reaching confluency, generally within four days. Aliquots of cells, designated BHK(SIN-1), were prepared in cryotubes after the fifth passage for long term storage in liquid nitrogen. BHK(SIN-1) cells were indistinguishable from the original, uninfected BHK cells in terms of growth rate or morphology.

B. Molecular Cloning of SIN-1

To characterize the mutation(s) in the Sindbis genome which correlate with the development of the substantially reduced cytopathogenicity of SIN-1, genomic RNA from SIN-1 virions was isolated, reverse transcribed, and the resultant cDNA encompassing the nonstructural protein genes sequenced, as described more fully below.

Briefly, the SIN-1 virus was plaque purified three times before preparation of a stock that was used for the isolation of RNA. The BHK(SIN-1) cells were grown as described above, the culture fluid was collected, and various dilutions were used to infect primary chicken embryo fibroblast monolayers (CEF, grown in minimal essential medium supplemented with 3% fetal calf serum). Following infection, medium containing 0.5% noble agar was added to the monolayers. Additionally, DEAE-dextran (100 $\mu$g/mL) can be included in the agar-overlay medium to increase the size of the SIN-1 plaques. Individual discreet plaques were observed after 3 days of incubation at 30° C. in plates infected with suitably dilute inoculums of the BHK(SIN-1) culture fluid. After the third round of purification, the cloned SIN-1 virus was passaged once at 30° C. in CEF cells infected at a MOI=0.1. The plaque-purified SIN-1 virus preparations were determined to be free of DI particles by the interference assay and RNA analysis in BHK infected cells, as described above.

BHK cells were infected (MOI=10) with the plaque purified SIN-1 stock to determine the ability of this wild-type Sindbis virus variant strain to establish persistence. As described above, establishment of persistent infection in BHK cells with wild-type Sindbis virus requires the presence of DI particles in the virus preparation and considerable time to allow those few surviving cells to grow out. In contrast, persistent infection was readily established in BHK cells infected at 37° C. with the SIN-1 variant whether or not DI particles are present in the virus inoculum. At six days post infection with SIN-1, the BHK cells were completely resistant to superinfection with wild-type Sindbis virus, demonstrating establishment of a persistent infection. However, these cells were susceptible to infection by the heterologous virus, VSV, demonstrating that interferon is not involved in the establishment of SIN-1 persistent infection.

CEF cells were infected (MOI=10) with the plaque purified SIN-1 stock to generate a high titered stock of virus for the isolation of RNA. Ninety ml of culture fluid ($2\times10^{10}$ PFU/ml) was clarified by centrifugation for 5 min at 2,500 rpm in a Sorvall GSA rotor. The SIN-1 virus was pelleted from the clarified culture fluid by centrifugation in an SW27.1 rotor for 2 h at 24,000 rpm, at 4° C. The virus pellet was then resuspended in 3 ml of culture media, homogenized by repeated pipetting, and layered on top of a 25–40% (w/w) sucrose gradient. This was followed by centrifugation in an SW27.1 rotor for 4 h at 24,000 rpm, at 4° C. The virus band was visualized with incandescent light illumination, and collected with a 22 gauge needle/syringe. The RNA was purified further by Proteinase K (Boehringer Mannheim, Indianapolis, Ind.) digestion (56° C., 1 hr), followed by extraction with an equal volume of $H_2O$-saturated phenol:chlorform (1:1 v/v, pH 7.0), followed by precipitation with 2 volumes of ethanol and 0.3 M sodium acetate, pH 5.2.

Alternatively, the SIN-1 virus can be further purified by polyethylene glycol precipitation of infected BHK cell culture media (Strauss et al. *Virology* 133:154–168, 1976), or alternatively by pelleting through a sucrose cushion (Polo et al. *J. Virol.* 62:2124–2133, 1988).

Two rounds of first strand cDNA synthesis were performed with the purified viral RNA, using the Moloney murine leukemia virus or SuperScript II reverse transcriptases (Gibco-BRL, Gaithersburg, Md.) according to the manufacturer's recommended conditions. Six separate reactions were performed, using the Sindbis virus specific primers complementary to the positive strand (primers denoted by R) shown below. All primers denoted by R were phosphorylated at their 5' end with polynucleotide kinase (New England Biolabs) prior to the first strand synthesis reaction to facilitate cloning.

| Primer | Location | Seq. ID No. | Sequence (5' -> 3') | Enzyme Site |
|---|---|---|---|---|
| T7/1F | Sac I/T7/1–20 | 2 | GGTGGAGCTCTAA TACGACTCACTAT AGATTGACGGCGT AGTACACAC | Sac I |
| 1465R | 1465–1451 | 3 | AATTTCTGCCTCA GC | Eco 47 III |
| 1003F | 1003–1019 | 4 | TATGCAAAGTTAC TGAC | Eco 47 III |
| 2823R | 2823–2806 | 5 | CTGTCATTACTTCA TGTC | Bsp HI |
| 1003F | 1003–1019 | 4 | TATGCAAAGTTAC TGAC | Eco 47 III |
| 4303R | 4303–4289 | 6 | GCGTGGATCACTT TC | Avr II |
| 4051F | 4051–4069 | 7 | ATTGCGTGATTTCG TCCGT | Avr II |
| 8115R | 8115–8101 | 8 | TAAATTTGAGCTT TG | Pml I |
| 1680F | 1680–1689 | 9 | GGCATATGGCATT AGTTG | Bsp HI |
| 8115R | 8115–8101 | 8 | TAAATTTGAGCTT TG | Pml I |
| 8034F | 8034–8052 | 10 | CTGGCCATGGAAG GAAAGG | Pml I |
| 11,703R | Xho I/dT$_{21}$/ 11703–11677 | 11 | CCCCTCGAGGGT (21)GAAATGTTAAA AACAAAATTTTGT TG | Xho I |

Synthesis of the second strand from the cDNA template above was accomplished in six separate reactions with the Klenow fragment of DNA polymerase I (New England Biolabs, Beverly, Mass.) according to the manufacturer's recommended conditions. Sindbis virus specific primers complementary to the negative strand (primers denoted by F shown above) were used. The double-stranded DNA products were substituted, stepwise, for the corresponding regions in the plasmid Toto1101, which contains the full-length Sindbis virus genome (Rice et al., *J. Virol,* 61:3809–3819, 1987). For example, the T7/1F-1465R product was digested with Sac I and Eco 47III, and inserted into Sac I/Eco 47III digested and CIAP treated Toto1101 plasmid, which was purified away from the Sac I/Eco 47III small fragment (SP6 promoter, Sindbis virus nts. 1–1407) by 1% agarose/TAE (5033 /liter: 242 g Tris base/57.1 ml glacial acetic acid/100 ml 0.5 M EDTA pH 8.0) electrophoresis, and GENECLEAN II. This construct was then digested with Eco 47III and Avr II (Sindbis virus nt nos. 1407 and 4281, respectively), treated with CIAP, and followed by insertion of the 3300 bp fragment isolated from the 1003F-4303R product, digested with Eco 47 III and Avr II. The fully assembled clone is designated as pRSIN-1g (g, as a reference to full-length genomic clone), and contained all 11,703 bp of viral genome. A subset of the primers listed in the table above generate redundant double-stranded DNA reaction products within the SIN-1 genome. For example, the sequences in the 4051F/8115R product are within the 1680F/8115R product. These redundant products are provided as construction alternatives for the SIN-1 genomic clone; i.e., in general, the efficiency of cDNA cloning is inversely proportional to the length of the desired fragment.

To clone portions of the viral genome not obtained by the above method, the SIN-1 RNA viral genome was cloned by reverse transcription polymerase chain reaction (RT-PCR). First strand synthesis was accomplished as described above. PCR amplifications of Sindbis cDNA with the primer pairs shown above were performed as separate reactions, using the Klentaq1 enzyme, and the reaction conditions. as described in Barnes (*Proc. Natl. Acad. Sci. USA* 91:2216–2220, 1994). Alternatively, the Thermalase thermostable DNA polymerase (Amresco Inc., Solon, Ohio) was substituted for the Klentaq 1 enzyme, using a buffer containing 1.5 mM MgCl, that was provided by the supplier. Alternatively, the VentR thermostable DNA polymerase (New England Biolabs, Beverly, Mass.) was used in the amplification reactions. Additionally, the reactions contained 5% DMSO and "HOT START WAX" beads (Perkin-Elmer). The PCR amplification protocol used is shown below (The 72° C. extension incubation period was adjusted to 1 min per 1 kb of template DNA):

|     | Temperature (° C.) | Time (Min.) | No. Cycles |
|-----|--------------------|-------------|------------|
| (a) | 95                 | 2           | 1          |
| (b) | 95                 | 0.5         |            |
|     | 55                 | 0.5         | 35         |
|     | 72                 | 3.5         |            |
| (c) | 72                 | 10          | 1          |

Alternatively, cloning of the full-length SIN-1 RNA genome can be performed similar to methods which have previously been described (Dubensky et al., *J. Virol.* 70:508–519, 1996). Briefly, first strand cDNA synthesis is accomplished with a mixture of random hexamer primers (50 ng/ml reaction concentration) (Invitrogen, San Diego, Calif.), and primer 4B, whose sequence is shown in the table below. Genomic length Sindbis virus SIN-1 variant cDNA is then amplified by PCR. Six distinct segments using six pairs of overlapping primers is sufficient to clone the entire genome. In addition to viral complementary sequences, the SIN-1 5' end forward primer contains a 19 nucleotide sequence corresponding to the bacterial SP6 RNA polymerase promoter and the Apa I restriction endonuclease recognition sequence linked to its 5' end. The bacterial SP6 RNA polymerase is poised such that transcription in vitro results in the inclusion of only a single non-viral G ribonucleotide linked to the A ribonucleotide, which corresponds to the authentic Sindbis virus 5' end. Inclusion of the Apa I recognition sequence facilitates insertion of the PCR amplicon into the plasmid vector pKS II$^+$ (Stratagene, La Jolla, Calif.) polylinker sequence. A five nucleotide 'buffer sequence' extension is also linked upstream from the Apa I recognition sequence in order to facilitate efficient enzyme digestion. The sequence of the SP6-5' SIN-1 forward primer and all of the primer pairs necessary to amplify the entire SIN-1 genome are shown in the table below. (Note that "nt" and "nts" as utilized hereinafter refer to "nucleotide" and "nucleotides," respectively). The reference sequence (GenBank accession no. J02363, locus: SINCG) is from Strauss et al., *Virology* 133:92–110, 1984.

| Primer | Location | Seq. ID No. | Sequence (5' -> 3') | Recognition Sequence |
|---|---|---|---|---|
| SP6-1A | Apa I/SP6/ SIN nts. 1–18 | 12 | TATATGGGCCCGAT TTAGGTGACACTAT AGATTGACGGCGTAG TACAC | Apa I |
| 1B | 3182–3160 | 13 | CTGGCAACCGGTAAG TACGATAC | Age I |
| 2A | 3144–3164 | 14 | ATACTAGCCACGGCC GGTATC | Age I |
| 2B | 5905–5885 | 15 | TCCTCTTTCGACGTG TCGAGC | Eco RI |
| 3A | 5844–5864 | 16 | ACCTTGGAGCGCAAT GTCCTG | Eco RI |
| 7349R | 7349–7328 | 17 | CCTTTTCAGGGGATC CGCCAC | Bam HI |
| 7328F | 7328–7349 | 18 | GTGGCGGATCCCCTG AAAAGG | Bam HI |
| 3B | 9385–9366 | 19 | TGGGCCGTGTGGTCG TCATG | Bcl I |
| 4A | 9336–9356 | 20 | TGGGTCTTCAACTCA CCGGAC | Bcl I |
| 10394R | 10394–10372 | 21 | CAATTCGACGTACGC CTCACTC | Bsi WI |
| 10373F | 10373–10394 | 22 | GAGTGAGGCGTACGT CGAATTG | Bsi WI |
| 4B | Xba I/$T_{35}$/ 11703–11698 | 23 | TATATTCTAGA($T_{35}$) GAAATG | Xba I |

PCR amplifications of Sindbis cDNA with the primer pairs shown above are performed as separate reactions, using the Thermalase or $Vent_R$ DNA polymerases (cited above), reaction conditions, and the PCR amplification conditions, as described above.

The regions of sequence overlap between the amplification products correspond to unique enzyme recognition sites within the PCR amplicon. The PCR products are purified (QIAquick PCR purification kit, Qiagen, Chatsworth, Calif.) and inserted stepwise into the pKS II$^+$ vector, between the Apa I and Xba I sites. The fully assembled clone is designated as pKSRSIN-1g (g, as a reference to full-length genomic clone), and contains all 11,703 bp of viral genome.

C. Sequence of the SIN-1 phenotype

The SIN-1 specific nucleotide sequences of the pRSIN-1g clone was determined by the dideoxy-chain termination method. Sequence comparison of 8,000 bp of viral sequence revealed multiple differences between the SIN-1 clone described herein and the Sindbis virus (strain HRsp) sequence provided in GenBank (GenBank Accession no. J02363, locus: SINCG). Differences in the sequence among SIN-1 (FIG. 6), SINCG (FIG. 7), and Toto1101 (FIG. 8) are presented below.

| | | SINCG | | Toto 1101 | | SIN-1 | |
|---|---|---|---|---|---|---|---|
| nt. Position | Gene | nt | aa | nt | aa | nt | aa |
| 45 | 5'NTR | T | — | T | — | C | — |
| 120 | nsP1 | C | Gln | C | Gln | A | Lys |
| 1775 | nsP2 | G | null | G | null | A | null |
| 1971 | nsP2 | T | Phe | T | Phe | C | Leu |
| 2992 | nsP2 | C | Pro | T | Leu | T | Leu |
| 3579 | nsP2 | A | Lys | G | Glu | G | Glu |
| 3855 | nsP2 | C | Pro | C | Pro | T | Ser |
| 3866 | nsP2 | C | null | C | null | T | null |

-continued

| | | SINCG | | Toto 1101 | | SIN-1 | |
|---|---|---|---|---|---|---|---|
| nt. Position | Gene | nt | aa | nt | aa | nt | aa |
| 4339 | nsP3 | A | Glu | A | Glu | T | Val |
| 4864 | nsP3 | C | Ser | C | Ser | T | Phe |
| 5702 | nsP3 | A | null | T | null | T | null |
| 5854* | nsP4 | G | Arg | G | Arg | A | His |
| 7612 | junction | A | — | A | — | T | — |
| 7837 | Capsid | C | Arg | C | Arg | T | Cys |

*This mutation was found in one cDNA clone. It was not detected when the Sin-1 virus RNA was sequenced. It likely represents a minor species in the RNA population.

Verification that the sequence changes were unique to the clone (and not the result of cloning artifact) described herein, was determined by amplifying SIN-1 virion RNA by RT-PCR as described above, establishing the sequence containing the nucleotides in question by direct sequencing of the RT-PCR amplicon product, and comparing the sequence to the corresponding SIN-1 sequence.

Characterization and Genetic Mapping of the SIN-1 Phenotype with Molecular Clones:

Various regions of the SIN-1 genome were substituted for the corresponding wild-type Sindbis virus region in the Toto1101 plasmid (Rice et al., *J. Virol* 61:3809–3819, 1987) in order to map the location of the phenotype for establishment of persistence. The various SIN-1 nsP genes were substituted into the Toto 1101 wild-type Sindbis virus background using restriction enzyme fragments purified from pRSIN-1g, as illustrated in the table below.

| nsP Gene | Restriction Fragment | Nucleotide Coordinates | Clone Designation |
|---|---|---|---|
| nsP1 | Ple I/Eco 47III | 98-1407 | pRSIN-1nsP1 |
| nsP2 | Eco 47III/Avr II | 1407-4281 | pRSIN-1nsP2 |
| nsP2-N terminus | Eco 47III/Bgl II | 1407-2289 | pRSIN-1nsP2-N |
| nsP2-C terminus | Bgl II/Avr II | 2289-4281 | pRSIN-1nsP2-C |
| nsP3-4 | Avr II/Eco RI | 4281-5870 | pRSIN-1nsP3 |
| nsP3 | Avr II/Spe I | 4281-5262 | pRSIN-1nsP3 |
| nsP4 | Spe I/Aat II | 5263-5870 | pRSIN-1nsP4 |
| nsP1-4 | Ple I/Aat II | 98-8000 | pRSIN-1nsP1-4 |

The coordinates of the nonstructural gene coding regions are provided in the following table:

| nsP Gene | Coordinates of Sindbis virus genome (nt. no.) |
|---|---|
| nsP1 | 60-1680 |
| nsP2 | 1680-4101 |
| nsP3 | 4101-5769 |
| nsP4 | 5769-7597 |
| nsP1-4 | 60-7597 |

The various SIN-1, Toto, and chimeric SIN-1/Toto clones. pRSIN-1g, Toto, pRSIN-1nsP1, pRSIN-1nsP2, pRSIN-1nsP2-N, pRSIN-1nsP2-C, pRSIN-1nsP3. pRSIN-1nsP4, and pRSIN-1nsP1–4 were linearized by digestion with Xho I, which makes a single cut in the cDNA clones immediately adjacent and downstream of a 21 nucleotide poly dA:dT tract following the Sindbis virus 3' end (viral nt. 11703). The linearized clones were purified with GENECLEAN II (BIO 101, La Jolla, Calif.), and adjusted to a concentration of 0.5 $\mu g/\mu l$. Transcription of the linearized clones was performed in vitro at 40° C. for 90 minutes according to the following reaction conditions: 2 $\mu l$ DNA/4.25 $\mu l$ $H_2O$); 10 $\mu l$ 2.5 mM NTPs (UTP, ATP, GTP, CTP); 1.25 $\mu l$ 20 mM Me7G(5')ppp (5')G cap analogue; 1.25 $\mu l$ 100 mM DTT; 5 $\mu l$ 5×transcription buffer (Promega, Madison Wis.); 0.5 $\mu l$ RNasin (Promega); 0.25 $\mu l$ 10 $\mu g/\mu l$ bovine serum albumin; and 0.5 $\mu l$ T7 RNA polymerase (Promega). The in vitro transcription reaction products were digested with DNase I (Promega), purified by sequential phenol:$CHCl_3$ and ether extraction, and followed by ethanol precipitation. Alternatively, the in vitro transcription reaction products can be used directly for transfection. The in vitro transcription reaction products or purified RNA were complexed with a commercial cationic lipid compound (LIPOFECTIN, GIBCO-BRL, Gaithersburg, Md.) and applied to Baby Hamster Kidney-21 (BHK-21) cells maintained in a 60 mm petri dish at 75% confluency. Alternatively, BHK cells were electroporated with the in vitro transcription reaction products or purified RNA, exactly as described previously (Liljestrom, *Bio/Technology* 9:1356–1361, 1991). The transfected cells were incubated at 37° C. At 48 hours post-transfection, culture media were collected and the titer of each virus was determined by plaque assay, as described above. The titered virus stocks derived from these in vitro transcription reactions were designated as shown in the table below.

| Clone Designation | Virus Designation |
|---|---|
| pRSIN-1nsP1 | SIN-1nsP1 |
| pRSIN-1nsP2 | SIN-1nsP2 |
| pRSIN-1nsP2-N | SIN-1nsP2-N |
| pRSIN-1nsP2-C | SIN-1nsP2-C |
| pRSIN-1NSp3-4 | SIN-1nsP3-4 |
| pRSIN-1nsP3 | SIN-1nsP3 |
| pRSIN-1nsP4 | SIN-1nsP4 |
| pRSIN-1nsP1-4 | SIN-1nsP1-4 |
| Toto 1101 | Toto |

To map the SIN-1 persistent phenotype, $8\times10^5$ BHK cells were infected (MOI=5) with each of the virus stocks prepared above. At 3 days post infection, the culture viability was determined by trypan blue dye exclusion. The results of this experiment (shown below), demonstrate that the SIN-1 phenotype of establishing persistent non-cytocidal infections maps to the nonstructural genes, and to nsP2 gene in particular. The number of cells in the mock-infected culture represents continued growth of these cells until they reached the stationary phase. At 3 dpi, cells infected with SIN-1nsP1, SIN-1nsP3, SIN-1-nsP3–4 and SIN-1nsP4 had all died. The cells that survived infection with SIN-1nsP2 and SIN-1nsP1–4 continued to grow and were persistently infected based on staining with antibodies specific for Sindbis virus.

| Virus | Number of Cells at 3 dpi |
|---|---|
| SIN-1nsP1 | 0 |
| SIN-1nsP2 | $3 \times 10^5$ |
| SIN-1nsP3-4 | 0 |
| SIN-1nsP3 | 0 |
| SIN-1nsP4 | 0 |
| SIN-1nsP1-4 | $5 \times 10^5$ |
| Toto | 0 |
| Mock | $1 \times 10^7$ |

As shown above, the observed SIN-1 phenotype of establishing non-cytocidal persistent infections maps to the viral nsPs, as opposed to the sPs. This conclusion was demonstrated clearly by comparison of cell survival levels between cultures infected with the Toto or SIN-1nsP1–4 virus stocks Both the Toto and SIN-1nsP1–4 viruses contain the wild-type sPs; cell survival was observed, however, only in those cultures infected with the virus (SIN-1nsP1–4) containing nsPs derived from the SIN-1 clone. In these experiments, cell survival was not dependent upon the source of the Sindbis virus sPs. Importantly, the SIN-1 phenotype was mapped further to nsP2. The level of cell survival was comparable between cultures infected with the SIN-1nsP1–4 or SIN-1nsP2 viruses. Further, a C->T transition at nucleotide 3855, in the SIN-1 nsP2 gene is responsible for the characteristic phenotype of establishment of persistent infection in cells infected with the SIN-1 virus. The single proline to serine change in the nsP2 protein produced in cells infected with the chimeric virus SIN-1nsP2-C, was all that was required to convert wild-type Sindbis virus (Toto 1101) from a virus that killed all of the infected cells into a virus which permitted many of the infected cells to survive and continue to produce virus. The phenotypes of chimeric viruses derived from insertion of the SIN-1 nsP1, nsP3, or nsP4 genes into the Toto background were indistinguishable from wild-type and complete lysis was observed in cultures infected with these viruses.

Figure 2:
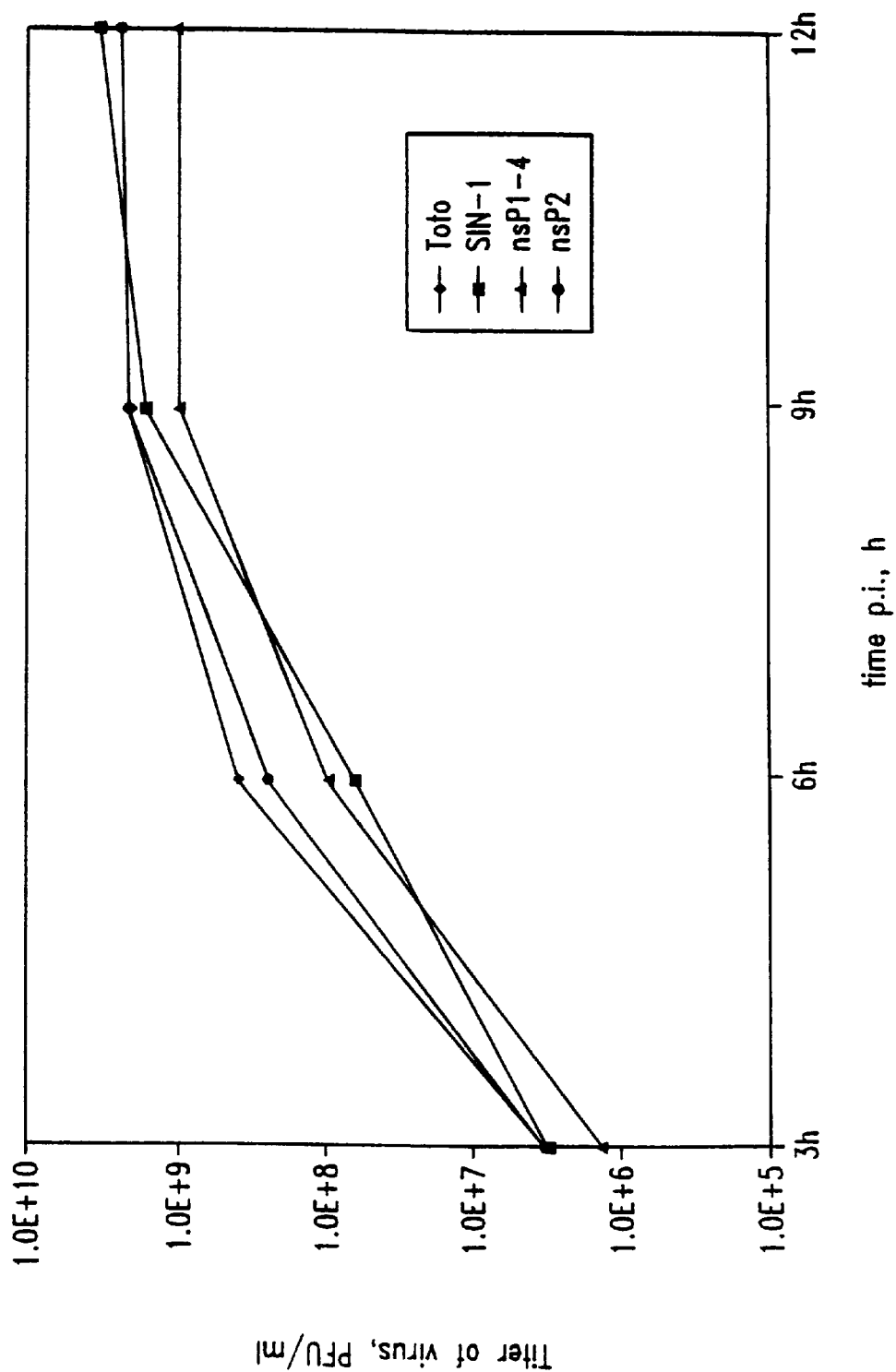
FIG. 2 is a graph of virus release from BHK cells infected at an MOI of 10 with SIN-1, SIN-1/nsP1–4, Toto1101, or Sin-1/nsP2 viruses. Cell culture fluids were collected at 3, 6, 9 and 12 hours post-infection. Virus titers were determined by plaque assay.

The possible effect of amino acid changes in the SIN-1 nsPs on the level of productive infection in BHK cells was determined by comparing the virus yield over a time course in BHK cells inoculated with the various SIN-1, wild-type (Toto), or SIN-1/Toto chimeric strains. Briefly, BHK cells were infected (MOI=20) with SIN-1(plaque purified stock described above), Toto, SIN-1nsP1–4, or SIN-1nsP2 viruses, and the culture fluids were collected at 3, 6, 9, and 12 hours post infection. The titers of virus in the culture fluids were then determined by plaque assay, as described above. The results of this study, shown in FIG. 2, demonstrate that equivalent levels of virus were produced in BHK cells infected with wild-type or SIN-1 strains. The actual virus titers at the 12 hpi time point are set forth in the table below. More than half of the BHK cells survived infection with SIN-1 virus (and chimeric viruses containing SIN-1 nsPs1–4, or SIN-1nsP2) in combination with levels of virus production equivalent to wild-type strains.

| Virus | Titer (PFU/ml) at 12 hpi ($\times 10^9$) |
|---|---|
| SIN-1 | 3.6 |
| Toto | 2.7 |
| SIN-1nsP1-4 | 1.8 |
| SIN-1nsP2 | 2.6 |

The possible effect of amino acid changes in the SIN-1nsPs on the level of viral-specific RNA synthesis was determined by comparing the level of [$^3$H]-uridine incorporation over a time course in BHK cells inoculated with the various SIN-1, wild-type (Toto), or SIN-1/Toto chimeric strains. BHK cells ($3\times10^5$ cells/35 mm dish) were grown at 37° C., according to the conditions described herein. The cells were infected (MOI=20) with SIN-1, Toto1101, SIN-1nsP1–4, or SIN-1nsP2 viruses. At 30 min. post infection, the culture medium was adjusted to 1 µg/ml actinomycin D. After incubation for an additional 30 min, the culture medium was adjusted to 10 µCi/ml [$^3$H]-uridine. At 3, 6, 9, and 12 hpi, the treated cells were washed with PBS, and lysed by addition of 200 µl of TTE buffer (0.2% Triton X-100, 10 mM Tris-HCl, pH 8.0, 1 mM EDTA). The RNA was precipitated at 4° C. by addition of 200 µl of a 25% trichloroacetic acid (TCA) solution. The RNA was pelleted by microcentrifugation for 5 min at 14,000 rpm, rinsed once with 5% TCA, and dissolved in a solution consisting of 50 mM NaOH/0.1% SDS, at 55° C. The solution containing the dissolved RNA was transferred into scintillation vials and the level of incorporated [$^3$H]-uridine was determined using EcoLume (ICN, Irvine, Calif.) scintillation fluid. The results of this study, shown in FIG. 3, demonstrate that levels of virus-specific RNA were dramatically lower in BHK cells infected with SIN-1 compared to wild-type virus. This phenotype of low level of virus-specific RNA synthesis maps to the nsPs, as shown by the equivalently low levels of RNA produced in BHK cells infected with the SIN-1 or SIN-1nsP1–4 strains, compared to wild-type.

| Virus | [$^3$H]uridine incorporation ($\times 10^3$ cpm) |
|---|---|
| SIN-1 | 22 |
| Toto 1101 | 86 |
| SIN-1nsP1-4 | 28 |
| SIN-1nsP2 | 62 |
| Mock | 8 |

Figure 4:
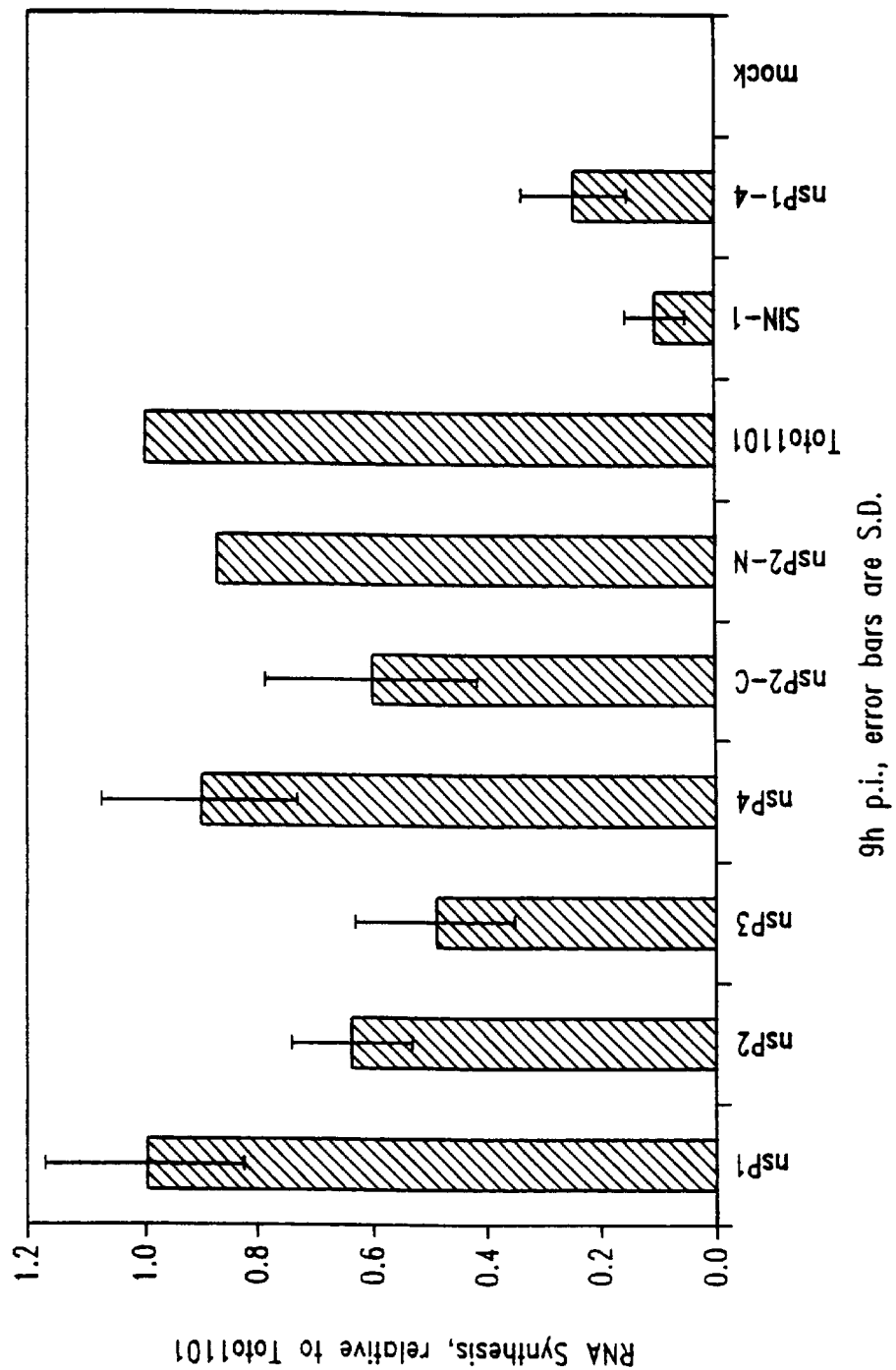
FIG. 4 is a graph depicting viral RNA synthesis in BHK cells infected by SIN-1/nsP1, SIN-1/nsP2, SIN-1/nsP3, SIN-1/nsP3–4, SIN-1/nsP4, SIN-1/nsP2-C, SIN-1/nsP2-N, Toto1101, SIN-1, or SIN-1/nsP1–4. The levels of 3H-uridine incorporation are expressed relative to wild-type (Toto 1101) infection.

Virus-specific RNA synthesis in infected BHK cells was also determined using all of the SIN-1, Toto, and SIN-1/Toto chimeric, strains. The levels of [$^3$H]uridine incorporation, relative to wild-type infection (Toto) at 9 hpi, are shown in FIG. 4, and given in the table below.

| Virus | No. of Experiments | Relative RNA Synthesis Level | Standard Deviation |
|---|---|---|---|
| Toto1101 | 9 | 1.0 | |
| SIN-1 | 9 | 0.1 | ±0.1 |
| SIN-1nsP1-4 | 8 | 0.2 | ±0.1 |
| SIN-1nsP1 | 7 | 1.0 | ±0.2 |
| SIN-1nsP2 | 8 | 0.6 | ±0.1 |
| SIN-1nsP3 | 4 | 1.0 | ±0.0 |
| SIN-1nsP3-4 | 7 | 0.4 | ±0.1 |
| SIN-1nsP4 | 6 | 0.8 | ±0.1 |
| SIN-1nsP2-N | 1 | 0.9 | |
| SIN-1nsP2-C | 3 | 0.6 | ±0.2 |
| Mock | 9 | 0.0 | |

Thus, BHK cells survive infection with SIN-1 virus (and chimeric viruses containing SIN-1nsPs1–4, or SIN-1 nsP2), SIN-1 virus levels equivalent to wild-type strains are produced in BHK cells, and, the level of viral-specific RNA synthesized is 10-fold lower compared to wild-type virus.

Figure 5:
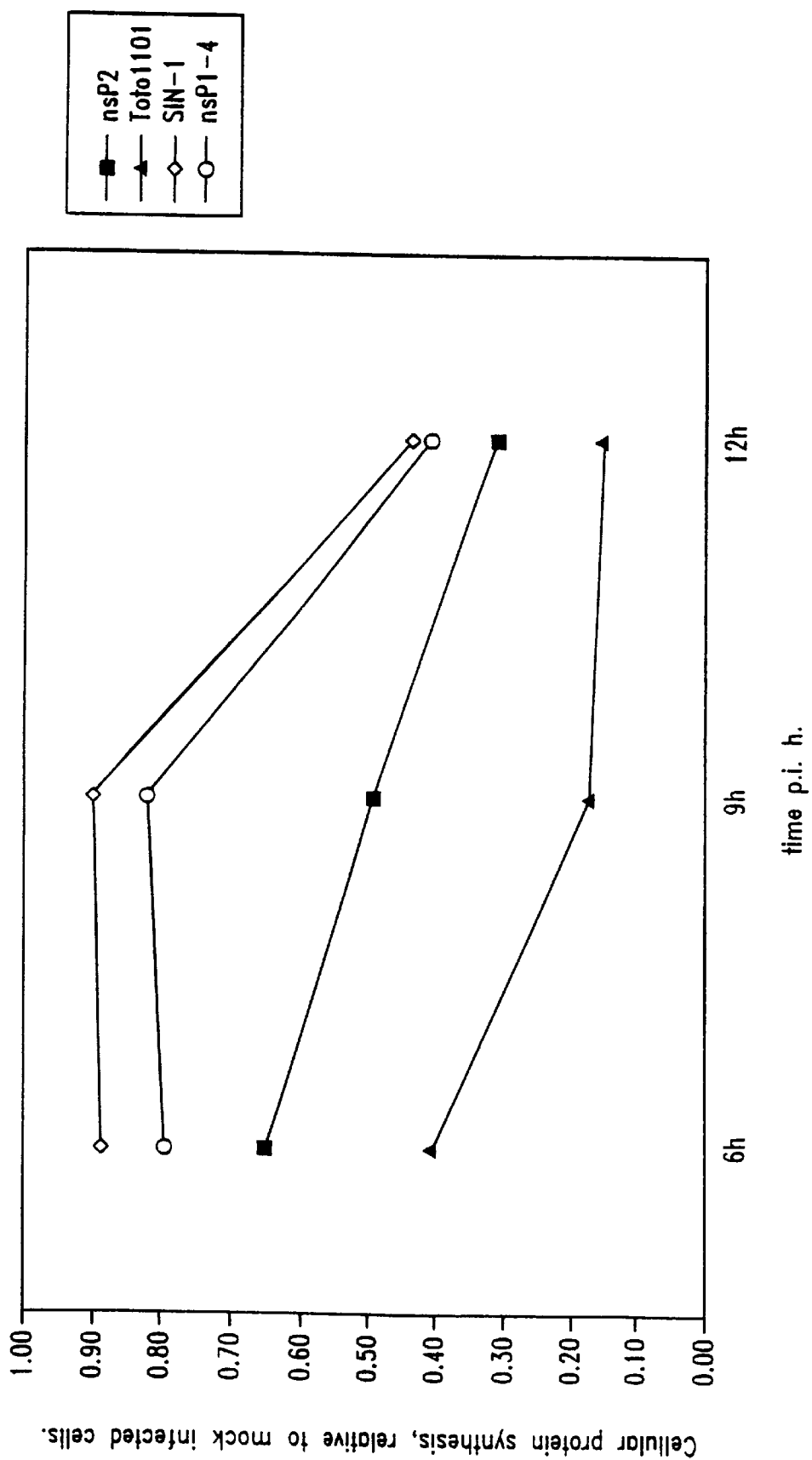
FIG. 5 is a graph depicting the shut-off of host cell protein synthesis in BHK cells infected by SIN-InsP1–4. SIN-1, SIN-1nsP2, or Toto1101 viruses.

The possible effect of amino acid changes in the SIN-1 nsPs on the level of inhibition of host cell protein synthesis was determined by comparing the level of protein synthesis, relative to uninfected cells, over a time course in BHK cells inoculated with the various SIN-1, wild-type (Toto), or SIN-1/Toto chimeric strains. Briefly, 35 mm dishes seeded with $2\times10^5$ BHK cells were infected (MOI=20) with the various Sindbis virus strains in a 0.5 ml virus inoculum in a buffer consisting of PBS/1% fetal calf serum. The plates were incubated at 4° C. for 1 hr with continuous gentle shaking. The inoculum was replaced with 2 ml of medium, described previously, containing 10% fetal calf serum. and the dishes were placed in a $CO_2$ incubator at 37° C. At 5, 8, and 11 hr later, the media was replaced with 2 ml of MEM lacking methionine (Met-), with 2% fetal calf serum, and incubated 30 min. The medium was then replaced with 1 ml of MEM (Met-) containing 2% fetal calf serum and 10

μCi/ml of [$^{35}$S]methionine. Following a 30 min incubation period at 37° C., 1 ml of medium containing 10% fetal calf serum was added to each well, and the dishes were incubated for another 30 min at 37° C. This dilution is sufficient to inhibit further incorporation of radioactive label into protein and significantly decreases the background of free [$^{35}$S]-methionine detected in polyacrylamide gels. The medium was then removed from the well. Cells were washed three times with PBS, scraped from the dish into PBS, pelleted by centrifugation, and dissolved in 25 μl of loading buffer (0.06 M Tris-HCl, pH 6.7, 2% SDS, 5% β-mercaptoethanol, 5% glycerol, 0.05% bromophenol blue). One-fifth of the sample was analyzed on the gel. After electrophoresis, the gels were stained with Coomassie brilliant blue R, dried, and autoradiographed. The rates of inhibition of host cell protein synthesis were compared by quantitating the amount of radioactivity in the section of the gel containing only host proteins. The results of this study are shown in FIG. 5, and demonstrate that the level of inhibition of host cell protein synthesis is significantly lower in SIN-1 virus infected cells, compared to wild-type virus infected cells, particularly at the earlier 6 and 9 hour time points post infection.

In summary, BHK cells survive SIN-1 infection, virus levels equivalent to wild-type strains are produced in BHK cells, the level of viral-specific RNA synthesized is 10-fold lower than wild-type virus, and the level of inhibition of host cell protein synthesis in SIN-1 virus infected cells is significantly lower compared to wild-type virus infected cells. The phenotypes of the SIN-1 virus described herein map to the viral nsP genes.

Example 2

Isolation and Characterization of Positive Strand RNA Viruses which Exhibit Reduced Inhibition of Host Macromolecular Synthesis The derivation of virus variants exhibiting the desired phenotypes of reduced, delayed or no inhibition of host cell macromolecular synthesis is dependent on the generation, characterization, and isolation of sequences which differ from that of wild-type virus. However, in addition to example 1, there are no obvious or previously disclosed methods to select for or identify coding or non-coding viral sequence changes that result in alteration of this virus-based inhibition of macromolecular synthesis, or the generation of viruses that lead to persistent, rather than lytic, infection. The present invention provides specific methods, using alphaviruses as an example, that enable one to overcome these obstacles.

A. Biological Selection of Virus Variants

The biological derivation of virus variants which result in reduced, delayed, or no inhibition of host macromolecular synthesis, or which establish persistent infections, can be performed by allowing for natural, spontaneous mutation within a cell, or first subjecting the desired virus stock to physical, chemical or other artificial mutagenesis, followed by infection of susceptible cells, and successive enrichments for those cell populations which harbor mutated virus. It is possible that prior mutagenesis, although not required, will facilitate the generation of appropriate mutations. The selection is based on the ability of cells infected with the desired variant to survive for significantly longer periods than wild-type virus infected cells. The following examples provide representative methods in detail, using Sindbis virus as an example; however. other viruses are readily substituted, as noted in the detailed description.

Specifically, in the case of chemical mutagenesis, a Sindbis virus stock suspension with a titer of greater than or equal to $10^9$ pfu/ml is treated with nitrosoguanidine at a final concentration of 100 ug/ml. After 15 minutes at room temperature, the nitrosoguanidine is removed by dialysis at 4° C. and the mutagenized stock is subsequently used for infection. Approximately $5 \times 10^6$ cells of the desired type (for example BHK-21), grown in flat stock culture, are infected with the mutagenized virus at a multiplicity of infection (M.O.I.) of approximately 5, to ensure that every cell is infected. At 12, 24, 36, and 48 hours post-infection, the cell monolayer is washed twice with fresh media to remove dead cells, and replaced with media consisting of a mixture of 50% fresh media and 50% conditioned media. After a desired time post-infection (for example 72 hours), the remaining cells are gently trypsinized to detach them from the culture dish and strip away any cell-associated extracellular virus, which is then separated from the cells by differential centrifugation. The remaining cells are then re-seeded directly into a tissue culture dish containing a semi-confluent uninfected cell monolayer, at a ratio of 1 infected cell for every $10^3$ uninfected cells. Additional rounds of selection are performed by seeding onto uninfected cells for amplification, followed by the above washing and harvesting steps. Alternatively, the initial infections may be done using a wild-type virus stock at low M.O.I., allowing for spontaneous mutation during replication within the cell. Using this approach, a heterogenous population of mutant virus is produced by the infected cells. In those instances where the population of infected cells recovered after trypsinization includes a significant number of non-viable or severely damaged cells, a brief treatment (5 minutes at room temperature) with 0.75% $NH_4Cl$ in 17 mM Tris (pH 7.65 with HCl), or centrifugation through Percoll™, is included to remove remaining dead or damaged cells, prior to re-seeding onto uninfected cell monolayers. After a minimum of two successive rounds of selection virus variants displaying the desired phenotype are isolated by limiting dilution or plaque purification, and subjected to cDNA cloning as described in Example 1. Isolation and characterization of specific sequences responsible for the variant phenotype are accomplished by substitution of defined regions of cDNA into a genomic clone or expression vector and testing for the accompanying phenotypic change, as outlined in the Examples.

B. Genetic Selection of Virus Variants

In a related approach, natural mutation or random mutagenesis is performed, not on a virus stock, but rather, using cloned genomic cDNA of the virus that can be transcribed into infectious viral RNA in vitro or in vivo. For example, in the case of prior mutagenesis, plasmid pRSINg, which contains a full-length genomic Sindbis cDNA functionally linked to a bacteriophage SP6 promoter (Dubensky, et al., *J. Virol.* 70:508–519, 1996), is transformed into competent *E. coli* XL1-Red mutator cells and plated on ampicillin plates to obtain colonies. At least 200 colonies are chosen at random, pooled, and inoculated for overnight growth in a 10 ml broth culture containing ampicillin. Plasmid DNA is prepared from the culture to obtain a heterogeneous population of pRSINg harboring various mutations. The DNA is linearized with Xba I and transcribed in vitro using SP6 polymerase, as described previously (Rice et al., *J. Virol.* 61:3809–3819, 1987). RNA transcripts are subsequently transfected into the desired cell type (for example, BHK cells) by electroporation (Liljestrom and Garoff, *Bio/Technology* 9:1356–1361, 1991), for initiation of the Sindbis virus infection cycle. Alternatively, in vitro transcribed RNA from an unmutagenized template also may be transfected. Selection of virus mutants which establish a persistent infection or exhibit reduced, delayed, or no inhibition of host macromolecular synthesis is performed as above. The selected virus variants with the desired phenotype are isolated by limiting dilution or plaque purification, subjected to cDNA cloning, and the sequences responsible for the variant phenotype are isolated and characterized, as described previously.

C. Genetic Selection of Variants Using Virus-Derived Vectors

1. Vectors Expressing an Immunogenic Protein

In another approach, spontaneous intracellular mutation, or random mutagenesis is performed on virus-derived sequences of a viral-based expression vector. These sequences include non-coding and regulatory regions, as well as nonstructural protein encoding regions. In certain instances, structural protein-encoding sequences also may be included. Such random mutagenesis or spontaneous intracellular mutation may be performed using any of the techniques described in this invention, along with the cloned cDNA of a virus-derived vector which can be transcribed into RNA in vitro or in vivo. For example, a replication-competent Sindbis virus expression vector may be used to express an immunogenic cell surface protein or other peptide which may be bound by specific antibodies added to the infected cells. Cells which contain functional vector are identified by their expression of the vector-encoded heterologous antigen and ability to be bound by antibody specific for the encoded antigen. By limiting the selection process to cells surviving for extended periods (see above), only those harboring vector variants exhibiting the desired phenotype are enriched.

Specifically, in the case of random mutagenesis, plasmid pTE3'2J (Hahn et al., *J. Virol.* 89:2679–2683, 1992). comprising an SP6 promoter operably linked to a full-length genomic Sindbis cDNA with a duplicated subgenomic promoter for expression of heterologous genes, is mutagenized as described above. This process results in isolation of a population of heterogeneous plasmid containing the random mutations. In parallel, the desired heterologous cell surface protein or marker peptide gene is cloned into a shuttle vector for insertion into the mutagenized pTE3'2J vector. Preferred cell surface proteins for use as markers include, but are not limited to, human B7.1 (Freeman et al., *J. Immunol.* 143:2714–2722, 1989) and the murine H-2K$^b$ class I molecule (Song et al., *J. Biol. Chem.* 269:7024–7029, 1994). The human B7.1 gene is amplified by standard three-cycle PCR, with 1.5 minute extension, from a pCDM8 vector containing the full-length cDNA sequence (Freeman et al., ibid), using the following oligonucleotide primers that are designed to contain flanking Xba I and Bam HI sites.

Forward primer: hB7.1 FX (5'-rest. site/B7.1 sequence) (SEQ. ID. NO. 24)

5'-ATATATCTAGA/
GCCATGGGCCACACACGGAGGCAG-3'

Reverse primer: hB7.1 RB (5'-rest. site/B7. I sequence) (SEQ. ID. NO. 25)

5'-ATATAGGATCC/
CTGTTATACAGGGCGTACACTTTC-3'

Following amplification, the approximately 875 bp DNA fragment is purified using a QIAquick-spin PCR purification kit (Qiagen, Chatsworth, Calif.), digested with Xba I and Bam HI and ligated into Sindbis shuttle vector pH3'2J1 (Hahn et al., ibid) that also has been digested with Xba I and Bam HI and treated with calf intestinal alkaline phosphatase, to create the construct pH3'B7. 1.

Following random mutagenesis of the pTE3'2J double subgenomic vector, as described above, plasmid pH3'B7.1 and the mutated population of plasmid pTE3'2J are digested with Apa I and Xho I, purified from 0.7% agarose gels using GENECLEAN II II™ (Biol101, Vista, Calif.), and ligated to form a heterogeneous population of a B7.1 expression vector, designated pTE3'B7.1. Without transforming *E. coli* and isolating individual clones, the entire population of ligated vector is linearized with Xho I and used as template for in vitro SP6 transcription reactions, as described above. The heterogeneous population of randomly mutagenized B7.1 vector transcripts is then electroporated into the desired cell type (for example, BHK cells) for initiation of the Sindbis virus replication cycle. Selection for virus mutants which establish a persistent infection or exhibit reduced, delayed, or no inhibition of host macromolecular synthesis is performed using a monoclonal antibody specific for B7.1 (Pharmingen, San Diego, Calif.) and either magnetic- or fluorescence-activated cell sorting protocols. The preferred secondary antibody tags include rat-anti-mouse IgG conjugated with magnetic microbeads for magnetic cell sorting (miniMACS Magnetic Separation System, Miltenyi Biotec, Auburn, Calif.; Miltenyi et al., *Cytometry* 11:231–238, 1990), and FITC-conjugated rat anti-mouse IgG (Pharmingen, San Diego, Calif.) for fluorescence activated cell sorting. Using such an approach and harvesting cells after an extended period (see above), only viable cells which contain a functional virus-derived vector (as evidenced by B7.1 expression), displaying the desired phenotype, are enriched.

Specifically, the heterogeneous population of randomly mutagenized B7.1 vector transcripts is electroporated into $1\times10^7$ cells, according to the procedure of Liljestrom and Garoff(1991, ibid), and plated as a flat stock culture. At 12, 24, 36, and 48 hour post-infection. the cell monolayer is washed twice with fresh media to remove dead cells, and replaced with media consisting of a mixture of 50% fresh media and 50% conditioned media. After a desired time post-infection (for example 72 hours), the remaining cells are gently trypsinized to detach them from the culture dish, and pelleted by centrifugation at 1000 rpm, 4° C. The cells are resuspended in 2 ml of blocking solution (PBS+10% fetal calf serum+1% BSA), incubated on ice for 10 minutes, and re-pelleted. Next, the cells are resuspended in 200 ul of the primary anti-B7.1 antibody solution (diluted in PBS+0.5% BSA). and incubated on ice for 30 minutes. The cells are washed twice with PBS+0.5% BSA, pelleted, and resuspended in 200 ul of magnetic bead solution (200 ul washed magnetic rat anti-mouse coated beads in PBS+0.5% BSA+5 mM EDTA). Following incubation at 4° C. for 30 minutes, the bead-bound cells are washed twice with PBS+0.5% BSA+5 mM EDTA, and resuspended in 1 ml of the same buffer. The bead-bound cells are then purified using the MiniMacs magnet column, according to the manufacturer's directions. The eluted positive cells are then re-seeded directly into a tissue culture dish containing a semi-confluent uninfected cell monolayer, at a ratio of 1 infected cell for every $10^4$ uninfected cells. Additional rounds of selection are performed as above for amplification/enrichment. The selected vector variants with the desired phenotype are isolated by limiting dilution or plaque purification, subjected to cDNA cloning, and the sequences responsible for the variant phenotype are isolated and characterized, as described previously.

Alternatively, the B7.1 expression vector, pTE3'B7.1, may be used directly for in vitro transcription without prior mutagenesis. Following transfection of these RNA transcripts, selection for mutants of the desired phenotype is performed as described above.

2. Vectors Expressing a Selectable Marker

Figure 8F:
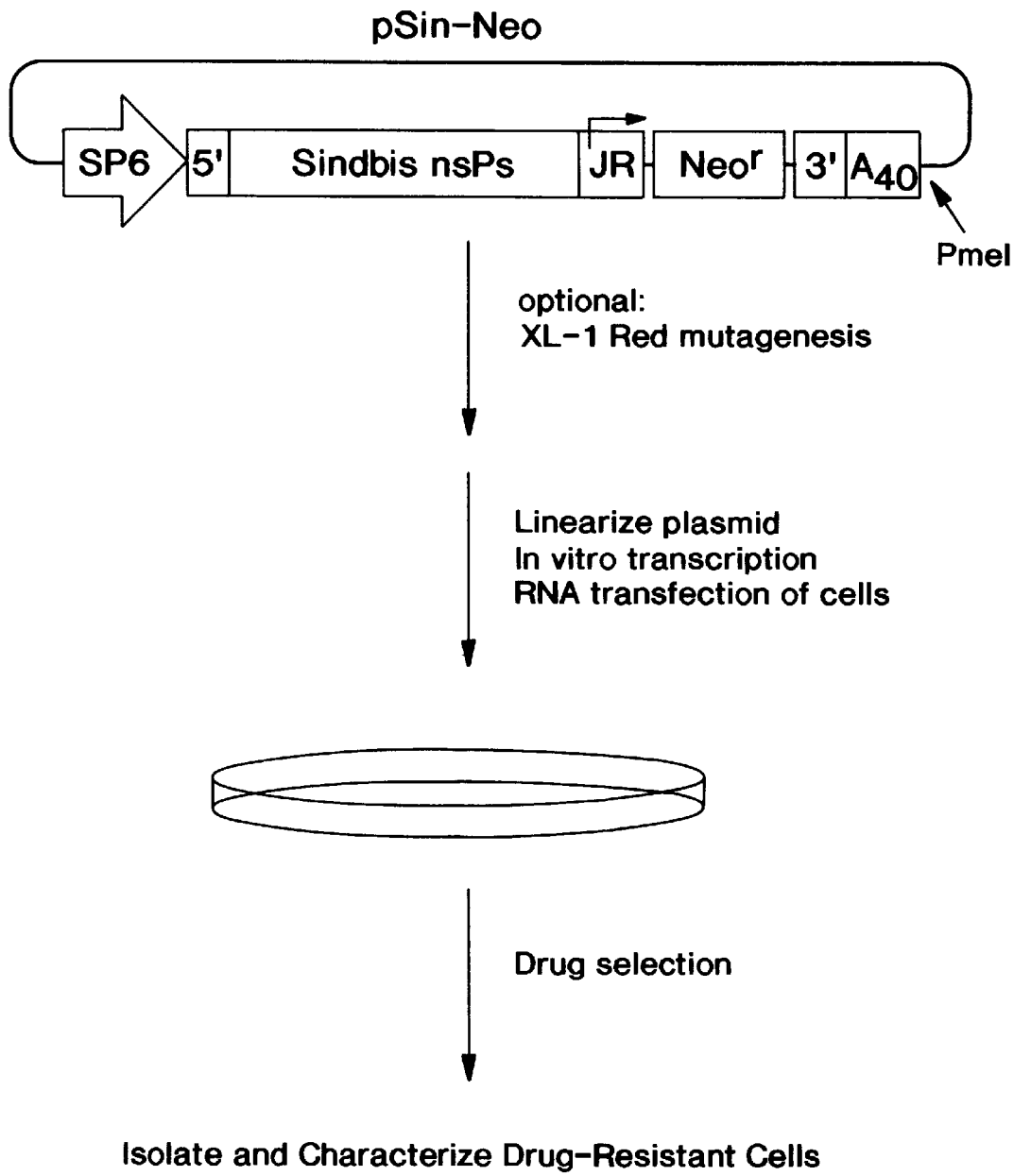
FIGS. 8A–8E are the cDNA sequence of Toto 1101 virus (SEQ. ID NO. 103).

Alternatively, an antibiotic resistance marker can be used for selection of virus vector variants exhibiting the desired phenotype (FIG. 8F). For example. the Sindbis vector pRSIN-βgal (Dubensky et al., ibid) was modified by replacement of the βgalactosidase reporter gene with a neomycin phosphotransferase selectable marker and either subjected to prior mutagenesis or used directly. The gene encoding neomycin (G418) resistance was isolated by standard three-cycle PCR amplification, with 1.5 minutes extension, from plasmid pcDNA3 (Invitrogen, San Diego, Calif.), using the following oligonucleotide primers that were designed to contain flanking Xho I and Not I restriction sites:

Forward primer: NeoFX (5'-rest. site/neo sequence) (SEQ. ID. NO. 26)

5'-ATATACTCGAG/ACCATGATTGAACAAGATGGATTG-3'

Reverse primer: NeoRN (5'-rest. site/neo sequence) (SEQ. ID. NO. 27)

5'-TATATAGCGGCCGC/TCAGAAGAACTCGTCAAGAAG-3'

Following amplification. the DNA fragment was purified with QIAquick-spin, digested with Xho I and Not I, and ligated into pRSIN-βgal vector that also had been digested with Xho I and Not I, treated with calf intestinal alkaline phosphatase, and purified from a 0.7% agarose gel, away from its previous βgalactosidase insert, using GENECLEAN II. The newly constructed Sindbis expression vector containing the neomycin resistance marker was designated pSin-Neo. Plasmid βSin-Neo was linearized with Pme I, either directly or with 1, 2, or 3 rounds of prior mutagenesis by passage through $E.$ $coli$ strain XL-1 Red. The linear DNA was used as template for. in vitro SP6 transcription reactions and vector transcripts were then transfected into the desired cell type (for example, BHK cells) for initiation of the Sindbis replication cycle and heterologous gene expression. Approximately 24 hour post-transfection, the BHK cells were trypsinized and replated in media containing 0.5 mg/ml 418. Subsequently, the media was changed at approximately 24 hour intervals to remove dead cells, and replaced with G418-containing media consisting of a mixture of 50% fresh media and 50% conditioned media. Media changes were reduced after the majority of dead cells were washed away, and cell foci began to form. At this time, all cells in control plates transfected with Sindbis vector RNA expressing only a reporter gene were killed by the drug. Using this selection, only viable cells which contained a functional Sindbis virus-derived vector, exhibiting the desired phenotype (as evidenced by neomycin resistance), were enriched. Stably transformed neomycin-resistant pools were obtained using this approach for both mutagenized and unmutagenized templates, and the pools were subsequently characterized. Similar selection approaches were demonstrated to work in cells that express higher levels of interferon(s), for example L929 cells.

Figure 8G:
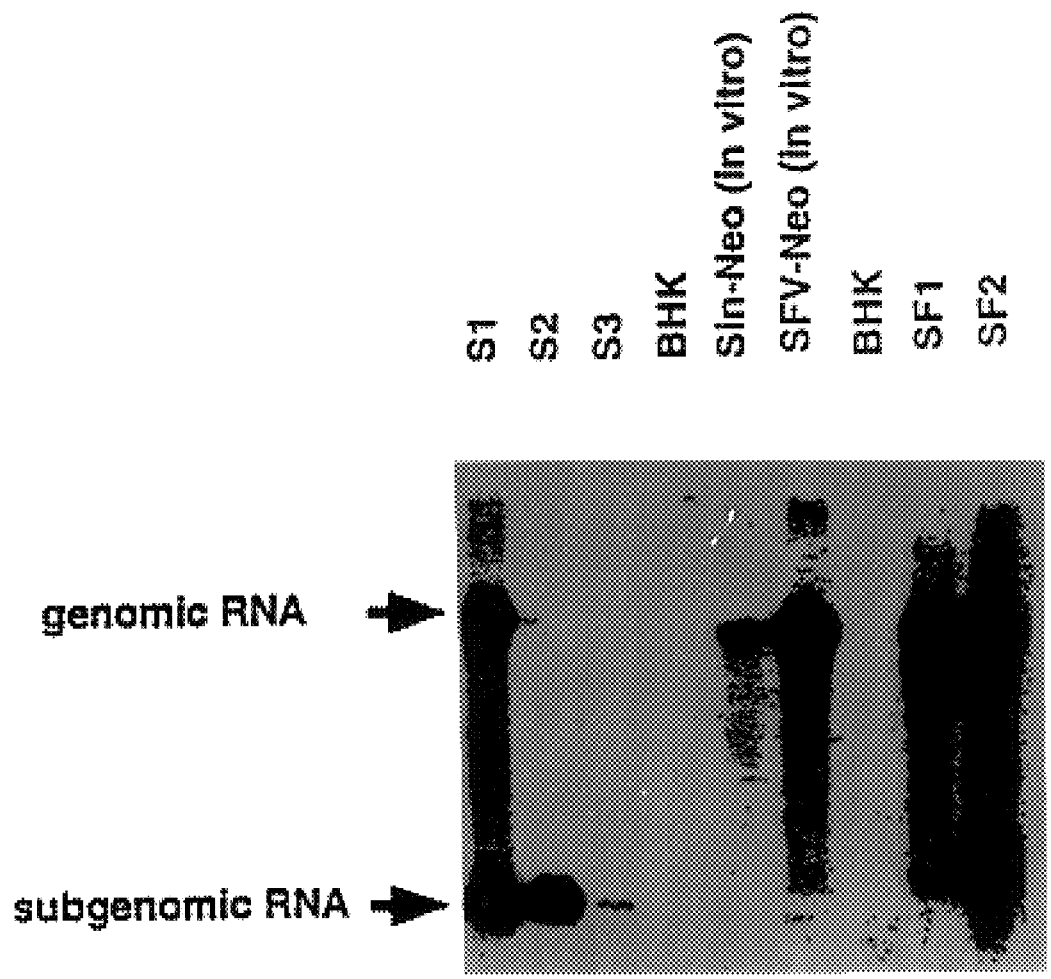

Mutant vector variants displaying the desired phenotype were isolated by harvesting RNA directly from the stably transformed cells using RNAzol B (Tel-Test, Friendswood, Tex.), followed by polyA selection. The RNAs were analyzed by northern blot, using a neomycin phosphotransferase gene probe, to demonstrate the presence of both genomic and subgenomic viral vector RNA species (FIG. 8G). Lanes S1, S2, and S3 represent RNA from three independently derived G418-resistant pools. The BHK lane represents untransfected cellular RNA, while the Sin-Neo lane represents the original in vitro transcribed RNA vector.

Clearly. significant differences in the ratios of genomic to subgenomic RNA are observed among the pools. suggesting their derivation from vectors containing different causal mutations. The isolated RNA also was used to transfer the neomycin resistance phenotype to naive cells. Specifically, BHK-21 cells were transfected with the above isolated RNA or a control template RNA and treated with the G418 drug. Those cells transfected with the isolated RNA were immediately resistant to the drug and grew to confluence within days, unlike the control transfections. Finally, complementation assays were performed using a defective Sindbis virus β-galactosidase vector (designated Sin-dl-βgal), which is deleted of nonstructural gene sequences between nucleotides 422 and 7054. Expression of the β-galactosidase reporter from such a defective vector can occur only after the deleted nonstructural proteins are provided in trans. Transfection of Sin-dl-βgal RNA into the above G418-resistant pools resulted in expression levels of β-galactosidase not seen in similarly transfected control BHK cells.

To map the genetic locus of the Sindbis vectors responsible for reduced cytopathogenicity, PCR primer pairs were synthesized, allowing division and gene substitution of the vector sequences (excluding the 3'-end UTR) in three distinct sections: nts. 1–2288. nts. 2289–4845, and nts. 4846–7644 (FIG. 8H). These primer pairs may be used to amplify cDNA directly from vector variant RNA isolated from G418-resistant cells. For example. RNA from the S2 pool (see FIG. 8G) was subjected to cDNA cloning and substitution into a wild-type pSin-Neo vector. Following in vitro transcription, wild-type and S2 mutant vector RNA was transfected into BHK cells and G418 drug selection was applied. Only the S2 mutant vector RNA resulted in rapid drug resistance and confluent cell growth within days, suggesting that the causal mutation resided within this region of gene replacement. Sequence analysis between the wild-type and S2 mutant vectors within this region, revealed a Proline to Threonine substitution at nsP2 amino acid 726, within the highly conserved alphavirus Leu-Xaa-Pro-Gly-Gly motif (SEQ. ID. NO.: 119). In addition, gene replacement of the same region with cDNA derived from pool S1 (see FIG. 8G) did not result in a vector producing similar G418 resistant cells (FIG. 8H), nor did the substituted sequence contain a mutation within the conserved Leu-Xaa-Pro-Gly-Gly motif (SEQ ID NO.: 125). These data indicate that an alternative mutation outside the region of replacement is required for the observed phenotype.

| Alphavirus Strain* | Pro-Gly-Gly Region | nsP2 a.a.'s (P-G-G) |
|---|---|---|
| 1. Sindbis virus (SEQ ID NO.: 120) | Leu-Asn-Pro-Gly-Gly-Thr | a.a. = 726–728 |
| 2. Sin-Neo S2 vector (SEQ ID NO.: 124) | Leu-Asn-Thr-Gly-Gly-Thr | a.a. = 726–728 |
| 3. S.A.AR86 virus (SEQ ID NO.: 120) | Leu-Asn-Pro-Gly-Gly-Thr | a.a. = 726–728 |
| 4. Ockelbo virus4 (SEQ ID NO.: 120) | Leu-Asn-Pro-Gly-Gly-Thr | a.a. = 726–728 |
| 5. Aura virus (SEQ ID NO.: 121) | Leu-Lys-Pro-Gly-Gly-Thr | a.a. = 725–727 |
| 6. Semliki Forest virus (SEQ ID NO.: 122) | Leu-Lys-Pro-Gly-Gly-Ile | a.a. = 718–720 |
| 7. VEE virus (SEQ ID NO.: 120) | Leu-Asn-Pro-Gly-Gly-Thr | a.a. = 713–715 |
| 8. Ross River virus (SEQ ID NO.: 123) | Leu-Xaa-Pro-Gly-Gly-Ser | a.a. = 717–719 |

In another example, a Semliki Forest virus-derived vector, pSFV-1 (GIBCO/BRL), was used for insertion of the antibiotic resistance marker and subsequent selection of the desired phenotype. The gene encoding neomycin (G418) resistance was isolated by standard three-cycle PCR amplification, with 1.5 minutes extension, from plasmid pcDNA3 (Invitrogen, San Diego, Calif.), using the following oligonucleotide primers that were designed to contain flanking BamH I restriction sites:

Forward primer: 5'BAMHI-Neo (SEQ. ID. NO. 118)
5'-ATATAGGATCCTTCGCATGATTGAACAAGAT GGATTGC-3'

Reverse primer: 3' BAMHI-Neo (SEQ. ID. NO. 57)
5'-ATATAGGATCCTCAGAAGAACTCGTCAAGA AGGCGA-3'

Following amplification. the DNA fragment was purified with QIAquick-spin, digested with BamH I, and ligated into pSFV-1 vector that also had been digested with BamH I, treated with calf intestinal alkaline phosphatase, and purified from a 0.7% agarose el, using GENECLEAN II. The resulting SFV vector construct containing the neomycin resistance marker was designated SFV-Neo. In vitro transcription of RNA vector from mutagenized or unmutagenized SFV-Neo DNA template was performed and transfection. followed by selection for mutants of the desired phenotype, was carried out essentially as described above for Sindbis virus vectors. Several independently-derived, stably transformed G418-resistant pools were obtained and characterized. Northern blot analysis for two such pools, SF1 and SF2, are shown in FIG. 8G, along with the original control RNA vector transcript (SFV-Neo). These data demonstrate that the selection methods described in the present invention have utility for multiple RNA virus vector systems.

Example 3

Preparation of SIN1Based RNA Vector Replicons

A. Construction of the SIN-1 Basic Vector

SIN-1 derived vector backbones were constructed and inserted into a plasmid DNA containing a bacteriophage RNA polymerase promoter, such that transcription in vitro produced an RNA molecule that acts as a self-replicating molecule (replicon) upon introduction into susceptible cells. The basic SIN-1 RNA vector replicon was comprised of the following ordered elements: SIN-1nsPs genes, subgenomic RNA promoter region, a polylinker sequence, which may contain heterologous sequence insertions, the SIN-1 3' non translated region (NTR), and a poly adenylate sequence. In addition, nsP genes of the desired phenotype, derived using methods such as those of Example 2, also may be substituted. Following transfection into susceptible cells, autonomous replication of the RNA vector replicon occurs as for virus, and the heterologous sequences are synthesized as highly abundant subgenomic mRNA molecules, which in turn serve as the translational template for the heterologous gene product.

The 5' region of the vector, comprised of the SIN-1nsP genes and subgenomic promoter, extends to within two nucleotides of the capsid gene translational initiation point. This region was first inserted into the pKSII+ plasmid (Stratagene) between the Apa I and Xho I sites. The 5' region of the vector was amplified by PCR from the pRSIN-1 g plasmid in two overlapping fragments. The first fragment was generated in a PCR reaction with the following primer pair:

Forward primer: SP6-1F(Apa I site/SP6 promoter/SIN nts 1–18): (SEQ. ID NO. 12) TATATGGGCCCGATTTAG-GTGACACTATAGATTGACGGCGTAGTACAC Reverse primer: SIN5160R (SIN nts 5160–5140): (SEQ. ID NO. 28)
5'-CTGTAGATGGTGACGGTGTCG The second fragment was generated in a PCR reaction with the following primer pair:

Forward primer: 5079F (SIN nts 5079–5100): (SEQ. ID NO. 29)
5'-GAAGTGCCAGAACAGCCTACCG Reverse primer: SIN7643R (buffer sequence/Xho I site/SIN nts 7643–7621): (SEQ. ID NO. 30)
5'-TATATCTCGAGGGTGGTGTTGTAGTAFTAGTCAG The two PCR reactions were performed with the primer pairs shown above using the Thermalase (Amresco, Solon, Ohio), Vent (New England Biolabs, Beverly, Mass.) or KlenTaq thermostable DNA polymerases. Additionally, the reactions contained 5% DMSO and "HOT START WAX" beads (Perkin-Elmer, Foster City, Calif.). The PCR amplification protocol shown below was used. The extension period was 5 minutes or 2.5 minutes for reactions with the SP6-1F/SIN5160R or 5079F/SIN7643R primer pairs, respectively.

| Temperature (° C.) | Time (Min) | No. Cycles |
|---|---|---|
| 95 | 2 | 1 |
| 95 | 0.5 | |
| 55 | 0.5 | 35 |
| 72 | 5.0 or 2.5 | |
| 72 | 10 | 10 |

Following PCR, the two amplified products of 5142 bp (SP6 -1F/SIN516OR primer pair) and 2532 bp (5079F/SIN7643R primer pair) were purified (PCR purification kit, Qiagen, Chatsworth, Calif.), and digested with Apa I and Sfi I (5142 bp amplicon product) or Sfi I and Xho I (2532 bp amplicon product). The digested products were purified with GENECLEAN II (Bio 101, Vista, Calif.) and ligated together with pKS+ plasmid (Stratagene, La Jolla, Calif.) prepared by digestion with Apa I and Xho I, and phosphatased with CIAP. This construction is known as pKSSIN-1-BV5'.

The 3' region of the vector, comprised of the viral 3' end, a polyadenylate tract, and a unique restriction recognition sequence were inserted between the Not I and Sac I sites of the plasmid pKSSIN-1-BV5'. The 3' region of the vector was amplified by PCR from the pRSIN-1 g plasmid in a reaction containing the following primer pair:

Forward primer: SIN11386F (buffer sequence/Not I site/SIN nts 11386–11407): (SEQ. ID NO. 31)
5'-TATATATATATGCGGCCGCCGCTACGCCCCA ATGATCCGAC Reverse primer: SIN11703R (buffer sequence/Sac I and Pme I sites/T40/SIN nts 11703–11698): (SEQ. ID NO.32)
5'-CTATAGAGCT CGTTTAAACT TTTTTTTTT TTTTTTTTT TTTTTTTTT TTTTTTTTG AAATG In addition to the primer pairs shown above, the PCR reaction contained Thermalase, Vent or KlenTaq thermostable DNA polymerase, 5% DMSO, and "Hot Start Wax" beads (Perkin-Elmer). The amplification protocol was as shown above, but with a 72° C. extension period of 30 seconds.

The 377 bp amplified product corresponding to the 3' vector end was purified, digested with Not I and Sac I, purified, and ligated into pKSSIN-1-BV5', which was prepared by digestion with Not I and Sac I and treatment with CIAP. This plasmid is known as pKSSIN-1-BV.

Using techniques described above, the lacZ gene encoding the β-galactosidase reporter protein was liberated from the plasmid pSV-β-galactosidase (Promega Corp., Madison, Wis.) with Bam HI and Hind III, and inserted into pKS+ at the corresponding enzyme recognition sites. The lacZ gene was digested from this plasmid, pKS-β-gal, with Xho I and Not I, and inserted into pKSSIN-1-BV, between the Xho I and Not I sites. This plasmid is known as SINrep/SIN-1 nsP1–4/lacZ Alternatively, the firefly luciferase gene encoding the luciferase reporter protein was liberated from the plasmid pT3/T7-LUC (Clontech. Palo Alto, Calif.) by digestion with Hind III, and inserted into pKS+ (Stratagene, La Jolla. Calif.) at the corresponding enzyme recognition sites contained in the multiple cloning sequence to generate pKS-luc. The luciferase gene was liberated from pKS-luc by digestion with Xho I and Not I and inserted into Xho I/Not I digested pKSSIN-1-BV. This plasmid is known as SINrep/SIN-1 nsP1–4/luc.

Additionally, the gene encoding the secreted form of alkaline phosphatase (SEAP) was inserted into pKSSIN-1-BV. Briefly, the SEAP gene was liberated from the plasmid pCMV/SEAP (Tropix, Bedford, Mass.) by digestion with Hind III and Xba I, and inserted in pSK+ (Stratagene, La Jolla, Calif.) at the corresponding recognition sites contained in the multiple cloning sequence. to generate pSK-SEAP. The SEAP gene was then liberated from pSK-SEAP by digestion with Xho I and Not I, and inserted into the corresponding enzyme recognition sites of pKSSIN-1-BV. This plasmid is known as SINrep/SIN-1 nsP 1–4/SEAP.

The individual SIN-1 nsP genes were substituted into the corresponding wild-type virus region of the Sindbis virus-based lac Z replicon described previously (Bredenbeek et al., *J. Virol.* 67:6439–6446, 1993), in order to compare the expression properties of the SIN-1 and wild-type expression vectors. Substitution of the SIN-1 nsP genes into the Toto 1101-derived lac Z replicon was accomplished as described in Example 1. These vectors were designated as shown in the table below.

| | nsP Genes Origin | |
|---|---|---|
| Replicon Designation | Toto1101 | SIN-1 |
| SINrep/lacZ | nsP 1–4 | |
| SINrep/SIN-1 nsP2/lacZ | nsP 1, 3–4 | nsP 2 |
| SINrep/SIN-1 nsP3/lacZ | nsP 1–2, 4 | nsP 3 |
| SINrep/SIN-1 nsP1-4/lacZ | | nsP 1–4 |

SP6 transcripts were prepared from the replicons shown in the table above, after linearization with Xho I, as described in Example 1. RNA transcripts contained a 5' sequence that is capable of initiating transcription of Sindbis virus, Sindbis virus nonstructural protein genes 1–4, RNA sequences required for packaging, a Sindbis virus junction region, the lacZ gene, and the Sindbis virus 3' end proximal sequences required for synthesis of the minus strand RNA.

The in vitro transcription reaction products or purified RNA. were electroporated into baby hamster kidney-21 (BHK-21) cells as described previously (Liljestrom and Garoff, *Bio/Technology* 9:1356–1361, 1991). Alternatively, BHK-21 cells were complexed with a commercial cationic lipid compound as described in Example 1 and applied to BHK-21 cells maintained at 75% confluency. Transfected cells were propagated in 35 mm dishes, and incubated at 37° C.

The efficiency of transfection of BHK-21 cells with SINrep/lac Z RNAs after 9 hours was determined by two alternative methods. In the first method, transfected cells expressing β-galactosidase were determined by direct staining with X-gal (5-bromo-4-chloro-3-indolyl-b-D-galactopyranoside), after first fixing cells with 2% cold methanol, as described previously (MacGregor et al., *Cell idol. Genet.* 13:253–265, 1987). In the second method, expression of β-galactosidase were determined by immunofluorescence, using a rabbit anti-β-galactosidase antibody. A portion of the cells transfected by either method described above were propagated on circular glass coverslips, contained in 35 mm dishes. At 9 hours post transfection (hpt). the media was removed by aspiration, and the cells were rinsed twice with PBS, and fixed with methanol by incubation overnight at −20° C. The methanol was removed by aspiration, the cells were rinsed three times with PBS, then incubated with 2% BSA (fraction V, Sigma, St. Louis, Mo.) for 30 minutes at room temperature. Following incubation with BSA to prevent non-specific antibody binding, the cells were incubated with the primary anti-β-galactosidase antibody (diluted 1:800 in 0.1% BSA/PBS) for 1 hour at room temperature. Excess primary antibody was then removed by aspiration and rinsing three times with 0.1% BSA in PBS. Following 1:100 dilution in 2% BSA in PBS, 100 ml of goat anti-rabbit-FITC conjugate secondary antibody (Sigma. St. Louis, Mo.) were added to the coverslips and incubated for 45 minutes at room temperature, in the dark. Excess secondary antibody was removed by rinsing the coverslips twice with 0.1% BSA in PBS, and once with PBS. The coverslips were then mounted cell side down on a drop of Cytoseal 60 mounting media (Stephens Scientific, Riverdale, N.J.), placed on a microscope slide. Fluorescence microscopy was used to determine the frequency of cells expressing β-galactosidase, in order to determine the transfection efficiency.

The level of β-galactosidase in whole transfected cell lysates was determined at 9 hpt, by two alternative methods. In the first method, transfected cells were rinsed with PBS after aspiration of the media and 250 $\mu$l of reporter lysis buffer (Promega. Madison, Wis.) per $10^6$ cells was added to each dish. β-galactosidase expression levels were determined by mixing the supernatant fraction from cell lysates, processed by micro centrifugation at 14,000 r.p.m. for 1 minute at room temperature, with a commercially available substrate detection system (Lumi-gal, Clontech, Palo Alto, Calif.), followed by luminometry (Analytical Luminescence Laboratory. San Diego, Calif.). In the second method, the activity of β-galactosidase was determined as described previously by Sambrook and Maniatis (1989, 2nd ed. Cold Spring Harbor Laboratory Press, NY). Briefly, transfected cells were rinsed with PBS after aspiration of the media, and 200 $\mu$l of TTE lysis buffer (10 mM Tris-HCl pH 8.0/1 mM EDTA/0.2% Triton X-100) per $10^6$ cells was added to each dish. Following pelleting of cell debris from the cell lysate by micro centrifugation at 14,000 r.p.m. for 1 minute at room temperature, 50 $\mu$l of the supernatant was added to 0.5 ml of Z buffer pH 7.0 (60 mM $Na_2HPO_4$/40 mM $NaH_2PO_4$/10 mM KCl/10 mM MgSO04/50 mM 2-mercaptoethanol) and incubated at 37° C. for 5 minutes. β-galactosidase activity in samples was then determined by spectrophotometry (420 nm) after addition of 0.2 ml of a solution containing 4 mg/ml of the chromogenic substrate o-nitrophenyl-b-D-galactopyranoside (ONPG; SIGMA, St. Louis, Mo.), in Z buffer. The samples were incubated at 37° C. until the yellow color developed (approximately 5 minutes), and the reactions were terminated by addition of 0.5 ml of 0.5 M $Na_2CO_3$.

The level of β-galactosidase expression in transfected BHK-21 cells was determined according to the methods described above, and is illustrated in the table shown below.

The data indicated are normalized for varying transfection efficiency, as described above.

| Replicon Transfected | Expression of β-gal, relative to SINrep/lacZ | Standard Deviation |
|---|---|---|
| SINrep/lacZ | 1.0 | |
| SINrep/SIN-1 nsP2/lacZ | 3.2 | ±0.4 |
| SINrep/SIN-1 nsP3/lacZ | 0.2 | ±0.0 |
| SINrep/SIN-1 nsP1-4/lacZ | 5.2 | ±1.3 |

The results demonstrate that the replicon vectors derived from the SIN-1 variant strain are indeed functional. When transfected into BHK-21 cells, the level of expressed reporter protein are higher than that observed in wild type virus-derived vector transfected cells. Furthermore, as with the phenotype for establishment of productive persistent infection, the higher level of β-galactosidase expression in BHK-21 cells transfected with the SIN-1-derived replicon vectors mapped primarily to the nsP 2 gene.

Example 4

Preparation of SIN1-Based DNA Vectors

A. Construction of Plasmid DNA SIN-1 Derived Expression Vectors

Efficient initiation of the Sindbis virus infectious cycle can occur in vivo from a genomic cDNA clone contained within an RNA polymerase II expression cassette (Dubensky et al., *J. Virol* 70:508–519, 1996.). The ability to express functional alphavirus genes from a DNA format has enabled two new alphavirus-based gene expression systems to be developed: (1) a plasmid DNA-based vector with applications for genetic immunization, and (2) the production of packaged alphavirus particles in cells co-transfected with vector replicon and DH plasmid DNAs. Previously, molecular approaches to produce infectious Sindbis virus RNA and its derived complementary vectors were restricted primarily to in vitro transcription of cDNA clones from a bacteriophage RNA polymerase promoter followed by transfection into permissive cells.

The plasmid DNA-based alphavirus derived expression vector is known as ELVS™ (Eukaryotic Layered Vector System). The ELVS™ plasmid DNA vector involves the conversion of a self-replicating vector RNA (replicon) into a layered DNA-based expression system. Within certain embodiments the first layer has a eukaryotic (e.g. RNA polymerase II) expression cassette that initiates transcription of a second layer. which corresponds to the RNA vector replicon. Following transport of the replicon expressed from the first layer from the nucleus to the cytoplasm, autocatalytic amplification of the vector proceeds according to the viral (e.g. alphavirus) replication cycle, resulting in expression of the heterologous gene.

Construction of plasmid DNA expression vectors derived from SIN-1 virus or those variants selected as taught in Example 2 were performed with modifications of methods previously described (Dubensky et al., *J. Virol* 70:508–519. 1996). The expression vector was assembled on the plasmid vector pBGS131 (ATCC No. 37443), which is a knamycin resistant analogue of pUC 9 (Spratt et al., *Gene* 41:337–342, 1986). pBGS131 and its derived plasmids were propagated in LB medium containing 20 µg/ml kanamycin.

To facilitate insertion of heterologous sequences into the expression vector, the Xho I recognition sequence, located within the translational reading frame of the kanamycin gene in pBGS131, was removed by inserting a partially complementary 12-mer oligonucleotide pair that contained Xho I sticky ends. The Xho I recognition site was lost as a result of the insertion, as shown below:

Oligonucleotide 1: (SEQ. ID NO.33)
  5'-TCGATCCTAGGA

| Original pBGS131 Paired sequence Oligonucleotides | pBGS131 sequence after insertion of 12-mer |
|---|---|
| SerArg<br>CTCGAGGC TCGATCCTAGGA<br>GAGCTCCG AGGATCCTAGT | SerIleLeuGlySerArg<br>CTCGATCCTAGGATCGAGGC<br>GAGCTAGGATCCTAGCTCCG |

(Xho I site: CTCGAG) (SEQ. ID NOS. 33–36 and 104).

The oligonucleotide is gel annealed in equal molar concentrations in the presence of 10 mM MgCl$_2$, heated to 100° C. for 5 min, cooled slowly to room temperature. and phosphorylated with polynucleotide kinase. The oligonucleotide was ligated at a 200:1 ratio of insert:plasmid vector to pBGS131, which was prepared by Xho I digestion and CIAP treatment. The resulting plasmid is called pBGS131 dlXho I. The growth rates of XL1-Blue (Stratagene) transformed with pBGS131 or pBGS131 dlXho I plasmids in LB medium containing 20 µg/ml kanamycin was indistinguishable over a time course between 1.5 and 8 hours.

The bovine growth hormone (BGH) transcription termination/polyadenylation signal was inserted between the Sac I and Eco RI sites of pBGS131 dlXho I. The BGH transcription termination sequences were isolated by PCR amplification using the primer pair shown below and the pcDNA3 plasmid (Invitrogen, San Diego, Calif.) as template.

Forward primer BGHTTF (buffer sequence/Sac I site/ pcDNA3 nts 1132–1161): (SEQ. ID NO. 37)
  5'-TATATATGAGCTCTAATAAAATGAGGAAATT GCATCGCATTGTC Reverse primer BGHTTR (buffer sequence/Eco RI site/ pCDNA3 nts 1180–1154): (SEQ.ID NO. 38)
  5'-TATATGAATTCATAGAATGACACCTACTCA GACAATGCGATGC The primers shown above were used in a PCR reaction with a three temperature cycling program, using a 30 sec extension period. The 58 bp amplified product was purified with the PCR purification kit (Qiagen Chatsworth, Calif.), digested with Sac I and Eco RI, purified with GENECLEAN II, and ligated into Sac I/Eco RI digested, CIAP treated pBGS131. The plasmid is known as pBGS131 dlXho I-BGHTT.

The 3' end of the Sindbis virus-derived plasmid DNA expression vector was then inserted into the pBGS131 dlXho I-BGHTT construct. This region of the vector contains the following ordered elements: Sindbis virus 3' end non-translated region (3' NTR); a 40-mer poly(A) sequence; the hepatitis delta virus (HDV) antigenomic ribozyme; and a Sac I recognition sequence. Construction of these ordered elements was accomplished by nested PCR, using the primers shown below and the pKSSIN-1-BV plasmid (Example 4) as template.

Forward primer: SIN11386F (buffer sequence/Not I site/SIN nts 11386–11407): (SEQ. ID NO. 31)
  5'-TATATATATATGCGGCCGCCGCTACGCCCC AATGATCCGAC Nested primer: pAHDVIF (poly(A)/HDV RBZ nts 1–46): (SEQ. ID NO. 39)

5'-AA AAAAAAA GGGTCGGCAT GGCATCTCCA CCTCCTCGCGGTCCGACCTG GGCATC

Reverse primer: SacHDV77R (buffer sequence/Sac I site/ HDV RBZ nts 77–27): (SEQ. ID NO. 40)

5'-TATATGAGCTCCTCCCTTAGCCATCCGAGTGG ACGTGCGTCCTCCTTCGGATGCCCAG GTCG-GACCGCG

The primers shown above were used in a PCR amplification according to the reaction conditions and three temperature cycling program described in Example 4, with an extension time of 30 sec. The 422 bp amplified product was purified with a PCR purification kit (Qiagen Chatsworth, Calif.), digested with Not I and Sac I, purified with GENECLEAN II, and ligated into Not I/Sac I digested. CIAP-treated pKSSIN-1-BV. This construct is known as pKSSIN-1BV/HDVRBZ and contains Sindbis virus-derived plasmid DNA expression vector sequences from the Bgl II site at Sindbis nt 2289 extending through the 3' end of the vector including the HDV ribozyme sequence.

Plasmid pKSSIN-1BV/HDVRBZ was then digested with Bgl II and Sac I, the 5815 bp fragment was isolated by 1% agarose/TBE gel electrophoresis, purified with GENECLEAN II, and was inserted into Bgl II/Sac I digested, CIAP-treated pBGS131 dlXho I-BGHTT to generate the plasmid construct known as pBG/SIN-1BglLF. This construct contains the region of the Sindbis virus expression vector from plasmid pKSSIN-1BV/HDVRBZ described above with the 3' end fused to the BGH transcription termination sequence on the pBGS131 dlXho I plasmid.

Assembly of the Sindbis virus plasmid DNA vector was completed by insertion of the CMV promoter juxtaposed with the first 2289 nts of the Sindbis virus genome (includes the 5' viral end and a portion of the nsPs genes) into the pBG/SIN-1BglLF plasmid. Using an overlapping PCR approach, the CMV promoter was positioned at the 5' viral end such that transcription initiation results in the addition of a single non-viral nucleotide at the 5' end of the Sindbis virus vector replicon RNA. The CMV promoter was amplified in a first PCR reaction from pcDNA3 (Invitrogen, San Diego, Calif.) using the following primer pair:

Forward primer: RCBgl233F (buffer sequence/Bgl II recognition sequence/CMV promoter nts 1–22): (SEQ. ID NO. 41)

5'-TATATATAGATCTTTGACATTGATTATTGACTAG

Reverse primer: SNCMV1142R (SIN nts 8–1/CMV pro nts 1142–1108): (SEQ. ID NO. 42)

5'-CCGTCAATACGGTTCACTAAACGAGCTC GCTTATATAGACC

The primers shown above were used in a PCR reaction according to the reaction conditions and three temperature cycling program described in Example 4, with an extension time of 1 min.

The SIN-1 5' end was amplified in a second PCR reaction from pKSRSIN-1g clone (Example 1) using the following primer pair:

Forward primer: CMVSIN1F (CMV pro nts 1124–1142/SIN nts 1–20): (SEQ. ID NO. 43)

5'-GCTCGTTTAGTGAACCGTATTGACGGCGTA GTACACAC

Reverse primer: SIN 3182R (SIN nts 3182–3160): (SEQ. ID NO. 44)

5'-CTGGCAACCGGTAAGTACGATAC

The primers shown above were used in a PCR reaction with a three temperature cycling program using a 3 min extension period.

The 930 bp and 3200 bp amplified products were purified with a PCR purification kit (Qiagen) and used together in a PCR reaction with the following primer pair:

Forward primer: pCBgl233F: (SEQ. ID NO. 41)

5'-TATATATAGATCTTTGACATTGATTATTGACTAG

Reverse primer: (SIN nts 2300–2278): (SEQ. ID NO. 45)

5'-GGTAACAAGATCTCGTGCCGTG

The primers shown above were used in a PCR reaction with a three temperature cycling program using a 3.5 min extension period.

The 26 3' terminal bases of the first PCR amplified product overlap with the 26 5' terminal bases of the second PCR amplified product; the resultant 3200 bp overlapping secondary PCR amplified product was purified by 1% agarose/TBE electrophoresis, digested with Bgl II, and ligated into Bgl II digested, CIAP-treated pBG/SIN-1BglLF. This construct is called pBG/SIN-1 ELVS 1.5.

As discussed within Example 1, relatively few nucleotide point changes in the nsP gene sequence of wild-type Sindbis virus result in the phenotype characteristic of SIN-1. No new restriction enzyme recognition sites are generated as a result of these nucleotide changes which facilitate clones derived from wild-type and SIN-1 genotypes to be easily distinguished. A PCR-based diagnostic assay was therefore devised as a rapid method for identification of SIN-1 derived clones. Briefly, forward primers were designed so that a particular base change between SIN-1 and wild-type was positioned at the 3' terminal base of the primer. One primer contained the SIN-1nucleotide while another contained the wild-type nucleotide. A reverse primer in a region downstream conserved between both genotypes was used in combination with each forward primer. At the correct annealing temperature, SIN-1 templates were only amplified in reactions containing SIN-1 forward primers. The primer sequences used to distinguish wild-type and SIN-1 genotypes is given below. The reaction conditions were as described throughout the examples contained herein.

Primer Set I

Forward primers:
WT100F: 5'-GTC CGT TTG TCG TGC AAC TGC (SEQ. ID NO. 105)
SIN-1100F: 5'-GTC CGT TTG TCG TGC AAC TGA (SEQ. ID NO. 106)
Reverse primer:
SIN2300R
PCR Program: (95° C.-30", 72° C.-2') 20 cycles Primer Set 2:

Forward primers:
WT3524F 5'-CAA TCT TCC TCA CGC CTT AGC (SEQ. ID NO. 107)
SIN-13524F 5'-CAA TCT TCC TCA CGC CTT AGT (SEQ. ID NO. 108)
Reverse primer:
SIN5448R
PCR Program: (95° C.-30", 60° C.-30", 72° C.-2') 20 cycles Primer Set 3:

Forward primers:
WT7592F 5'TCC TAA ATA GTC AGC ATA GTA (SEQ. ID NO. 109)
SIN-17592F 5'TCC TAA ATA GTC AGC ATA GTT (SEQ. ID NO. 110)
Reverse primer:
SIN7643R
5'-TATATCTCGAGGGTGGTGTTGTAGTATTA GTCAG
(SEQ. ID NO. 111)

PCR Program: (95° C.-30", 60° C.-30 ", 72° C.-2') 20 cycles

Reporter protein expression vectors were constructed by inserting the lacZ, SEAP, or luciferase reporter genes into the pBG/SIN-1 ELVS 1.5 vector backbone. In separate reactions, the pKS-β-gal, pSK-SEAP, and pKS-luc plasmids (Example 4), were digested with Xho I and Not I. The fragments containing the lacZ, SEAP, or luciferase genes were isolated by 1% agarose/TBE gel electrophoresis and purified subsequently with GENECLEAN II. These reporter genes were then ligated in separate reactions with Xho I/Not I digested, CIAP-treated pBG/SIN-1 ELVS 1.5 plasmid. These constructs are known as pBG/SIN-1ELVS 1.5-β-gal, pBG/SIN-1 ELVS 1.5-SEAP, and pBG/SIN-1ELVS 1.5-luc.

B. Expression of Heterologous Proteins in Cells Transfected with pBG/SIN-1 ELVS 1.5-SEAP, pBG/SIN-1 ELVS 1.5-luc or pBG/SIN-1 ELVS 1.5-β-gal Expression Vectors The pattern of secreted alkaline phosphatase, luciferase, and β-galactosidase reporter gene expression in BHK cells transfected with pBG/SIN-1 ELVS 1.5 or pBG/wt ELVS 1.5 vectors was compared. The pBG/wt ELVS 1.5 plasmid contains sequences derived from wild-type Sindbis virus, rather than the SIN-1 variant. Construction of the pBG/wt ELVS 1.5 expression vectors was exactly as described herein for the pBG/SIN-1 ELVS 1.5 expression vectors, except that full-length genomic cDNA derived from wild-type Sindbis virus (Dubensky et al., WO 95/07994) was used as the template for the vector construction. Construction of the pBG/wt ELVS 1.5 expression vector has been described previously (Dubensky, supra.); thus, although the strains, and therefore the sequences, are different, the Sindbis virus-specific regions contained in the pBG/wt ELVS 1.5 and pBG/SIN-1 ELVS 1.5 expression vectors are the same.

Baby hamster kidney-21 (BHK-21) cells maintained at 75% confluency in 12 mm dishes were transfected with 1.0 μg of pBG/SIN-1 ELVS 1.5 or pBG/wt ELVS 1.5 expression vector plasmid DNAs complexed with 4.0 μl of a commercially available lipid (Lipofectamine, GIBCO-BRL). Otherwise, transfection conditions were as suggested by the lipid manufacturer. Eagle minimal essential medium supplemented with 5% fetal bovine sera was added to the cells at 4 hours post transfection (hpt); unless otherwise indicated. Transfected cells were incubated at 37° C. At various times post transfection, as indicated below. several assays were performed to compare vector-specific RNA synthesis, and expression of secreted alkaline phosphatase, luciferase, or β-galactosidase reporter gene expression in cells transfected with pBG/SIN-1 ELVS 1.5 or pBG/wt ELVS 1.5 plasmid DNAs.

The levels of alkaline phosphatase secreted into the culture medium of BHK cells transfected with pBG/SIN-1 ELVS-1 1.5-SEAP or pBG/wt ELVS 1.5-SEAP plasmid DNA were compared. Cell culture medium was assayed for the presence of alkaline phosphatase with the Phospha-Light™ chemiluminescent reporter gene assay, according to the directions of the manufacturer (Tropix. Inc.. Bedford, Mass.). Briefly, 10μl of cell culture supernatant was mixed with 30μl of Dilution Buffer and incubated for 30 minutes at 65° C. The sample was allowed to cool to room temperature before mixing with 40μl of Assay Buffer. The sample was incubated for five minutes at room temperature followed by the addition of 40μl of Reaction Buffer. Samples were incubated for 20 minutes at room temperature. Total luminescence was measured on an ML3000 microtiter plate luminometer (Dynatech, Inc..Chantilly. Va.) in cycle mode. and alkaline phosphatase (AP) in the culture medium of BHK cells transfected with pBG/SIN-1 ELVS-1 1.5-SEAP or pBG/wt ELVS 1.5-SEAP plasmid DNAs. were determined at 48 hpt, and the results are shown in the table below.

| Plasmid Transfected | RLU at 48 hpt |
|---|---|
| pBG SIN-1 ELVS 1.5-SEAP | 18 ± 1.7 |
| pBG wt ELVS 1.5-SEAP | 94 ± 10.7 |
| pCDNA3 | 0.13 ± 0.04 |

Figure 9A:
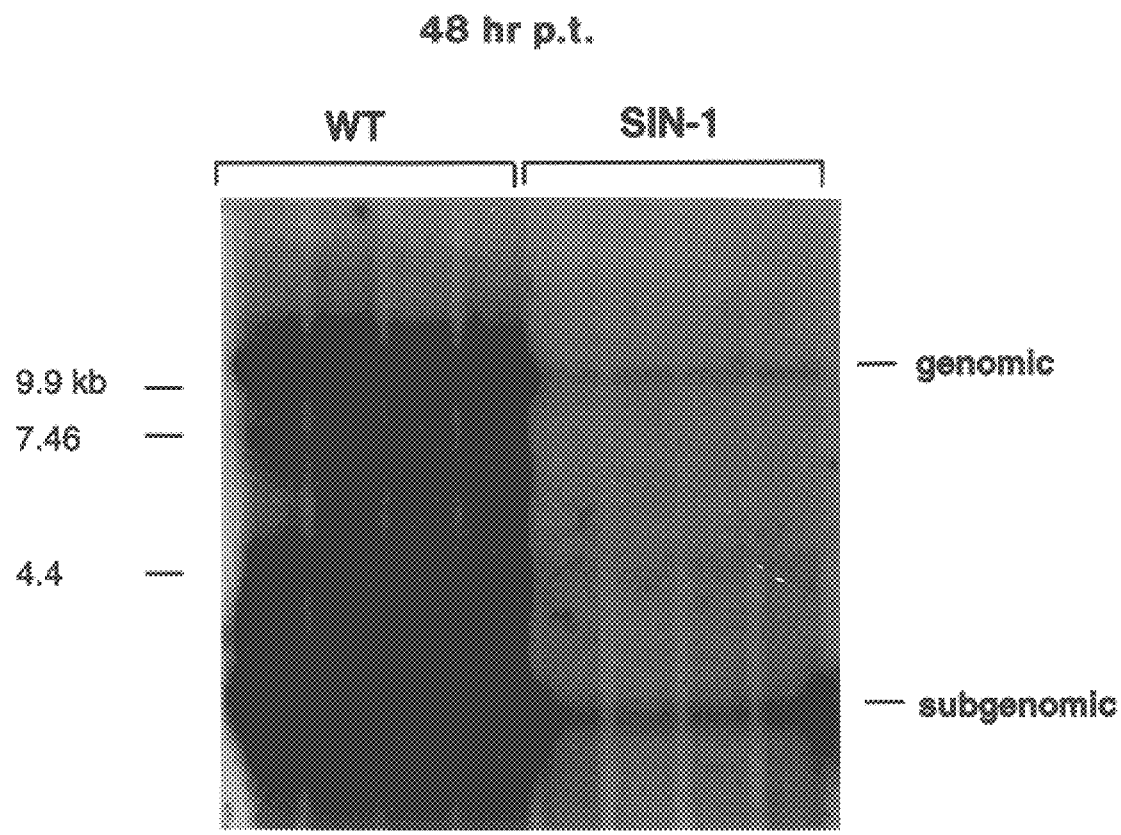

Additionally, the levels of vector-specific RNAs synthesized in BHK-21 cells transfected with pBG/SIN-1 ELVS 1.5-SEAP or pBG/wt ELVS 1.5-SEAP plasmids were determined by Northern blot analysis, exactly as described previously (Dubensky, supra.), at 48 hours post-transfection. The results of this experiment are shown in FIG. 9A. Total cellular RNA was isolated from transfected BHK cells with Tri-Reagent as described by the manufacturer (Molecular Research Center. Inc., Cincinnati, Ohio). Total cellular RNA concentrations present in samples from transfected BHK cells were determined spectrophotometrically. Additionally, material isolated from transfected cells was determined to be intact by electrophoresis of 0.5 ug of total cellular RNA through 0.7% agarose/TBE mini gels, stained 10 ul/ml of ethidium bromide. Northern blot analysis was performed according to Sambrook and Maniatis (1989, 2nd ed. Cold Spring Harbor Laboratory, Cold Spring Harbor, N.Y.). In order that RNA from all transfected samples could be visualized on a autoradiogram from a single Northern blot analysis, 2.5 ug and 30 ug of RNA were loaded per lane from pBG/wt ELVS 1.5-SEAP and pBG/SIN-1ELVS 1.5-SEAP transfected cells, respectively. Four samples of RNA, from individual transfections with both plasmids tested, were electrophoresed through 0.7% formaldehyde agarose gels and transferred to Zeta-probe membrane (Bio-Rad, Richmond, Calif.). The blot was hybridized with random-primed probes corresponding to the alkaline phosphatase gene. The results of this experiment in which the levels of vector-specific RNA synthesis and AP expression in transfected BHK cells were compared at 48 hpt, demonstrate that while the level of vector-specific RNA synthesized in cells transfected with pBG/SIN-1 ELVS 1.5-SEAP DNA was at least100-fold lower than in pBG/wt ELVS 1.5-SEAP transfected cells, the levels of AP were only 5-fold lower in cells transfected with pBG/SIN-1ELVS 1.5-SEAP DNA, compared to pBG/wt-ELVS 1.5-SEAP DNA.

Figure 9B:
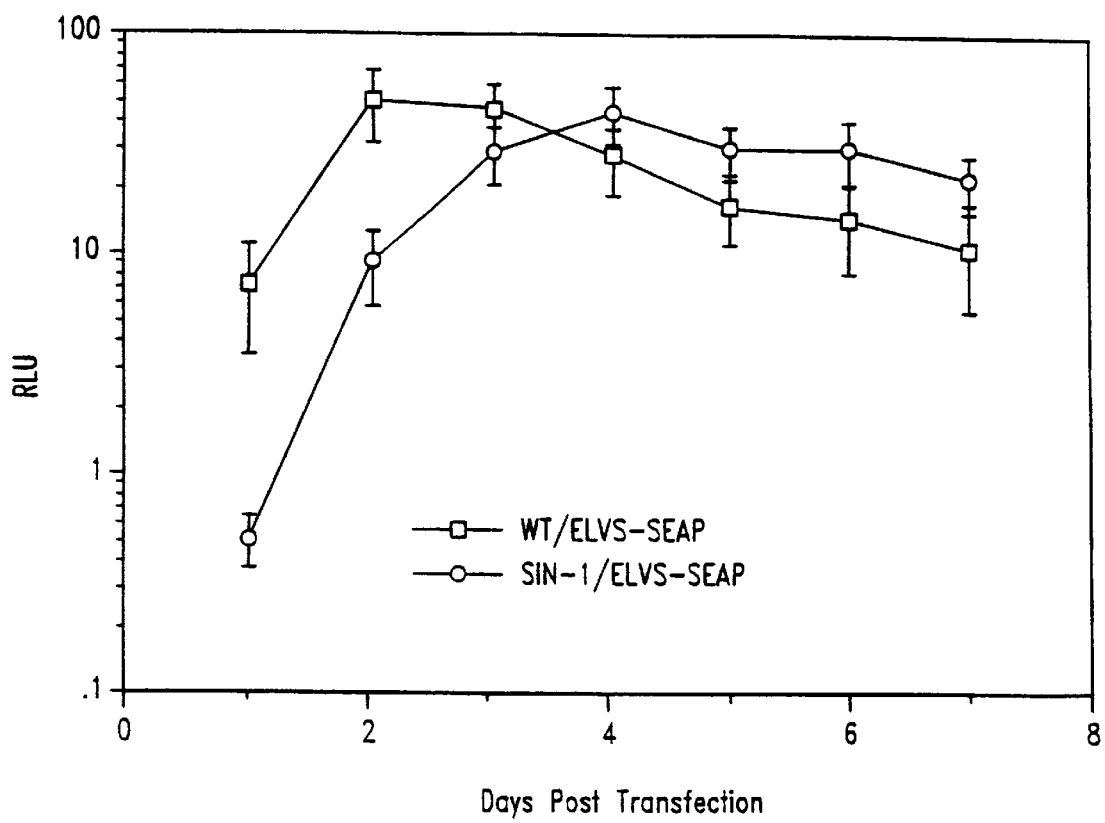

The levels of alkaline phosphatase secreted into the culture medium of BHK cells transfected with pBG/SIN-1ELVS-1 1.5-SEAP or pBG/wt ELVS 1.5-SEAP plasmid DNA were also compared over a 7 day time-course. The results of this study, illustrated in FIG. 9B, demonstrate that the levels of AP present in the culture medium at early time points were much lower in cells transfected with pBG/SIN-1ELVS-1 1.5-SEAP plasmid, compared to pBG/wt ELVS 1.5-SEAP plasmid. However, the level of AP expressed in cells transfected with the SIN-1 Sindbis virus variant strain-derived vectors rapidly increased and was higher than in cells transfected with wild-type virus-derived vectors by the 96 hpt time point.

Figure 10:
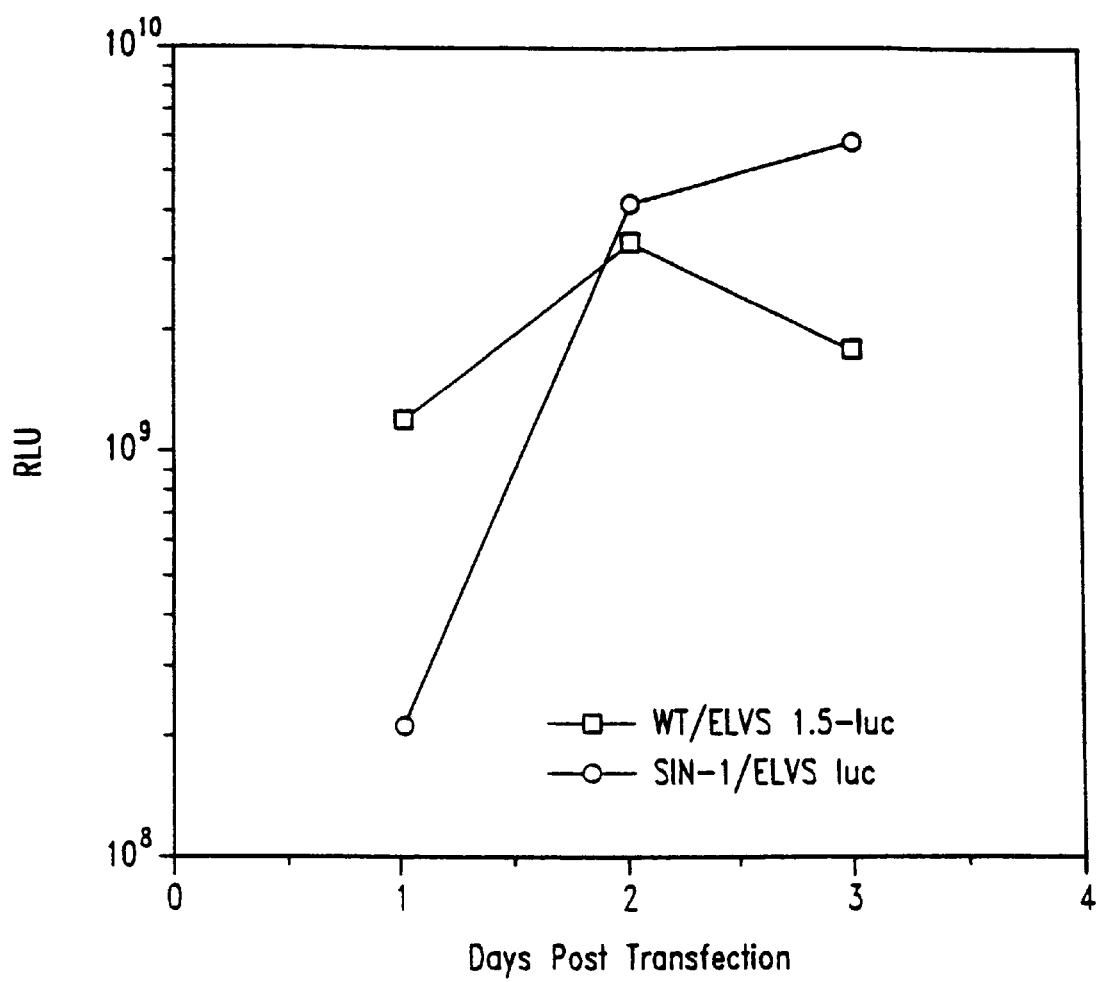

The luciferase levels present in BHK cells transfected with pBG/SIN-1 ELVS-1 1.5-luc or pBG/wt ELVS 1.5-luc plasmid DNA were compared at 24, 48, and 72 hpt. The luciferase expression levels were quantitated by adding 250 μl of reporter lysis buffer (Promega, Madison Wis.) per $10^6$ transfected cells, centrifuging the lysate at 14,000 rpm for 1 min, and then mixing the supernatant fraction from the cell lysates with a commercially available substrate detection system (Promega, Madison Wis.), followed by luminometry (Analytical Luminescence Laboratory, San Diego, Calif.). The results from this experiment (shown in the table below), and shown graphically in FIG. 10, parallel the results observed with the alkaline phosphatase expression vectors. At early times post transfection the luciferase expression levels were lower in BHK cells transfected with pBG/SIN-1 ELVS 1.5-luc plasmid, compared to pBG/wt ELVS 1.5-luc plasmid. However, at the 48 and 72 hpt time points, the luciferase levels were similar in BHK cells transfected with Sindbis virus SIN-1 variant strain- and wild-type-derived expression vectors.

| Plasmid Transfected | Hr. Post Trans-fection | Relative Light Units (Ave. ± SD) |
|---|---|---|
| pBG/SIN-1 ELVS 1.5-luc | 24 | $1.2 \times 10^9$ |
| pBG/wt ELVS 1.5-luc |  | $2.1 \times 10^8$ |
| pBG/SIN-1 ELVS 1.5-luc | 48 | $3.3 \times 10^9$ |
| pBG/wtELVS 1.5-luc |  | $4.1 \times 10^9$ |
| pBG/SIN-1 ELVS 1.5-luc | 72 | $1.8 \times 10^9$ |
| pBG/wt ELVS 1.5-luc |  | $5.8 \times 10^9$ |
| pCDNA3 | 48 | 482 |

The efficiency of transfection of the pBG/SIN-1 ELVS 1.5-β-gal and pBG/wt ELVS 1.5-β-gal plasmids in BHK cells at 48 hpt was determined by direct X-gal (5-bromo-4-chloro-3-indolyl-b-D-galactopyranoside) staining of the cell monolayer (MacGregor, *Cell Mol. Genet.* 13:253–265, 1987), in order to measure directly the number of cells expressing β-galactosidase. The transfection efficiencies were equivalent, and are shown in the table below.

| Plasmid Transfected | No. Blue Cells/100X Field |
|---|---|
| pBG/SIN-1 ELVS 1.5-β-gal | 24 ± 3 |
| pBG/wt ELVS 1.5-β-gal | 26 ± 7 |

Figure 11A:
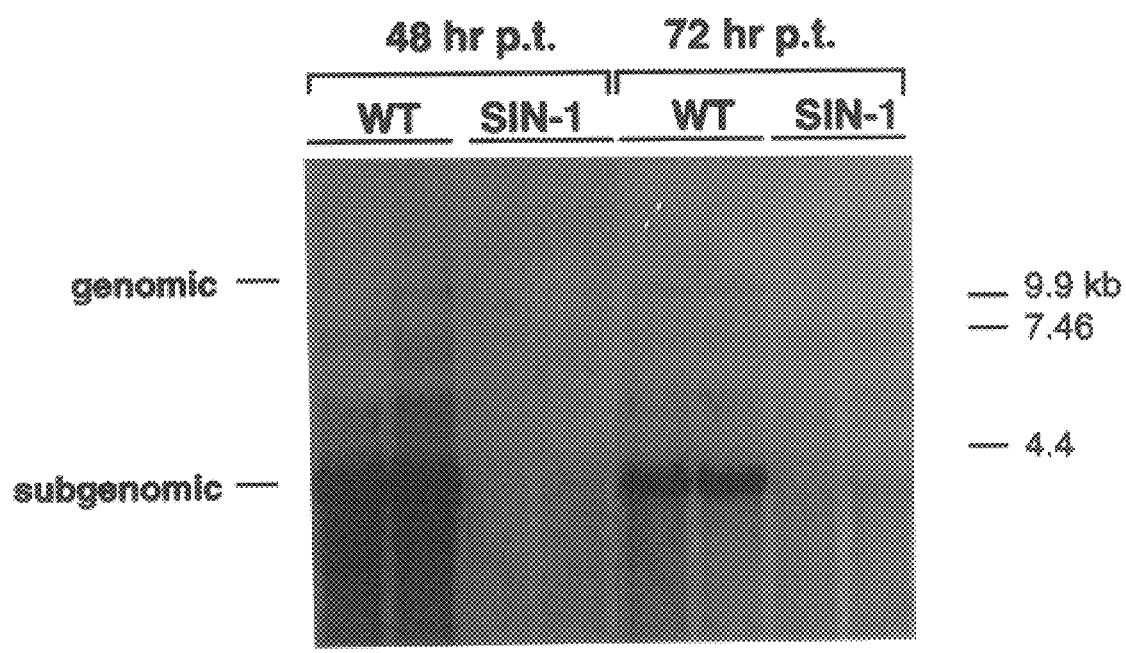
Figure 11B:
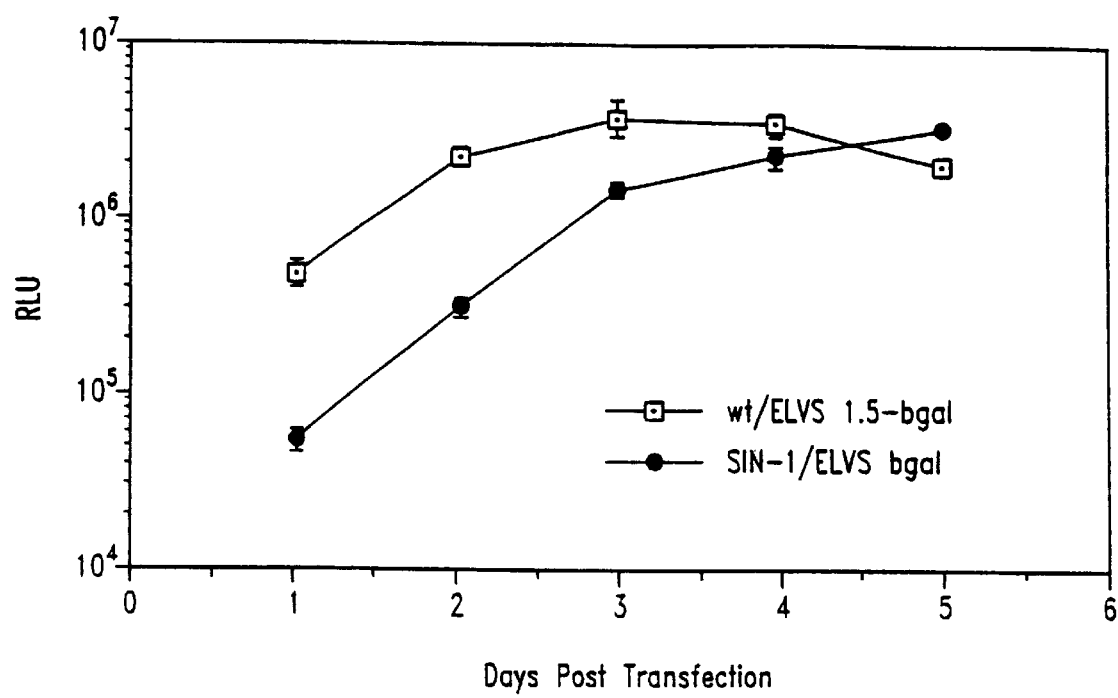

The levels of vector-specific RNAs synthesized in BHK-21 cells transfected with pBG/SIN-1 ELVS 1.5-β-gal or pBG/wt ELVS 1.5-β-gal plasmids were determined by Northern blot analysis, exactly as described previously (Dubensky, supra.), at 48 and 72 hours post-transfection. Total cellular RNA was isolated from transfected BHK cells with Tri-Reagent as described by the manufacturer (Molecular Research Center, Inc., Cincinnati, Ohio). Total cellular RNA concentrations present in samples from BHK cells transfected with pBG/SIN-1 ELVS 1.5-β-gal or pBG/wt ELVS 1.5-β-gal plasmids were determined spectrophotometrically. Additionally, material isolated from transfected cells was determined to be intact by electrophoresis of 0.5 ug of total cellular RNA through 0.7% agarose/TBE mini gels, stained 10 ul/ml of ethidium bromide. Northern blot analysis was performed according to Sambrook and Maniatis (1989, 2nd ed. Cold Spring Harbor Laboratory, Cold Spring Harbor, N.Y.). In order that RNA from all transfected samples could be visualized on a autoradiogram from a single Northern blot analysis, 2.5 ug and 5 ug of RNA were loaded per lane from pBG/wt ELVS 1.5-β-gal and pBG/SIN-1 ELVS 1.5-β-gal transfected cells, respectively. Two samples of RNA, from individual transfections with both plasmids tested, at 48 and 72 hpt, were electrophoresed through 0.7% formaldehyde agarose gels and transferred to Zeta-probe membrane (Bio-Rad, Richmond, Calif.). The blot was hybridized with random-primed probes corresponding to the β-galactosidase gene. The results of this experiment, shown in FIG. 11A. demonstrate that the level of vector specific RNA synthesized in cells transfected with pBG/SIN-1 ELVS 1.5-β-gal DNA at 48 and 72 hours post transfection was at least 100-fold lower than the level of RNA detected in pBG/wt ELVS 1.5-β-gal transfected cells.

Additionally the β-galactosidase expression levels were quantitated in transfected whole cell lysates by adding 250 µl of reporter lysis buffer (Promega, Madison Wis.) per $10^6$ transfected cells, centrifuging the lysate at 14,000 rpm for 1 min, and then mixing the supernatant fraction from the cell lysates with a commercially available substrate detection system (Clontech, Palo Alto, Calif.), followed by luminometry (Analytical Luminescence Laboratory, San Diego, Calif.). The results from this experiment (shown in the table below, and graphically in FIG. 9C) demonstrate that at early times post transfection the β-galactosidase expression levels were significantly lower in BHK cells transfected with pBG/SIN- 1 ELVS 1.5-β-gal plasmid, compared to pBG/wt ELVS 1.5-β-gal plasmid. However, reporter expression rapidly increased over the time-course in pBG/SIN-1 ELVS 1.5-β-gal transfected cells such that the β-galactosidase levels were higher than in wild-type virus transfected cells at the final 120 hr time point.

Figure 11C:
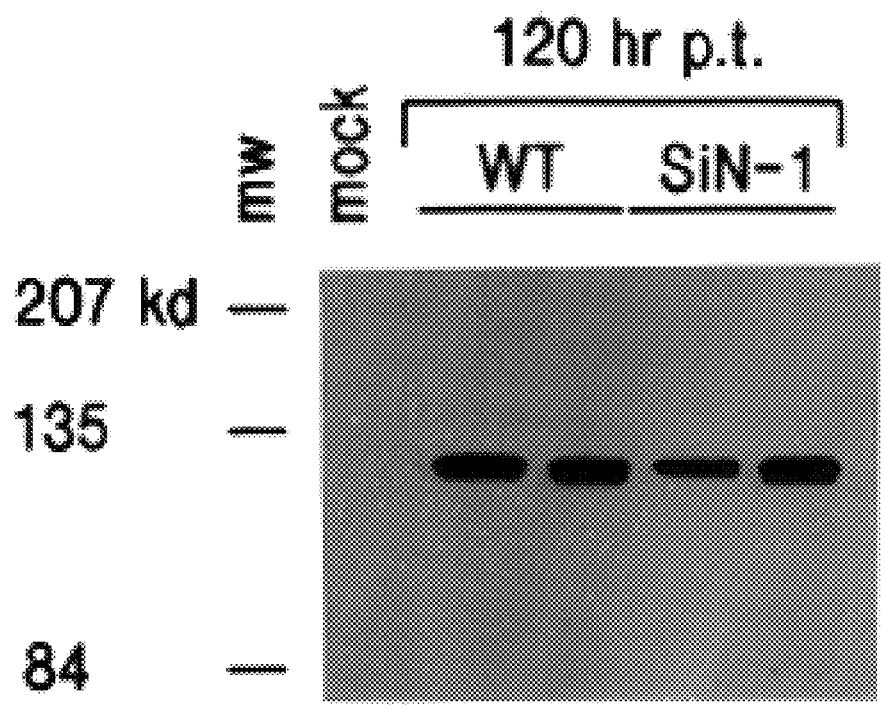

Expression of β-galactosidase in cells transfected with the pBG/SIN-1 ELVS-1 1.5-β-gal or pBG/wt ELVS 1.5-β-gal plasmid DNAs was also measured directly by Western blot analysis using a monoclonal antibody specific for the reporter protein (Boehringer Mannheim), at the final 120 hpt time point. In parallel with the reporter protein activity determined at 120 hpt, the level of β-galactosidase protein was at the same level, or greater, in PBG/SIN-1 ELVS-1 1.5-β/-gal transfected BHK cells, compared to pBG/wt ELVS 1.5-β-gal, and is demonstrated in FIG. 11C.

Taken together, the results described herein demonstrate that the level of vector-specific RNA synthesized is at least 100-fold less in pBG/SIN-1 ELVS transfected cells, compared to pBG/wt ELVS transfected cells. Importantly however, after a 48–72 hour lag, the levels of reporter gene expression are equivalent, or higher, in pBG/SIN-1 ELVS transfected cells, compared to pBG/wt ELVS transfected cells. The phenotype of pBG/SIN-1ELVS, characterized by high expression levels combined with low vector-specific RNA synthesis in transfected cells, is due likely to the diminished, or absent, inhibition of host cell protein synthesis. This property of pBG/SIN-1 ELVS thus results in much higher levels of expressed reporter protein per subgenomic mRNA translation template in transfected cells, compared to pBG/wt ELVS. In summary, the phenotype of the plasmid DNA expression vectors derived from the SIN-1 variant strains follows the parent virus, in terms of equivalent expression levels, combined with relatively low levels of RNA synthesis, compared to wild-type virus derived-vectors. As vectors do not contain any of the Sindbis virus structural proteins, this phenotype must map to the nonstructural genes of the SIN-1 virus variant.

Example 5

Modifications of Plasmid DNA SIN-1 Derived Expression Vectors

Figure 12A:
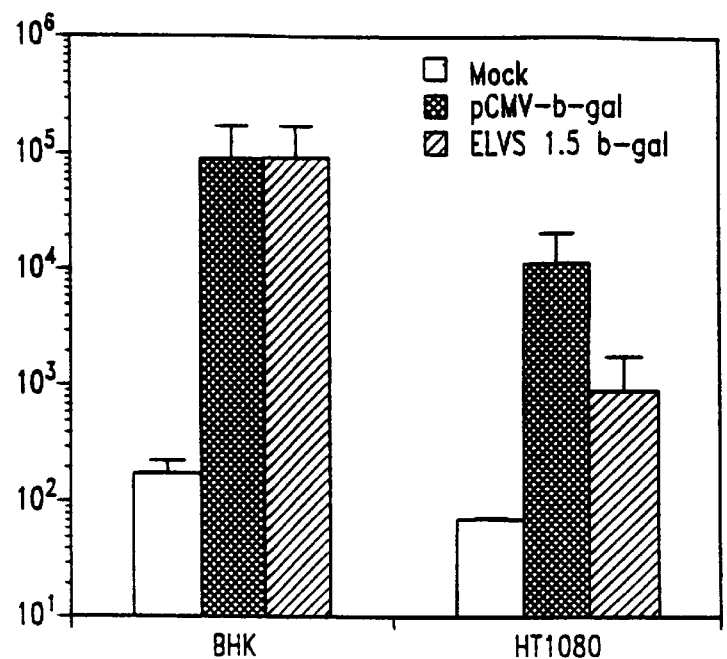

Expression levels of heterologous genes in target cells from alphavirus-based vectors are affected by several factors, including host genus and vector configuration. For example, β-galactosidase expression levels are 10- to 100-fold higher in BHK cells, compared to some human cells, such as HT1080, transfected with pBG/ELVS vectors. The levels of reporter gene expression in BHK and several human cell lines transfected with pBG/wt ELVS 1.5-βgal plasmid DNA (see example 4) were compared in order to establish the relative level of vector-specific expression in cell types derived from the intended in vivo target genus. The levels of β-galactosidase expression in BHK cells and HT1080 (ATCC CCL 121) cells, a human fibrosarcoma line, transfected with pBG/wt ELVS 1.5-βgal plasmid, or with a conventional plasmid expression vector, were determined. The conventional plasmid vector was constructed by insertion of the lac Z gene (Promega, Madison, Wis.) into the CMV promoter-driven pUC-derived expression plasmid multiple cloning site (Invitrogen, San Diego, Calif.), and is known as pCMV-β-gal. The results of this study, given in FIG. 12A, demonstrate that the level of β-galactosidase expression was nearly 100-fold lower in HT1080 cells transfected with pBG/wt ELVS 1.5-βgal plasmid DNA, compared to BHK cells. Cells were also transfected with pCMV-β-gal in order to segregate RNA polymerase II expression from Sindbis virus vector replicon expression. In this experiment, while the expression decreased 5- to 10-fold in HT1080 cells transfected with pCMV-β-gal plasmid, compared to BHK cells, expression decreased nearly 100-fold in HT 1080 cells transfected with pBG/wt ELVS 1.5-βgal plasmid DNA. Thus, the results indicate that the dramatic decrease of reporter gene expression in HT1080 cells transfected with pBG/wt ELVS 1.5-βgal plasmid DNA is due in part to the diminished activity of the Sindbis virus vector replicon in these human cells.

Given the overall plasticity of the RNA alphaviral genome and the propagation of virus in BHK cells. it is not surprising that the expression levels of heterologous genes are highest in the host cell lines from which the vectors were derived. Thus, selection of alphaviruses with the SIN-1 phenotype (as described in Examples 1 and 2), characterized by comparatively low viral RNA levels and equivalent virus production levels, combined with delayed or absent inhibition of host cell protein synthesis, can be performed in any human primary. or diploid or polyploid human cells.

In addition to selecting alphaviruses with desired phenotypes in cells (e.g., human) which more closely parallel target cells in vivo, several alternative modifications of the prototype plasmid DNA expression cassette components can also be performed. For example, substitution of the MoMLV RNA polymerase II promoter with the stronger CMV immediate early (IE) promoter significantly enhances the level of heterologous gene expression in transfected cells (Dubensky et al., *J. Virol.* 70:508–519, 1996, and Dubensky et al., W/O 95/07994). Further, juxtaposition of introns, for example SV40 small t antigen or CMV intron A, either upstream or downstream from the heterologous gene, can increase the level of heterologous gene expression in some transfected cell types (Dubensky et al. supra.).

Several further alternative modifications of the prototype plasmid DNA expression cassette components can also be utilized in order to enhance the overall expression in transfected cells in vitro or in vivo. In one modification, the Hepatitis B virus (HBV) posttranscriptional regulatory element (PRE) was inserted in the pBG/wt ELVS 1.5-βgal plasmid DNA. The PRE sequence activates the transport of HBV S transcripts in cis from the nucleus to the cytoplasm. The PRE sequence appears to function independently of splice donor and acceptor sites, and has been shown to activate cytoplasmic expression of a β-globin transcript not containing introns. It has been proposed that the PRE functions in cis to allow the export of nuclear transcripts that do not interact efficiently with the splicing pathway and hence are not exported well from the nucleus (Huang et al., *Molecular and Cellular Biology* 15:3864–3869, 1995).

The PRE sequence was cloned into pBG/SIN-1 ELVS 1.5-βgal by isolating first a PCR-generated 564 bp fragment of HBV from the full length genomic clone of the ADW viral strain, pAM6 (ATCC No. 39630). The amplified fragment extends from base 1238–1802 of the HBV genome. The primer sequences are given below.

Forward Primer: NTPRE1238F (SEQ. ID NO. 46)
  5'-CCTATGCGGCCGCGTGGAACCTTTGTGGCT CCTC Reverse Primer: EAPRE 1802R (SEQ. ID NO. 47)
  5'-CCTATTGGCCAGCAGACCAATTTATGCCTAC The primers introduce a Not I recognition site at the 5' end of the fragment and an Eae I recognition site at the 3' end. Not I and Eae I have compatible sticky ends. The Eae I recognition site is internal to the Not I site, so Eae I cuts both sites.

The PCR fragment was digested with Eae I and cloned into Not I digested/CIAP treated pBG/wt ELVS 1.5-βgal. The correct clone retains the Not I site at the 5' terminus of the PRE and is called pBG/wt ELVS/PRE 1.5-βgal.

The possible effect of the PRE sequence contained in ELVS plasmids on heterologous gene expression in transfected cells was determined. Briefly, BHK and HT1080 cells were cultured in 12 mm dishes to 75% confluency and transfected with 500 ng of pCMV-β-gal, pBG/wt ELVS 1.5-βgal, or pBG/wt ELVS/PRE 1.5-βgal plasmid DNA complexed with Lipofectamine (GIBCO-BRL, Gaithersburg, Md.), and the level of β-galalactosidase expression was determined 48 hr later. Transfection efficiencies were determined by direct Xgal staining of transfected monolayers, as described in Example 4, and are shown in the table below.

The results demonstrate clearly that the number of BHK or HT1080 cells transfected with ELVS plasmids expressing β-galalactosidase was increased dramatically by inclusion of the RNA transport PRE sequence in the vector. Further, these results indicate that one cause for the diminished heterologous gene expression levels in HT1080 cells, compared to BHK cells, transfected with ELVS plasmid DNA is the inefficient transport of the primary transcript from the nucleus.

Figure 12B:
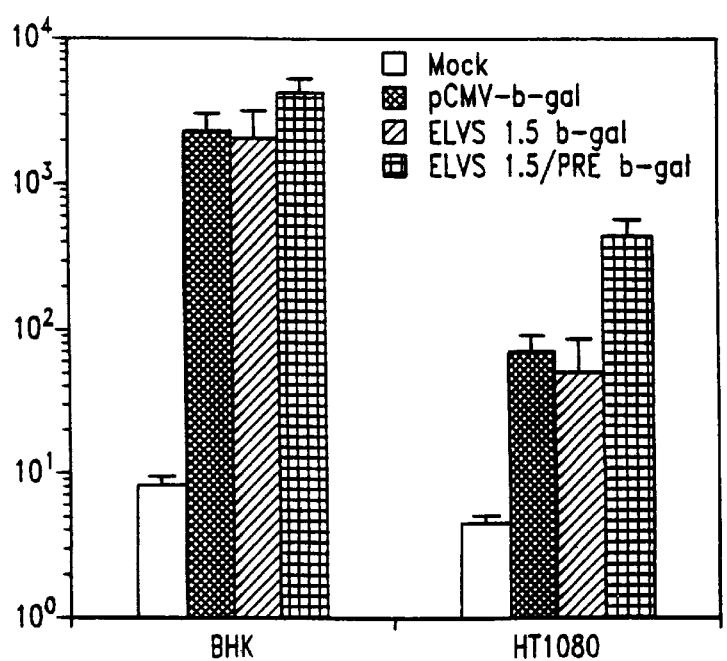
Figure 13:
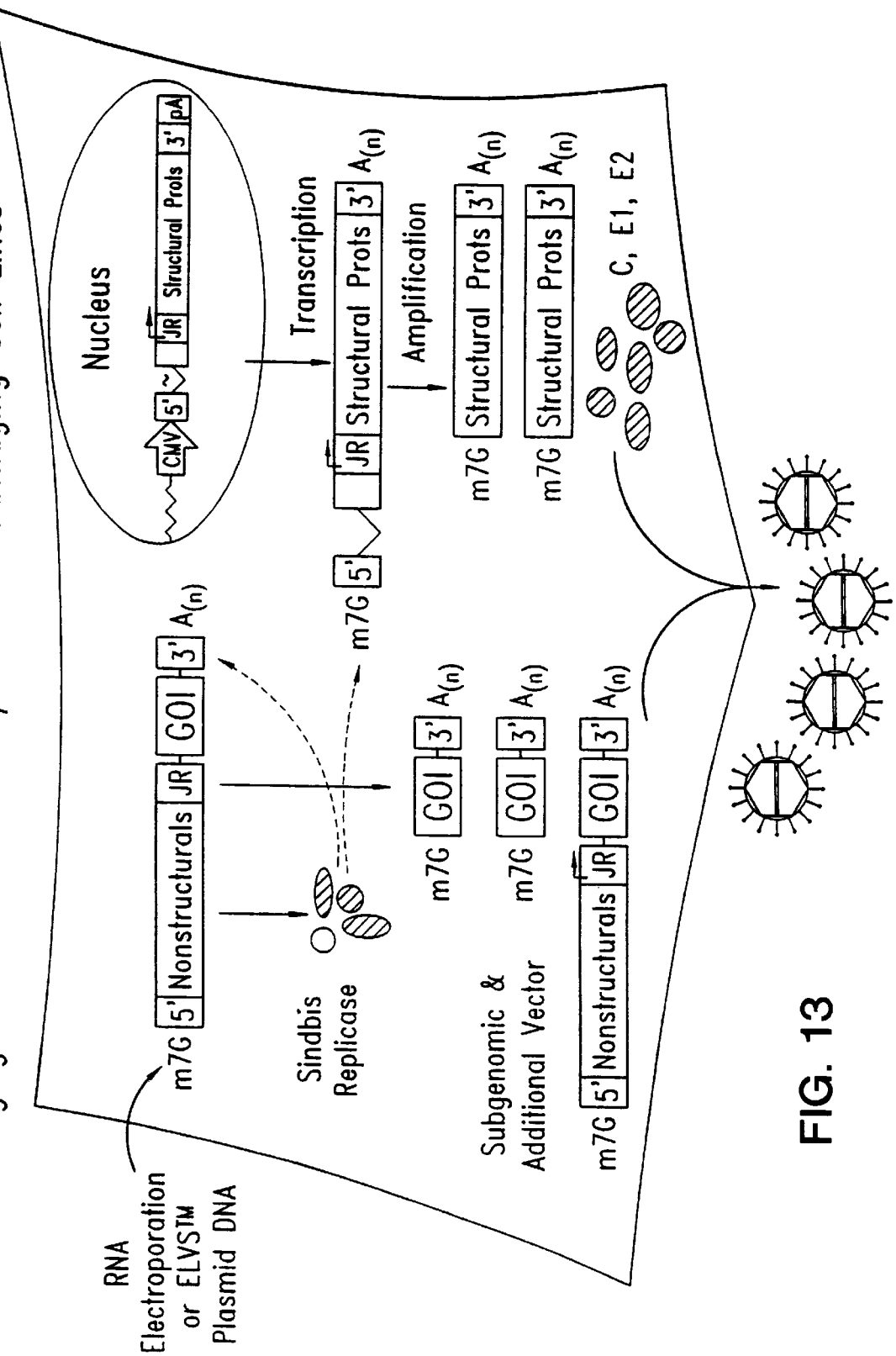

In parallel with the higher frequency of reporter protein expressing HT1080 cells transfected with ELVS plasmids containing the PRE sequence, the levels of β-galalactosidase were dramatically higher in lysates from HT1080 cells transfected with ELVS vectors containing the PRE sequence. These results are illustrated in FIG. 12B, and taken together with the results shown in the table above, demonstrate that functional vector replicons are transported inefficiently from the nucleus in human cells transfected with ELVS plasmids. Further, inclusion of the PRE sequence in the ELVS plasmid construct increases the level of heterologous gene expression in all cells tested, demonstrating a clear relationship between efficiency of cytoplasmic vector replicon transport and overall heterologous gene expression level.

Figure 14:
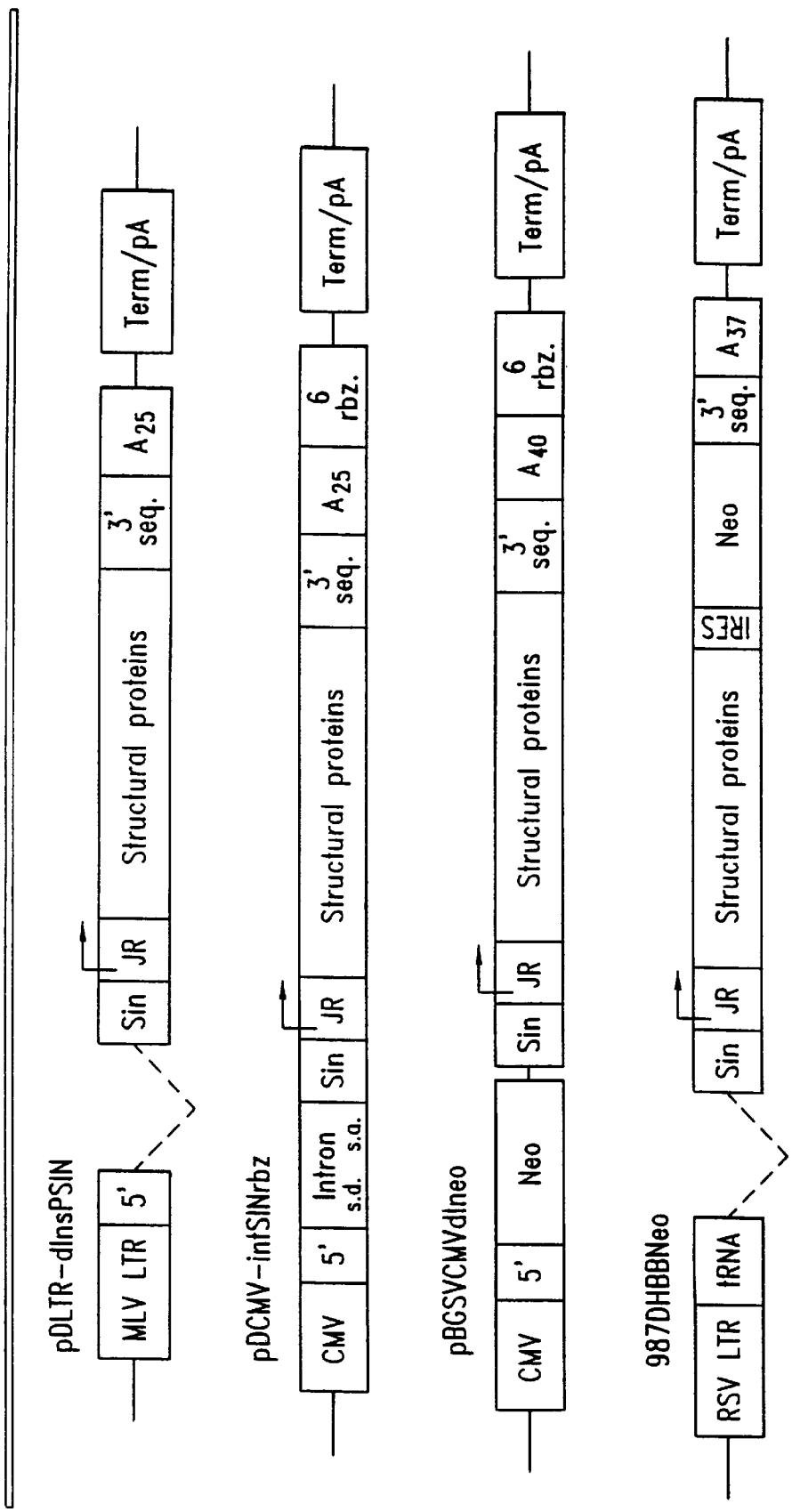

Several other viral sequence elements which operate in cis to transport unspliced RNAs have also been identified. For example, a 219 bp sequence, located between nts 8022 and 8240 near the 3' end of the Mason-Pfizer monkey virus (MPMV) genome, has been shown to enable Rev independent human immunodeficiency virus type 1 (HIV-1) replication (Bray et al., *PNAS* 91:1256–1260, 1994). The MPMV RNA transport element, known as the constitutive transport element (CTE), is inserted into the pBG/SIN-1 ELVS 1.5-βgal plasmid by first isolating a PCR-generated 219 bp fragment of MPSV from the full length genomic clone template (Sonigo et al., *Cell* 45:375–385, 1986), or the MPSV subgenomic clone pGEM7FZ(-)MPSV 8007–8240 (D. Rekosh, Ham-Rek Laboratories, SUNY at Buffalo, 304 Foster Hall, Buffalo, N.Y.). The amplified fragment extends from base 8022–8240 of the MPSV genome. The primer sequences are given below.

Forward Primer: NMPVM8021F (SEQ. ID NO. 48)

5'-CCTATGCGGCCGCTAGACTGGACAGCCAATGACG

Reverse Primer: EMPMV8241R (SEQ. ID NO. 49)

5'-CCTATTGGCCAGCCAAGACATCATCCGGGCAG

The primers introduce a Not I recognition site at the 5' end of the fragment and an Eae I recognition site at the 3' end. Not I and Eae I have compatible sticky ends. The Eae I recognition site is internal to the Not I site, so Eae I cuts both sites.

The PCR fragment is digested with Eae I and cloned into Not I digested/CIAP treated pBG/wt ELVS 1.5-βgal. The correct clone retains the Not I site at the 5' terminus of the PRE and is called pBG/wt ELVS/CTE 1.5-βgal.

In addition to the HBV PRE and MPSV CTE sequences, several RNA transport elements from other viral or cellular sources can be inserted into the ELVS plasmid constructs, as described above. For example, some of these elements include the HIV Rev responsive element (Malim et al., *Nature,* 338:254–257, 1989), the HTLV 1 Rex element (Ahmed et. al., Genes Dev., 4:1014–1022, 1990), and another cis-acting sequence from simian retrovirus type 1 (Zolotukhin et al., *J. Virol.,* 68:7944–7952, 1994). In addition, each of the above RNA transport elements also may be incorporated into the structural protein expression casettes, packaging cell lines, or producer cell lines described in Examples 6 and 7.

In yet another modification of prototype ELVS vectors, expression of the alphavirus replicons can be driven from an RNA polymerase I promoter. Briefly, because RNA polymerase I promoters are not tissue specific and are expressed in essentially all human cells in the body they provide an attractive alternative for plasmid DNA-directed alphavirus replicon expression in transfected cells. For example, the human rDNA promoter (plasmid prHU3. Learned and Tjian, *J Mol. Appl. Gen.,* 1:575–584, 1982), has been used to construct a vector for heterologous gene expression (Palmer et al., *Nuc. Acids Res.* 21:3451–3457, 1993).

Thus, within one embodiment of the invention a RNA polymerase I promoter can be juxtaposed with the 5' end of the replicon cDNA such that the first nucleotide transcribed in transfected cells corresponds to the authentic alphavirus 5' end. Identification of the RNA polymerase I promoter (e.g.. plasmid prHU3) nucleotide at which transcription initiation occurs is determined as described previously (Dubensky et al., W/O 95/07994).

All modifications described herein can be performed with ELVS constructs containing the Sindbis virus wild-type or SIN-1 nsPs, or nsP genes from any alphavirus. For example, all of the constructions provided in Example 5 can also be performed with plasmid pBG/SIN-1 ELVS 1.5-βgal, whose construction is described in Example 4.

Example 6

Construction of Alpha Virus Packaging Cell Lines

In the present invention, alphavirus packaging cell lines (PCL) are provided, whereby the virus-derived structural proteins necessary for RNA packaging and formation of recombinant alphavirus vector particles are encoded by one or more stably transformed structural protein expression cassette(s). Synthesis of these proteins preferably occurs in an inducible manner, and in particularly preferred embodiments, via transcription of subgenomic mRNA from their native "junction region" promoter. Inducible subgenomic transcription is mediated by the input alphavirus vector RNA itself (FIG. 13). Following primary transcription from the structural protein expression cassette(s), cytoplasmic amplification of the RNA transcript is initiated by vector-encoded nonstructural proteins, and ultimately leads to transcription from the junction region promoter and high level structural protein expression. The structural protein expression casettes may include any of the previously described elements of the present invention, including RNA transport elements (e.g., HBV PRE and MPMV CTE) and splicing sequences. Such PCL and their stably transformed structural protein expression cassettes can be derived using methods described within PCT application WO 95/07994, or using novel approaches described within this invention. PCL may be derived from almost any existing parental cell type, including both mammalian and non-mammalian cells. Preferred embodiments for the derivation of PCL are cell lines of human origin.

A. Construction of Vector-Inducible Alphavirus PCL

For example, an alphavirus structural protein expression cassette was constructed, whereby primary transcription from a CMV immediate early promoter produces an RNA molecule capable of efficient cytoplasmic amplification and structural protein expression only after translation of nonstructural replicase proteins from the vector RNA. Specifically, plasmid pDCMV-dlnsPSIN (Dubensky et al., *J. Virol.* 70:508–519; 1996), a DNA-based Sindbis defective helper (DH) vector, was modified to contain both a hepatitis delta virus (HDV) antigenomic ribozyme sequence (Perotta and Been, *Nature* 350:434–436, 1991) for 3'-end RNA processing, and an SV40 small t antigen intron inserted within the region of nonstructural protein gene deletion. Due to restriction site duplications associated with insertion of the HDV ribozyme sequence, an additional plasmid from Dubensky et al, (ibid), pDLTRSINgHDV, was used as starting material to reconstruct the modified CMV-based DH construct. Plasmid pDLTRSINgHDV, an LTR-based Sindbis genomic clone containing the HDV ribozyme, was digested with Bgl II to remove the existing LTR promoter and Sindbis nucleotides 1–2289 (numbering according to Strauss et al., *Virology* 133:92–110, 1984). treated with calf intestinal alkaline phosphatase, and purified from a 0.7% agarose gel using GENECLEAN II™ (Biol101, San Diego, Calif.). The corresponding 5'-end fragment with a CMV promoter was obtained by Bgl II digestion of the Sindbis genomic clone pDCMVSINg (Dubensky et al., ibid) and purification from a 1% agarose gel using GENECLEAN II, and then ligated into the Bgl II-deleted pDLTRSINgHDV vector to generate the construct pDCMVSINgHDV. This CMV-based genomic plasmid with an HDV ribozyme was shown to produce infectious Sindbis virus and cytopathic effect within 24 hr after transfection into BHK cells. Defective helper plasmid pDCMVdlnsPSINgHDV, containing the HDV ribozyme, was then constructed by BspE I digestion and relegation under dilute conditions, to remove nonstructural gene sequences between nucleotides 422 and 7054. Subsequently, the SV40 intron was synthesized by PCR and inserted into the region of nonstructural protein gene deletion. Amplification of the SV40 intron sequence was accomplished by standard three-cycle PCR with a 30 second extension time, using plasmid pBR322/SV40 (strain 776, ATCC #45019) as template and the following oligonucleotide primers that were designed to contain flanking BspE I or Bam HI sites.

Forward primer: BspSVSDF (5'-rest. site/SV40 intron seq.) (SEQ. ID. NO. 50)
5'-TATATATCCGGA/
AAGCTCTAAGGTAAATATAAAATTTTT-3'
Reverse primer: BamSVSAR (5'-rest. site/SV40 intron seq.) (SEQ. ID. NO. 51)
5'-TATATAGGATCC/
TAGGTTAGGTTGGAATCTAAAATACACAAAC-3'
Following amplification, the DNA fragment was purified using a QIAquick-spin PCR purification kit (Qiagen, Chatsworth, Calif.), digested with BspE I and Bam HI, purified from a 1.2% agarose gel using Mermaid™ (Bio 101, San Diego, Calif.), and ligated into the defective helper plasmid pDCMV-dlnsPSIN, which was also digested with BspE I and Bam HI, treated with calf intestinal alkaline phosphatase, and purified from a 0.7% agarose gel using GENECLEAN II, to generate the construct pDCMV-intSINrbz (FIG. 14). Plasmid pDCMV-intSINrbz., which also contains an SV40 promoter-driven neomycin resistance selectable marker on another portion of the plasmid, was transfected into BHK cells using Lipofectamine™ (Gibco/BRL, Gaithersburg, Md.), as described by the manufacturer. Approximately 24 hr post-transfection, the cells were trypsinized and re-plated in media containing 600 μg/ml G418 (neomycin). The media was exchanged periodically with fresh G41 8-containing media and foci of resistant cells were allowed to grow. Cells were trypsinized and cloned by limiting dilution in 96 well tissue culture dishes, and individual cell clones were grown and expanded for screening.

Figure 15:
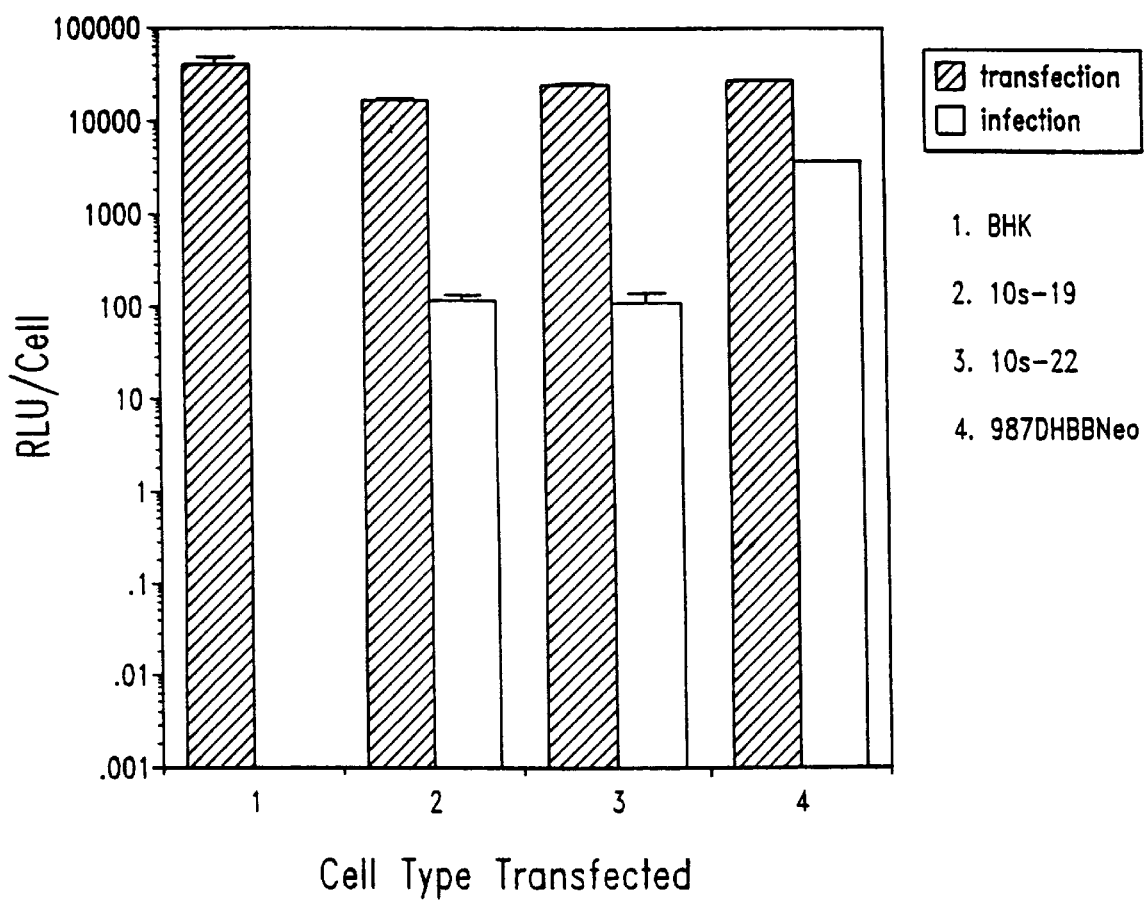

Positive packaging activity for the individual clones was identified by Lipofectin™ (Gibco/BRL. Gaithersburg, Md.)-transfection with Sindbis vector RNA that expresses a luciferase reporter gene (described in Dubensky et al., ibid), harvesting the culture supernatants at approximately 24 hr post-transfection, and assaying for the presence of packaged Sindbis-luciferase vector particles. In addition, initial transfection levels were determined by harvesting the transfected cell lysates using reporter lysis buffer (Promega, Madison, Wis.), and testing for the presence of luciferase activity by using luciferin substrate (Promega), as described by the manufacturer. To assay for packaged vector particles in the culture supernatants. 1 ml of undiluted, clarified supernatant was used to infect fresh BHK cell monolayers for approximately 18 hr. The cells were subsequently lysed as above, and luciferase activity was determined. The presence of luciferase activity in the infected BHK cells was confirmation of packaged vector particles in the transfected cell supernatants. Several positive cell clones harboring integrated copies of the pDCMV-intSINrbz structural protein expression cassette, and functioning as PCL. were identified. Packaging data for two of the individual PCL clones (#10s-19 and #10s-22), that were representative of the group, are shown in FIG. 15. In addition. the titer of packaged vector particles being produced was determined by transfecting an individual PCL clone (#10s-22) with SIN-β-gal vector RNA (described in Dubensky et al., ibid). The culture supernatant was recovered at 48 hr post-transfection, clarified by passage through a 0.45 mm filter, and fresh BHK monolayers were infected with 10-fold dilutions of the supernatant Approximately 14 hr post-infection, the cells were washed with PBS, fixed with 2% formaldehyde, washed again with PBS, and stained with X-gal. Vector particle units were then determined by counting individual blue-stained cells. Packaged β-gal vector titers from this PCL clone were approximately $10^6$ infectious units/ml of supernatant. Vector-controlled inducibility of Sindbis structural protein expression was demonstrated by western blot analysis using a polyclonal rabbit antiserum specific for the structural proteins. Positive 10s-22 PCL and negative control BHK cell lysates were made in Lameli sample buffer, either before (U; uninduced) or after (I; induced) transfection with SIN-β-gal vector RNA. As shown in FIG. 16, the only cell lysate that showed expression of Sindbis structural proteins was the 10s-22 PCL clone after transfection with vector RNA. Differences in the apparent levels of expression between the capsid protein and envelope glycoproteins do not reflect the actual amounts of protein being made, rather, the lower stability of the envelope glycoproteins during the cell lysis procedure used for this particular experiment.

Figure 17B:
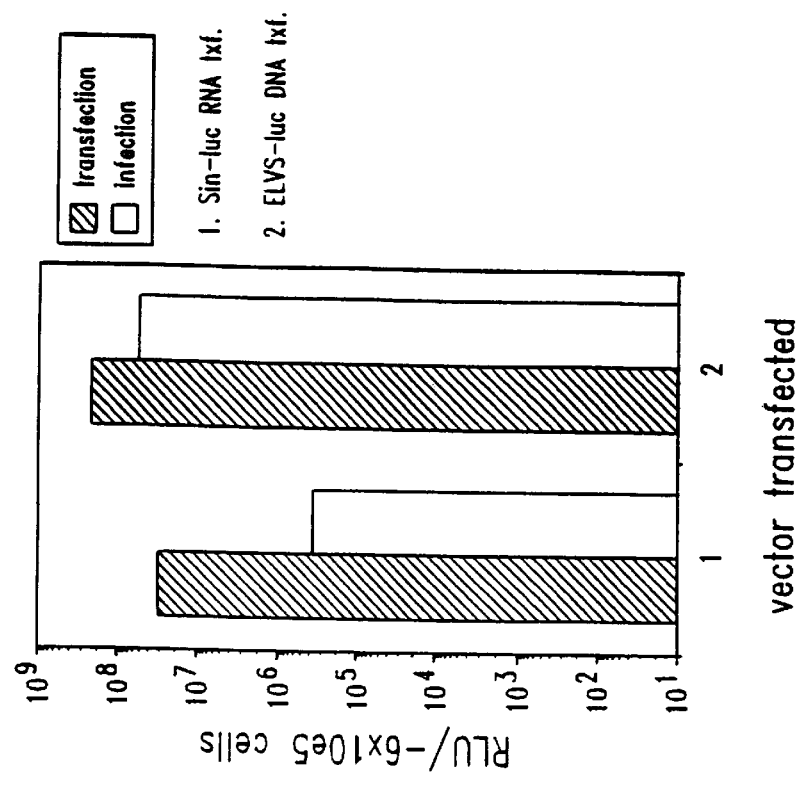
FIG. 17B is a graph depicting luciferase vector packaging by human 293 packaging cells stably transformed with plasmid pBGSVCMVdlneo.
Figure 17A:
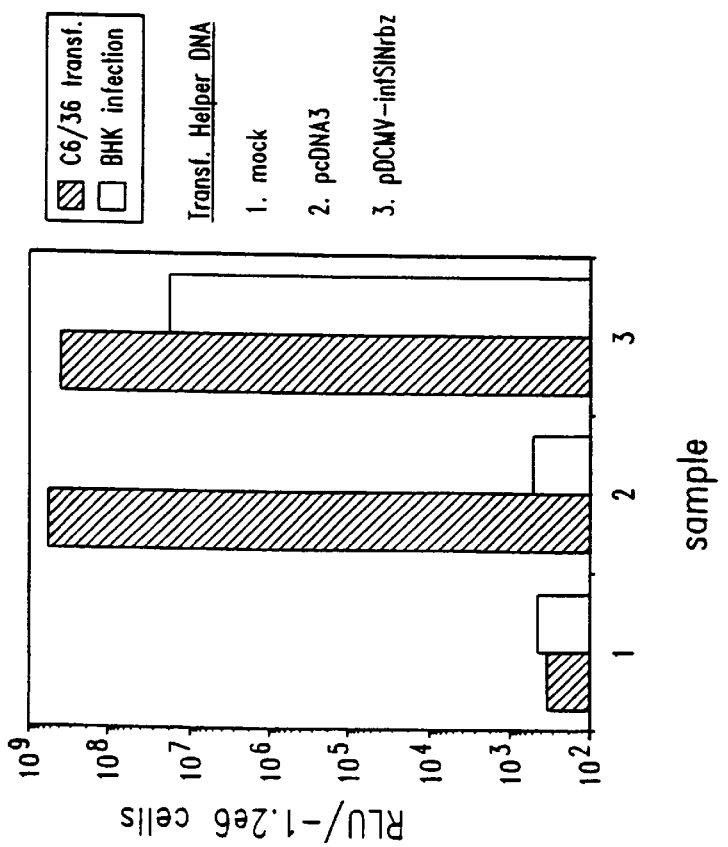

Packaging activity of the CMV-based DH construct was also highly efficient in non-mammalian cells. for example, C6/36 mosquito cells. The use of such a non-mammalian parental cell type for derivation of PCL may be particularly advantageous when the PCL are intended for subsequent use as starting material for the generation of vector producer cell lines. The advantage of this cell type is the natural ability of alphaviruses to establish a persistent infection, without the mammalian cell-associated phenotype of inhibition of host macromolecular synthesis and resulting cytopathic effect (CPE). Thus a DNA-based alphavirus vector (Examples 4 and 5), with an appropriate selectable marker. may be stably transformed into mosquito or other on-mammalian cell-derived PCL. FIG. 17A shows that both a DNA-based luciferase reporter vector and DH helper vector expressing Sindbis structural proteins, under the control of the CMV promoter, were fully functional in C6/36 cells, as demonstrated by luciferase vector packaging.

B. Construction of PCL with operably-linked selection marker

In other embodiments of the present invention, a selectable marker is operably linked to transcription of the alphavirus structural protein expression cassette. In preferred embodiments, this operable linkage is accomplished either by insertion of the marker into the region of nonstructural protein gene deletion, as a fusion with remaining nsP 1 amino acids. or by insertion downstream of the structural protein genes, under the translational control of an internal ribosomal entry site (IRES) sequence. Again, amplification of the primary structural protein gene mRNA transcript and induction of structural protein expression is controlled by the input vector RNA molecule and its synthesized non-structural proteins.

Specifically, for construction of the structural protein expression cassette, plasmid pBGS131 (Spratt et al., *Gene* 41.337–342, 1986; ATCC #37443) was modified to remove extraneous sequences, and to render an existing Xho I site within the kanamycin resistance gene non-functional. Plasmid pBGS131 was digested with Xho I and a synthetic double-stranded oligonucleotide linker with Xho I-compatible ends was ligated into the site. The synthetic 12-mer oligonucleotide, shown below, was designed as a partial palindrome that would anneal to itself generating Xho I sticky ends for ligation, and maintaining the kanamycin resistance gene open reading frame by inserting four in-frame amino acids.

dLXholinker (SEQ. ID. NO. 52)
5'-TCGATCCTAGGA

Insertion of this oligonucleotide resulted in a Xho I site-deleted plasmid, designated pBGS131dXhoI. The plasmid was next digested with BspH I and religated to itself under dilute conditions to remove 829 bp of extraneous sequence between the ColE1 replicon and kanamycin resistance marker, generating the plasmid pBGS131dlB. The BspH I site next was changed to a Pac I site by digesting pBGS131dlB with BspH I, making the termini blunt with Klenow enzyme and dNTPs, and ligating with excess Pac I linker.

Pac I linker (SEQ. ID. NO. 53)
  5'-GCTCTTAATTAAGAGC

This new construct, designated pBGS 131 dlB-P, was further modified by digesting with Fsp I and Pvu II to remove an additional 472 bp, including the multiple cloning site (MCS) and purifying the remaining vector from a 1% agarose gel using GENECLEAN II. A replacement MCS was inserted into the modified vector by annealing two complimentary oligonucleotides, PME.MCSI and PME.MCSII, and ligating with the linear plasmid.

PME.MCSI (SEQ. ID. NO. 54)
  5'-CTGTTTAAACAGATCTTATCTCGAGTATGCG GCCGCTATGAATTCGTFTAAACGA-3'

PME.MCSII (SEQ. ID. NO. 55)
  5'-TCGTTTAAACGAATCATAGCGGCCGCATAC TCGAGATAAGATCTGTTTAAACAG-3'

The new, approximately 2475 bp, cloning vector was designated pBGSVG, and contained the following multiple cloning site: <Pme I-Bgl II-Xho I-Not I-EcoR I-Pme I>. Insertion of the structural protein expression cassette containing an operably linked selectable marker proceeded stepwise, as follows. A DNA fragment comprising the 3'-end of Sindbis virus, a synthetic $A_{40}$ tract, the antigenomic HDV ribozyme, and a BGH transcription termination signal, was removed from plasmid pBG/SIN-1 ELVS 1.5 (Example 5) by digestion with Not I and EcoR I, and purification from a 1% agarose gel using GENECLEAN II. Plasmid pBGSVG also was digested with Not I and EcoR I, purified from a 1% agarose gel using GENECLEAN II, and ligated with the purified 3'-end/A40/HDV/BGH fragment, to generate the construct pBGSV3'. Next, an approximately 9250 bp Sindbis cDNA fragment, containing the structural protein genes and much of the nonstructural protein-encoding region, was removed from plasmid pDLTRSINg (Dubensky et al., ibid) by digestion with Bgl II and Fsp I, and purified from a 0.7% agarose gel using GENECLEAN II. The Sindbis cDNA fragment was then ligated into plasmid pBGSV3', which was also digested with Bgl II and Fsp I, treated with alkaline phosphatase, and purified from a 0.7% agarose gel using GENECLEAN II. The new construct was designated pBGSV3'BF. Subsequently, this construct was digested with Bgl II, treated with alkaline phosphatase, and purified with GENECLEAN II for insertion of remaining 5'-end and nonstructural gene sequences, along with a CMV IE promoter. The remaining sequences. were obtained by digestion of plasmidpDCMVSINg (Dubensky et al., ibid) with Bgl II, purification of the fragment from a 1% agarose gel using GENECLEAN II, and ligation with the linear pBGSV3'BF vector, to create the CMV-driven Sindbis genomic construct, pBGSVCMVgen. Functionality of this construct for initiation of the Sindbis virus replication cycle was determined by Lipofectamine-mediated transfection of pBGSVCMVgen plasmid into BHK cells, and the observance of CPE within 24 hr post-transfection.

Plasmid pBGSVCMVgen was subsequently used to construct a DH structural protein expression cassette by deleting most of the nonstructural protein gene sequences and inserting a neomycin resistance gene as an in-frame fusion with remaining codons of the nsP1 open reading frame. Briefly, the neomycin resistance gene was amplified by standard three-cycle PCR from the pcDNA3 vector (Invitrogen, San Diego, Calif.), using the following oligonucleotide primers that were designed to contain flanking BspE I and BamHI sites.

Forward primer: NEO5'FUSE (5'-rest. site/neo gene) (SEQ. ID. NO. 56)
  5'-ATATATCCGGA/ GTCCGGCCGCTTGGGTGGAGAGGCTA Reverse primer: NEO3'BAM (5'-rest. site/neo gene) (SEQ. ID. NO. 57)
  5'-ATATAGGATCC/ TCAGAAGAACTCGTCAAGAAGGCGA Following amplification, the DNA fragment was purified with QIAquick-spin, digested with BspE I and BamH I, purified using GENECLEAN II, and ligated into plasmid pBGSVCMVgen that had also been digested with BspE I and BamH I, treated with alkaline phosphatase, and purified from a 0.7% agarose gel using GENECLEAN II. The resulting construct was designated pBGSVCMVdlneo, and is shown schematically in FIG. 14. The configuration of pBGSVCMVdlneo includes, as part of the structural protein expression cassette and controlled by the same CMV promoter, a fusion protein comprising the initiator methionine and amino-terminal 121 amino acids of nsP1 and the neomycin resistance gene lacking its methionine initiator codon and next ten amino acids.

Figure 18:
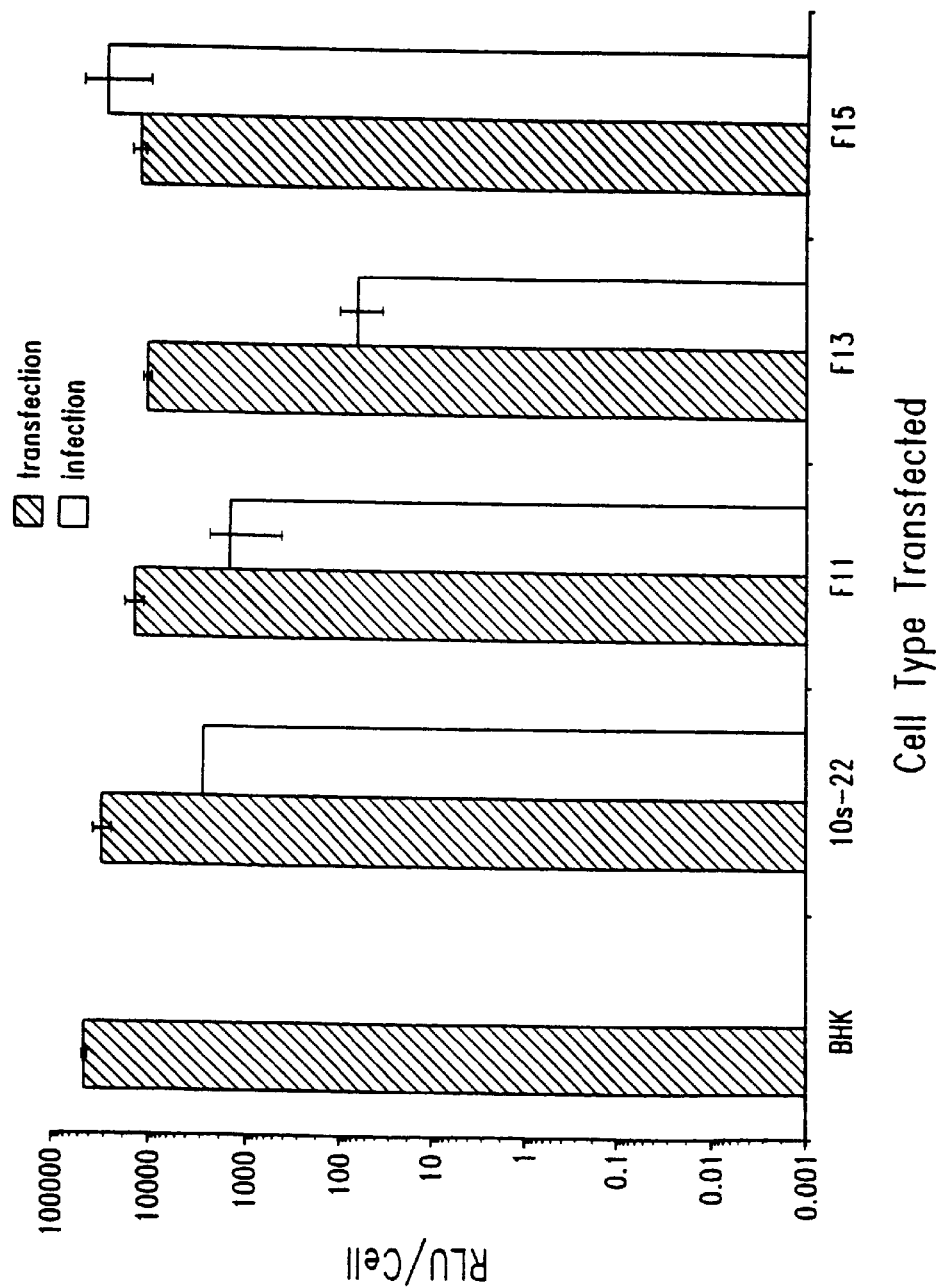
FIG. 18 is a graph depicting luciferase vector packaging by different alphavirus packaging cell lines.

Plasmid pBGSVCMVdlneo was transfected into BHK cells using Lipofectamine, as described by the manufacturer. Approximately 24 hr post-transfection, the cells were trypsinized and re-plated in media containing 600 µg/ml of the drug G418 (neomycin). The media was exchanged periodically with fresh G418-containing media and foci of resistant cells were allowed to grow. Cells were trypsinized and cloned by limiting dilution in 96 well tissue culture dishes, and individual cell clones were grown and expanded for screening. Positive packaging activity for the individual clones was identified by transfecting with Sindbis luciferase vector RNA and assaying for the presence of packaged Sindbis-luciferase vector particles as described in the previous section. Several positive cell clones harboring integrated copies of the pBGSVCMVdlneo structural protein gene expression cassette, and functioning as PCL, were identified. SNBS™-luciferase vector packaging data for individual clones (F11, F13, F15) that are representative of the group, as well as the previously described 10s-22 PCL line, are shown in FIG. 18.

In addition to demonstrating functional packaging activity with Sindbis-lucifease vectors, additional experiments performed using the same PCL also showed that vectors derived from other alphaviruses also could be packaged. For example, both Sindbis (Dubensky et al., ibid.) and Semliki Forest (pSFV3-lacZ; GIBCO BRL, Gaithersburg, Md.) vector RNAs expressing β-galactosidase, were transfected into the F15 packaging cell line. Approximately 48 hr post-transfection, the culture supernatants were harvested, clarified, diluted serially, and used to infect fresh BHK cell monolayers for determination of vector particle titers. At 18 hr post-infection, the BHK cells were fixed, stained with X-gal, and the blue-staining cells were counted, as described previously. The vector titers obtained for Sindbis β-gal were approximately $5 \times 10^6$ IU/ml, while the titers for SFV β-gal were approximately $4 \times 10^6$ IU/ml. These data demonstrate that the two different alphaviruses and their corresponding vectors have similar packaging signals and that PCL derived for the Sindbis systems described herein are fully functional when used with another alphavirus.

Packaging activity of the pBGSVCMVdlneo construct also was highly efficient in cells of human origin, for example, 293 cells. The use of such a human parental cell type for derivation of PCL may be particularly advantageous in the generation of complement resistant recombinant alphavirus particles. FIG. 17B shows that both RNA and DNA-based luciferase reporter vectors were efficiently packaged following transfection into G418 resistant. pBGSVCMVdlneo-transformed 293 PCL, as demonstrated by supernatant transfer of luciferase expression into BHK cells.

Another selectable drug-resistance marker also was shown to function in a similar PCL configuration, as a fusion protein with remaining nsP1 amino acids at its N-terminus. Briefly, the hygromycin phosphotranferase gene (hygromycin resistance marker, hygro$^r$) was substituted into plasmid pBGSVCMVdlneo, in place of the existing neomycin resistance marker. The hygro$^r$ gene was amplified by standard three-cycle PCR from plasmid p3'SS (Stratagene, La Jolla, Calif.), using the following oligonucleotide primers that were designed to contain flanking EcoRV and BamHI sites.
Forward primer: 5'HYGROEV (5'-rest. site/hygro gene) (SEQ. ID. NO. 112)
5'-TATATGATATC/ AAAAAGCCTGAACTCACCGCGACG
Reverse primer: 3'HYGROBA (5'-rest. site/hygro gene) (SEQ. ID. NO. 113)
5'-ATATAGGATCC/ TCAGTTAGCCTCCCCCATCTCCCG
Following amplification, the DNA fragment was purified with QIAquick-spin, digested with EcoRV and BamHI, purified using GENECLEAN, and ligated into plasmid pBGSVCMVdlneo that had been digested with BspEI, blunt-ended with Klenow, digested further with BamHI, treated with alkaline phosphatase. and purified from a 0.7% gel using Geneclean. The resulting construct was designated pBGSVCMVdlhyg.

Figure 39:
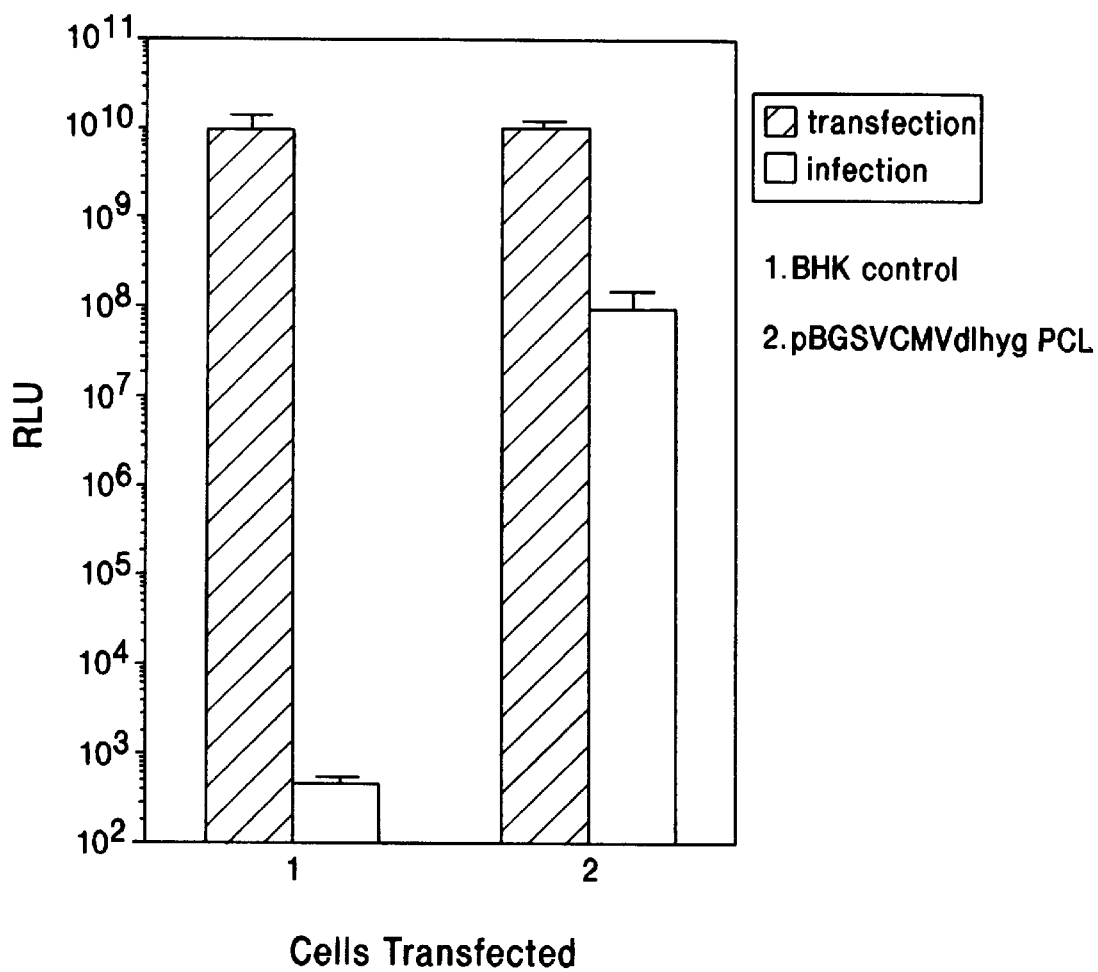

Plasmid pBGSVCMVdlhyg was transfected into BHK cells using Lipofectamine, as described by the manufacturer. Approximately 24 hr post-transfection, the cells were trypsinized and re-plated in media containing 1.2 mg/ml of the drug hygromycin (Boehringer Mannheim). The media was exchanged periodically with fresh hygromycin-containing media and foci of resistant cells were allowed to grow into a pool. Functionality of the selected packaging cells was demonstrated by transfecting with Sindbis luciferase vector RNA and assaying for the presence of packaged Sindbis-luciferase vector particles as described in the previous section. Positive results from these packaging experiments are shown in FIG. 39.

In an alternative packaging cell line structural protein expression cassette, the selectable marker (in this case neomycin resistance) was inserted downstream of the Sindbis structural protein genes and under the translational control of an internal ribosome entry site (IRES). Thus, transcription of the mRNA encoding neomycin resistance occurs both at the genomic level (from the RSV promoter) and also from the subgenomic junction region promoter. Additional features unique to this construct include the Rous sarcoma virus (RSV) LTR promoter for primary transcription and a tRNA$^{Asp}$ 5'-end sequence derived from Sindbis defective-interfering RNA clone DI25 (Monroe and Schlesinger, *Proc. Natl. Acad. Sci. USA* 80:3279–3283, 1983). This particular PCL expression cassette configuration was designated 987DHBBNeo, and is shown schematically in FIG. 14. Specifically, plasmid 987DHBBNeo may be constructed stepwise using the modified plasmid vector pBGS131dlB-P (described above) as starting material. A cDNA fragment containing the junction region promoter, the structural protein gene sequences. and 3'-untranslated region+polyA is obtained by digestion of the full-length Sindbis cDNA clone pRSINg (Dubensky et al., ibid) with BamH I and Xba I, and purification from a 0.7% agarose gel using GENECLEAN II. The Sindbis cDNA DNA fragment is ligated with plasmid vector pBGS 131 dlB-P that also has been digested with BamH I and Xba I, treated with alkaline phosphatase, and purified from a 0.7% agarose gel using GENECLEAN II, to generate the construct pBGSINsp.

Next, the transcription termination signal from the SV40 early region is inserted between the Sac I and Eco RI sites of pBGSINsp, immediately downstream of the Sindbis sequence. The SV40 viral nucleotides 2643 to 2563, containing the early region transcription termination sequences, are isolated by PCR amplification using the primer pair shown below and the pBR322/SV40 plasmid (ATCC #45019), as template
Forward primer: FSVTT2643 (5'-rest. site/SV40 nts 2643–2613) (SEQ. ID. NO. 58)
5'-TATATATGAGCTCTTACAAATAAAGCAATA GCATCACAAATTTC
Reverse primer: RSVTT2563 (rest. site/SV40 nts 2563–2588) (SEQ. ID. NO. 59)
5'-TATATGAATTCGTTTGGACAAACCACAACT AGAATG
The primers are used in a standard three-cycle PCR reaction with a 30 second extension period. The amplification products are purified with QIAquick-spin, digested with Sac I and Eco RI, purified again with the Mermaid kit, and the 90 bp fragment is ligated into plasmid pBGSINsp that also has been digested with Sac I and EcoRI, treated with alkaline phosphatase, and purified from a 0.7% agarose gel using GENECLEAN II. This construction is known as pBGSINspSV.

Next the RSV promoter and Sindbis 5'-end sequences, including the DI tRNA$^{Asp}$ structure, are assembled by overlapping PCR and the entire fragment is inserted into the structural protein gene vector pBGSINspSV. In PCR reaction #1, the RSV promoter fragment is amplified by standard three cycle PCR, with a 1 minute extension, from an RSV promoter-containing template plasmid (e.g. pRc/RSV, Invitrogen, San Diego, Calif.), using the following oligonucleotide primers that are designed to also contain a flanking Bgl II site in one primer and sequences overlapping the tRNA 5'-end in the other. The Sindbis tRNA 5'-end is positioned immediately adjacent to the RSV promoter transcription start site.
Forward primer: 5'RSVpro (5'-rest. site/RSV seq.) (SEQ. ID. NO. 60)
5'-TATATAGATCT/ AGTCTTATGCAATACTCTFGTAGT
Reverse primer: 3'RSVtR (5'-Sin tRNA seq/RSV seq.) (SEQ. ID. NO. 61)
5'-GGGATACTCACCACTATATCTCGACGGTATC GAGGTAGGGCACT
In PCR reaction #2, the Sindbis 5'-end plus tRNA sequence is amplified by standard three cycle PCR with a 1 minute extension. from template plasmid Toto110(5'tRNA$^{Asp}$) (Bredenbeek et al.. *J. Virol.* 6/:6439–6446, 1993), using the following oligonucleotide primers that are designed to also contain a flanking BamH I site in one primer and sequences overlapping the 3'RSVtR primer in the other.
Forward primer: 5'tRNASin (5'-Sindbis+tRNA seq. only) (SEQ. ID. NO. 62)
5'-GATATAGTGGTGAGTATCCCCG
Reverse primer: 3'SinBam (3'-rest. site/Sindbis seq.) (SEQ. ID. NO. 63)
5'-TATATGGATCC/ AGTACGGTCCGGAGATCCTTAATCTTCTCATG
Following amplification, the DNA fragments are purified with QIAquick-spin and used together as templates in a subsequent three-cycle PCR reaction with 2 minute extension, using additional 5'RSVpro and 3'SinBam primers. The resulting overlapping PCR amplicon is purified using GENECLEAN II, digested with Bgl II and BamH I, and ligated into plasmid pBGSINspSV that also has been digested with Bgl II and BamH I, treated with alkaline phosphatase, and purified from a 0.7% agarose gel using GENECLEAN II. The resulting structural protein expressing, defective helper is designated 987DHBB.

Next, the IRES sequence from encephalomycodarditis virus (EMCV), is positioned immediately upstream of the neomycin phosphotransferase gene, as a selectable marker, by overlapping PCR, and the entire amplicon is inserted into the Nsi I site of 987DHBB. Insertion at the Nsi I site will position the selectable marker immediately downstream of the structural protein ORF. In PCR reaction #1, the EMCV IRES fragment (nucleotides 260–827) is amplified by standard three cycle PCR, with a 30 second extension, from template plasmid pBS-ECAT (Jang et al., J Virol 63:1651, 1989), using the following oligonucleotide primers that are designed to also contain a flanking Nsi I site in one primer and sequences overlapping the neo gene in the other.

Forward primer: 5'EMCVIRES (5'-rest. site/EMCV seq.) (SEQ. ID. NO. 64)

5'-TATATATGCAT/CCCCCCCCCCCCCAACG

Reverse primer: 3'EMCVIRES (5'-pcDNA+neo seg/EMCV seq.) (SEQ. ID. NO. 65)

5'-CATGCGAAACGATCCTCATC/ CTTACAATCGTGGTTTTCAAAGG

In PCR reaction #2, the neo resistance marker is amplified by standard three cycle PCR. with a 1.5 minute extension, from template plasmid pcDNA3 (Invitrogen, San Diego, Calif.), using the following oligonucleotide primers that are designed to also contain a flanking Nsi I site in one primer and sequences overlapping the 3'EMCVIRES primer in the other.

Forward primer: 5Neo/pcDNA (5'-pcDNA+neo seq. only) (SEQ. ID. NO. 66)

5'-GATGAGGATCGTTTCGCATGATTGA

Reverse primer: 3'Neo/pcDNA (3'-rest. site/neo seq.) (SEQ. ID. NO. 67)

5'-TATATATGCAT/ TCAGAAGAACTCGTCAAGAAGGCGA

Following amplification, the DNA fragments are purified with QIAquick-spin and used together as templates in a subsequent three-cycle PCR reaction with 2 minute extension, using additional 5'EMCVIRES and 3'Neo/pcDNA primers. The resulting overlapping PCR amplicon is purified using GENECLEAN II, digested with Nsi I, and ligated into plasmid 987DHBB that also has been digested with Nsi I, treated with alkaline phosphatase, and purified from a 0.7% agarose gel using GENECLEAN II. The resulting structural protein expression construct, with the IRES/neo insert in the Sindbis 3'-untranslated region, is designated 987DHBBNeo.

Figure 19:
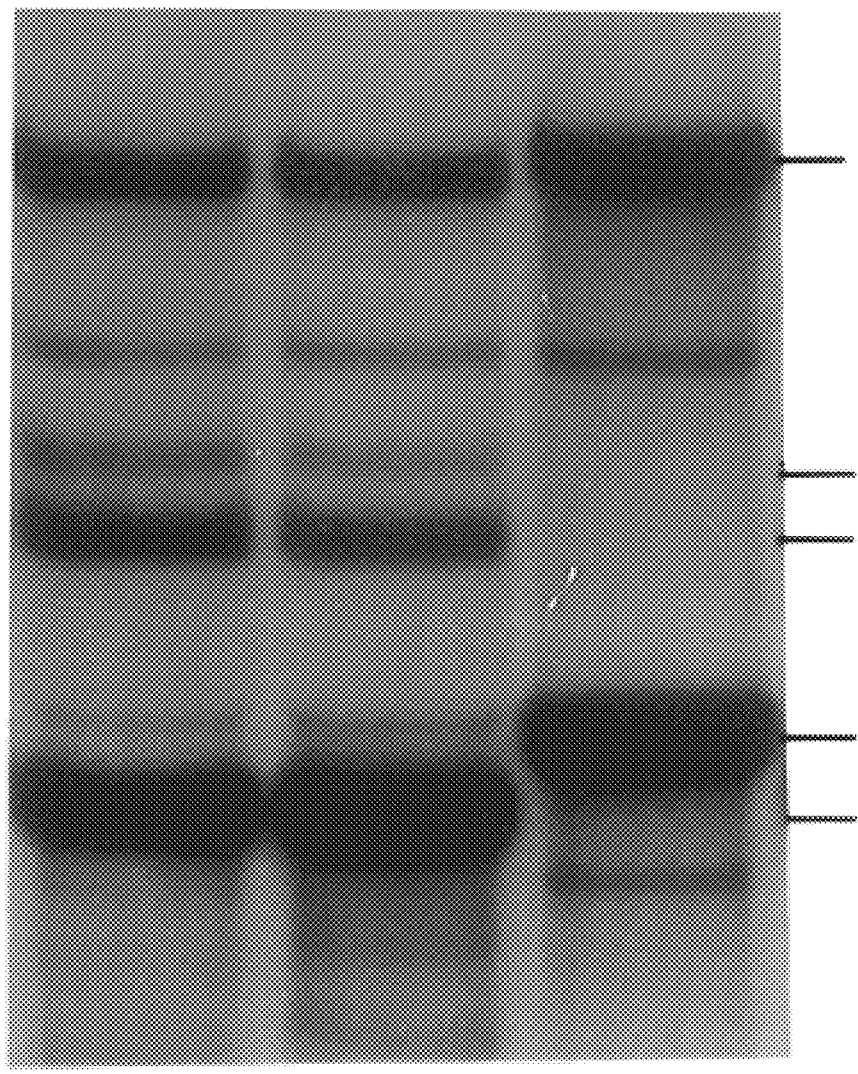
FIG. 19 is an RNA gel autoradiograph depicting $^{3}H$ uridine-labeled RNAs from BHK cells infected with SINrep/LacZ vector particles produced from an alphavirus packaging cell line.

To generate stable packaging cell lines, BHK cells were transfected with 10 μg of plasmid 987DHBBNeo, using a standard calcium phosphate precipitation protocol. Approximately 24 hr post-transfection, the media was replaced with fresh media containing 1 mg/ml of the drμg G418. After one additional day, the cells were trypsinized and re-plated at 1/10 density in media containing 500 μg/ml G418. After several more passages, the cells were subjected to dilution cloning and individual clones were expanded. The ability of individual clones to function as packaging cell lines was determined by calcium phosphate transfection of plasmid RSV/Sinrep/LacZ, a Sindbis DNA vector expressing β-gal, and assaying for the presence of packaged vector particles in the supernatants after 48 hr. The packaged vector replicons were titered by the CPE assay described in Frolov and Schlesinger (J. Virol. 68:1721–1727, 1994) and one that gave high titers of packaged particles, designated 987DH-BBNeo, was used for further characterization. Packaged vector titers were determined at 48 hr, following transfection of either RNA- or DNA-based Sindbis vectors expressing β-gal, using several different transfection techniques. The results were as follows:

In addition, SINrep/LacZ particles that were packaged using 987DH-BB cell lines subsequently were used to infect fresh BHK cell monolayers and examine both RNA and protein expression patterns. FIG. 19 shows the RNA pattern after BHK cells were infected with two different preparations of SINrep/LacZ particles at a MOI of 150 infectious units per cell (lanes 1 and 2), or wild-type Sindbis virus (lane 3), as a control. Seven hours post-infection, dactinomycin (1 μg/ml) and [$^3$H]uridine (20 uCi/ml) were added, followed by harvest and analysis of RNA 4 hr later, according to Bredenbeek et al. (J. Virol. 67:6439–6446, 1993). The high MOI was used in order to detect possible recombinants. Horizontal lines to the right of the gel lanes indicate the Sindbis and β-gal RNAs of interest. The highest molecular weight band indicates the genomic RNA of the replicon or virus (lanes 1 and 2. SINrep/LacZ; lane 3 Sindbis virus). The next two RNAs indicated are the genomic RNA of the 987DH-BBNeo PCL expression cassette and the inducible subgenomic structural protein mRNA from the same 987DH-BBNeo PCL cassette. The presence of the latter two bands demonstrates that the helper genomic RNA derived from the packaging cell line is also co-packaged. The next RNA bands. those present in greatest abundance, are the subgenomic RNAs derived from either SINrep/LacZ (lanes 1 and 2) or the Sindbis virus genome (lane 3).

Figure 20:
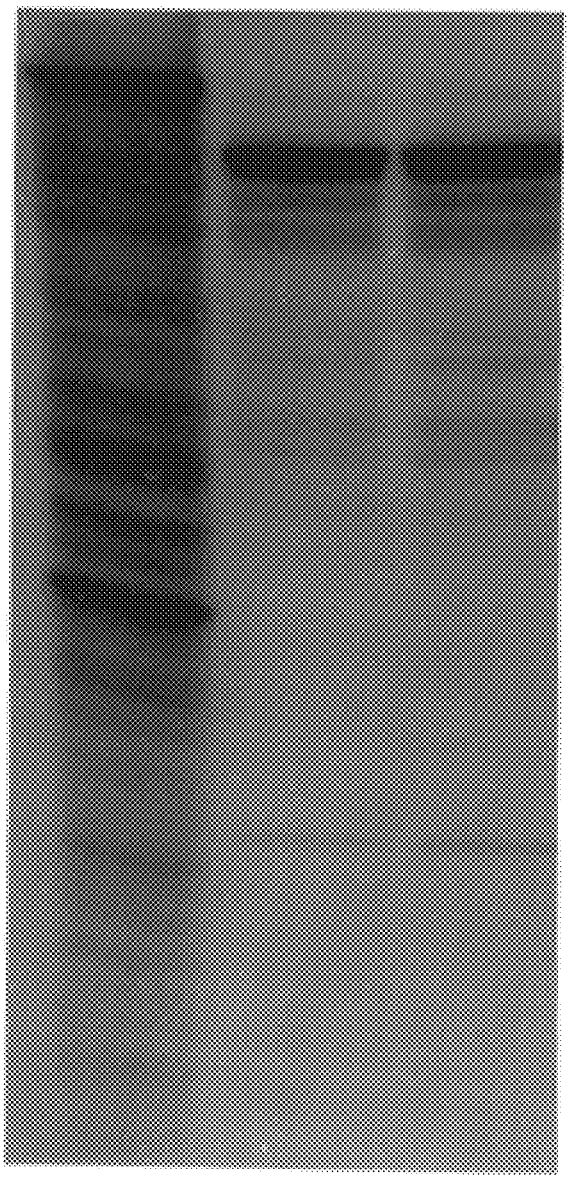
FIG. 20 is a protein gel autoradiograph depicting $^{35}S$ methionine-labeled proteins from BHK cells infected with SINrep/LacZ vector particles produced from an alphavirus packaging cell line.

Protein analysis was performed following infection of BHK 21 cells with packaged SINrep/LacZ replicons at a MOI of 20 infectious units/cell. Fifteen hours post-infection. the cells were labeled with [$^{35}$S] methionine for 30 minutes, lysates made, and the proteins analyzed by SDS-PAGE. As shown in FIG. 20 (lanes2 and 3), both beta-galactosidase and the Sindbis virus capsid protein are labeled in the vector particle-infected cells, but not in uninfected cells (lane 1). The presence of capsid shows that some of the packaged particles also contain structural protein gene RNA transcripts from the PCL.

C. Construction of "split structural gene" PCL configurations

Figure 21A:
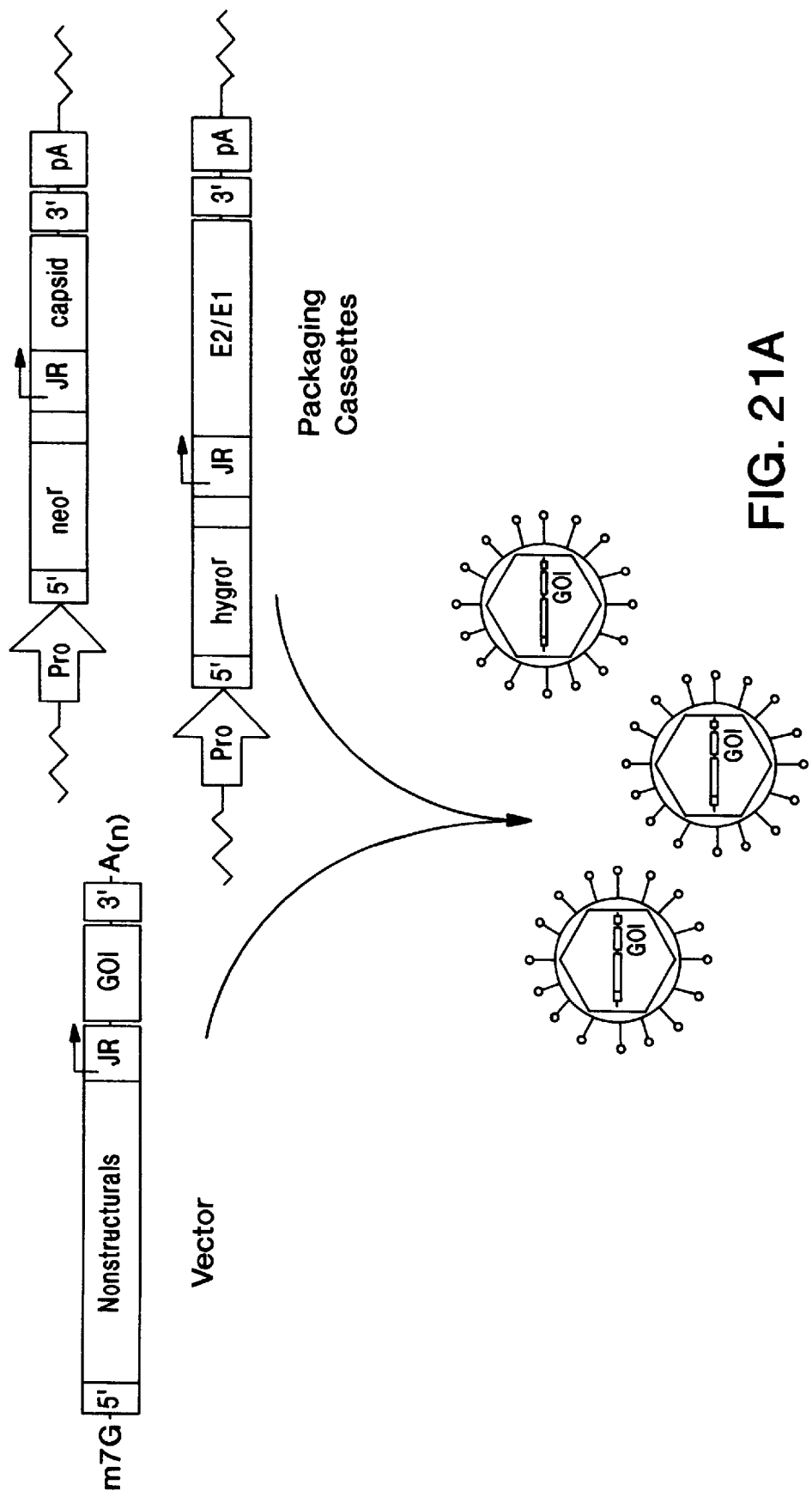
FIG. 21A is a schematic illustration depicting packaging of alphavirus vectors with structural proteins in which the capsid protein and glycoproteins are expressed from distinct, or "split", expression cassettes.

In other embodiments of the present invention, PCL are provided wherein the alphavirus structural proteins are expressed, not as a polyprotein from a single mRNA, with its native post-translational processing, but rather, as separate proteins from independent mRNAs that are transcribed via multiple cassettes. This approach is depicted schematically in FIG. 21A. Such a configuration greatly minimizes the possibility of recombination or co-packaging events that lead to formation of replication-competent or infectious virus. In preferred embodiments, the capsid protein is expressed from one stably transformed cassette and the envelope glycoproteins are expressed together from a second stably transformed cassette, and each is expressed in a vector-inducible manner from the junction region promoter (described above).

For example, the Sindbis virus capsid protein gene was amplified from plasmid pDLTRSINg (Dubensky et al., ibid), by standard three-cycle PCR with a 1.5 minute extension, using the following oligonucleotide primers that were designed to contain a flanking Xho I site and capsid protein gene initiation codon or a flanking Not I site and translation stop codon.

Forward primer: SIN5'CXho (5'-rest. site/capsid seq.) (SEQ. ID. NO. 68)
5'-ATATACTCGAG/ACCACCACCATGAATAGAGGATTC
Reverse primer: SIN3'CNot (5'-rest. site/stop codon/capsid seg.) (SEQ. ID. NO. 69)
5'-TATATGCGGCCGC/TATTAICCACTCTTCTGTCCCTTCCGGGGT Following amplification, the capsid DNA fragment was purified with QIAquick-spin, digested with Xho I and Not I, purified using GENECLEAN II, and ligated into the DNA-based Sindbis expression vector pDCMVSIN-luc (Dubensky et al., ibid), that also had been digested with Xho I and Not I to remove its luciferase reporter gene insert, treated with alkaline phosphatase, and purified from a 0.7% agarose gel using GENECLEAN II. The resulting capsid protein expression construct was designated pDCMVSIN-C. Plasmid pDCMVSIN-C was subsequently digested with BspE I to remove most nonstructural protein gene sequences, and re-ligated to itself under dilute conditions to create the DH vector construct, pDCMVSINdl-C.

Alternatively, the vector backbone may be first modified to contain the RSV promoter and/or 5'-end tRNA sequences described previously for 987DHBB. Specifically, this was accomplished by step-wise replacements using plasmid pBGSV3' (see above) as starting material. The junction region promoter plus Xho I and Not I cloning sites were obtained as a luciferase reporter-containing fragment from pDCMVSIN-luc (see above). Plasmid pDCMVSIN-luc was digested with Bam HI and Fsp I, and the luciferase reporter-containing fragment was purified from a 0.7% agarose gel using GENECLEAN II. The fragment was ligated into plasmid pBGSV3' that also had been digested with Bam HI and Fsp I, and treated with alkaline phosphatase to produce a plasmid designated pBGSV3'BaFLuc. The RSV promoter/5'-end tRNA sequence was then obtained from 987DHBB by digestion with Bgl II and Bam HI and purification from a 1% agarose gel using GENECLEAN II. This fragment was ligated into pBGSV3'BaFLuc that was similarly digested with Bgl II and Bam HI, to produce the construct pBRSV987dl-Luc, which may be used as starting material for either capsid or envelope glycoprotein expression constructs.

To generate a capsid gene expression construct with the RSV promoter and tRNA 5'-end sequence, the existing luciferase reporter gene insert was removed by digestion with Xho I and Not I, and replaced with a PCR-amplified capsid protein gene (see above), that also was digested with Xho I and Not I. The resulting construct was designated pBRSV987dl-C. Insertion of a neomycin phosphotransferase selectable marker into the region of nonstructural protein gene deletion was accomplished by digestion with BspE I and Bam HI, and replacement with a PCR-amplified neo$^r$ gene (see above) that also was digested with BspE I and Bam HI, and purified from a 1% agarose gel. The resulting construct was designated pBRSV987dlneo-C and is shown schematically in FIG. 21B.

Plasmids pDCMVSINdl-C and pBRSV987dlneo-C, which contain neomycin resistance selectable markers, were transfected into BHK-21 cells using Lipofectamine, as described by the manufacturer. Approximately 24 hr post-transfection, the cells were trypsinized and re-plated in media containing 600 µg/ml of the drug G418 (neomycin). The media was exchanged periodically with fresh G418-containing media and foci of resistant cells were allowed to grow. Cells were trypsinized and cloned by limiting dilution in 96 well tissue culture dishes, and individual cell clones were grown and expanded for screening. Cells which inducibly expressed capsid protein in response to input vector were identified by transfecting with Sindbis luciferase vector RNA or Sindbis β-galactosidase DNA vectors, making cell lysates approximately 24 or 48 -hr post-transfection, and performing western blot analysis with a rabbit anti-Sindbis polyclonal antibody. Several positive cell clones harboring integrated copies of the capsid protein gene expression cassette and inducibly expressing the protein were identified and are shown in FIG. 21D.

In order to demonstrate both inducibility and functionality of the expressed capsid in the context of "split structural gene" cassettes, an additional construct that expressed the Sindbis virus envelope glycoproteins was generated from pDCMVSIN-luc. Briefly, the Sindbis envelope glycoprotein genes were amplified from plasmid pDLTRSINg by standard three-cycle PCR, with a 2.5 minute extension, and using the following oligonucleotide primers that are designed to contain a flanking Xho I site and translation initiation codon in good Kozak context, or a flanking Not I site and the translation stop codon.

Forward primer: 5'GLYCO-X (5'-rest. site/initiation codon/glycoprotein seg.) (SEQ. ID. NO. 70)
5'-ATATACTCGAG/AGCAATG/TCCGCAGCACCACTGGTCACGGCA
Reverse primer: 3'GLYCO-N (5'-rest. site/glycoprotein seq.) (SEQ. ID. NO. 71)
5'-ATATAGGCGGCCGC/TCATCTTCGTGTGCTAGTCAGCATC Following amplification, the glycoprotein gene DNA fragment was purified with QIAquick-spin, digested with Xho I and Not I, purified using GENECLEAN II, and ligated into the DNA-based Sindbis expression vector pDCMVSIN-luc, that also had been digested with Xho I and Not I to remove its luciferase reporter gene insert, treated with alkaline phosphatase, and purified from a 0.7% agarose gel using GENECLEAN II. The resulting glycoprotein expression construct was designated pDCMVSIN1.5PE.

Figure 21C:
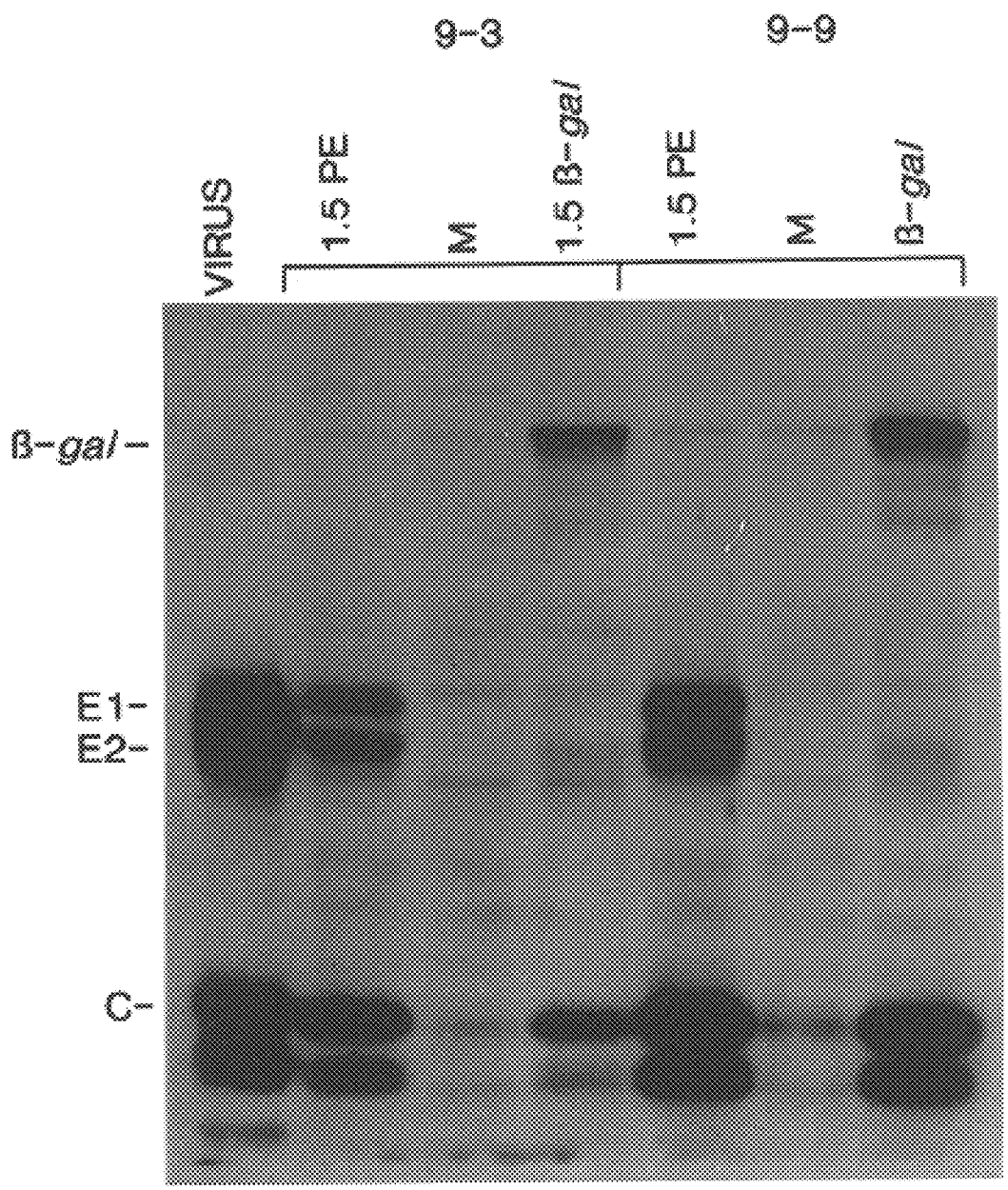
FIG. 21C is a western blot analysis demonstrating induction of alphavirus capsid protein synthesis by several clonal cell lines following transfection and subsequent synthesis of alphavirus glycoproteins or βgal from an alphavirus expression vector (ELVS-1.5PE [1.5PE], or ELVS-βgal [βgal]).

FIG. 21C is a western blot demonstrating vector controlled inducibility of two different clonal capsid lines (9-3 and 9-9) cell lines, that were transfected with Sindbis DNA vectors expressing the envelope glycoproteins (1.5PE lanes) or a β-galactosidase reporter, pDCMVSIN-β-gal (Dubensky et al., ibid ; 1.5 β-gal lanes), or "mock" transfected (M lanes), using Lipofectamine. Cell lysates were made at 48 hr post-transfection, separated by SDS-PAGE, and transferred to membranes, where they were probed with a combination of antibodies specific for Sindbis structural proteins and β-galactosidase. The blot clearly shows the inducibility of capsid protein in response to the nonstructural proteins supplied by either vector, as well as the expression of β-galactosidase and the envelope glycoproteins. Functionality of the "split structural gene" capsid cell lines, by complementation and vector particle packaging, was demonstrated by co-transfecting the β-galactosidase and envelope glycoprotein vectors into a capsid cell line using Lipofectamine, and assaying for packaged particles in the culture supernatants. Approximately 48 hr post-transfection, the supernatants were harvested and clarified for the packaging assays and vector titer determination. In addition. the cells were lysed using Lameli sample buffer and examined by western blot analysis with polyclonal anti-Sindbis antibody, demonstrating expression of both capsid protein and the vector supplied envelope glycoproteins. The supernatants were then tested for the presence of packaged vector particles by infecting naive BHK cells for approximately 18 hr, and staining for β-gal reporter gene expression, as described previously in this example. Functionality of the cell lines for complementation and packaging was demonstrated by the observance of blue-stained β-gal expressing cells.

To generate stable "split structural gene" PCL that have separate vector inducible expression cassettes for both capsid protein and the envelope glycoproteins, any of the above described capsid cell lines may be used. in conjunction with an additional envelope glycoprotein expression construct that contains a different selectable marker (for example, hygromycin B resistance). In one example, pBRSV987dl-Luc was used as starting material to generate a glycoprotein gene expression construct with the RSV promoter and tRNA 5'-end sequence. The existing luciferase reporter gene insert of pBRSV987dl-Luc was removed by digestion with Xho I and Not I, and replaced with a PCR-amplified glycoprotein gene (pE2/E1) product (see above), that also was digested with Xho I and Not I, and purified from a 0.7% agarose gel. The resulting construct was designated pBRSV987dl-Glyco. Insertion of a hygromycin phosphotransferase selectable marker into the region of nonstructural protein gene deletion was accomplished by digestion of plasmid pBRSV987dl-Glyco with BspE I, blunt-ending with Klenow, and further digesting with Bam HI. The hygromycin insert was obtained as a PCR-amplified product (see above) that was digested with EcoR V and BamH I, and ligated into the prepared pBRSV987dl-Glyco vector. This construct was modified further to include an RNA export element. The PRE sequence was inserted by first isolating a PCR-generated 564 bp fragment of HBV from the full-length genomic clone of the ADW viral strain, pAM6 (ATCC No. 39630), as described in Example 5. Following amplification and purification, the purified HBV PRE fragment was cloned into the pCR-Blunt (INVITROGEN, San Diego. Calif.) plasmid vector, to yield the construct pHBV-PRE. The HBV PRE element then was isolated from pHBV-PRE by digestion with Not I and 2% agarose gel electrophoresis, and ligated into the hygromycin resistance marker containing construct derived from pBRSV987dl-Glyco, that was also digested with Not I and treated with CIAP, to yield the final construct, pBRSV987dlhyg-Glyco.

In certain embodiments, it may be desirable to also include a translation enhancement element that may derived from capsid gene sequences of homologous or heterologous alphaviruses. For inclusion of a Ross River virus translation enhancer, an appropriate sequence may be obtained from the DH-BB CΔ3rrv construct described in example 8. Specifically, DH-BB CΔ3rrv was digested with Bam HI and Bsi WI, and a fragment containing the junction region promoter, Ross River virus translation enhancer, and the amino terminal sequences of the pE2 gene, was isolated using a 1.2% agarose gel and GENECLEAN II. This fragment was ligated into plasmid pBRSV987dlhyg-Glyco that was similarly digested with Bam HI and Bsi WI, to produce the expression cassette designated pBRSV987dlhyg-rrv-Glyco, and shown schematically in FIG. 21B.

Alternatively, plasmid pBG/SIN-1 ELVS 1.5-β-gal (Example 5) may be used as starting material, by digestion with BamH I and Fsp I to isolate the sequences comprising the junction region promoter, the β-gal reporter gene, and some 3'-end sequences. The desired fragment is purified from a 1% agarose gel using GENECLEAN II, and ligated into plasmid pBGSVCMVdlneo (see above) that also has been digested with Bam HI and Fsp I to eliminate all structural protein gene sequences, treated with alkaline phosphatase, and purified from a 0.7% agarose gel using GENECLEAN II. The resulting construct is designated as pBGSVCMVdlsP-luc. Plasmid pBGSVCMVdlsP-luc is next digested with 2Xho I and Not I to remove the luciferase reporter gene, treated with alkaline phosphatase, and purified from a 0.7% agarose gel using GENECLEAN II, and the Xho I- and Not I-digested envelope glycoprotein PCR amplicon from above is subsequently ligated into the digested pBGSVCMVdlsP-luc vector to generate the envelope glycoprotein expressing DH construct, pBGSVCMVdl-G. Insertion of a hygromycin resistance marker cassette into this plasmid, as well as flanking HSV TK promoter and polyadenylation sequences, is accomplished by PCR amplification, using a standard three-cycle protocol with 2.5 minute extension, plasmid pDR2 (Clontech, Palo Alto, Calif.) as template, and the following oligonucleotide primers that are designed to contain flanking Pac I sites.

Forward primer: 5'HYGRO/Pro-P (5'-rest. site/pDR2 seq.) (SEQ. ID. NO. 72)
   5'-ACACATTAATTAA/
     CGATGCCGCCGGAAGCGAGAA Reverse primer: 3'HYGRO/pA-P (5'-rest. site /DR2 seq.) (SEQ. ID. NO. 73)
   5'-ACACATTAATTAA/
     GTATTGGCCCCAATGGGGTCT Following amplification, the DNA fragment is purified with QIAquick-spin, digested with Pac I, purified using GENECLEAN II, and ligated into plasmid pBGSVCMVdl-G that also has been digested with Pac I, treated with alkaline phosphatase, and purified using GENECLEAN II. The resulting construct is designated as pBGSVhygro-G.

Figure 26B:
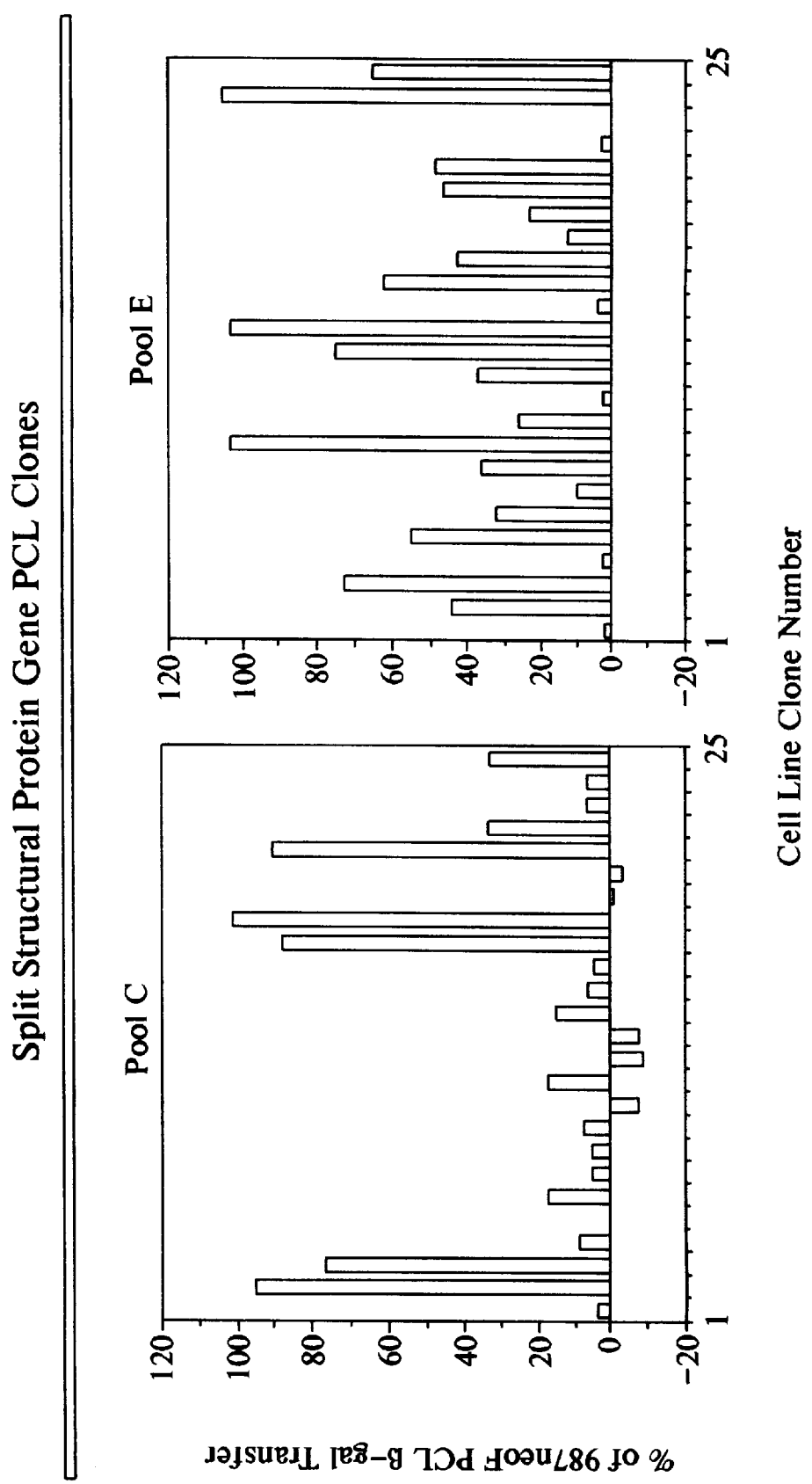
Figure 26C:
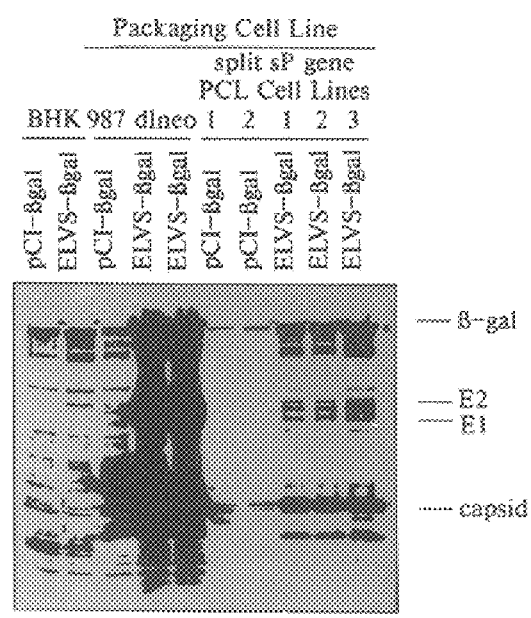

Plasmid pBRSV987dlhyg-rrv-Glyco, which contains a hygromycin selectable marker, was transfected into a clonal capsid cell line using Lipofectamine, as described by the manufacturer. Approximately 24 hr post-transfection, the cells were trypsinized and re-plated in media containing 500 μg/ml of hygromycin (Calbiochem, La Jolla, Calif.). The media was exchanged periodically with fresh hygromycin-containing media and foci of resistant cells were allowed to grow. Cells were trypsinized and cloned by limiting dilution in 96 well tissue culture dishes, and individual cell clones were grown and expanded for screening. Split structural gene PCL derived in this manner were designated C/GLYCO PCL. Positive cells which inducibly express biologically active capsid protein and envelope glycoproteins in response to input vector were identified in two ways. Initially, transfer of expression experiments were performed to demonstrate that transfected vector molecules could induce structural protein expression, resulting in packaging and secretion of vector particles that could in turn be used to infect naive cells. Sindbis virus plasmid DNA vectors expressing β-galactosidase were transfected into panels of potential C/GLYCO PCL clones derived from two independently selected pools (FIG. 26B, pools C and E). At 48 hr post-transfection, supernatants were harvested and used to infect naive BHK-21 cells for an additional 18 hr. Infected cell lysates were harvested and enzymatic β-galactosidase activity determined. As shown in the figure, several clones were able to package vector, resulting in the high level transfer of vector to naive cells. In a second experiment, transfected PCL were lysed and subjected to western blot analysis as described previously. As shown in FIG. 26C, induction of both capsid and envelope glycoprotein occurs after introduction of vector into the PCL.

D. Construction of PCL with "hybrid" structural proteins

An additional approach which may be utilized to decrease the level of co-packaging or recombination between DH and vector RNA molecules, to enhance translation of the glycoprotein genes, or to alter the cell or tissue specificity of the packaged recombinant alphavirus vector particles, makes use of structural protein genes derived from other alphaviruses or togaviruses. More specifically, numerous combinations of alphavirus or togavirus structural protein genes for use with Sindbis virus or different alphavirus vectors can be envisioned. For example, the capsid protein gene of Ross River virus (RRV), may be used in conjunction with the envelope glycoprotein genes of Sindbis virus (expressed from the same or a different construct), to package a Sindbis virus-derived vector described in examples 3, 4, or 5. In addition, a deleted form of the RRV capsid protein gene may be positioned immediately upstream of the Sindbis glycoprotein gene sequences to serve as a translational enhancer elements. As another example, the structural proteins of Sindbis virus may be used to package Semliki Forest virus RNA vectors.

Figure 22:
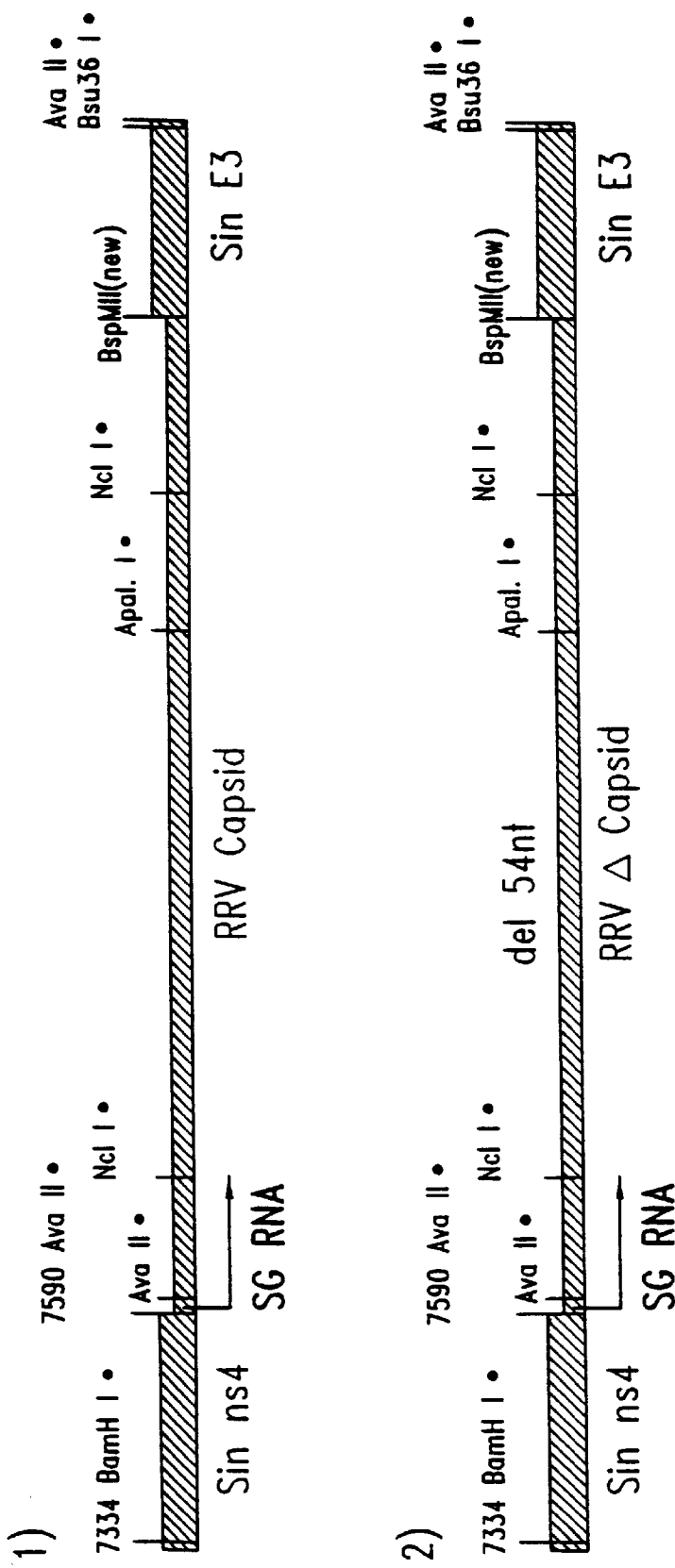
FIG. 22 is a schematic illustration of the region of structural protein expression cassettes comprising a wild-type or deletion mutant Ross River virus capsid protein gene.

Specifically, defective helper (DH) structural protein constructs that contain an intact or deleted form of the RRV capsid gene (FIG. 22), plus the Sindbis glycoprotein genes, were constructed by PCR amplification of Sindbis virus or Ross River virus sequences from plasmid templates Toto 1101 (Rice et al., *J. Virol.* 61:3809–3819, 1987) and RR6415 (Kuhn et al., *Virology* 182:430–441, 1991), respectively, and incorporation of those sequences into the previously described DH constructs DH-BB or DH-BB(5'SIN) (Bredenbeek et al., *J. Virol.* 67:6439–6446, 1993), for transcription in vitro with SP6 polymerase. The DH constructs DH-BB or DH-BB(5'SIN) different by the presence (DH-BB) or absence (DH-BB(5'SIN)) of a DI-derived tRNA$^{Asp}$ sequence at the Sindbis 5'-end. The following table indicates the specific PCR primer sequences and their corresponding Sindbis or Ross River nucleotide positions, with capital letters indicating viral nucleotides and lower case letters indicating additional nucleotides of restriction sites used in cloning steps or specific point mutations. Point mutations in primer 6 (RRV Bsp) did not change the resulting amino acid sequence.

Primers used for PCR
1. RRV Ava: (nt.7510–7525) (SEQ. ID. NO.74)
   5'-ccacgaattcGGTCCTAAATAGATGC
2. RRV Nci1: (nt.7606–7620) (SEQ. ID. NO.75)
   5'-ccacaagcttCCGGGCGAGGCCGCC
3. RRV Nci2: (nt.7616–7630) (SEQ. ID. NO.76)
   5'-ccacggatCCCGGCGTTCCGTCC
4. RRV Apa1. (nt.8088–8102) (SEQ. ID. NO.77)
   5'-ccacaagcttGTGCACTGGGATCTG
5. RRV Apa2: (nt.8097–81 11) (SEQ. ID. NO.78)
   5'-ccacggatccGTGCACATGAAGTCC
6. RRV Bsp: (nt.8339–8361) (SEQ. ID. NO.79)
   5'-ccacaagCTTCcGGaGTTACCCGAGTGACC
7. RRV Afl1: (nt.7820–7836) (SEQ. ID. NO.80)
   5'-ccaccttaaGCGTCGGCTTTTTCTTC
8. RRV Afl2: (nt.7892–7907) (SEQ. ID. NO.81)
   5'-ccaccttaaGAGAAGAGAAAGAATG
9. SIN Ava: (nt.7591–7594) (SEQ. ID. NO.82)
   5'-ccacaagcttGGACCACCGTAGAG
10. SIN Bam: (nt.7325–7343) (SEQ. ID. NO.83)
    5'-CCGCGTGGCGGATCCCCTG
11. SIN Bsp: (nt.8418–8433) (SEQ. ID. NO.84)
    5'-ccacggatCCGGAAGGGACAGAAG
12. SIN Bsu: (nt.8887–8902) (SEQ. ID. NO.85)
    5'-CACGGTCCTGAGGTGC PCR reactions were performed using the primer pairs indicated below, in a standard three cycle protocol, with 30 sec extensions and Vent polymerase, to produce the corresponding DNA fragments, which are also indicated below.

PCR fragments: primer pairs, plasmid temp late
Fragment 1: pr1+pr2, RRV6415 plasmid
Fragment 2: pr3+pr4, RRV6415 plasmid
Fragment 3: pr5+pr6, RRV6415 plasmid
Fragment 4: pr3+pr7, RRV6415 plasmid
Fragment 5: pr4+pr8, RRV6415 plasmid
Fragment 6: pr9+pr10, Toto1101 plasmid
Fragment 7: pr1+pr12, Toto1101 plasmid Following amplification, the PCR products were digested with the indicated enzymes, and ligated into the pUC18 plasmid analog, pRS2, which contains additional polylinker sites and which had also been digested with the same enzyme combinations: fragment 1 was cut with EcoR I+Hind III; fragment 2 with BamH I+Hind III; fragment 3 with BamH I+Hind III; fragment 4 with BamH I+Afl II, fragment S with Hind III+Afl II, fragment 6 with BamH I+Hind III; and fragment 7 with BamH I+Bsu 36I. All insertions were sequenced to verify that artifacts had not been acquired during PCR.

Subsequently, the fragments were released from the pRS2 plasmids using the enzymes indicated below, and ligated exactly as indicated to generate the next set of constructs. To generate FR8, fragment 6 (cut by Bam HI and Ava II) was ligated with fragment 1 (cut by Ava II and Nci I), fragment 2 (cut by Nci I and Hind III) and plasmid pRS2 (cut by Bam HI and Hind III). To generate FR9, fragment 6 (cut by BamH I and Ava II) was ligated with fragment 1 (cut by Ava II and Nci I), fragment 4 (cut by Nci I and Afl II) and plasmid pRS2 (cut by BamH I and Afl II). To generate FR10, fragment 5 (cut by Afl II and ApaL I) was ligated with fragment 3 (cut by ApaL I and Hind III) and plasmid pRS2 (cut by Afl II and Hind III). After transformation of *E. coli*, plasmids were analyzed by restriction analysis and their inserts were again isolated by digestion and used for the next steps of cloning.

The FR8 insert (cut by BamH I and ApaL I) was ligated with fragment 3 (cut by ApaL I and BspM II), fragment 7 (cut by BspM II and Bsu36 I) and plasmid DH-BB (cut by BamH I and Bsu36 I). The same fragments also were used to replace the BamH I-Bsu36 I fragment of plasmid DH-BB (5'SIN). The resulting plasmids were designated DH-BB Crrv and DH-BB(5'SIN) Crrv, respectively (see FIG. 23). The FR9 insert (cut by BamH I and Afl II) was ligated with the FR10 insert (cut by Afl II and BspM II), fragment 7 (cut by BspM II and Bsu36 I) and plasmid DH-BB (cut by BamH I and Bsu36 I). The same fragments also were used to replace the BamH I-Bsu36 I fragment of plasmid DH-BB (5'SIN). The resulting plasmids were designated DH-BB CΔrrv and DH-BB(5'SIN) CΔrrv (see FIG. 23).

Figure 24:
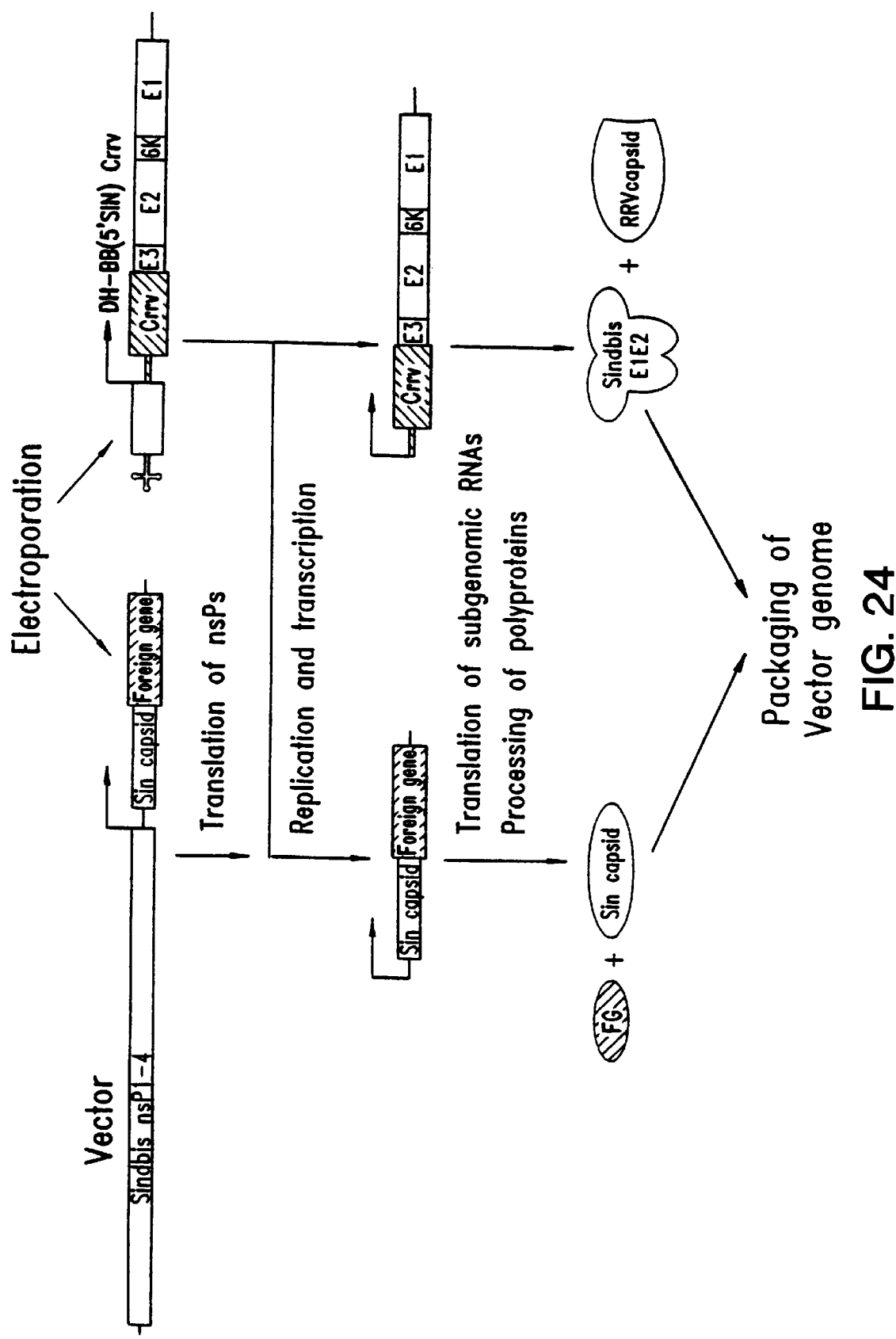
Figure 25:
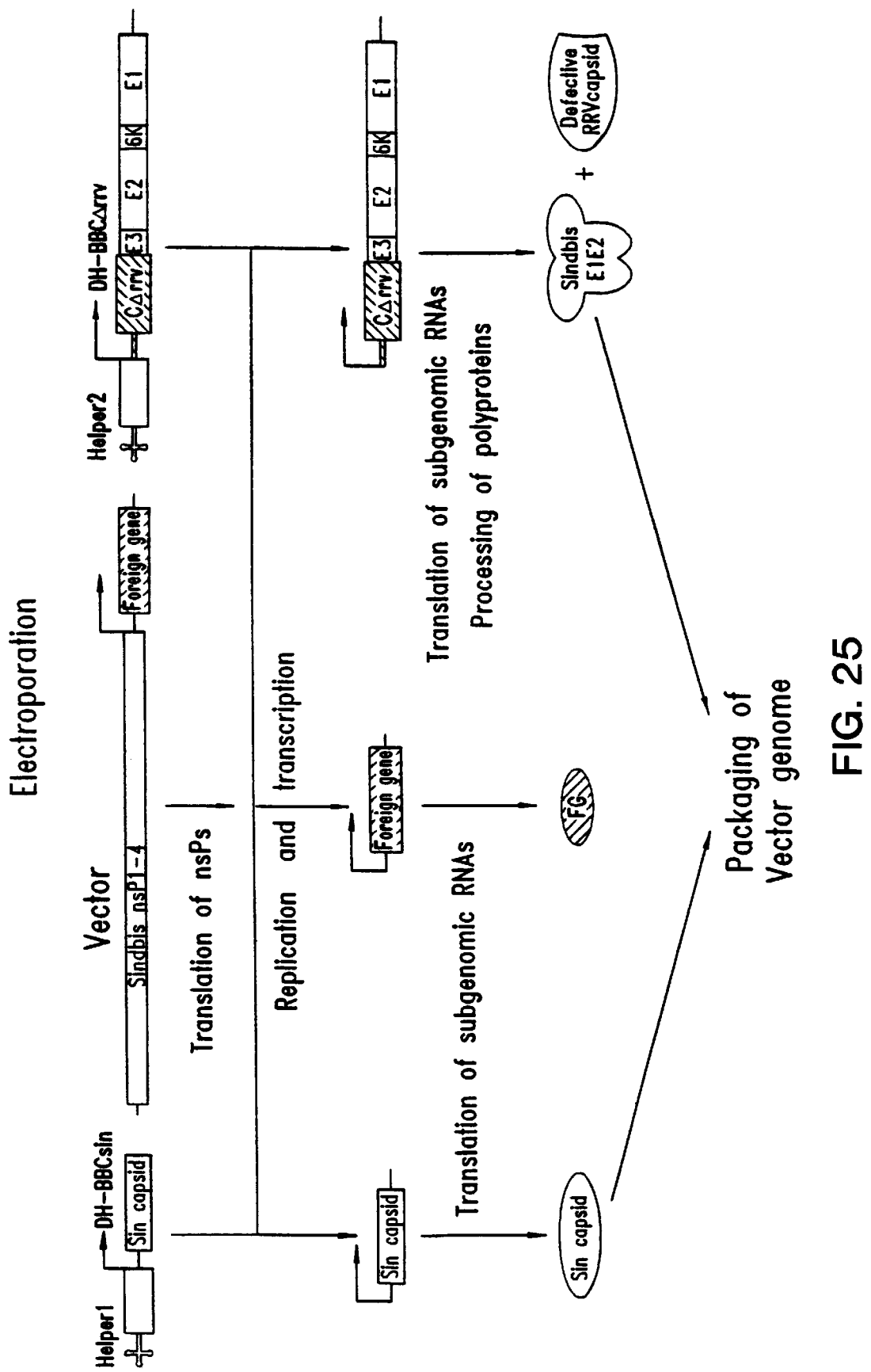

Multiple uses for DH constructs that contain chimeric structural protein genes are possible, and two such approaches are illustrated in FIGS. 24 and 25. In FIG. 24, the intact Ross River capsid protein gene is linked with the Sindbis glycoprotein gene sequences (DH-BB Crrv or DH-BB(5'SIN) Crrv), as part of a defective helper construct, and co-transfected with a Sindbis reporter RNA vector replicon to demonstrate packaging into recombinant alphavirus particles (FIG. 26). In FIG. 25, the deleted form of the Ross River capsid protein gene is linked with the Sindbis glycoprotein gene sequences (DH-BB CΔrrv and DH-BB(5'SIN) CΔrrv), as a translational enhancer and part of the DH construct, while the Sindbis capsid protein gene expressed from a second DH construct. Both DH constructs are co-transfected with a Sindbis reporter RNA vector replicon to demonstrate packaging into recombinant alphavirus particles (FIG. 26). Additionally, the Ross River capsid protein gene may be expressed alone from one DH construct, while the Sindbis glycoproteins are expressed from another, for use in packaging. Using this knowledge and the availability of several other alphaviruses from which to derive structural protein gene sequences, a large number of different protein combinations may be generated in similar approaches.

Alternatively, the entire complement of structural protein genes from one alphavirus, or other members of the Togaviridae (e.g., rubella virus) may be used to package an RNA vector derived from another, as shown above for SFV vectors and Sindbis structural proteins. In an-alternative embodiment, the structural protein genes from Venezuelan equine encephalitis (VEE) virus may be used to package a Sindbis-virus derived vector (wild-type or displaying the phenotype described in Example 4 or 5). Such a method provides recombinant alphavirus particles containing vector RNAs which exhibit the desirable properties of the present invention, such as delayed, reduced or no inhibition of host macromolecular synthesis, plus, structural proteins which redirect the tropism of the recombinant particle. Venezuelan equine encephalitis virus (VEE) is an alphavirus which exhibits tropism for cells of lymphoid origin, unlike its Sindbis virus counterpart. Therefore, Sindbis-derived vector constructs packaged by a cell line expressing the VEE structural proteins will display the same lymphotropic properties as the parental VEE virus from which the packaging cell structural protein gene cassette was obtained.

Specifically, the Trinidad donkey strain of VEE virus (ATCC #VR-69) is propagated in BHK-21 cells, and virion RNA is extracted using procedures similar to those described in Example 1. The entire structural protein coding region is amplified by PCR with a primer pair whose 5'-ends map, respectively, to the authentic AUG translational start site, including the surrounding Kozak consensus sequence, and the UGA translational stop site. The forward primer is complementary to VEE nucleotides 7553–7579, and the reverse primer is complementary to VEE nucleotides 11206–11186 (sequence from Kinney et al., *Virology* 170:19–30. 1989). PCR amplification of VEE cDNA corresponding to the structural protein genes is accomplished using a two-step reverse transcriptase-PCR protocol as described above, the VEE genome RNA as template, and the following oligonucleotide pair, which contain flanking Xho I and Not I sites:

Forward primer: VEE 7553F (5'-rest. site/VEE capsid seq.) (SEQ. ID. NO. 86)
   30 5'-TATATATATCTCGAGACCGCCAAGATGTTC CCGTTCCAGCCA-3'
Reverse primer: VEE 11206R (5'-rest. site/VEE E1 glyco seq.) (SEQ. ID. NO. 87)
   5'-TATATATATGCGGCCGCTCAATTATGTTTCTG GTTGGT-3'

Following PCR amplification, the approximately 3800 bp fragment is purified from a 0.7% agarose gel using GENECLEAN II, and digested with Xho I and Not I. The resulting fragment is then ligated into the DNA-based Sindbis expression vector pDCMVSIN-luc (see above), that also has been digested with Xho I and Not I to remove its luciferase reporter gene insert, treated with alkaline phosphatase, and purified from a 0.7% agarose gel using GENECLEAN II. The resulting VEE structural protein expression construct is designated pDCMV-VEEsp. Plasmid pDCMV-VEEsp subsequently is digested, under limiting partial digest conditions, with BspE I to remove most nonstructural protein gene sequences, and re-ligated to create the structural protein-expressing DU vector construct, pDCMV-VEEdl.

Plasmid pDCMV-VEEdl, which also contains a neomycin resistance marker, is transfected into BHK cells using Lipofectamine, as described by the manufacturer. Approximately 24 hr post-transfection, the cells are trypsinized and re-plated in media containing 600 µg/ml of the drug G418. The media is exchanged periodically with fresh G418-containing media and foci of resistant cells are allowed to grow. Cells are trypsinized and cloned by limiting dilution in 96 well tissue culture dishes, and individual cell clones are grown and expanded for screening. Cells which inducibly express VEE structural proteins in response to input vector are identified by transfecting with Sindbis luciferase vector RNA, and assaying for VEE structural protein expression in cell lysates or packaged luciferase vector in the supernatants, as described previously. Structural protein genes obtained from variants of VEE, or other alphaviruses and their variants differing in tissue tropism, also are useful when following this approach. In addition, each of the various structural protein gene expression cassette configurations described in this example, including split structural gene PCL, may be used.

E. Production of Packaged Alphavirus Vectors from PCL

Alphavirus derived PCL described throughout this example may be used in a number of different ways to produce recombinant alphavirus particle stocks, and include the introduction of vector by either transfection of RNA or DNA molecules, infection with previously produced packaged vector-containing particles, or the intracellular production of vector from stably transformed expression cassettes. The utility of alphavirus PCL for the production of vector particles is demonstrated first with a reporter vector construct, and later may be applied to any other vector constructs which express a desired heterologous sequence. For example, a stock of packaged Sindbis-β-gal vector particles is obtained by electroporation of approximately $10^7$ alphavirus C/GLYCO or other PCL cells (see above, and for example, FIGS. 15, 17, 18) with 5–10 ug pKSSIN-1-BV-β-gal or -luciferase RNA (Example 4) or pBG/SIN-1 ELVS 1.5-β-gal or -luciferase DNA (Example 5), using the procedure described in (Liljestrom and Garoff, *Bio/Technology* 9:1356–1361, 1991). The transfected PCL are incubated at a desired temperature (e.g., 37° C.), and at approximately 48 hr. post-transfection, the supernatants are harvested and clarified by passage through a 0.45 micron filter. Additional formulation may be performed using parameters illustrated in the detailed description of this invention.

Alternatively, a stock of packaged recombinant alphavirus particles (obtained using PCL as above, or by co-transfection of vector and DH constructs) is used to infect a naive culture of PCL, for further amplification. For example, $5 \times 10^7$ of alphavirus C/GLYCO or other PCL cells are infected with a stock of packaged pKSSIN-1-BV-β-gal vector at an approximate multiplicity of infection (MOI) of 1 infectious unit/cell. Upon reaching the cell cytoplasm, the particle delivered RNA vector is autocatalytically amplified and packaged into additional progeny particles. After incubation at the desired temperature (e.g., 37° C.) for approximately 48 hr., the culture supernatants are harvested, clarified by passage through a 0.45 micron filter, and formulated as desired.

Figure 27:
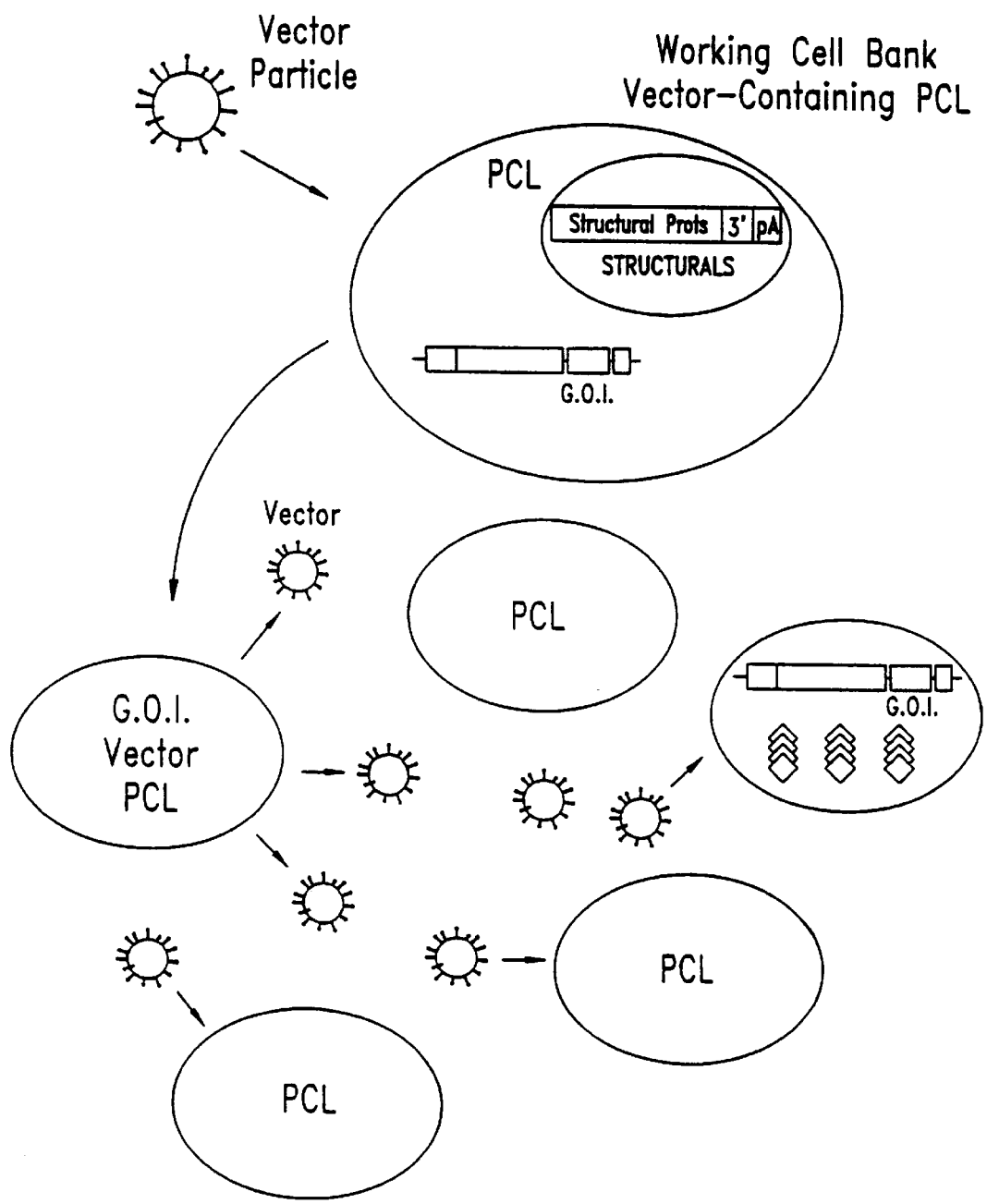

In still another method which exploits the ability of PCL to further amplify packaged recombinant alphavirus vector particles, stocks of packaged particles are used to infect naive cultures of PCL to create a working cell bank of vector-containing PCL (vector producing cells, FIG. 27), which may subsequently be used to seed another naive culture of PCL. For example, such a working cell bank is obtained by infection of alphavirus C/GLYCO or other PCL cells with the packaged vector stock at a M.O.I.=5. Approximately 2–3 hr post-infection, the vector containing PCL are gently detached and cell number is determined. The vector containing PCL may now be used directly, or aliquoted and stored in liquid $N_2$ as a vector producing cell bank. When desired, the cells are seeded directly into a previously growing culture of naive alphavirus C/GLYCO or other PCL at a ratio of approximately 1 vector producing cell per 1000 fresh PCL, for production of large quantities of high titer packaged vector particles. Aliquots of culture supernatant are harvested at various times post-coculture to determine the time of maximal recombinant alphavirus particle production, and that time is chosen for further harvest, purification and formulation, as described above. The same sequential amplification methodology using vector producing cells also is useful for large-scale production of any desired recombinant protein (FIG. 27). For the production of recombinant protein, supernatants or cell lysates may be harvested. depending on the nature of the recombinant protein.

In yet another method for producing high titer or large scale stocks of packaged recombinant alphavirus particles, the desired expression vector is introduced into 1–5% of a naive alphavirus PCL culture by transfection of in vitro transcribed RNA or plasmid DNA vector using a commonly accepted reagent or method (for example, Lipofectin or Lipofectamine, respectively, or infection with vector particles at low MOI [$\leq 0.1$]), as described herein. The recombinant vector particles produced by the initial cells, into which vector was introduced, subsequently infect other naive packaging cells in the culture, which in turn, produce even more packaged particles. This process of temporal amplification continues until packaged recombinant alphavirus particles are produced in all cells of the PCL culture.

Figure 28:
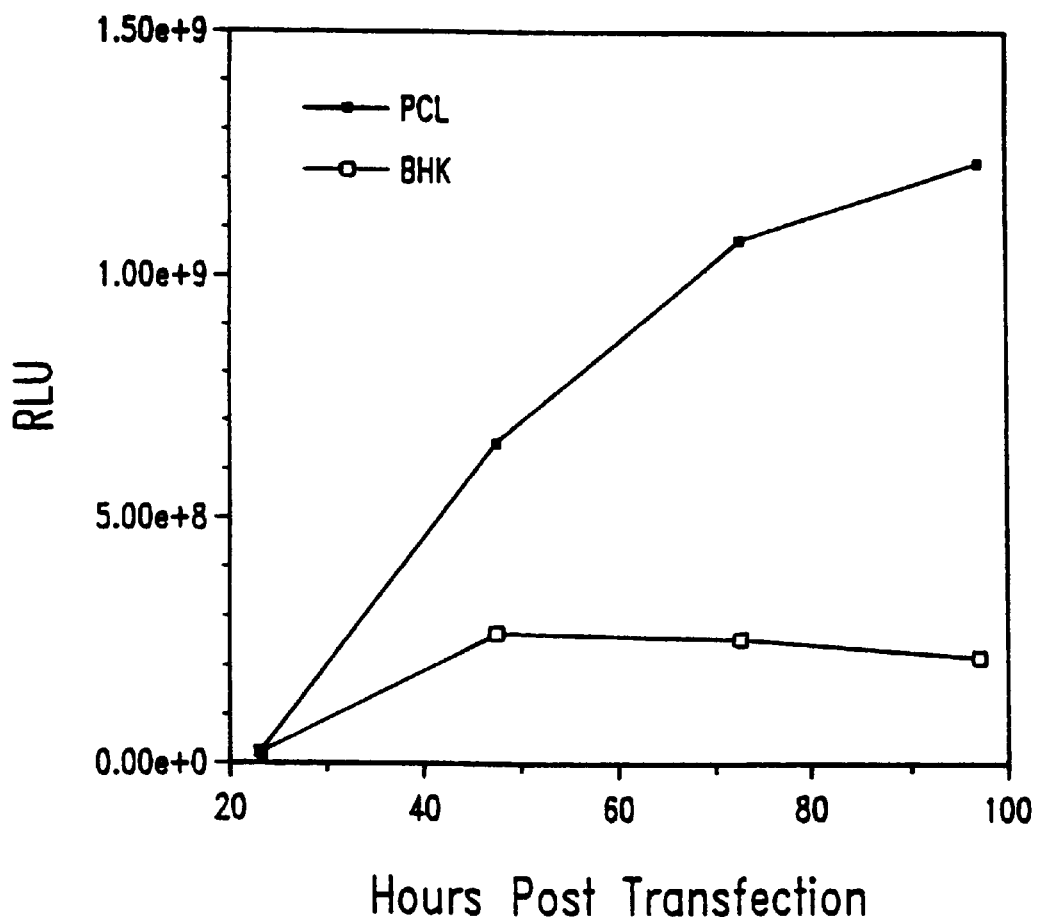

The amplification process is demonstrated in FIGS. 26D and 28. ELVS 1.5-β-gal plasmid DNA was transfected into 987DHBBNeo packaging cells or into BHK-2 1 cells, and the levels of β-galactosidase present in cell lysates was measured, as described previously, at the indicated times post-transfection. In BHK-21 cells, the level of β-galactosidase expression reached a maximum by approximately 48 hpt, and plateaued. In contrast, the level of β-galactosidase expression continued to increase over a longer period of time in the ELVS 1.5-β-gal transfected 987DHBBNeo PCL culture, reflecting the recombinant vector particle amplification process, and the ultimate expression of β-galactosidase in all of the cells of the culture. Further, infection of split structural gene PCL with Sindbis vector particles (FIG. 26D) also resulted in particle amplification. In all cases, stocks of recombinant alphavirus vector particles may be formulated so as to be pharmaceutically acceptable, using any of the methods described herein.

Example 7

Construction of Alphavirus Producer Cell Lines

The generation of alphavirus PCL, as described above, coupled with the construction of DNA-based alphavirus vectors exhibiting reduced, delayed, or no inhibition of host cell macromolecular synthesis (Examples 1, 2, 4 and 5), provides a relatively straightforward mechanism to derive alphavirus vector producer cell lines. In certain embodiments of the present invention, the vector producer cell lines contain one or more stably transformed structural protein gene expression cassettes, and also alphavirus RNA expression vector molecules with the above phenotype, that are transfected, transduced, or intracellularly produced, leading to the production of packaged vector particles. In preferred embodiments, an RNA vector replicon is produced intracellularly from a stably transformed DNA molecule (eukaryotic layered vector initiation system) that exists in either an integrated form or as an episomal DNA, with transcription of vector RNAs being controlled inducibly by one or more stimuli provided at a desired time. This type of alphavirus producer cell line configuration essentially provides a cascade of events that include: inducible production of vector RNA and resulting autocatalytic cytoplasmic amplification of the RNA, the induction of high level structural protein expression by vector-supplied nonstructural proteins, the packaging of vector RNA by the expressed structural proteins, and the release of packaged vector particles. Tightly regulated, inducible expression of vector RNA from the DNA molecule, once producer cell population reaches as desired number, is preferred, due to the potential for low level cytotoxicity of vector replication, or the necessity to control nonstructural protein synthesis. as it relates to the regulation of positive strand versus negative strand vector RNA ratios.

A. Alphavirus DNA Vectors with Single Level Regulation

In certain embodiments of the present invention, a DNA-based alphavirus vector is provided, wherein in vivo transcription of an alphavirus vector RNA molecule that is capable of autocatalytic amplification occurs from a promoter which is regulatable by applying a stimulus at a desired time. Such a DNA-based alphavirus vector subsequently may be stably transformed into an alphavirus packaging cell line (PCL) to create an inducible alphavirus producer cell line. The producer cell line configuration described herein, is therefore, a "feed-forward" system in which: 1) a stimulus is applied to the cell, resulting in efficient transcription of alphavirus vector RNA; 2) the vector RNA replicates autocatalytically and produces nonstructural proteins; 3) the nonstructural proteins stimulate amplification of the structural protein expression cassette mRNAs and high level structural protein expression; and 4) the structural proteins interact with the vector RNA and result in the subsequent packaging of recombinant alphavirus particles which are released into the culture media. Any previously described alphavirus PCL, which is stably transformed with one or more inducible alphavirus structural protein expression cassettes, may serve as the parental line with which to derive the producer cell line.

Figure 29:
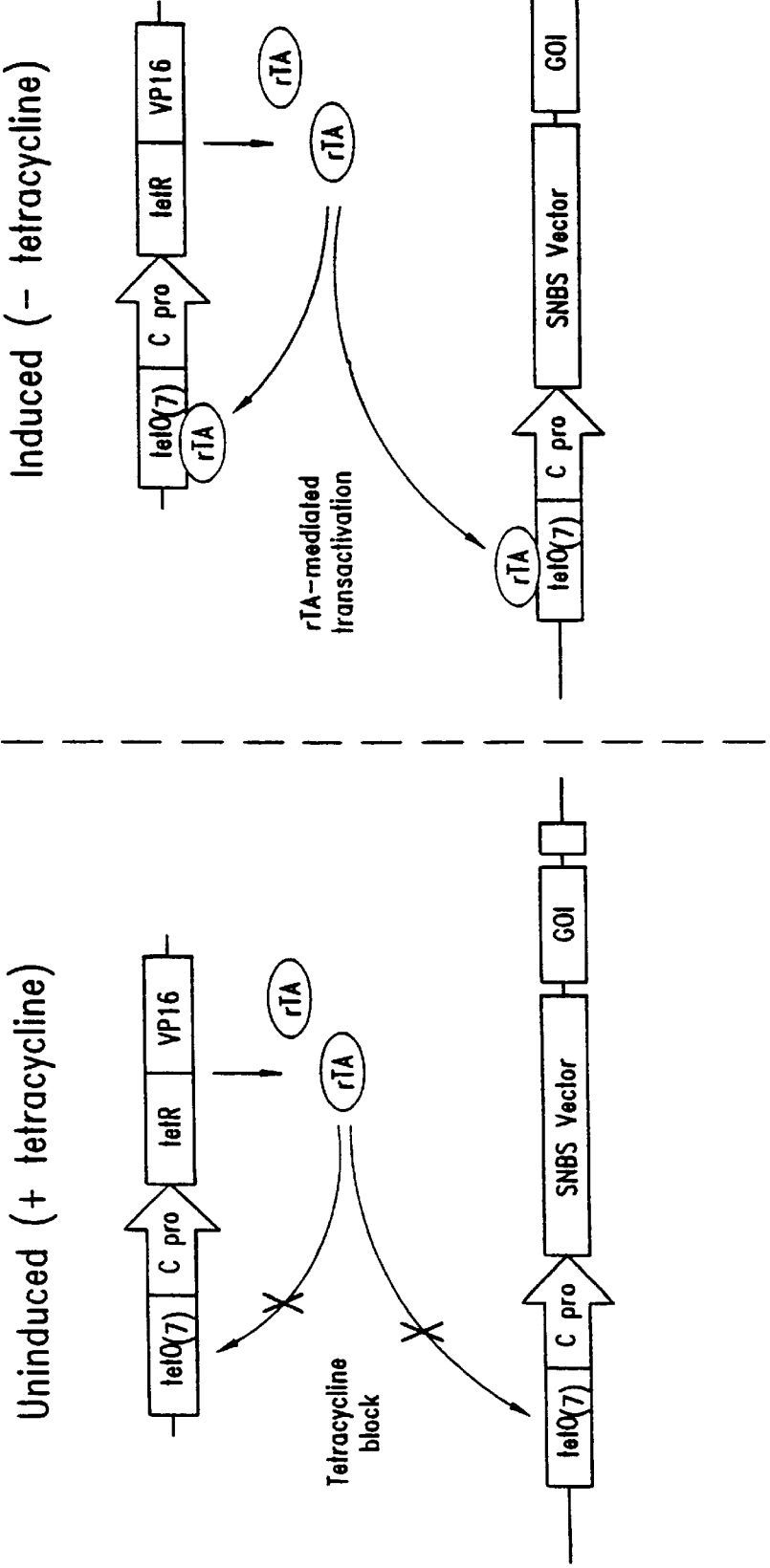
Figure 33A:
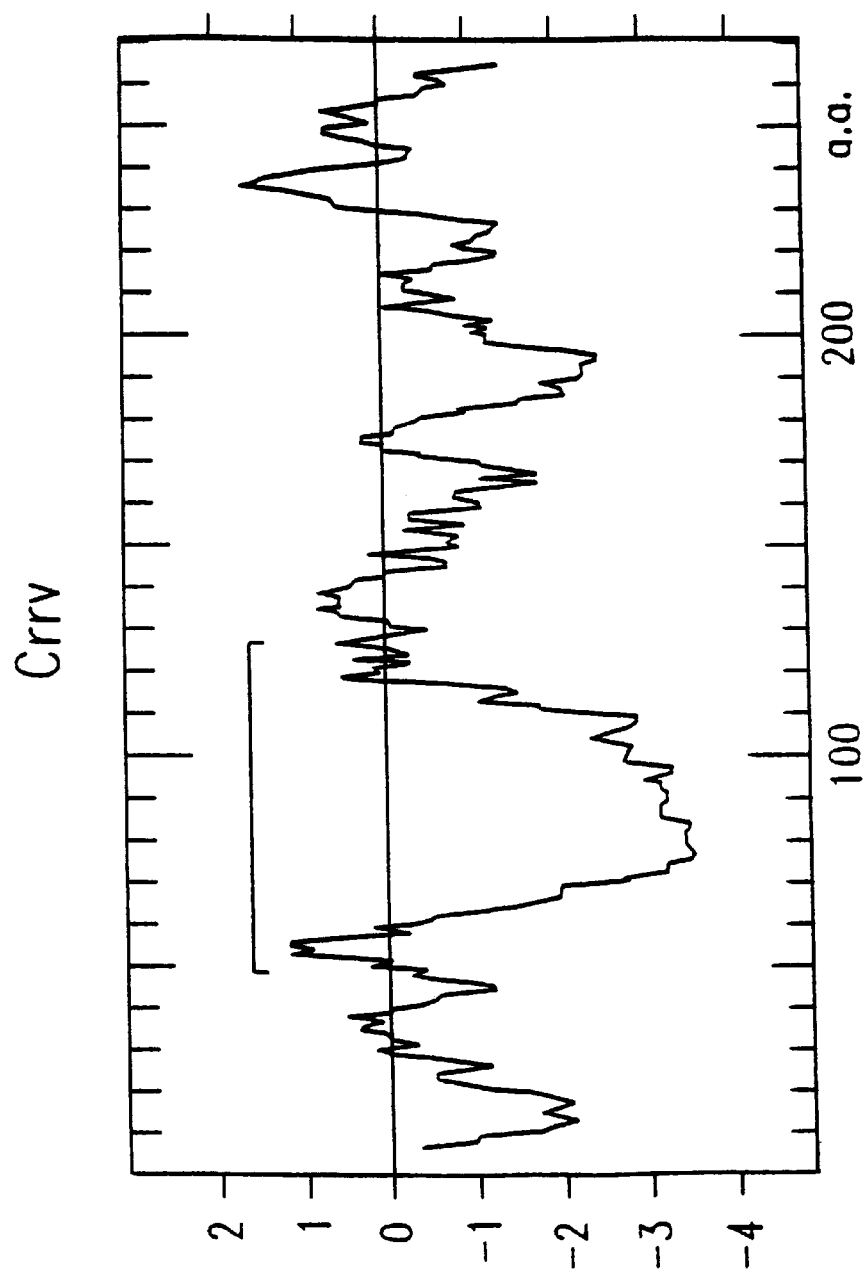
Figure 33B:
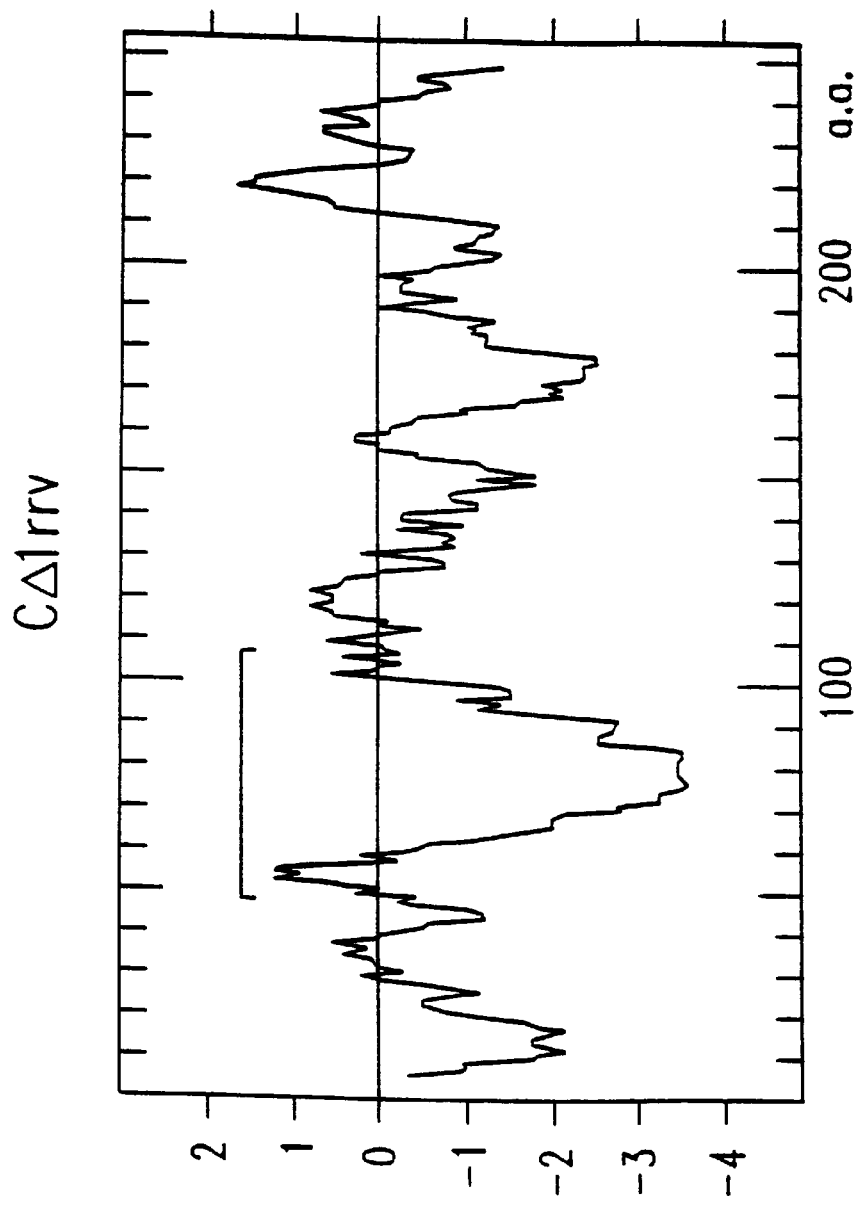
Figure 33C:
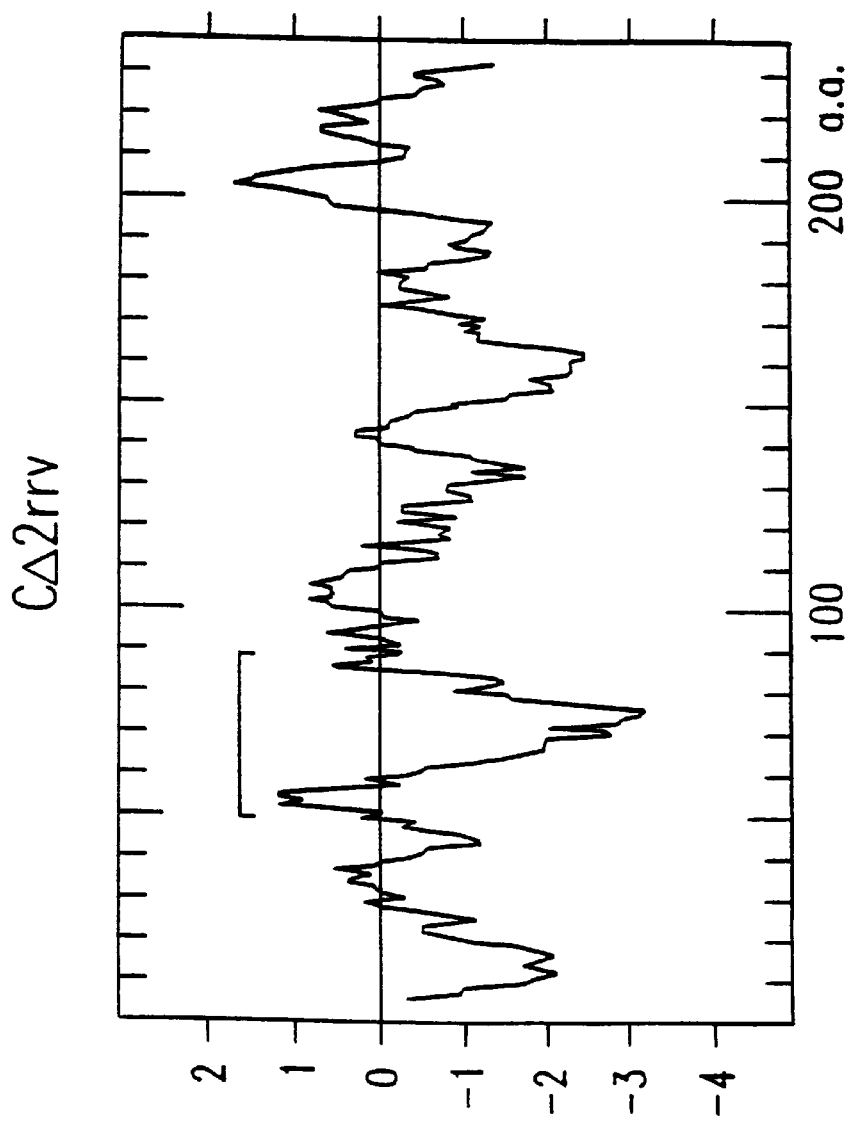
Figure 33D:
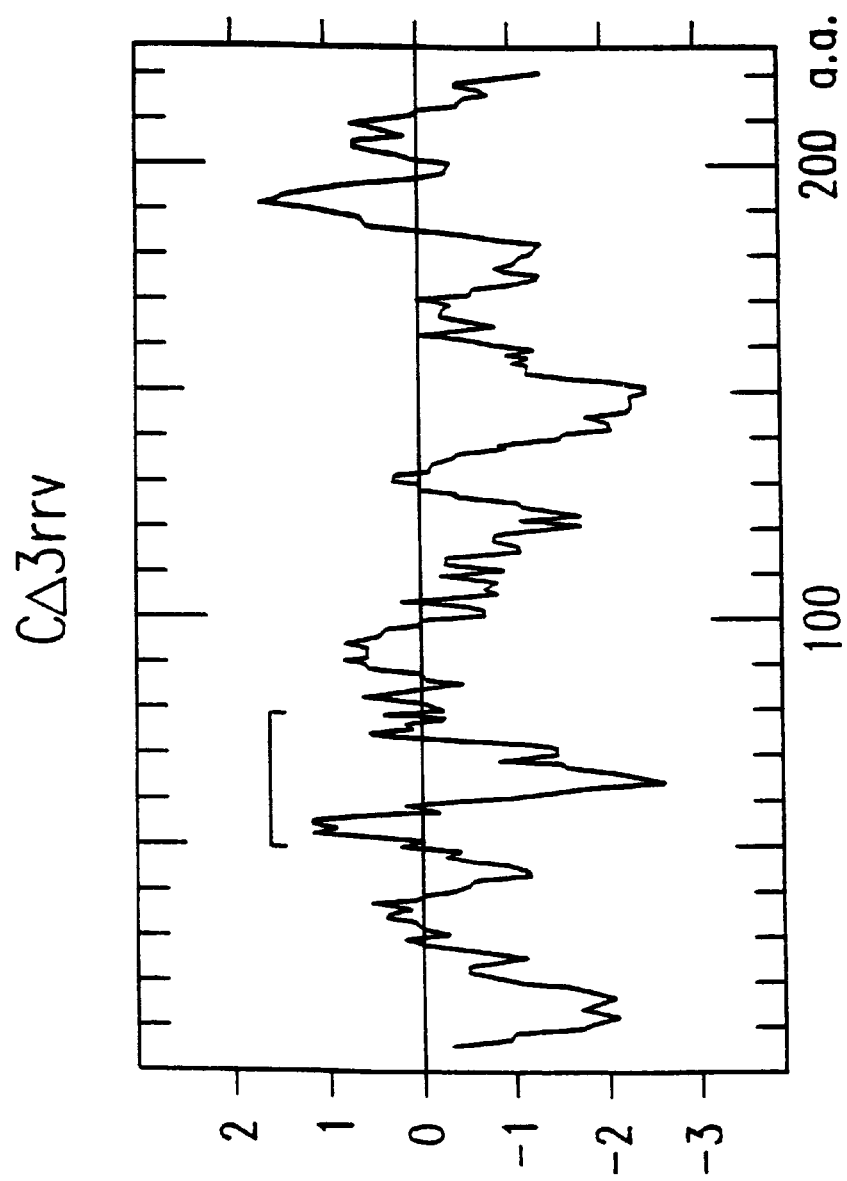

For example, a tetracycline-responsive promoter system (Gossen and Bujard, *Proc. Natl. Acad. Sci.* 89:5547–5551, 1992) may be utilized for inducible transcription of an alphavirus vector RNA, as depicted in FIG. 29. In this system, the expression of a tetracycline repressor and HSV-VP16 transactivator domain, as a "fusion" protein (rTA), stimulates in vivo transcription of the alphavirus vector RNA by binding specifically to a tetracycline operator sequence (tetO) located immediately adjacent to a minimal "core" promoter (for example, CMV). The binding and transactivation event is reversibly blocked by the presence of tetracycline, and may be "turned on" by removing tetracycline from the culture media. As uninduced basal levels of transcription will vary among different cell types, other different minimal core promoters (for example HSV-tk) may be linked to the tetracycline operator sequences, provided the transcription start site is known, to allow juxtaposition at or in the immediate proximity of alphavirus vector nucleotide 1.

The rTA transactivator is provided by an additional expression cassette also stably transformed into the same cell line; and in certain embodiments, the rTA expression cassette may itself be autoregulatory. The use of an autoregulatory rTA expression cassette circumvents potential toxicity problems associated with constitutive high level expression of rTA by linking expression to transcriptional control by the same tetO-linked promoter to which rTA itself binds. This type of system creates a negative feedback cycle that ensures very little rTA is produced in the presence of tetracycline, but becomes highly active when the tetracycline is removed (FIG. 29). Such an autoregulatory rTA expression cassette is provided in plasmid pTet-tTAk (Shockett et al., *Proc. Natl. Acad. Sci. USA* 92:6522–6526, 1995).

Functionality of such a tetracycline-regulated DNA-based alphavirus vector is demonstrated by constructing a modified SIN-1-derived luciferase plasmid vector, which is driven by a tetracycline operator/CMV minimal promoter. Using plasmids pBG/SIN-1 ELVS1.5-luc (Example 4) and pBGSV3' (Example 6) as starting material, an approximately 7200 bp fragment, including much of the SIN-1 nonstructural-encoding region, the junction region promoter and luciferase reporter gene, and a portion of the 3'-UTR, is isolated by digestion of pBG/SIN-1 ELVS1.5-luc with Bgl II and Fsp I, and purification from a 0.7% agarose gel using GENECLEAN II. The 7200 bp fragment is subsequently ligated into plasmid pBGSV3' that has also been digested with Bgl II and Fsp I, treated with alkaline phosphatase, and purified from a 0.7% agarose gel using GENECLEAN II. The resulting construct is designated pBGSVdlB/SIN1-luc. Insertion of the remaining sequences, which include the heptamerized tetracycline operator and minimal CMV promoter (tetO/CMV) linked to Sindbis nucleotides 1–2289, such that transcription will initiate with one additional nonviral nucleotide 5' of Sindbis nucleotide 1, is accomplished by overlapping PCR. In PCR reaction #1,the approximately 370 bp tetO/CMV portion of the sequence is amplified by standard three-cycle PCR with a 30 second extension from template plasmid pUHC13-3 (Gossen and Bujard, ibid) using the following oligonucleotide primers that are designed to also contain flanking Bgl II and Asc I sites on one primer and sequences overlapping 5'-Sindbis nucleotides on the other.

Forward primer: 5'BAtetOF (5'-rest. sites/tetO nts.) (SEQ. ID. NO. 88)

5'-TATATAGATCTGGCGCGCC/
   TTTACCACTCCCTATCAGTGATAG-3'

Reverse primer: 3' CMVpro/SINR (5'-Sindbis nts./CMV nts.) (SEQ. ID. NO. 89)

5'-TACGCCGTCAAT/
   ACGGTTCACTAAACGAGCTCTGC-3'

In PCR reaction #2, the 2289 bp Sindbis 5'-end portion of the sequence is amplified by standard three-cycle PCR with a three minute extension, from template plasmid pKSRSIN-1 (Example 1), using the following oligonucleotide primers that are designed to also contain sequences overlapping the CMV promoter nucleotides on one primer.

Forward primer: CMVSIN5'endF (5'-CMV nts./Sindbis nts.) (SEQ. ID. NO. 90)

5'-TAGTGAACCGT/
   ATTGACGGCGTAGTACACACTATT

Reverse primer: SIN2400R (all Sindbis nts.) (SEQ. ID. NO. 91)

5'-CGTTGAGCATAACCGAATCTAC

Following amplification, the DNA fragments are purified with QIAquick-spin and used together as templates in a subsequent three-cycle PCR reaction with 3.5 minute extension, using additional 5'BAtetOF and SIN2400R primers. The resulting overlapping PCR amplicon of approximately 2660 bp is purified using GENECLEAN II, digested with Bgl II, and ligated into plasmid pBGSVdlB/SIN1-luc that has also been digested with Bgl II, treated with alkaline phosphatase and purified from a 0.7% agarose gel using GENECLEAN II. The resulting construct is designated ptetSIN1-luc. Vector constructs containing other heterologous sequences-of-interest are generated using a similar approach, or by direct cloning into the Xho I and/or Not I sites. Subsequently, a selectable *E. coli* gpt gene (xanthine-guanine phosphoribosyltransferase) expression cassette is generated and inserted into the unique Pac I site of plasmid ptetSINl-luc, to provide an additional selectable marker. First, a fragment containing the SV40 promoter linked to a gpt gene open reading frame is amplified from plasmid pMAM (Clontech. Palo Alto, Calif.) by standard three-cycle PCR with a 2 minute extension, and using the following oligonucleotide primers that are designed to contain upstream flanking Sac I and Pac I sites and a downstream Sac I site.

Forward primer: SV40proSPF (5'-rest. sites/SV40 promoter seq.) (SEQ. ID. NO.92)

5'-ATATAGAGCTCTTAATTAA/
   TCTTTGTGAAGGAACCTTACTTC

Reverse primer: 3'ECgptR (5'-rest. site/gpt gene seq.) (SEQ. ID. NO. 93)

5'-ATATAGAGCTC/AGG
   (:GTTGAAAAGATTAGCGACCG

Following amplification the SV40 promoter/gpt gene DNA fragment is purified with QIAquick-spin, digested with Sac I, purified using GENECLEAN II. and ligated into plasmid pBGS131 d1Xhol-BGHTT (Example 5) that also had been digested with Sac I, treated with alkaline phosphatase, and purified from a 0.7% agarose gel using GENECLEAN II. Clones with proper orientation of the insert are identified by restriction analysis. This configuration positions the promoter and gpt gene immediately adjacent to a bovine growth hormone transcription termination signal. The resulting gpt expression construct is designated pBGS131 d1XhoI-gpt. Next the entire expression cassette is amplified from plasmid pBGS131 d1XhoI-gpt by standard three-cycle PCR with a 2 minute extension, and using the following oligonucleotide primers that are designed to contain flanking Pac I sites.

Forward primer: SV40proSPF. as shown above (SEQ. ID. NO. 92)

Reverse primer: BGHTTpacR (5'-rest. site/BGH seq.) (SEQ. ID. NO. 94)

5'-TATATATTAATTAA/
   ATAGAATGACACCTACTCAGACAATGCGATGC

Following amplification, the gpt-gene expression cassette fragment is purified with QIAquick-spin, digested with Pac I, purified using GENECLEAN II, and ligated into the tet-inducible alphavirus vector construct ptetSIN1-luc that also had been digested with Pac I, treated with alkaline phosphatase, and purified from a 0.7% agarose gel using GENECLEAN II. The resulting construct is designated ptetSIN1gpt-luc.

For construction of an initial tetracycline-inducible alphavirus vector producer cell line, the ptetSIN1gpt-luc construct and a tetracycline repressor/VP16 transactivator (rTA) expression cassette are stably transformed into the desired alphavirus PCL. For example, alphavirus C/GLYCO PCL cells (from above) are stably transformed with plasmid pTet-tTAk (see above) by cotransfection with another plasmid encoding a selectable marker. Plasmids pTet-tTAk and pSV2-His, encoding a histidinol dehydrogenase marker (Schatz et al., 1989, *Cell* 59:1035–1048), are co-transfected into C/GLYCO PCL cells (or other PCL) at a molar ratio of 40:1, respectively, using Lipofectamine, as described by the manufacturer. Approximately 24 hours post-transfection, the cells are trypsinized and re-plated in media containing histidinol and 0.5 ug/ml tetracycline. The media is exchanged periodically with fresh drug-containing media, and foci of resistant cells are allowed to grow. Cells are trypsinized and cloned by limiting dilution in 96 well tissue culture dishes, and individual cell clones are grown are expanded for screening. Positive pTet-tTAk-containing packaging cell clones, designated C/GLYCO/TAk cells. are identified by transfecting the luciferase reporter plasmid pUHC 13-3 (Gossen and Bujard, ibid), under the control of a tetO/promoter, in both the presence or absence of tetracycline. In the absence of tetracycline, positive C/GLYCO/TAk PCL cells will provide induction from the tetO/promoter and inducible, high levels of luciferase.

Subsequently, the DNA-based alphavirus vector construct ptetSIN1gpt-luc is stably transfected into the C/GLYCO/TAk cells using Lipofectamine, as described by the manufacturer. Approximately 24 hr post-transfection, the cells are trypsinized and re-plated in selection media, optimized for the particular cell type (DMEM+10% dialyzed fetal calf serum; 250 ug/ml xanthine; 15 ug/ml hypoxanthine; 10 ug/ml thymidine; 2 ug/ml aminopterin; 25 ug/ml mycophenolic acid), and containing 0.5 ug/ml tetracycline. The media is exchanged periodically with fresh selection media, and foci of resistant cells are allowed to grow. Cells are trypsinized and cloned by limiting dilution in 96 well tissue culture dishes, and individual cell clones are grown are expanded for screening. Positive producer cell lines, stably transformed with ptetSIN1gpt-luc. are identified by removing tetracycline from the media for at least 24 hr and testing for luciferase in cell lysates and also testing for packaged luciferase vector in the culture supernatants. as described previously.

B. Alphavirus DNA Vectors with Two Level Regulation

In preferred embodiments, it may be desirable to construct a DNA-based alphavirus vector (wild-type or with the desired phenotype of reduced, delayed or no inhibition of host macromolecular synthesis), wherein transcription of the RNA vector molecule. capable of autocatalytic amplification, occurs from a promoter which is very tightly controlled by two levels of regulation to eliminate all basal levels of transcription. Such an approach may combine one inducible component (e.g. the tet system from above) with a reversible transcriptional silencing component. For example, the KRAB repression domain of a certain zinc finger protein may be used.

Briefly, KRAB (Krüppel-associated box) domains are highly conserved sequences present in the amino-terminal regions of more than one-third of all Krüppel-class $Cys_2His_2$ zinc finger proteins. The domains contain two predicted amphipathic α-helicies and have been shown to function as DNA binding-dependent RNA polymerase II transcriptional repressors (for example, Licht et al., *Nature* 346: 76–79, 1990). Like other transcription factors, the active repression domain and the DNA-binding domain are distinct and separable. Therefore. the repression domain can be linked as a fusion protein to any sequence specific DNA binding protein for targeting. Ideally, the DNA binding protein component can be reversibly prevented from binding in a regulatable fashion. thus turning "off" the transcriptional silencing. For example, within one embodiment the KRAB domain from human Kox1 (Thiesen. *New Biol.* 2:363–374, 1990) is fused to the DNA-binding lactose (lac) repressor protein, forming a hybrid transcriptional silencer with reversible, sequence-specific binding to a lac operator sequence engineered immediately adjacent to the tet-responsive promoter (FIG. 30). In this configuration, constitutive expression of the lac repressor/KRAB domain fusion (rKR) will result in binding to the lac operator sequence and the elimination of any "leaky" basal transcription from the uninduced tet-responsive promoter. When vector expression is desired and tetracycline is removed from the system, IPTG is added to prevent rKR-mediated transcriptional silencing.

In addition. the KRAB domains from other zinc finger proteins, for example, ZNF133 (Tommerup et al., *Hum. Vol. Genet.* 2:1571–1575, 1993), ZNF91 (Bellefroid et al., *EMBO J* 12:1363–1374, 1993), ZNF2 (Rosati et al., *Nucleic Acids Res.* 19:5661–5667, 1991), and others, as well as other transferable repressor domains, for example, Drosophila en or eve genes (Jaynes and O'Farrell, *EMBO J.* 10:1427–1433, 1991; Han and Manley, *Genes Dev.* 7:491–503, 1993), human zinc finger protein YY1 (Shi et al., *Cell* 67;377–388. 1991). Wilms' tumor suppressor protein WT1 (Madden et al., *Science* 253:1550–1553. 1991), thyroid hormone receptor (Baniahmad et al., *EMBO J.* 11: 1015–1023, 1992), retinoic acid receptor (Baniahmad et al., ibid), Kid-I (Witzgall et al., *Proc. Natl. Acad. Sci. USA* 91:4514–4518, 1994), are readily used in such a system. Furthermore, the lac repressor/lac operator component of this system may be substituted by any number of other regulatable systems derived from other sources, for example, the tryptophan and maltose operons, GAL4, etc.

Specifically, an expression cassette that contains the lac repressor (lacI) protein fused to the KRAB domain of human Kox1, with a linked nuclear localization sequence (NLS; Pro-Lys-Lys-Lys-Arg-Lys (SEQ. ID. NO. 100); Kalderon et al., *Cell* 39:499–509, 1984) to more efficiently direct the protein back to the nucleus, is constructed by overlapping PCR. In PCR reaction #1, the approximately 1100 bp lacI sequence is amplified by standard three-cycle PCR with a 1.5 minute extension, from template plasmid p3'SS (Stratagene, La Jolla, Calif.), using the following oligonucleotide primers that are designed to also contain a flanking Xho I site and AUG start codon in good translation initiation context on the upstream primer, and the SV40 large-T-antigen nuclear localization sequence on the other.
Forward primer: LacI5'F (5'-rest. site/AUG+lacI sequence) (SEQ. ID. NO. 95)
   5'-ATATACTCGAGTAGCA/
    ATGGTGAAACCAGTAACGTTATAC
Reverse primer: LacI3'NLSR (5'-NLS/lacI sequence) (SEQ. ID. NO. 96)
   5'-GCCCTTTCTCTTCTTTTTTGG/
    CTGCCCGCTTTCCAGTCGGGAAAC In PCR reaction #2, the an approximately 400 bp amplicon, comprising the amino-terminal 121 residue KRAB domain of human Kox1 is amplified by standard three-cycle PCR with a one minute extension, from template plasmid pKox1 (Thiesen. *New Biol.* 2-363–374, 1990), using the following oligonucleotide primers that are designed to also contain sequences overlapping NLS and lad on one primer and a Sac I restriction site and stop codon on the other.
Forward primer: KRAB5° F (5'-NLS+lacI overlap sequence/ KRAB sequence) (SEQ. ID. NO. 97) p1
   5'-CCAAAAAAGAAGAGAAAG/
    GGCGGTGGTGCTTTGTCTCCT
Reverse primer: KRAB3'R (5'-rest. site+stop codon KRAB sequence) (SEQ. ID. NO. 98)

5'-ATATAGAGCTCTTA/
AACTGATGATTTGATTTCAAATGC

Following amplification, the DNA fragments are purified with QIAquick-spin and used together as templates in a subsequent three-cycle PCR reaction with 2.5 minute extension, using additional LacI5'F and KRAB3'R primers. The resulting overlapping PCR amplicon of approximately 1500 bp is purified using GENECLEAN II. digested with Xho I and Sac I, and ligated into the eukaryotic expression vector plasmid pEUK-C1 (Clontech. Palo Alto, Calif.) that has also been digested with Xho I and Sac I, treated with alkaline phosphatase, and purified from a 0.7% agarose gel using GENECLEAN II. The resulting lacI/KRAB expression construct is designated pEUK-rKR.

To generate stable PCL transformants containing the lacI/KRAB expression cassette, an alphavirus PCL which has already been selected for transformation with an rTA tet/transactivator fusion protein cassette is used for starting material. For example, alphavirus C/GLYCO/TAk PCL cells (from above) are stably transformed with plasmid pEUK-rKR by cotransfection with another plasmid encoding a selectable marker. Plasmids pEUK-rKR and pPUR, encoding a puromycin acetyltransferase selectable marker (Clontech), are co-transfected into C/GLYCO/TAk PCL cells (or other PCL) at a molar ratio of 40:1, respectively, using Lipofectamine, as described by the manufacturer. Approximately 24 hr post-transfection, the cells are trypsinized and re-plated in media containing 5 ug/ml puromycin and 0.5 ug/ml tetracycline. The media is exchanged periodically with fresh drug-containing media. and foci of resistant cells are allowed to grow. Cells are trypsinized and cloned by limiting dilution in 96 well tissue culture dishes. and individual cell clones are grown are expanded for screening. Positive pEUK-rKR-containing packaging cell clones, designated C/G/TAk/rKR cells, are identified by immunostaining with a polyclonal antiserum specific for LacI (Stratagene, La Jolla, Calif.).

Next, specific lac operator (lacO) sequences must be inserted into the desired ptet-based alphavirus vector (see above). For example, vector construct ptetSIN1gpt-luc is modified to contain multiple copies of lacO by using a synthetic oligonucleotide linker. The LacO oligonucleotide is designed to contain a symmetric lacO sequence, including the full 22 bp palindromic operator sequence (Simons et al., *Proc. Natl. Acad. Sci. USA* 81:1624–1628, 1984; Sadler et al., *Proc. Natl. Acad. Sci. USA* 80:6785–6789, 1983), and flanking Asc I sites when self-annealed into a double-stranded molecule.

LacOsymA (SEQ. ID. NO. 99)

5'-CGCGCCGAATTGTGAGCGCTCACAATTCGG

The LacOsymA oligo is self-annealed to form a Asc I "sticky-ended" DNA fragment, and then ligated into plasmid ptetSIN1gpt-luc that has been digested with Asc I, treated with alkaline phosphatase, and purified from a 0.7% gel using GENECLEAN II. Clones containing one, two, three, or more tandem copies of the lacO sequence are identified by sequence analysis, and given the designation pOItetSIN1gpt-luc, pOIItetSIN1gpt-luc, pOIIItetSIN1gpt-luc, etc. Individual clones with different lacO copy numbers are then transfected as detailed below, and tested for the tightest level of transcriptional regulation.

To generate an alphavirus vector producer cell line, the DNA-based pOtetSIN1gpt-luc vector constructs are stably transfected into C/G/TAk/rKR cells using Lipofectamine, as described by the manufacturer. Approximately 24 hr post-transfection, the cells are trypsinized and re-plated in selection media, optimized for the particular cell type (DMEM+ 10% dialyzed fetal calf serum; 250 ug/ml xanthine; 15 ug/ml hypoxanthine; 10 ug/ml thymidine; 2 ug/ml aminopterin; 25 ug/ml mycophenolic acid), and containing 0.5 ug/ml tetracycline. The media is exchanged periodically with fresh selection media and foci of resistant cells are allowed to grow. Cells are trypsinized and cloned by limiting dilution in 96 well tissue culture dishes, and individual cell clones are grown are expanded for screening. Positive producer cell lines, stably transformed with the pOtetSIN1gpt-luc constructs, are identified by the expression of luciferase (described previously) at least 24 hr after the removal of tetracycline from the media and the addition of 20 mM IPTG for induction. Luciferase activity is determined both on producer cell lysates and also after transfer-of-expression experiments using culture supernatants.

Additional levels of control may be incorporated by adding a third, or even fourth, level of regulation to the promoter responsible for transcription of the alphavirus vector molecule. Such extra level or regulation may be incorporated into the minimal promoter, and may involve other inducible systems and/or cell differentiation control. In each of the above cases, stable transformation may be accomplished as an integration into the host cell chromosome, or as an extrachromosomal episome, using for example, the EBV episomal-based vector promoter (for non-integrated).

Example 8

Methods for the Generation of Alphavirus-Derived Empty or Chimeric Viral Particles As illustrated in Example 6, individual defective helper (DH) expression cassettes can be constructed to contain elements from multiple alphaviruses or their variants. Thus, as described in Example 6, split structural gene DH cassettes for the expression of the viral glycoproteins can be constructed to contain the capsid and glycoprotein genes from different alphavirus species. For example, such a heterologous alphavirus glycoprotein DH cassette might contain the capsid gene from Ross River virus (RRV), and the glycoprotein genes from Sindbis virus. In this configuration. the RRV capsid gene serves to enhance the level of translation of the glycoprotein genes.

The configurations described herein for the heterologous alphavirus glycoprotein DH cassettes are designed to improve the packaging of vector replicons into alphavirus particles, yet diminish the possibility of recombination, resulting in the formation of replication competent alphavirus. The heterologous alphavirus glycoprotein DH expression cassette is a replacement of the Sindbis virus capsid gene in the DH expression cassettes described in Example 6 ("genomic" structural protein gene PCL), with a heterologous alphavirus capsid gene (e.g. RRV). The second DH expression cassette in the split structural gene PCL contains, for example, the Sindbis virus capsid gene. Thus, a split structural gene PCL for the generation of recombinant alphavirus vector particles having Sindbis virus structural proteins can be derived. for example, with the Sindbis virus glycoprotein genes and capsid genes on individual DH expression cassettes.

It has been shown previously that chimeric viruses containing all of the genes of RRV, but with the capsid gene from Sindbis virus. or the reciprocal chimeric virus, do not assemble into infectious virus particles (Lopez et. al., *J. Virol.* 68:1316–1323, 1994). The authors concluded in this report that the interaction between the carboxy terminus of glycoprotein E2 and capsid protein in virus assembly cannot occur between the structural proteins of heterologous alphaviruses. Thus, recombinant genomes arising in the split structural gene alphavirus PCLs described in Example 6. consisting of the Sindbis virus non-structural protein genes (originating from the vector replicon), the RRV capsid gene, and the Sindbis virus glycoprotein genes, should not be replication competent, resulting in the propagation of virus (replication competent Sindbis virus, RCSV). The packaging restriction between heterologous alphavirus species permits the construction of DH cassettes comprised of the capsid gene. including the translational enhancement element, from one alphavirus, and the glycoprotein genes from a different alphavirus.

However, as illustrated in FIG. 31, the observation of Lopez et. al. (ibid), that assembly cannot occur between the structural proteins of heterologous alphaviruses, is incorrect. Indeed, a DH cassette consisting of the RRV capsid gene. and the Sindbis virus glycoprotein gene produces infectious virus particles. Briefly. BHK cells were co-electroporated with SINrep/Lac Z replicon (Bredenbeek et. al., J Virol., 67:6439–6446, 1993). and DH-BB (5' tRNA/SIN) Crrv (Example 6 and FIG. 24; RRV capsid/Sindbis virus glycoproteins) in vitro transcribed RNAs. The electroporation and in vitro transcriptions were performed as described in Example 1. Following electroporation, the BHK cells were treated with dactinomycin and labeled with [$^3$H] uridine, exactly as described in Example 1. At 18 hours post electroporation. the culture medium was collected, and clarified by centrifugation at 6,000 rpm for 10 min. The vector particles remaining in the supernatant were pelleted by ultracentrifugation, after first layering over a sucrose cushion. RNA was isolated from the BHK cells at 18 hours post electroporation, and from the virus pellet electrophoresed on denaturing glyoxal agarose gels, and visualized by autoradiography. exactly as described in Example 1. The viral RNAs present in BHK cells electoporated with SINrep/LacZ and DH-BB Crrv RNAs, and in virus particles. are shown in FIG. 31 (lane 1, panel A, and lane 1, panel B). RNAs corresponding to the genomic and subgenomic replicative species for SINrep/LacZ and DH-BB Crrv RNAs were present in both electroporated BHK cells. and the produced virus particles. The results demonstrate, in contrast to Lopez et. al. (ibid), the formation of chimeric alphavirus particles consisting of RRV capsid protein and Sindbis virus glycoproteins. Further, the indiscriminate packaging of genomic and subgenomic SINrep/LacZ and DH-BB Crrv RNAs in chimeric alphavirus particles indicates the inability of the Ross River capsid protein to recognize specifically the Sindbis virus packaging sequence, which is present in the nsP1 gene of the SINrep/LacZ vector replicon.

The viral proteins present in BHK cells electoporated with SINrep/LacZ and DH-BB Crrv RNAs, at 18 hours post electroporation, and the produced virus particles are given in FIG. 32 (lane 1, panel A, and lane 1, panel B). The viral-specific structural proteins in electroporated cells and the produced chimeric alphavirus particles were indistinguishable. That is, FIG. 32 demonstrates clearly that virus particles produced from BHK cells electoporated with SINrep/LacZ and DH-BB Crrv RNAs contained the RRV capsid and the Sindbis virus glycoproteins E1 and E2. This result provides indisputable evidence that in contrast to Lopez et. al., (ibid), there is no restriction in assembly between heterologous alphavirus capsid and glycoproteins that prevents the formation of chimeric viral particles.

Thus, in distinct contrast to the results and discussion of Lopez et. al., the amino terminus of the RRV capsid protein is able to bind with the heterologous Sindbis virus genome, and form infectious chimeric alphavirus particles. Importantly, the previous conclusion that there is a restriction of virus assembly between heterologous alphavirus capsid proteins and glycoproteins is incorrect. The generation of chimeric alphavirus particles as described here would, then, also result in the formation of RCSV in the split structural gene PCLs described above, since a recombinant genome consisting of the Sindbis virus non-structural protein genes (originating from the vector replicon), the RRV capsid gene, and the Sindbis virus glycoprotein genes, would generate infectious virus. Alternatively, this lack of restriction of packaging between distinct alphavirus structural proteins and vector replicons permits the tropism of vector particles to be modified. For example, Sindbis virus replicons can be packaged with the Venezuelan Equine Ecephalitis virus structural proteins, in order to generate a lymphotropic recombinant vector particle.

The results described in two separate previous investigations have shown that ablation, in vitro, of the interaction between the capsid protein and the positive RNA-stranded genome of two icosahedral viruses having triangulation numbers (T)=3, turnip crinkle virus (TCV), and southern bean mosaic virus (SBMV), resulted in the disassociation of the virus particles, and the formation of nucleic acid-free T=1 particles (Sorger et. al. J. Mol. Biol., 191:639–656, 1986, and Erickson and Rossmann, Virology 116:128–136, 1982). In the absence of nucleic acid, T=3 particles similar to wild-type virus were not formed in vitro. Owen and Kuhn (J. Virol., 70:2757–2763, 1996), investigated the packaging properties of Sindbis virus genomes containing deletions in the capsid, in order to identify the region of the capsid protein that is required for dictating specificity of the encapsidation reaction, in vivo. One mutant virus [CD (97–106)] which contained a deletion corresponding to residues 97–106 of the capsid, encapsidated both genomic and subgenomic RNAs. indicating the domain of the capsid protein required for specific recognition of the genomic RNA packaging signal. In yet another report, the packaging properties of Aura alphavirus were investigated (Rumenapf et. al. J. Virol., 69:1741–1746, 1995). In this study, a mechanism for alphavirus packaging that involves a capsid protein-encapsidation sequence interaction initiation complex was proposed. This mechanism proposed is based on observations by the authors, and others (including Owen and Kuhn, ibid), in which 26S and 49S alphavirus RNAs are packaged into T=1, T=3, T=4, and T=7 virus particles, and that empty capsids arising during infection with alphaviruses have not been reported.

Based on the literature presented above and the discussions contained therein, a RRV capsid gene deleted of the region corresponding to the capsid protein domain that is required for dictating specificity of the encapsidation reaction, and, in addition, surrounding basic residues that bind electrostatically with viral RNA, should not be able to form stable capsid particles containing viral RNAs. Thus, the alphavirus structural proteins expressed from a heterologous alphavirus DH cassette, consisting of this deleted RRV capsid gene and the Sindbis virus glycoprotein genes, should not assemble into stable chimeric alphavirus particles. Thus, in the split structural gene PCL discussed above and in Example 6, a recombinant genome consisting of the Sindbis virus non-structural protein genes, the RRV capsid gene (deleted of the region corresponding to packaging specificity and the surrounding basic residues), and the Sindbis virus glycoprotein genes, could not generate infectious virus. As described in Example 6, the Sindbis virus capsid protein is expressed from a separate DH expression cassette; thus, the three Sindbis virus structural proteins are expressed in toto, resulting in the production of recombinant vector particles.

Nucleotides of the RRV capsid gene corresponding to predicted regions of the expressed protein that bind to the Sindbis virus packaging sequence (Weiss et. al., Nuc. Acids, Res., 22:780–786, 1994, and Lopez et. al., ibid), including the basic residues which bind electrostatically with the viral RNA, were deleted in order to construct a heterologous alphavirus capsid-glycoprotein DH that provided translational enhancement and correct pE2-6K-E 1 polyprotein processing by post-translational cleavage, yet could not assemble stable chimeric RRV/Sindbis virus particles. FIG. 33 illustrates the hydrophobicity profiles (Kyte-Dolittle) of the RRV capsid protein, and the capsid protein expressed from 3 individual RRV capsid gene mutants (CΔ1rrv, CΔ2rrv, and CΔ3rrv), in which varying amounts of the capsid gene encoding a lysine-rich protein that interacts with the viral packaging sequence RNA, was deleted. The lysine-rich basic region of the RRV capsid protein is shown in FIG. 33. Further, the hydrophobicity profiles demonstrate that this lysine-rich basic region is progressively eliminated in the 3 individual RRV capsid gene mutants CΔ1rrv. CΔ2rrv, and CΔ3rrv. FIG. 34 demonstrates the lysine residues eliminated in the expressed RRV capsid protein, as a result of the deletions in mutants CΔ1rrv, CΔ2rrv, and CΔ3rrv. The table shown below gives the nucleotides deleted in the RRV genome of constructs CΔ1rrv, CΔ2rrv, and CΔ3rrv.

Figure 23:
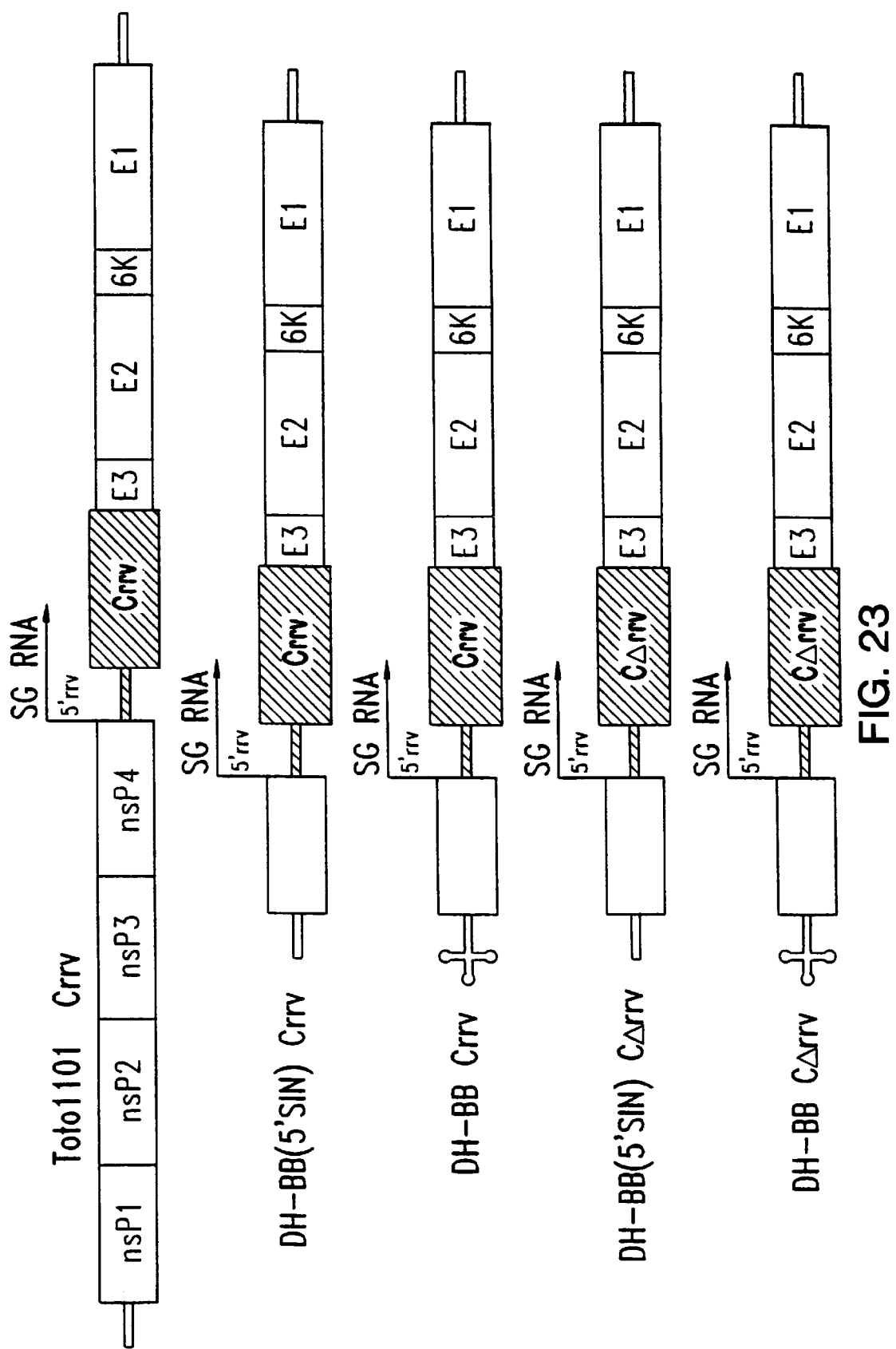
FIG. 23 is a schematic illustration of vector inducible structural protein expression cassettes containing a wild-type or deletion mutant Ross River virus capsid protein gene.

The RRV capsid gene deletions were constructed on the DH-BB Crrv plasmid DNA illustrated in FIG. 23, and described in Example 6. The indicated RRV capsid gene sequences were deleted by PCR, using the primers and other cloning steps given in Example 6.

FIGS. 31 and 32, discussed above, illustrate the virus-specific RNAs (FIG. 31) and proteins (FIG. 32) synthesized in BHK cells electroporated with SINrep/LacZ and the DH-BB CΔ1rrv, CΔ2rrv, or CΔ3rrv RNAs. and present in viral particles contained in the culture fluids of these cells. The genomic and subgenomic species were detected for both the SINrep/LacZ replicon and all the three DH-BB CΔ1rrv, CΔ2rrv, or CΔ3rrv DH RNAs in electroporated cells (FIG. 31, panel A). However, the SINrep/lacZ replicon was not packaged in vector particles in cells electroporated with DH RNA containing deletions in the RRV capsid gene, as demonstrated by the absence of replicon genomic RNA in virus particles (FIG. 31, panel B). Further, helper genomic and subgenomic RNAs were packaged very inefficiently and were barely visible in autoradiograms of denaturing gels (FIG. 31, panel B, lanes 3 and 4), when cells were electroporated with DH molecules containing larger deletions of the RRV capsid (CΔ2rrv or CΔ3rrv). In contrast. while SINrep/lacZ genomic RNA (and DH RNA in electroporations with CΔ2rrv or CΔ3rrv) was not detected in viral particles from BHK cells electroporated with the DHs containing deletions in the RRV capsid gene, equivalent RRV capsid protein and Sindbis virus glycoprotein levels were observed in virus particles from cells electroporated with all DH RNAs, regardless of whether the RRV capsid gene contained deletions (FIG. 32, panels A and B). This result demonstrates that stable chimeric virus particles not containing vector replicon, or other viral-specific RNAs, were formed in BHK cells electroporated with SINrep/lacZ genomic RNA and DH RNA. from which capsid protein unable to bind to the genomic RNA was expressed. The formation of stable empty heterologous alphavirus particles is unexpected and not predicted, based on the results and discussions of previous investigations (Lopez et. al.,*J. Virol.* 68:1316–1323, 1994, Sorger et. al. *J. Mol. Biol.,* 191:639–656, 1986, Erickson and Rossmann. *Virology* 116:128–136, 1982, and Rumenapf et. al. *J. Virol.,* 69:1741–1746, 1995).

Figure 35:
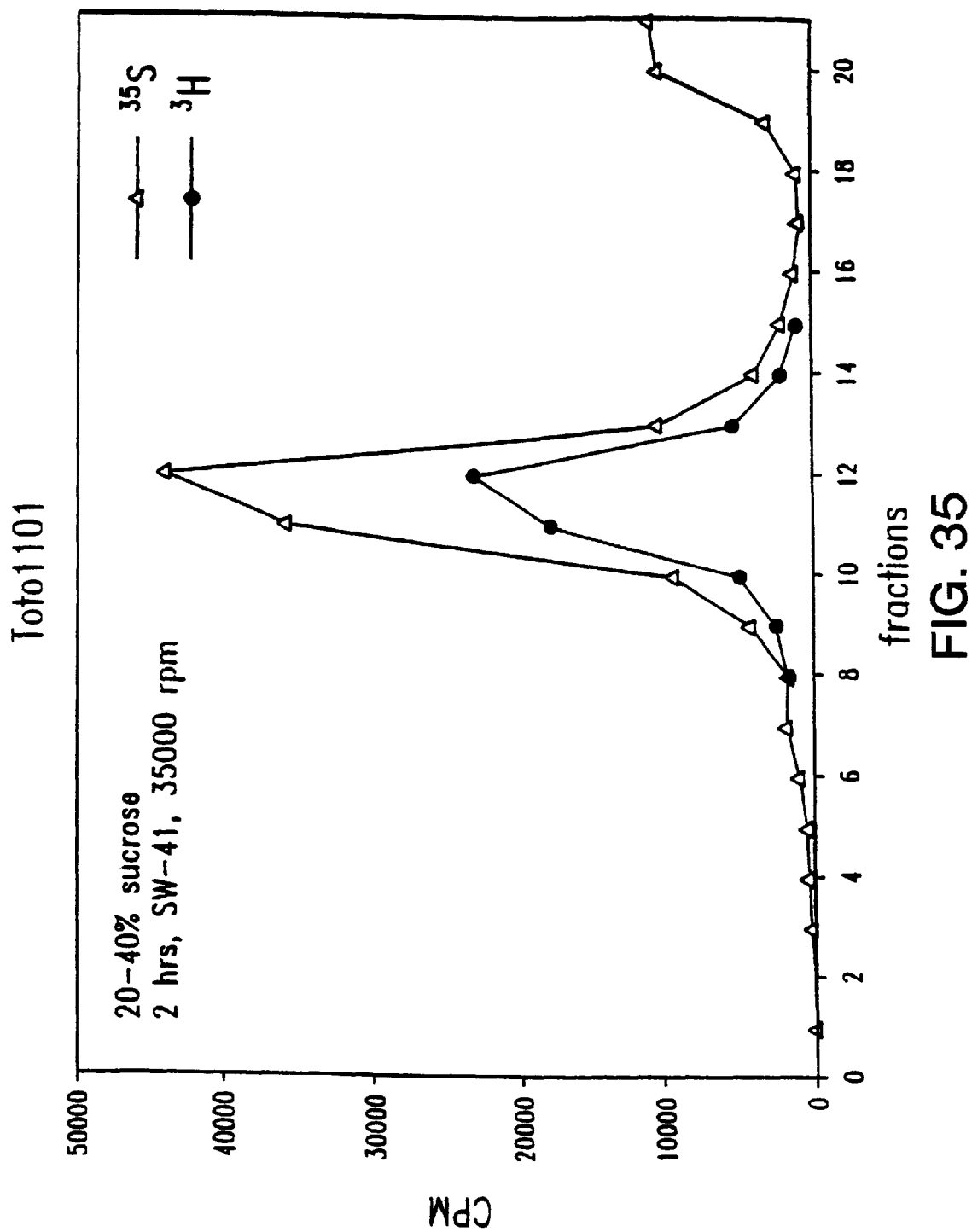
Figure 36:
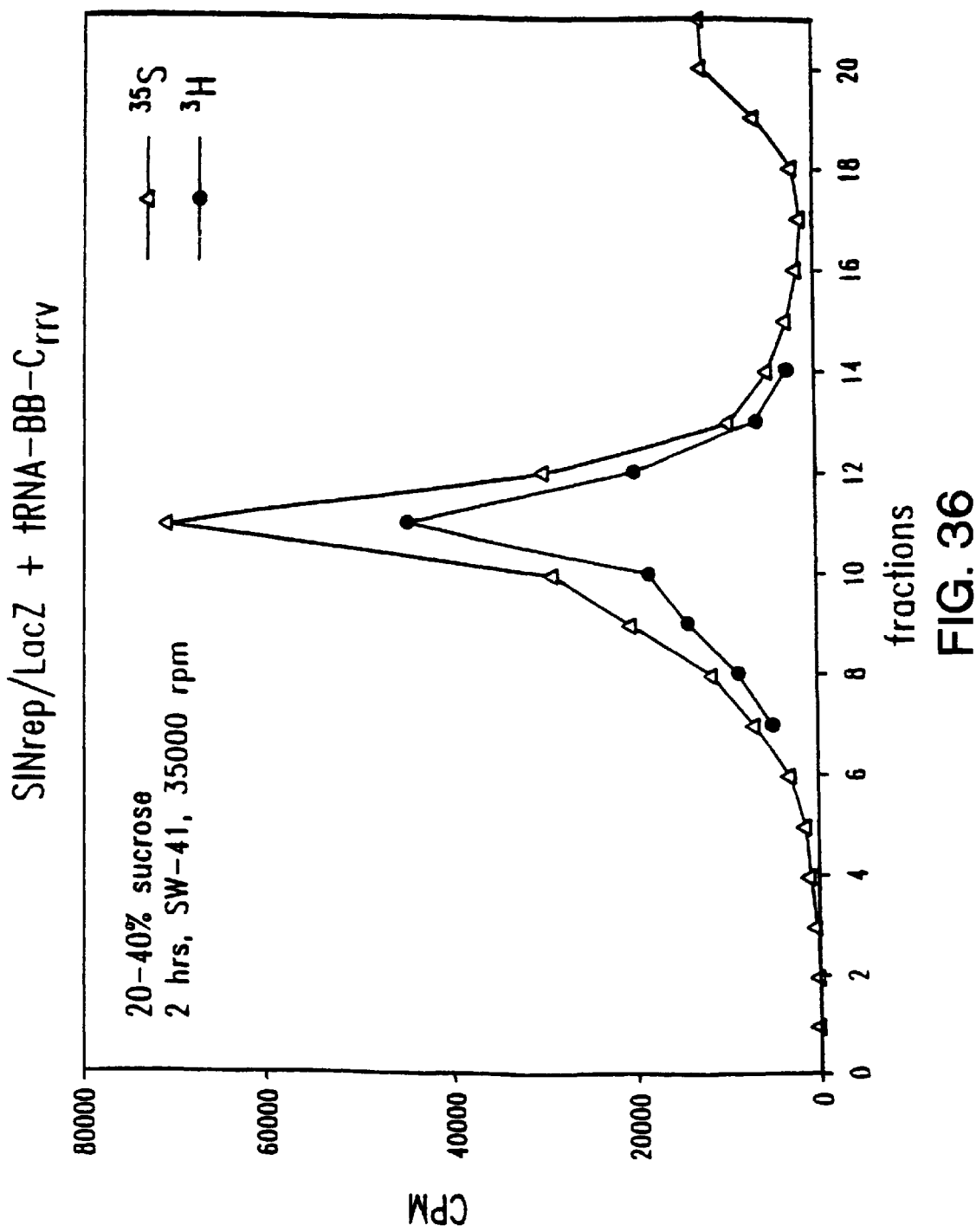
Figure 37:
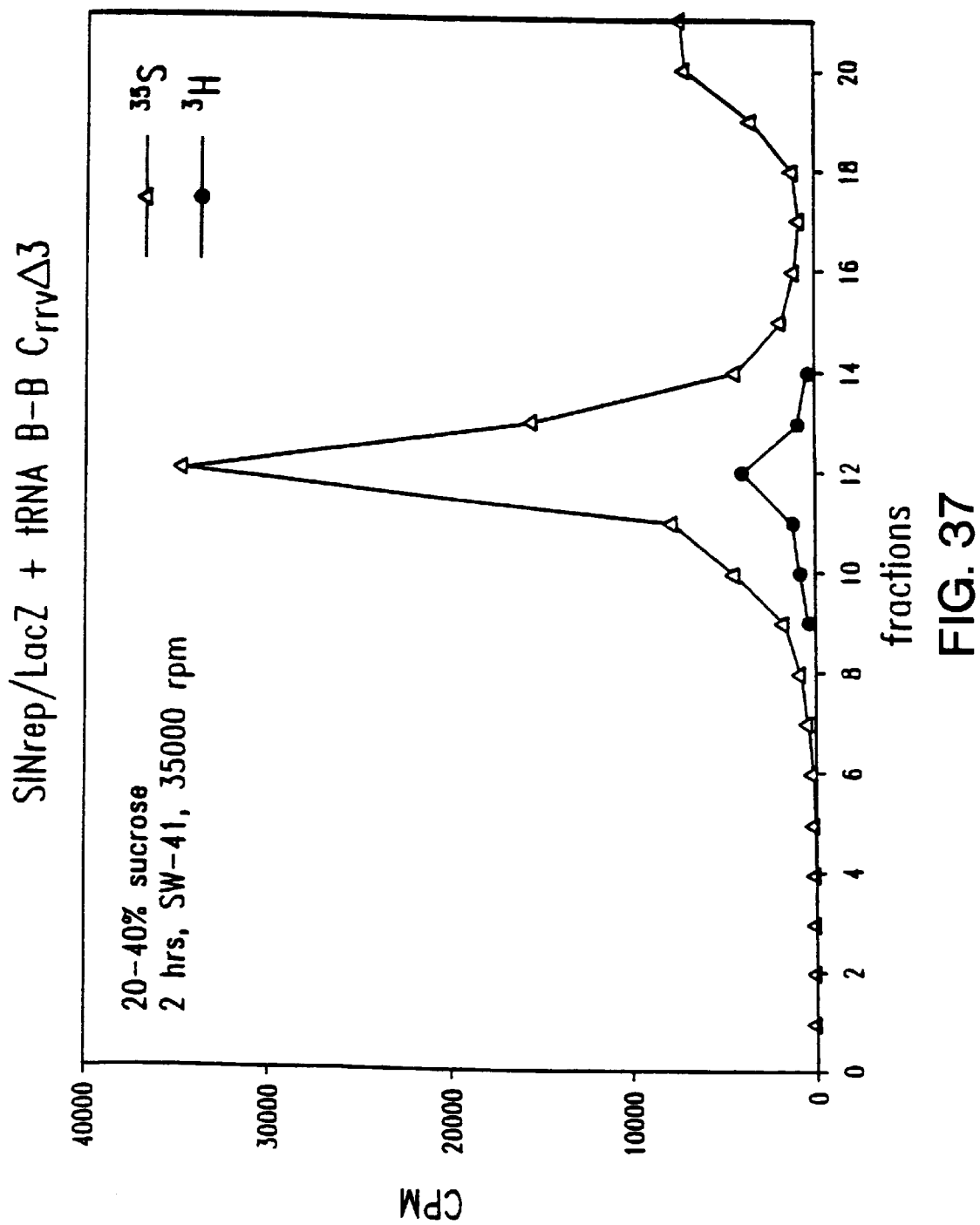
Figure 38:
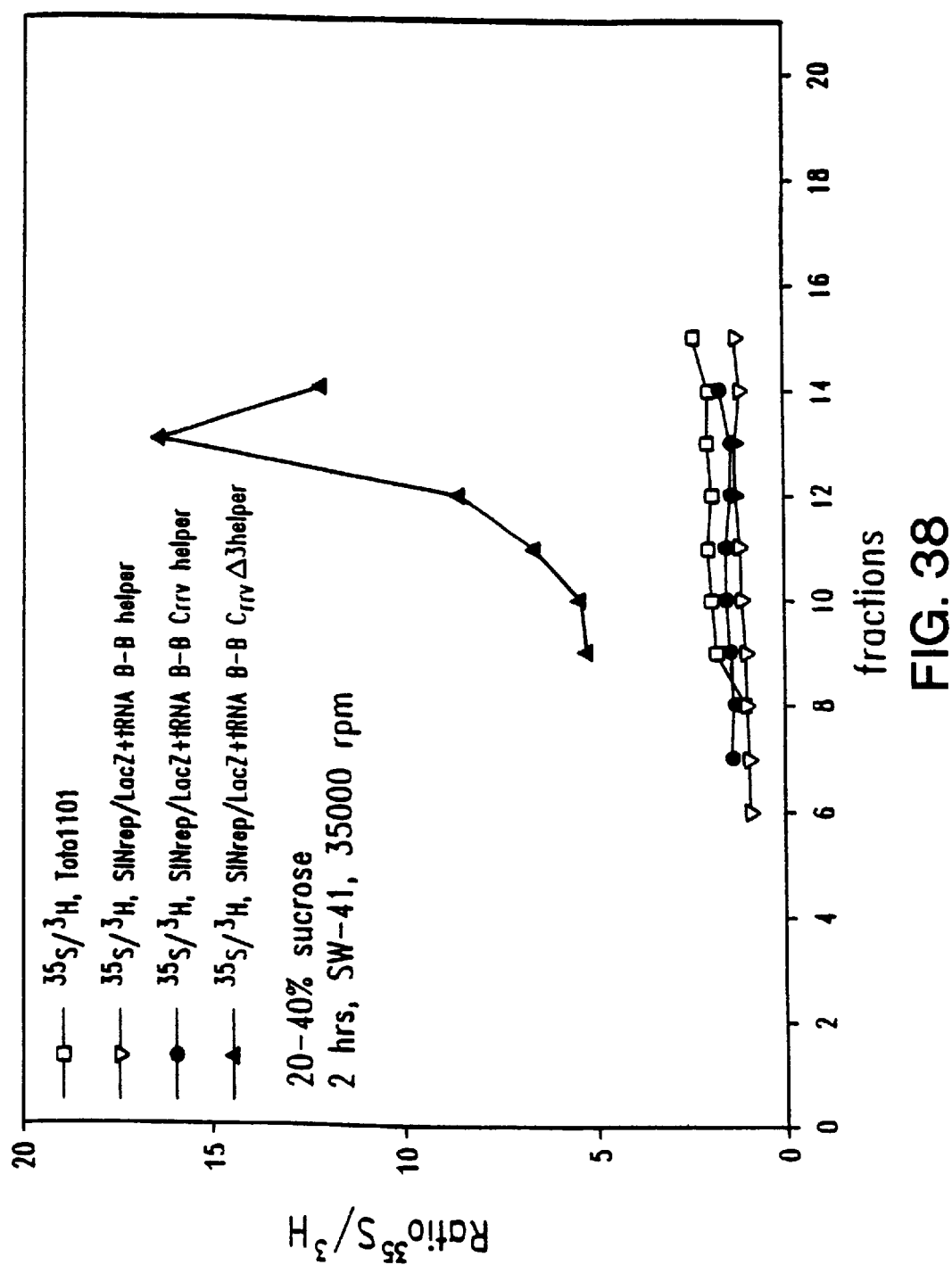

To determine the composition of the virus particles produced, BHK cells were electroporated with SINrep lacZ and the DH RNAs containing various RRV capsid gene configurations, as described herein, and were treated subsequently with dactinomycin, and labeled with [$^{35}$S] methionine and [$^3$H]uridine, as described in Example 1. The configuration of the viral particles produced were determined by ultracentrifugation of clarified cell culture media for 2 hrs at 35,000 rpm in a SWA4 rotor over a 20%–40% (w/w) sucrose gradient. The results of this study are shown in FIGS. 35–37, and demonstrate again the formation of stable empty heterologous alphavirus particles. FIG. 35 demonstrates the relative levels of [$^{35}$S]methionine and [$^3$H]uridine incorporated into particles synthesized in BHK cells infected at high MOI (5) with wild-type virus, Toto 1101. FIG. 36 demonstrates that the relative levels of [$^{35}$S]methionine and [$^3$H]uridine incorporated into particles synthesized in BHK cells electroporated with SINrep/LacZ and DH-BB (5' tRNA) Crrv (FIG. 23) RNAs was the same as in cells infected with wild-type virus. In contrast, FIG. 37 demonstrates that the particles produced in BHK cells electroporated with SINrep/LacZ and DH-BB (5' tRNA) CΔ3rrv contained very low levels of incorporated [$^3$H] uridine. FIG. 38 is a compilation of FIGS. 35–37. and illustrates clearly that while the relative levels of [$^{35}$S] methionine and [$^3$H]uridine incorporated into particles were similar in BHK cells infected or electroporated with RNAs containing wild-type alphavirus capsid genes, BHK cells electroporated with DH RNA containing deletions of nts. 7760–7891 of the RRV capsid gene formed stable chimeric empty alphavirus particles, devoid of SINrep/LacZ RNA. Titers of empty alphavirus particles, produced in cell lines electroporated with with SINrep/LacZ RNA and DH-BB CD3rrv in vitro transcribed RNAs, and labeled with [$^{35}$S] methionine, were determined by comparison with BHK cells, infected with Toto 1101 wild-type virus, and labeled with [35S]methionine. The level of radioactivity present in virus-containing sucrose gradient fractions from Toto 1101 -infected cells was quanitated, and related to the virus titer present in these same fractions, as determined by plaque assay, according to the methods described in Example 1. For empty alphavirus particle titer determinations, the level of radioactivity present in virus particle-containing sucrose gradient fractions from BHK cells electroporated with SINrep/LacZ RNA and DH-BB CD3rrv in vitro transcribed RNAs, was quantitated, and related to the [$^{35}$S]methionine/ virus titer, from Toto 1101 infected cells. The titer of empty chimeric virus particles, containing the deleted Ross River virus capsid and the Sindbis virus glycoproteins, produced in SINrep/LacZ RNA and DH-BB CD3rrv in vitro transcribed RNA electroporated cells was 1×10$^9$ particles/ml.

While the present invention has been described above both generally and in terms of preferred embodiments, it is understood that variations and modifications will occur to those skilled in the art in light of the description, supra. Therefore, it is intended that the appended claims cover all such variations coming within the scope of the invention as claimed.

Additionally, the publications and other materials cited to illuminate the background of the invention, and in particular, to provide additional details concerning its practice as described in the detailed description and examples, are hereby incorporated by reference in their entirety.

We claim:

1. A eukaryotic layered vector initiation system, comprising:
   (a) a 5' promoter which directs synthesis of alphavirus RNA in vivo from cDNA;
   (b) a 5' sequence which directs transcription of alphavirus RNA;
   (c) a nucleic acid sequence which operably encodes all four alphaviral nonstructural proteins;
   (d) an alphavirus RNA polymerase recognition sequence; and
   (e) a 3'polyadenylate tract;
   wherein said nucleic acid sequence which operably encodes all four alphaviral nonstructural proteins further comprises an altered nucleic acid sequence encoding for nonstructural protein 2 (nsP2) such that when said altered nucleic acid sequence is operably incorporated into an RNA vector replicon, the time required to reach 50% inhibition of host-cell directed macromolecular synthesis following expression in mammalian cells is increased, as compared to an RNA vector replicon having a wild-type alphavirus nsP2.

2. The eukaryotic layered vector initiation system according to claim 1 further comprising an alphavirus junction region promoter sequence.

3. The eukaryotic layered vector initiation system according to claim 2 wherein said eukaryotic layered vector initiation system further comprises a heterologous nucleic acid sequence.

4. The eukaryotic layered vector initiation system according to claim 3 wherein said heterologous nucleic acid sequence encodes an interferon.

5. The eukaryotic layered vector initiation system according to claim 3 wherein said heterologous nucleic acid sequence encodes a growth factor.

6. The eukaryotic layered vector initiation system according to claim 5 wherein said growth factor is basic Fibroblast Growth Factor (FGF).

7. The eukaryotic layered vector initiation system according to claim 5 wherein said growth factor is Platelet-derived Growth Factor (PDGF).

8. The eukaryotic layered vector initiation system according to claim 5 wherein said growth factor is a bone morphogenetic protein.

9. The eukaryotic layered vector initiation system according to claim 3 wherein said heterologous nucleic acid sequence encodes an antigen from a pathogenic agent.

10. The eukaryotic layered vector initiation system according to claim 9 wherein said pathogenic agent is a virus.

11. The eukaryotic layered vector initiation system according to claim 10 wherein said virus is selected from the group consisting of hepatitis B virus (HBV), hepatitis C virus (HCV) and human immunodeficiency virus (HIV).

12. The eukaryotic layered vector initiation system according to claim 1 wherein said 5' promoter which directs synthesis of alphavirus RNA in vivo from cDNA is a eukaryotic promoter.

13. The eukaryotic layered vector initiation system according to claim 12 wherein said eukaryotic promoter is a RNA polymerase II (pol II) promoter.

14. The eukaryotic layered vector initiation system according to claim 13 wherein said pol II promoter is a cytomegalovirus (CMV) or Rous sarcoma virus (RSV) promoter.

15. The eukaryotic layered vector initiation system according to claim 1 wherein said sequence encoding said altered nonstructural protein has a mutation within a Leu-Xaa-Pro-Gly-Gly motif SEQ ID NO: 119.

16. The eukaryotic layered vector initiation system according to claim 1 wherein said sequence encoding said altered nonstructural protein has a mutation one to three amino acids upstream or downstream of a Leu-Xaa-Pro-Gly-Gly motif SEQ ID NO: 119.

17. The eukaryotic layered vector initiation system according to claim 1 wherein said heterologous nucleic acid sequence encodes a lymphokine.

18. The eukaryotic layered vector initiation system according to claim 17 wherein said lymphokine is interleukin-2 (IL-2).

19. The eukaryotic layered vector initiation system according to claim 1 wherein said alphavirus is Sindbis virus and wherein said altered nsP2 has a mutation at amino acid residue 726.

20. A eukaryotic layered vector initiation system, comprising:

(a) a 5' eukaryotic promoter which directs synthesis of alphavirus RNA in vivo from cDNA;

(b) a 5' sequence which directs transcription of alphavirus RNA;

(c) a nucleic acid sequence which operably encodes all four alphaviral nonstructural proteins;

(d) alphavirus junction region promoter sequence;

(e) heterologous nucleic acid sequence;

(f) an alphavirus RNA polymerase recognition sequence; and (g) a 3'polyadenylate tract;

wherein said nucleic acid sequence which operably encodes all four alphaviral nonstructural proteins further comprises an altered nucleic acid sequence encoding for nonstructural protein 2 (nsP2) having a mutation at amino acid residue 726 such that when said altered nucleic acid sequence is operably incorporated into an RNA vector replicon, the time required to reach 50% inhibition of host-cell directed macromolecular synthesis following expression in mammalian cells is increased, as compared to an RNA vector replicon having a wild-type alphavirus nsP2.

21. The eukaryotic layered vector initiation system according to any one of claims 1 to 20 wherein said alphavirus is Sindbis virus.

22. The eukaryotic layered vector initiation system according to any one of claims 1 to 20 wherein said alphavirus is S.A.AR86 virus.

23. The eukaryotic layered vector initiation system according to any one of claims 1 to 20 wherein said alphavirus is Semliki Forest virus.

24. The eukaryotic layered vector initiation system according to any one of claims 1 to 20 wherein said alphavirus is Venezuelan equine encephalitis virus.

25. The eukaryotic layered vector initiation system according to any one of claims 1 to 20 wherein said alphavirus is Ross River virus.

* * * * *